United States Patent
Kobayashi et al.

(10) Patent No.: US 10,077,401 B2
(45) Date of Patent: *Sep. 18, 2018

(54) POLYMERIZABLE COMPOUND, POLYMERIZABLE COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Masahide Kobayashi, Chiba (JP); Yasuyuki Gotoh, Tokyo (JP); Takahiro Kobayashi, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/903,594

(22) PCT Filed: Mar. 13, 2014

(86) PCT No.: PCT/JP2014/056666
§ 371 (c)(1),
(2) Date: Jan. 7, 2016

(87) PCT Pub. No.: WO2015/004947
PCT Pub. Date: Jan. 15, 2015

(65) Prior Publication Data
US 2016/0152895 A1 Jun. 2, 2016

(30) Foreign Application Priority Data

Jul. 10, 2013 (JP) ................................. 2013-144613
Oct. 29, 2013 (JP) ................................. 2013-223998

(51) Int. Cl.
| | | |
|---|---|---|
| G02F 1/1333 | (2006.01) |
| C09K 19/56 | (2006.01) |
| C09K 19/30 | (2006.01) |
| C09K 19/34 | (2006.01) |
| C07C 69/017 | (2006.01) |
| C07C 69/653 | (2006.01) |
| C07D 303/23 | (2006.01) |
| C07D 407/12 | (2006.01) |
| C09K 19/20 | (2006.01) |
| C08G 59/32 | (2006.01) |
| C09K 19/04 | (2006.01) |

(Continued)

(52) U.S. Cl.
CPC ............ *C09K 19/56* (2013.01); *C07C 69/017* (2013.01); *C07C 69/653* (2013.01); *C07D 303/23* (2013.01); *C07D 407/12* (2013.01); *C08G 59/3218* (2013.01); *C09K 19/20* (2013.01); *C09K 19/3003* (2013.01); *C09K 19/3059* (2013.01); *C09K 19/3411* (2013.01); *C08F 222/1006* (2013.01); *C09K 2019/0448* (2013.01); *C09K 2019/0466* (2013.01); *C09K 2019/123* (2013.01); *C09K 2019/124* (2013.01); *C09K 2019/3004* (2013.01); *C09K 2019/3016* (2013.01)

(58) Field of Classification Search
CPC ........................ C09K 19/56; C09K 19/3059; C09K 19/3411; C09K 19/20; C09K 19/3003; C09K 2019/0448; C09K 2019/0466; C09K 2019/123; C09K 2019/124; C09K 2019/3004; C09K 2019/3016; G02F 1/1333; C07C 69/017; C07C 69/653; C07D 303/23; C07D 407/12; C08G 59/3218; C08F 222/1006
USPC ........................................ 252/299.4; 428/1.1
See application file for complete search history.

(56) References Cited

U.S. PATENT DOCUMENTS

| 7,927,671 B2* | 4/2011 | Kato | .................... C08F 26/06 252/299.5 |
| 9,714,210 B2* | 7/2017 | Furusato | ................ C07C 69/54 |

(Continued)

FOREIGN PATENT DOCUMENTS

| CN | 101437924 | 5/2009 |
| CN | 101687778 | 3/2010 |
| EP | 2990424 | 3/2016 |

(Continued)

OTHER PUBLICATIONS

Bonifacio et al., "Polycyclic Aromatic Hydrocarbons by Ring-Closing Metathesis", Journal of Organic Chemistry, Sep. 2005, pp. 8522-8526, vol. 70, No. 21.

(Continued)

*Primary Examiner* — Geraldina Visconti
(74) *Attorney, Agent, or Firm* — JCIPRNET

(57) ABSTRACT

A polymerizable compound having high polymerization reactivity, a high conversion ratio and high solubility in a liquid crystal composition, a polymerizable composition containing the compound, a liquid crystal composite prepared from the composition and a liquid crystal display device having the composite are shown. The polymerizable compound has three or four rings in a serial arrangement and not being mutually condensed, and has three or more polymerizable groups among which at least one is bonded with a ring which is not an either terminal of the three or four rings. The polymerizable composition contains the above polymerizable compound and a liquid crystal composition. The liquid crystal composite is prepared from the above polymerizable composition, and the liquid crystal display device has the liquid crystal composite.

18 Claims, No Drawings

(51) Int. Cl.
 *C09K 19/12* (2006.01)
 *C08F 222/10* (2006.01)

(56) References Cited

U.S. PATENT DOCUMENTS

2016/0075950 A1* 3/2016 Kobayashi .............. C08F 20/26
 252/299.01
2016/0376506 A1* 12/2016 Saito .................. C09K 19/3068
 252/299.61

FOREIGN PATENT DOCUMENTS

| JP | 2008-100982 | 5/2008 |
| JP | 2008-291218 | 12/2008 |
| JP | 2009-269957 | 11/2009 |
| JP | 2011246365 | 12/2011 |
| JP | 2012-018215 | 1/2012 |
| JP | 2012-140585 | 7/2012 |
| JP | 2013-014538 | 1/2013 |
| KR | 20080102795 | 11/2008 |
| TW | 201040135 | 11/2010 |
| TW | 201321483 | 6/2013 |
| WO | 2008/105538 | 9/2008 |
| WO | 2013/014733 | 1/2013 |
| WO | 2013/054682 | 4/2013 |
| WO | 2014/024648 | 2/2014 |

OTHER PUBLICATIONS

Kouno et al., "A New Triphenyl-Type Neolignan and a Biphenylneolignan from the Bark of Illicium simonsii", Chemical & Pharmaceutical Bulletin, Jan. 1994, pp. 112-114, vol. 42, No. 1.
"International Search Report (Form PCT/ISA/210)", dated May 20, 2014, pp. 1-4.
"Office Action of Taiwan Counterpart Application," with English translation thereof, dated May 23, 2017, p. 1-p. 14.
"Office Action of China Counterpart Application," with English tranaslation thereof, dated Jul. 20, 2017, p. 1-p. 17.
"Office Action of China Counterpart Application" dated Feb. 11, 2018, with English translation thereof, p. 1-p. 9.
"Office Action of China Counterpart Application" with English translation thereof, dated Dec. 2, 2016, p. 1-p. 15.
"Search Report of Europe Counterpart Application", dated Feb. 3, 2017, p. 1-p. 16.
"Office Action of Taiwan Counterpart Application," dated Jun. 22, 2018, with English translation thereof, p. 1-p. 13.

* cited by examiner

US 10,077,401 B2

POLYMERIZABLE COMPOUND, POLYMERIZABLE COMPOSITION AND LIQUID CRYSTAL DISPLAY DEVICE

CROSS-REFERENCE TO RELATED APPLICATION

This application is a 371 application of the International PCT application serial no. PCT/JP2014/056666, filed on Mar. 13, 2014, which claims the priority benefits of Japan application serial no. 2013-144613, filed on Jul. 10, 2013, and Japan application serial no. 2013-223998, filed on Oct. 29, 2013. The entirety of each of the above-mentioned patent applications is hereby incorporated by reference herein and made a part of this specification.

TECHNICAL FIELD

The present invention relates to a polymerizable compound, a polymerizable composition containing the polymerizable compound and a liquid crystal composition, a liquid crystal composite prepared from the polymerizable composition, and a liquid crystal display device.

BACKGROUND ART

A liquid crystal display device utilizes optical anisotropy, dielectric anisotropy and so forth of liquid crystal molecules in a liquid crystal composition. A classification based on an operating mode for the liquid crystal molecules includes a phase change (PC) mode, a twisted nematic (TN) mode, a super twisted nematic (STN) mode, a bistable twisted nematic mode (BTN), an electrically controlled birefringence (ECB) mode, an optically compensated bend (OCB) mode, an in-plane switching (IPS) mode, a fringe field switching (FFS) mode and a vertical alignment (VA) mode.

A liquid crystal display device having a mode in which a polymer is combined with the liquid crystal composition is known. Specific examples thereof include a polymer sustained alignment (PSA) mode or a polymer stabilized (PS) mode. In the liquid crystal display device having the mode, the liquid crystal composition to which a polymerizable compound is added is injected into the display device. The display device is irradiated with UV light in a state in which voltage is applied between electrodes, and the polymerizable compound is polymerized to form the polymer in the liquid crystal composition. The liquid crystal device is obtained in which a response time of the device is shortened, and image persistence is improved by the above method.

The above method above is applicable to the liquid crystal display devices having various operating modes, and such modes are known as a PS-TN mode, a PS-IPS mode, a PS-FFS mode, a PSA-VA mode and a PSA-OCB mode. The polymerizable compound used in the device having such a mode is considered to have high capacity for aligning liquid crystal molecules, but solubility in the liquid crystal composition is far from high. An attempt has been made so far on improving the solubility in the liquid crystal composition. However, if the solubility is improved, polymerization reactivity tends to reduce. Accordingly, a development has been desired for the polymerizable compound having a suitable balance between the solubility and the polymerization reactivity.

CITATION LIST

Patent Literature

Patent literature No. 1: JP 2012-018215 A
Patent literature No. 2: JP 2013-014538 A

SUMMARY OF INVENTION

Technical Problem

A first objective of the invention is to provide a polymerizable compound having high polymerization reactivity, a high conversion ratio and a high solubility in a liquid crystal composition. A second objective is to provide a liquid crystal composite satisfying at least one of physical properties such as a high maximum temperature of a nematic phase, a low minimum temperature of the nematic phase, a small viscosity, a suitable optical anisotropy, a large dielectric anisotropy, a suitable elastic constant, a large specific resistance and a suitable pretilt. The above objective is to provide a liquid crystal composite having a suitable balance regarding at least two physical properties. A third objective is to provide a liquid crystal display device having a wide temperature range in which the device can be used, a short response time, a high voltage holding ratio, a low threshold voltage, a large contrast ratio and a long service life.

Solution to Problem

The invention concerns a polymerizable compound serially formed of three or four rings not condensed with each other, in which the polymerizable compound also has three or more polymerizable groups, and at least one of the polymerizable groups is bonded with a ring not at both terminals among the three or four rings, a polymerizable composition containing the polymerizable compound and a liquid crystal composition, a liquid crystal composite prepared from the polymerizable composition, and a liquid crystal display device.

Advantageous Effects of Invention

A first advantage of the invention is in a polymerizable compound having high polymerization reactivity, a high conversion ratio and a high solubility in a liquid crystal composition. A second advantage is in a liquid crystal composite satisfying at least one of physical properties such as a high maximum temperature of a nematic phase, a low minimum temperature of the nematic phase, a small viscosity, a suitable optical anisotropy, a large dielectric anisotropy, a suitable elastic constant, a large specific resistance and a suitable pretilt. The above advantage is in a liquid crystal composite having a suitable balance regarding at least two physical properties. A third advantage is in a liquid crystal display device having a wide temperature range in which the device can be used, a short response time, a high voltage holding ratio, a low threshold voltage, a large contrast ratio and a long service life.

DESCRIPTION OF EMBODIMENTS

Usage of terms herein is as described below. "Liquid crystal compound" is a generic term for a non-polymerizable compound having a liquid crystal phase such as a nematic phase and a smectic phase, and a non-polymerizable compound having no liquid crystal phase but being mixed for the purpose of adjusting physical properties of a liquid crystal composition, such as a maximum temperature, a minimum temperature, viscosity and dielectric anisotropy. The compound has a 6-membered ring such as 1,4-cyclohexylene and 1,4-phenylene, and a rod like molecular structure. The liquid crystal composition is a mixture of liquid crystal compounds. A polymerizable compound is a compound to be added to the composition for the purpose of forming a polymer. The polymerizable composition is a composition containing the polymerizable compound, and a mixture of the polymerizable compound, the liquid crystal composition and an additive, for example. The liquid crystal composite is a composite formed by polymerization of the polymerizable composition. A liquid crystal display device is a generic term for a liquid crystal display panel and a liquid crystal display module. The maximum temperature of the nematic phase is a phase transition temperature between the nematic phase and an isotropic phase in the liquid crystal composition, the polymerizable composition or the liquid crystal composite, and may be occasionally abbreviated as the maximum temperature. The minimum temperature of the nematic phase may be occasionally abbreviated as the minimum temperature. Polymerization reactivity means a degree of easiness when a reactant is polymerized. A conversion ratio is expressed in terms of a weight ratio of the reactant consumed by a chemical reaction based on the reactant.

The liquid crystal composition is prepared by mixing the liquid crystal compounds. A proportion (content) of a liquid crystal compound is expressed in terms of weight percent (wt %) based on the weight of the liquid crystal composition. An additive such as an optically active compound, an antioxidant, a UV light absorber, a light stabilizer, a heat stabilizer, an antifoaming agent, a polymerization initiator and a polymerization inhibitor is added to the composition when necessary. A proportion (amount of addition) of the additive is expressed in terms of weight percent (wt %) based on the weight of the liquid crystal composition in a manner similar to the proportions of the liquid crystal compounds. Weight parts per million (ppm) may be occasionally used. A proportion of the polymerization initiator and the polymerization inhibitor is exceptionally expressed based on the weight of the polymerizable compound.

A compound represented by formula (1) may be occasionally abbreviated as "compound (1)." The abbreviation also applies to a compound represented by formula (2) or the like. Compound (1) means one compound or two or more compounds represented by formula (1). In formulas (1) to (8), a symbol such as $A^1$, $B^1$, $C^1$ surrounded by a circle or a hexagonal shape corresponds to ring $A^1$, ring $B^1$, ring $C^1$ or the like, respectively. In formula (1), an oblique line crossing the circle means that a bonding position on a ring can be arbitrarily selected for a $P^1$-$S^1$ group. A same rule also applies to a $P^2$-$S^2$ group or the like. A same rule also applies to an oblique line crossing a six-membered ring represented by formula (1-1) or the like. In formula (1), a subscript such as a1 represent the number of groups to be bonded with ring $A^1$ or the like. When a1 is 2, two of $P^1$-$S^1$ group exists on ring $A^1$. Two groups represented by two of $P^1$-$S^1$ group may be identical or different. A same rule also applies to arbitrary two when a1 is larger than 2. A same rule also applies to any other group. A symbol of $R^{11}$ is used for plurality of formulas such as formula (2) and formula (3). In the compounds, two terminal groups represented by two of arbitrary $R^{11}$ may be identical or different. In formula (8), when i is 2, two of symbol $D^1$ exists in one formula. In the compound, two rings represented by two of symbol $D^1$ may be identical or different. A same rule also applies to a symbol such as $Z^{17}$.

An expression "at least one of 'A' may be replaced by 'B'" means that a position of 'A' is arbitrary when the number of 'A' is one and also that the positions can be selected without restriction when the number of 'A' is two or more. An expression "at least one of A may be replaced by B, C or D" means inclusion of a case where at least one of A is replaced by B, a case where at least one of A is replaced by C, a case where at least one of A is replaced by D, and a case where a plurality of A are further replaced by at least two of B, C and D. For example, alkyl in which at least one —$CH_2$— (or —$CH_2CH_2$—) may be replaced by —O— (or —CH═CH—) includes alkyl, alkenyl, alkoxy, alkoxyalkyl, alkoxyalkenyl and alkenyloxyalkyl. In addition, a case where two successive —$CH_2$— is replaced by —O— to form —O—O— or the like is not preferred. In alkyl or the like, a case where —$CH_2$— of a methyl part (—$CH_2$—H) is replaced by —O— to form —O—H is not preferred, either.

Then, 2-fluoro-1,4-phenylene means two divalent groups described below. In a chemical formula, fluorine may be leftward (L) or rightward (R). A same rule also applies to a ring having an asymmetrical divalent group such as tetrahydropyran-2,5-diyl.

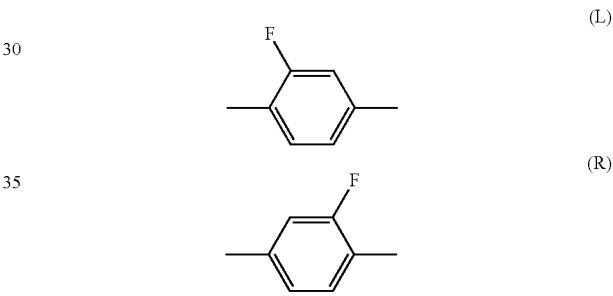

The invention includes a content described in items described below.

Item 1. A polymerizable compound serially formed of three or four rings not condensed with each other, wherein the polymerizable compound also has three or more polymerizable groups, and at least one of the polymerizable groups is bonded with a ring not at both terminals among the three or four rings.

Item 2. The polymerizable compound of item 1, represented by formula (1):

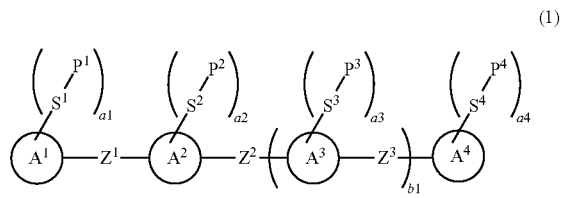

wherein, in formula (1), $P^1$, $P^2$, $P^3$ and $P^4$ are a polymerizable group;

$S^1$, $S^2$, $S^3$ and $S^4$ are independently a single bond or alkylene having 1 to 10 carbons, and in alkylene, at least one —$CH_2$— may be replaced by —O—, —COO—, —OCO— or —OCOO—, at least one —CH$_2$—CH$_2$— may be replaced by —CH=CH— or —C≡C—, and at least one hydrogen may be replaced by fluorine or chlorine;

a1, a3 and a4 are independently 0, 1, 2, 3 or 4, a2 is 1, 2, 3 or 4, and a sum of a1, a2, a3 and a4 is 3 to 10;

ring A$^1$ and ring A$^4$ are independently phenyl, pyrimidyl, pyridyl, naphthyl, cyclohexyl, cyclohexenyl, tetrahydropyranyl or 1,3-dioxanyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

ring A$^2$ and ring A$^3$ are independently 1,4-phenylene, pyrimidine-2,5-diyl, pyridine-2,5-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, 1,4-cyclohexylene, 1,4-cyclohexenylene, tetrahydropyran-2,5-diyl or 1,3-dioxane-2,5-diyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

Z$^1$, Z$^2$ and Z$^3$ are independently a single bond or alkylene having 1 to 10 carbons, and in the alkylene, at least one —CH$_2$— may be replaced by —O—, —CO—, —COO— or —OCO—, at least one —CH$_2$—CH$_2$— may be replaced by —CH=CH—, —C(CH$_3$)=CH—, —CH=C(CH$_3$)— or —C(CH$_3$)=C(CH$_3$)—, and at least one hydrogen may be replaced by fluorine or chlorine; and b1 is 0 or 1.

Item 3. The polymerizable compound of item 2, wherein, in formula (1) described in item 2, P$^1$, P$^2$, P$^3$ and P$^4$ are independently acryloyloxy or methacryloyloxy;

S$^1$, S$^2$, S$^3$ and S4 are independently a single bond or alkylene having 1 to 10 carbons, and in the alkylene, one of —CH$_2$— may be replaced by —O—, —COO—, —OCO— or —OCOO—, one of —CH$_2$—CH$_2$— may be replaced by —CH=CH— or —C≡C—, and at least one hydrogen may be replaced by fluorine or chlorine;

a1, a3 and a4 are independently 0, 1, 2, 3 or 4, a2 is 1, 2, 3 or 4, and a sum of a1, a2, a3 and a4 is 3 to 10;

ring A$^1$ and ring A$^4$ are independently phenyl, pyrimidyl, pyridyl or naphthyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

ring A$^2$ and ring A$^3$ are independently 1,4-phenylene, pyrimidine-2,5-diyl, pyridine-2,5-diyl, naphthalene-1,4-diyl, naphthalene-1,5-diyl, naphthalene-2,6-diyl, 1,4-cyclohexylene, tetrahydropyran-2,5-diyl or 1,3-dioxane-2,5-diyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

Z$^1$, Z$^2$ and Z$^3$ are independently a single bond, alkylene having 1 to 5 carbons, —CO—, 13 COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CO—CH=CH—, —CH=CH—CO—, —C(CH$_3$)=C(CH$_3$)—, —CH=CH—CH$_2$O—, —OCH$_2$—CH=CH—, —CH=CH—OCH$_2$— or —CH$_2$O—CH=CH—; and b1 is 0 or 1.

Item 4. The polymerizable compound of item 1 or 2, represented by formula (1-1):

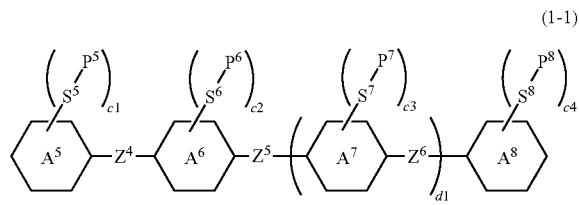

(1-1)

wherein, in formula (1-1),

P$^5$, P$^6$, P$^7$ and P$^8$ are independently acryloyloxy or methacryloyloxy;

S$^5$, S$^6$, S$^7$ and S$^8$ are independently a single bond or alkylene having 1 to 5 carbons, and in the alkylene, one of —CH$_2$— may be replaced by —O—, —COO— or —OCO—, and one of —CH$_2$—CH$_2$— may be replaced by —CH=CH—;

c1, c3 and c4 are independently 0, 1 or 2, c2 is 1 or 2, and a sum of c1, c2, c3 and c4 is 3 to 6;

ring A$^5$ and ring A$^8$ are independently phenyl in which at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

ring A$^6$ and ring A$^7$ are independently 1,4-phenylene in which at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

Z$^4$, Z$^5$ and Z$^6$ are independently a single bond, alkylene having 1 to 5 carbons, —CO—, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=O(CH$_3$)—, —CO—CH=CH—, —CH=CH—CO—, —C(CH$_3$)=C(CH$_3$)—, —CH=CH—CH$_2$O—, —OCH$_2$—CH=CH—, —CH=CH—OCH$_2$— or —CH$_2$—O—CH=CH—; and d1 is 0 or 1.

Item 5. The polymerizable compound of item 1, represented by any one of formula (1-1-1) or (1-1-2):

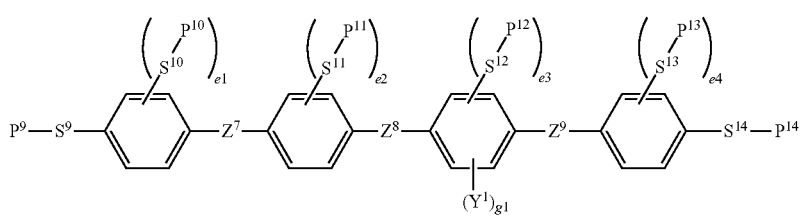

(1-1-1)

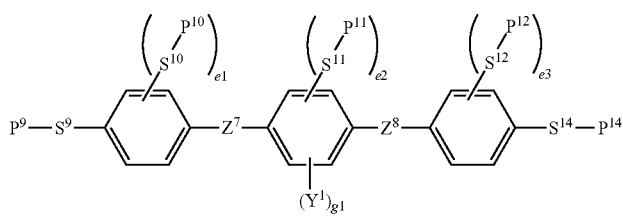

(1-1-2)

wherein, in formulas (1-1-1) and (1-1-2),
- $P^9$, $P^{10}$, $P^{11}$, $P^{12}$, $P^{13}$ and $P^{14}$ are independently acryloyloxy or methacryloyloxy;
- $S^{11}$, $S^{12}$, $S^{13}$, $S^{14}$, $S^{15}$ and $S^{16}$ are independently a single bond or alkylene having 1 to 5 carbons, and in the alkylene, one of —CH$_2$— may be replaced by —O—, —COO— or —OCO—, and one of —CH$_2$—CH$_2$— may be replaced by —CH=CH—;
- e1, e3 and e4 are independently 0, 1 or 2, e2 is 1 or 2, and a sum of e1, e2, e3 and e4 is 1 to 4;
- $Z^4$, $Z^5$ and $Z^6$ are independently a single bond, alkylene having 1 to 5 carbons, —CO—, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CO—CH=CH—, —CH=CH—CO—, —C(CH$_3$)=C(CH$_3$)—, —CH=CH—CH$_2$O—, —OCH$_2$—CH=CH—, —CH=CH—OCH$_2$— or —CH$_2$O—CH=CH—;
- g1 is 0, 1 or 2; and
- $Y^1$ is halogen, alkyl having 1 to 5 carbons, alkoxy having 1 to 5 carbons, alkyl having 1 to 5 carbons in which at least one hydrogen is replaced by halogen, or alkoxy having 1 to 5 carbons in which at least one hydrogen is replaced by halogen.

Item 6. The polymerizable compound of item 1 or 2, represented by formula (1-2) or (1-3):

wherein, in formulas (1-2) and (1-3),
- $P^9$, $P^{10}$, $P^{11}$, $P^{12}$, $P^{13}$ and $P^{14}$ are independently acryloyloxy or methacryloyloxy;
- $S^9$, $S^{10}$, $S^{11}$, $S^{12}$, $S^{13}$ and $S^{14}$ are independently a single bond or alkylene having 1 to 5 carbons, and in the alkylene, one of —CH$_2$— may be replaced by —O—, —COO— or —OCO—, and one of —CH$_2$—CH$_2$— may be replaced by —CH=CH—;
- e1, e3 and e4 are independently 0, 1 or 2, e2 is 1 or 2, and a sum of e1, e2, e3 and e4 is 1 to 4;
- $Z^7$, $Z^8$ and $Z^9$ are independently a single bond, alkylene having 1 to 5 carbons, —CO—, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CO—CH=CH—, —CH=CH—CO—, —C(CH$_3$)=C(CH$_3$)—, —CH=CH—CH$_2$O—, —OCH$_2$—CH=CH—, —CH=CH—OCH$_2$— or —CH$_2$—O—CH=CH—.

Item 7. The polymerizable compound of item 1 or 2, represented by formula (1-4) or (1-5):

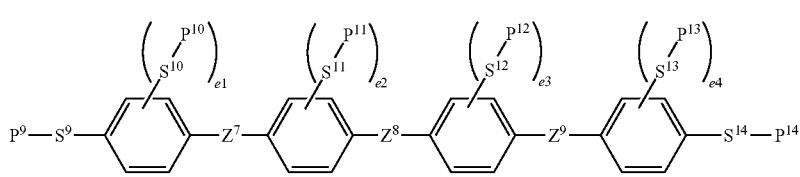

(1-2)

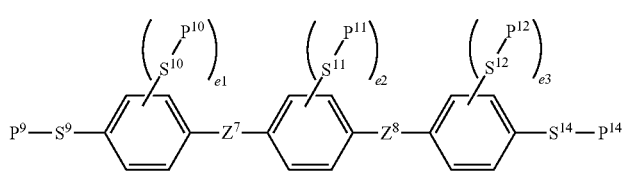

(1-3)

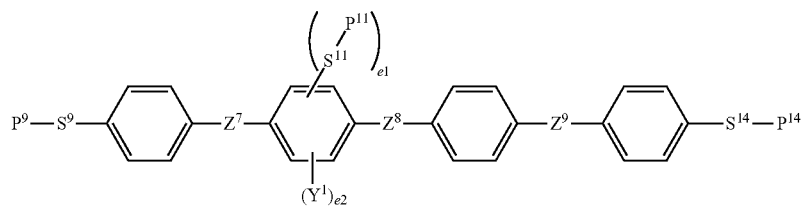
(1-4)

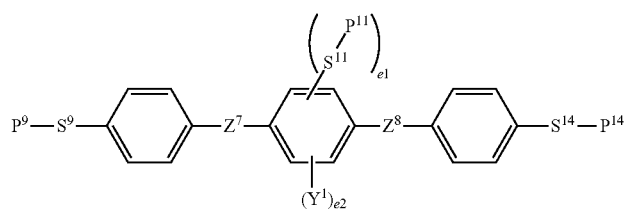
(1-5)

wherein, in formulas (1-4) and (1-5), $P^9$, $P^{11}$ and $P^{14}$ are independently acryloyloxy or methacryloyloxy;

$Y^1$ is halogen, alkyl having 1 to 5 carbons, alkoxy having 1 to 5 carbons, alkyl having 1 to 5 carbons in which at least one hydrogen is replaced by halogen, or alkoxy having 1 to 5 carbons in which at least one hydrogen is replaced by halogen;

$S^9$, $S^{11}$ and $S^{14}$ are independently a single bond, —CH$_2$—, —CH$_2$O—, —OCH$_2$—, —COO—, —OCO—, —CH=CH—, —C≡C—, —CH$_2$CH$_2$O—, —OCH$_2$CH$_2$—, —CH=CH—O— or —O—CH=CH—;

e1 is 1 or 2, and e2 is 0, 1 or 2; and $Z^7$, $Z^8$ and $Z^9$ are independently a single bond, —CO—, —COO—, —CH=CH—, —CH=CH—COO—, —C(CH$_3$)=CH—COO—, —CH=C(CH$_3$)—COO—, —C(CH$_3$)=C(CH$_3$)—COO—, —COCH=CH—, —C(CH$_3$)=C(CH$_3$)—, —CH=CH—CH$_2$O— or —CH=CH—OCH$_2$—.

Item 8. The polymerizable compound of item 7, wherein, in formula (1-4) or (1-5), at least one of $P^9$, e1 pieces of $P^{11}$, and $P^{14}$ is acryloyloxy, and at least one thereof is methacryloyloxy.

Item 9. The polymerizable compound of item 1 or 2, represented by formula (1-6) or (1-7):

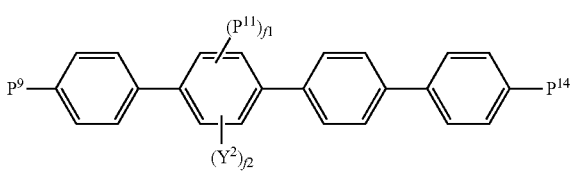
(1-6)

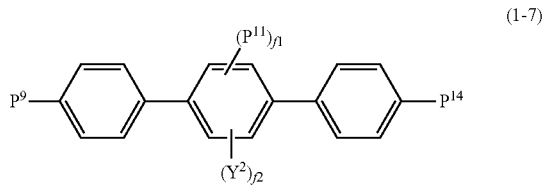
(1-7)

wherein, in formulas (1-6) and (1-7), $P^9$, $P^{11}$ and $P^{14}$ are independently acryloyloxy or methacryloyloxy;

$Y^2$ is halogen, alkyl having 1 to 5 carbons or alkoxy having 1 to 5 carbons; and f1 is 1 or 2, and f2 is 0, 1 or 2.

Item 10. The polymerizable compound of item 9, wherein, in formula (1-6) or (1-7), at least one of $P^9$, f1 pieces of $P^{11}$, and $P^{14}$ is acryloyloxy, and at least one thereof is methacryloyloxy.

Item 11. The polymerizable compound of item 1 or 2, represented by formula (1-8) or (1-9):

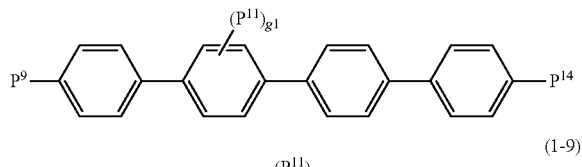
(1-8)

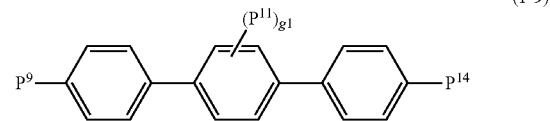
(1-9)

wherein, in formula (1-8) or (1-9), $P^9$, $P^{11}$ and $P^{14}$ are independently acryloyloxy or methacryloyloxy; and g1 is 1 or 2.

Item 12. A polymerizable composition, containing at least one of the compounds of any one of items 1 to 11.

Item 13. The polymerizable composition of item 12, further containing at least one compound selected from the group of compounds represented by formulas (2) to (4):

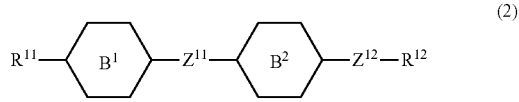
(2)

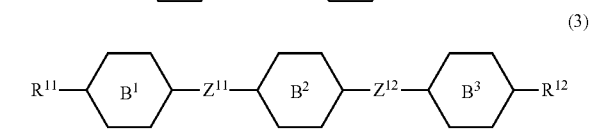
(3)

(4)

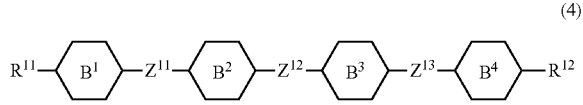

wherein, in formulas (2) to (4),
$R^{11}$ and $R^{12}$ are independently alkyl having 1 to 10 carbons or alkenyl having 2 to 12 carbons, and in the alkyl or the alkenyl, at least one —CH$_2$— may be replaced by —O— and at least one hydrogen may be replaced by fluorine;
ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$, and $Z^{13}$ are independently a single bond, —CH$_2$CH$_2$—, —CH=CH—, —C≡C— or —COO—.

Item 14. The polymerizable composition of item 12 or 13, further containing at least one compound selected from the group of compounds represented by formulas (5) to (7):

(5)

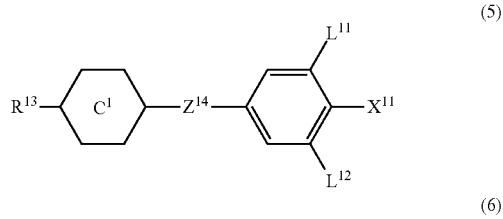

(6)

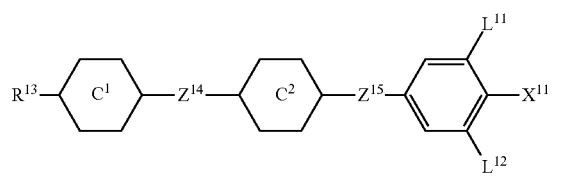

(7)

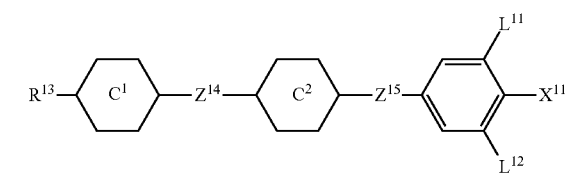

wherein, in formulas (5) to (7),
$R^{13}$ is alkyl having 1 to 10 carbons or alkenyl having 2 to 12 carbons, and in the alkyl or the alkenyl, at least one —CH$_2$— may be replaced by —O— and at least one hydrogen may be replaced by fluorine;
$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring $C^1$, ring $C^2$, and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diy;
$Z^{14}$, $Z^{15}$ and $Z^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and
$L^{11}$ and $L^{12}$ are independently hydrogen or fluorine.

Item 15. The polymerizable composition of any one of items 12 to 14, further containing at least one compound selected from the group of compounds represented by formula (8):

(8)

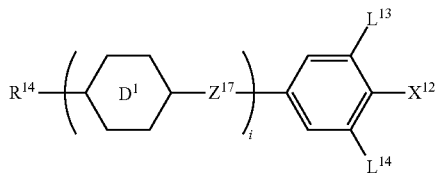

wherein, in formula (8),
$R^{14}$ is alkyl having 1 to 10 carbons or alkenyl having 2 to 12 carbons, and in the alkyl or the alkenyl, at least one —CH$_2$— may be replaced by —O— and at least one hydrogen may be replaced by fluorine;
$X^{12}$ is —C≡N or —C≡C—C≡N;
ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
$Z^{17}$ is a single bond, —CH$_2$CH$_2$—, —C≡C—, —COO—, —CF$_2$O—, —OCF$_2$— or —CH$_2$O—;
$L^{13}$ and $L^{14}$ are independently hydrogen or fluorine; and
i is 1, 2, 3 or 4.

Item 16. A liquid crystal composite, formed by polymerization of the polymerizable composition of any one of items 12 to 15.

Item 17. An optical anisotropic body, formed by polymerization of the polymerizable composition of any one of items 12 to 15.

Item 18. A liquid crystal display device, including the polymerizable composition of any one of items 12 to 15 or the liquid crystal composite of item 16.

Item 19. Use of at least one selected from the group of the compound of any one of items 1 to 11, the polymerizable composition of any one of items 12 to 15 and the liquid crystal composite of item 16 in a liquid crystal display device.

The invention further includes the following items: (a) the polymerizable composition, further containing at least one of additives such as an optically active compound, an antioxidant, a UV light absorber, a light stabilizer, a heat stabilizer, an antifoaming agent, a polymerization initiator and a polymerization inhibitor; (b) the polymerizable composition, further containing a polymerizable compound different from the compound represented by formula (1); (c) an AM device including the polymerizable composition; (d) a device that includes the polymerizable composition and has a mode of PS-TN, PS-IPS, PS-FFS, PSA-VA or PSA-OCB; (e) a transmissive device including the polymerizable composition; (f) use of the polymerizable composition as a composition having a nematic phase; and (g) use of the composition as an optically active composition by adding the optically active compound.

The invention further includes the following items: (h) a polymerizable composition that contains at least one compound selected from the group of compounds represented by formula (1) and has a positive dielectric anisotropy; (i) a polymerizable composition containing at least one compound selected from the group of compounds represented by formula (1), at least one compound selected from the group of compounds represented by formulas (2) to (4) and at least one compound selected from the group of compounds represented by formulas (5) to (7); (j) a polymerizable composition containing at least one compound selected from the group of compounds represented by formula (1), at least one compound selected from the group of compounds represented by formulas (2) to (4) and at least one compound selected from the group of compounds represented by a formula (8); (k) a polymerizable composition containing at least one compound selected from the group of compounds represented by formula (1), at least one compound selected from the group of compounds represented by formulas (2) to (4), at least one compound selected from the group of compounds represented by formulas (5) to (7) and at least one compound selected from the group of compounds represented by formula (8); (l) the polymerizable composition that further contains a liquid crystal compound having 2,3-difluorophenylene and a negative dielectric anisotropy; (m) a liquid crystal composite produced by polymerization of the polymerizable composition; and (n) use of the polymerizable composition or the liquid crystal composite in a liquid crystal display device having a PSA mode.

1. Polymerizable Compound

A polymerizable compound of the invention will be first described, and then a synthesis method, a polymerizable composition, a liquid crystal composite and a liquid crystal display device will be described in the order. The polymerizable compound is a compound serially formed of three or four rings not condensed with each other, in which the polymerizable compound also has three or more polymerizable groups, and at least one of the polymerizable groups is bonded with a ring not at both terminals among the three or four rings. Here, the rings may be condensed, and in the case of condensed ring, the condensed rings as a whole are to be counted as one ring.

Typified examples of the polymerizable compound include the compound represented by formula (1). First, compound (1) has features of having a rod like molecular structure. The liquid crystal composition used in a commercially available liquid crystal display device is a mixture of the liquid crystal compounds having the rod like molecular structure. A molecular structure of compound (1) is similar to the structure of the liquid crystal compound. Accordingly, compound (1) has a high solubility in the liquid crystal composition. Second, compound (1) has features of having a group having high polymerizability. Specific examples of the polymerizable group include acryloyloxy or methacryloyloxy. Compound (1) has at least three polymerizable groups. Accordingly, symmetry of a molecule is reduced, and therefore the solubility in the liquid crystal composition is expected to be improved.

(1)

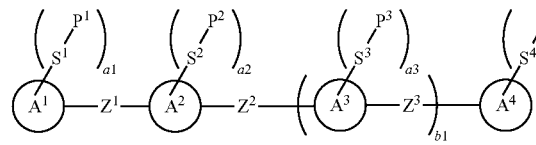

In formula (1), $P^1$, $P^2$, $P^3$ and $P^4$ are a polymerizable group. Preferred examples of the polymerizable group include acryloyloxy, methacryloyloxy, acrylamide, methacrylamide, vinyloxy, vinylcarbonyl, oxiranyl, oxetanyl, 3,4-epoxycyclohexyl or maleimide. In the groups, at least one hydrogen may be replaced by fluorine. Further preferred examples include —OCO-($M^1$)C=CH ($M^2$), in which $M^1$ and $M^2$ are independently hydrogen, fluorine, —$CH_3$ or —$CF_3$. Still further preferred $M^1$ or $M^2$ is hydrogen or —$CH_3$. Particularly preferred examples include acryloyloxy (—OCO—HC=$CH_2$) or methacryloyloxy (—OCO—($CH_3$)C=$CH_2$).

In formula (1), $S^1$, $S^2$, $S^3$, and S4 are independently a single bond or alkylene having 1 to 10 carbons, and in the alkylene, at least one —$CH_2$— may be replaced by —O—, —COO—, —OCO— or —OCOO—, at least one —$CH_2$— may be replaced by —CH=CH— or —C≡C—, and at least one hydrogen may be replaced by fluorine or chlorine.

Preferred examples of $S^1$, $S^2$, $S^3$ or $S^4$ include a single bond, —$CH_2$—, —$CH_2O$—, —$OCH_2$—, —COO—, —OCO—, —$CH_2CH_2$—, —CH=CH—, —C≡C—, —$(CH_2)_3$—, —$CH_2CH_2O$—, —$OCH_2CH_2$—, —CH=CH—O—, —O—CH=CH—, —C≡C—O—, —O—C≡C—, —$(CH_2)_4$—, —$(CH_2)_3$—O—, —O—$(CH_2)_3$—, —$(CH_2)_4O$— or —$O(CH_2)_4$—. Further preferred examples include a single bond, —$CH_2$—, —$CH_2O$—, —$OCH_2$—, —COO—, —OCO—, —CH=CH—, —C≡C—, —$CH_2CH_2O$—, —$OCH_2CH_2$—, —CH=CH—O— or —O—CH=CH—. Particularly preferred examples include a single bond, —$CH_2$—, —CH=CH—, —CH=CH—O—, —O—CH=CH—, —$CH_2CH_2O$— or —$OCH_2CH_2$—. Most preferred examples include a single bond. A configuration of a double bond of —CH=CH— may be a cis form or a trans form. The trans form is preferred to the cis form.

In formula (1), a1, a3, and a4 are independently 0, 1, 2, 3 or 4, a2 is 1, 2, 3 or 4, and a sum of a1, a2, a3 and a4 is 3 to 10. Then, a2 is one or more, and therefore ring $A^2$ not at both terminals has at least one polymerizable group. Preferred examples of a1, a3 or a4 include 1 or 2. Preferred examples of a2 include 1 or 2.

In formula (1), ring $A^1$ and ring $A^4$ are independently phenyl, pyrimidyl, pyridyl, naphthyl, cyclohexyl, cyclohexenyl, tetrahydropyranyl or 1,3-dioxanyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen.

Preferred examples of ring $A^1$ or ring $A^4$ include phenyl, naphthyl or cyclohexyl, and in the rings, at least one hydrogen may be replaced by fluorine, chlorine, alkyl having 1 to 3 carbons in which and at least one hydrogen is replaced by halogen, or alkoxy having 1 to 3 carbons in which at least one hydrogen is replaced by halogen. Further preferred examples include phenyl or naphthyl, and in the rings, at least one hydrogen may be replaced by fluorine, chlorine, alkyl having 1 to 5 carbons, alkoxy having 1 to 5 carbons, alkyl having 1 to 5 carbons in which at least one hydrogen is replaced by halogen, or alkoxy having 1 to 5 carbons in which at least one hydrogen is replaced by halogen. Preferred examples of alkyl in which at least one hydrogen is replaced by halogen include —$CH_2F$, —$CHF_2$, —$CF_3$, —$CClF_2$, —$CH_2CF_3$, —$CF_2CF_3$ or —$CH_2H_2CF_3$. Particularly preferred examples include phenyl.

Ring $A^2$ and ring $A^3$ are independently 1,4-phenylene, pyrimidine-2,5-diyl, pyridine-2,5-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, 1,4-cyclohexylene, 1,4-cyclohexenylene, tetrahydropyran-2,5-diyl or 1,3-dioxane-2,5-diyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen.

Preferred example of ring $A^2$ or ring $A^3$ include 1,4-phenylene, pyrimidine-2,5-diyl, pyridine-2,5-diyl, naphthalene-1,4-diyl, naphthalene-1,5-diyl, naphthalene-1,6-diyl, naphthalene-2,6-diyl, 1,4-cyclohexylene, tetrahydropyran-2,5-diyl or 1,3-dioxane-2,5-diyl, and in the rings, at least one or two hydrogens may be replaced by fluorine, chlorine, alkyl having 1 to 3 carbons, or alkyl having 1 to 3 carbons in which at least one hydrogen is replaced by halogen.

Preferred examples of ring $A^2$ or ring $A^3$ include 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-chloro-3-fluoro-1,4-phenylene, 2-methyl-1,4-phenylene, 2-ethyl-1,4-phenylene, 2-isopropyl-1,4-phenylene, 2-tert-butyl-1,4-phenylene, 2-methoxy-1,4-phenylene, 2-ethoxy-1,4-phenylene, 2-propyoxy-1,4-phenylene, 2-butoxy-1,4-phenylene, 2-difluoromethyl-1,4-phenylene, 2-trifluoromethyl-1,4-phenylene, pyrimidine-2,5-diyl or pyridine-2,5-diyl. Further preferred examples include naphthalene-1,4-diyl, naphthalene-1,5-diyl, naphthalene-1,6-diyl or naphthalene-2,6-diyl. Particularly preferred examples include 1,4-phenylene, naphthalene-1,4-diyl, naphthalene-1,5-diyl or naphthalene-2,6-diyl. Most preferred examples include 1,4-phenylene.

In formula (1), $Z^1$, $Z^2$ and $Z^3$ are independently a single bond or alkylene having 1 to 10 carbons, and in the alkylene, at least one —CH$_2$— may be replaced by —O—, —CO—, —COO— or —OCO—, at least one —CH$_2$—CH$_2$— may be replaced by —CH=CH—, —C(CH$_3$)=CH—, —CH=C(CH$_3$)— or —C(CH$_3$)=C(CH$_3$)—, and at least one hydrogen may be replaced by fluorine or chlorine.

Preferred examples of $Z^1$, $Z^2$ or $Z^3$ include a single bond, alkylene having 1 to 5 carbons, —CO—, —COO—, —OCO—, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CO—CH=CH—, —CH=CH—CO—, —C(CH$_3$)=C(CH$_3$)—, —CH=CH—CH$_2$O—, —OCH$_2$—CH=CH—, —CH=CH—OCH$_2$— or —CH$_2$O—CH=CH—. Further preferred examples include a single bond, —COO—, —OCO— or —CH=CH—. Most preferred examples include a single bond. When the bonding groups have —CH=CH—, a configuration may be a cis form or a trans form. A preferred configuration is the trans form.

In formula (1), b1 is 0 or 1. Preferred examples of b1 include 0.

In compound (1), preferred examples of polymerizable group P, linking group S, ring A and bonding group Z are as described above. The example also applies to a subordinate formula of formula (1) for compound (1). The polymerizable compound having objective physical properties can be obtained, with referring to the preferred examples described above, by suitably selecting a combination of the polymerizable groups ($P^1$ to $P^4$), the linking group S ($S^1$ to $S^4$), the rings ($A^1$ to $A^4$) and the bonding groups ($Z^1$ to $Z^3$). In addition, a case where oxygen is an element of $S^1$ to be bonded with $P^1$ is not preferred because a divalent group such as —COO—O— and —O—O— is formed. A same rule may apply to a bond between $P^2$ and $S^2$, or the like. No significant difference exists in the physical properties of compounds, and therefore compound (1) may contain an isotope such as $^2$H (deuterium) and $^{13}$C in an amount higher than natural abundance.

Preferred examples of compound (1) include compound (1-1). Further preferred examples include compound (1-2) or (1-3). Still further preferred examples include compound (1-4) or (1-5). Particularly preferred examples include compounds (1-2-a) to (1-2-i), compounds (1-3-a) to (1-3-g), (1-4-a) to (1-4-f) and (1-5-a) to (1-5-g).

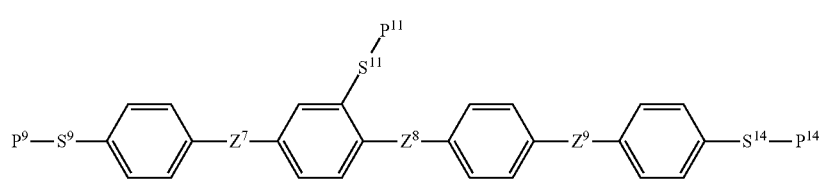

(1-2-a)

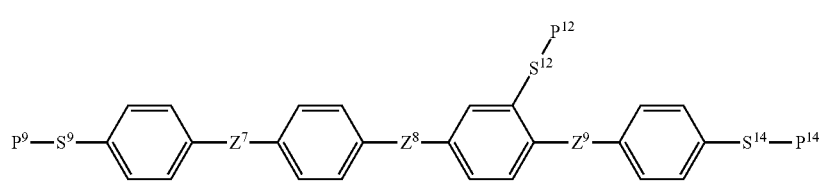

(1-2-b)

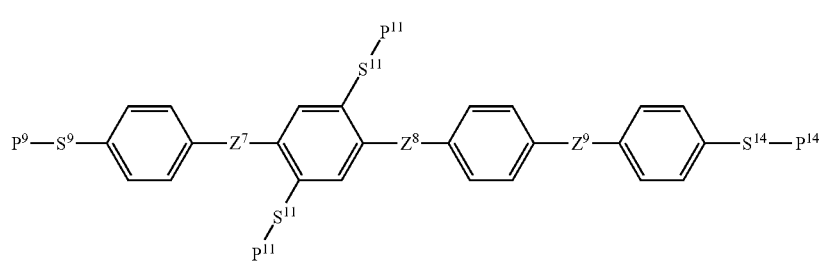

(1-2-c)

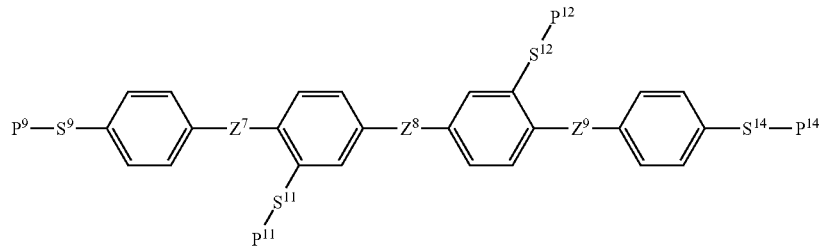
(1-2-d)
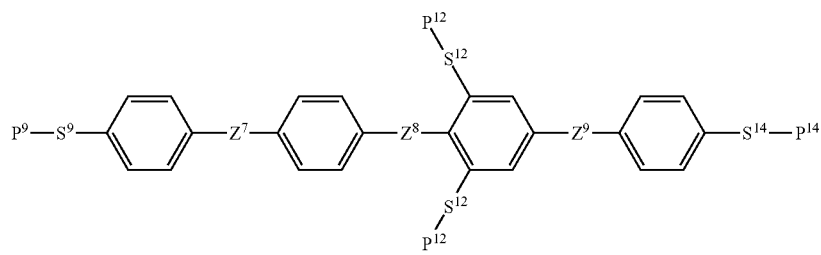
(1-2-e)
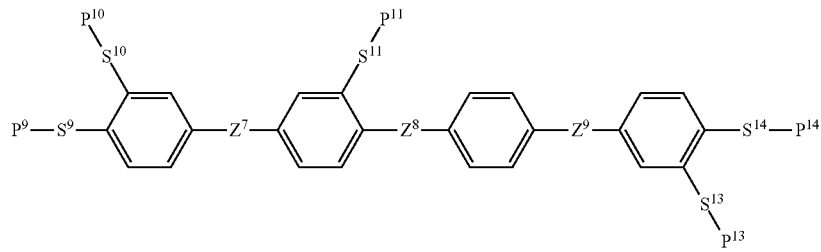
(1-2-f)
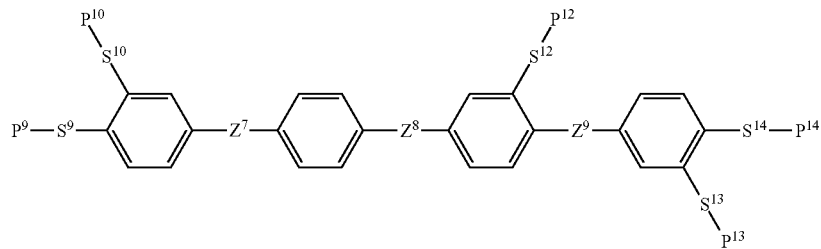
(1-2-g)
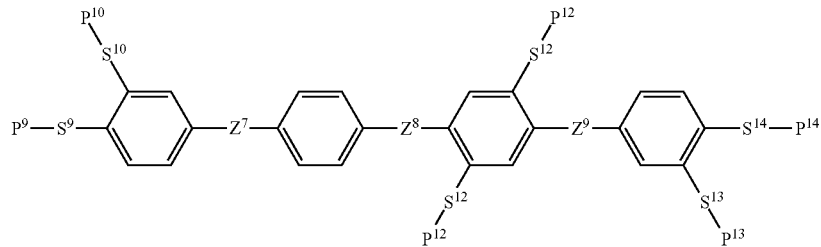
(1-2-h)
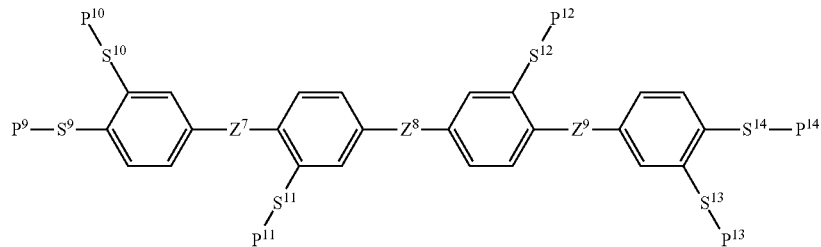
(1-2-i)

-continued
(1-3-a)
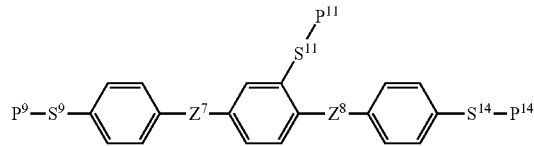
(1-3-b)
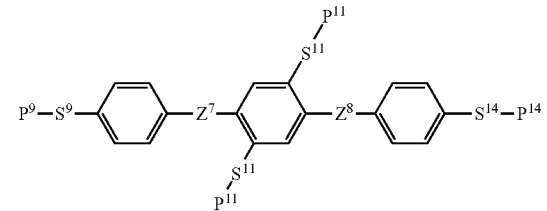
(1-3-c)
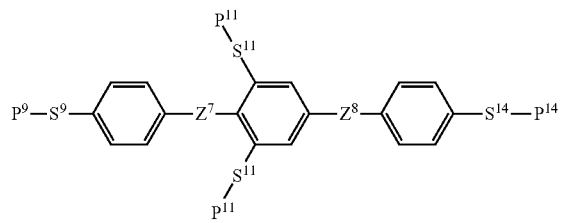
(1-3-d)
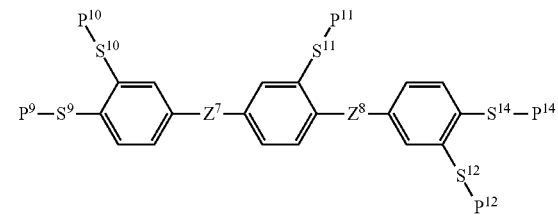
(1-3-e)
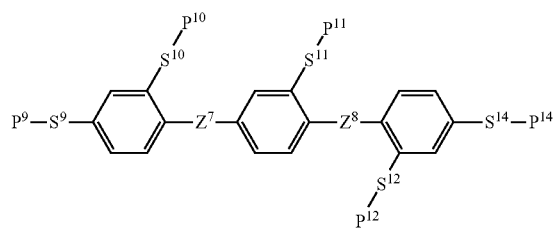
(1-3-f)
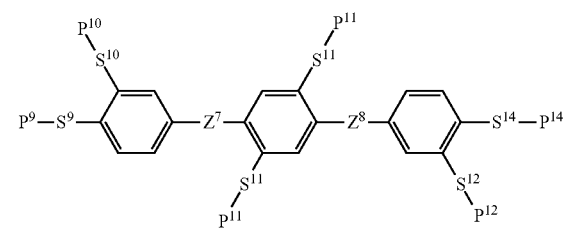
(1-3-g)
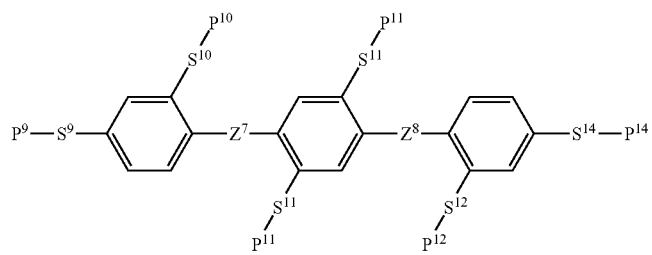
(1-4-a)
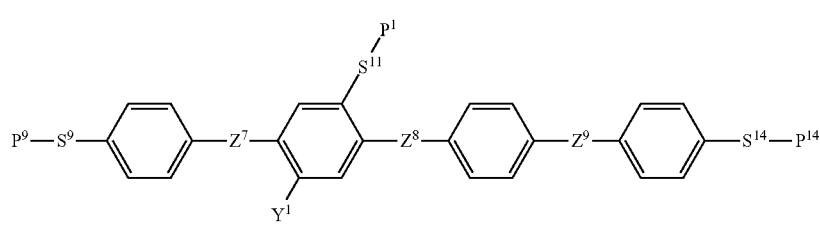
(1-4-b)
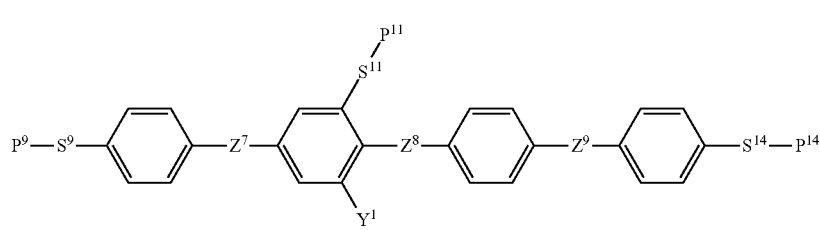
(1-4-c)
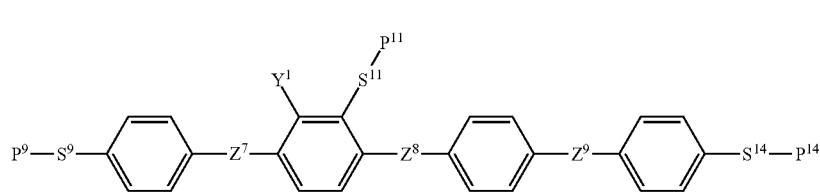

(1-4-d)
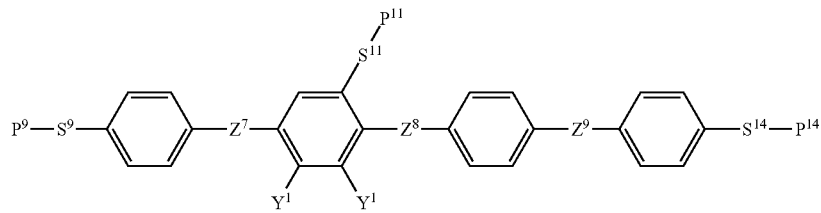
(1-4-e)
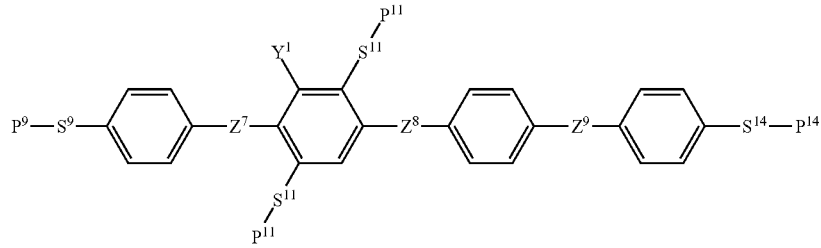
(1-4-f)
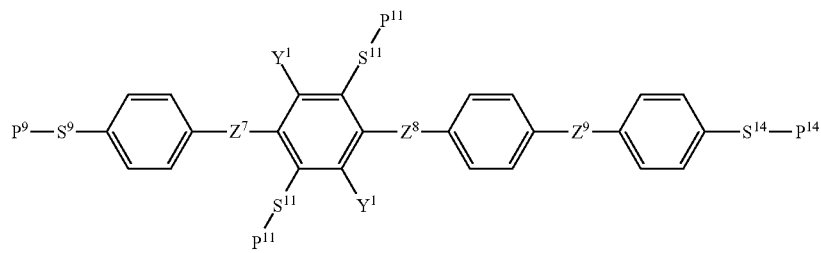
(1-5-a)
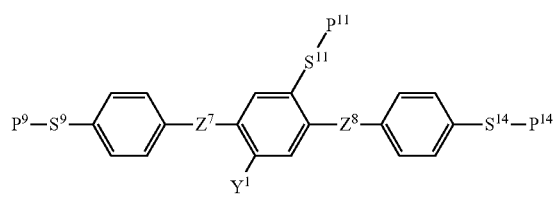
(1-5-b)
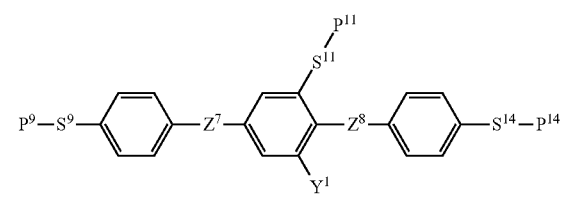
(1-5-c)
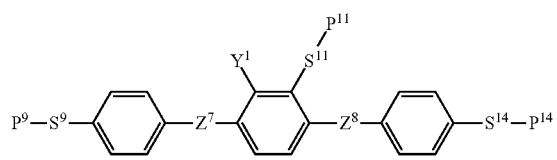
(1-5-d)
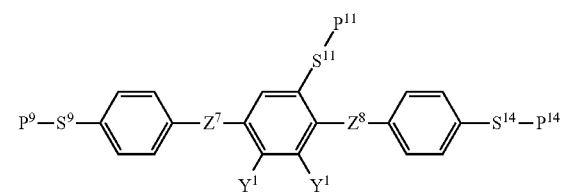
(1-5-e)
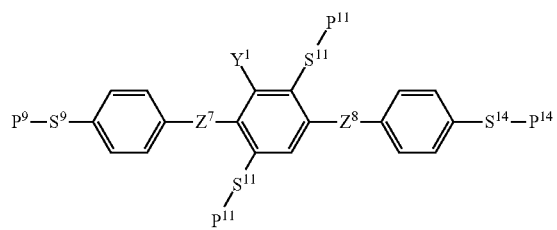
(1-5-f)
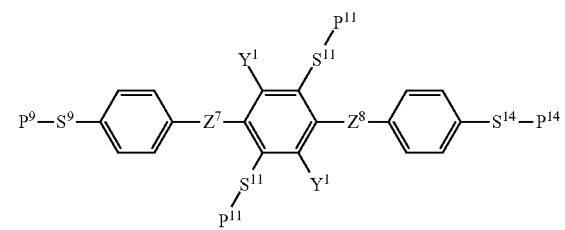

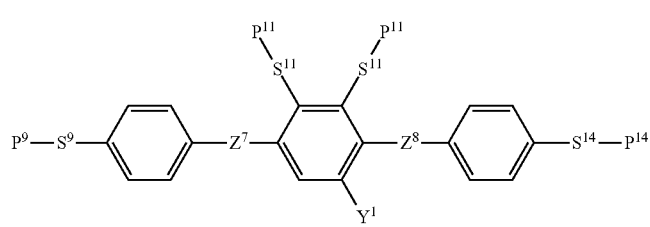

(1-5-g)

In compounds (1-2-a) to (1-2-i), compounds (1-3-a) to (1-3-g), compounds (1-4-a) to (1-4-f) and compounds (1-5-a) to (1-5-g), $P^9$, $P^{10}$, $P^{11}$, $P^{12}$, $P^{13}$ and $P^{14}$ are independently acryloyloxy or methacryloyloxy; $S^9$, $S^{10}$, $S^{11}$, $S^{12}$, $S^{13}$ and $S^{14}$ are independently a single bond, —$CH_2O$—, —$OCH_2$—, —COO—, —OCO—, —CH=CH—, —C≡C—, —$CH_2CH_2O$—, —$OCH_2CH_2$—, —CH=CH—O—, or —O—CH=CH—; $Y^1$ is halogen, alkyl having 1 to 5 carbons, alkoxy having 1 to 5 carbons, alkyl having 1 to 5 carbons in which at least one hydrogen is replaced by halogen, or alkoxy having 1 to 5 carbons in which at least one hydrogen is replaced by halogen; and $Z^7$, $Z^8$ and $Z^9$ are independently a single bond, —CO—, —COO—, —CH=CH—, —CH=CH—COO—, —C($CH_3$)=CH—COO—, —CH=C($CH_3$)—COO—, —C($CH_3$)=C($CH_3$)—COO—, —COCH=CH—, —C($CH_3$)=C($CH_3$)—, —CH=CH—$CH_2O$— or —CH=CH—$OCH_2$—.

Compounds (1-2-a) to (1-2-i), compounds (1-3-a) to (1-3-g), compounds (1-4-a) to (1-4-f) and compounds (1-5-a) to (1-5-g) are most preferred when $P^9$, $P^{10}$, $P^{11}$, $P^{12}$, $P^{13}$ and $P^{14}$ are independently acryloyloxy or methacryloyloxy; $S^9$, $S^{10}$, $S^{11}$, $S^{12}$, $S^{13}$ and $S^{14}$ are a single bond; and $Z^7$, $Z^8$, and $Z^9$ are a single bond. In the compounds, preferred examples include compounds (1-2-a), (1-2-b), (1-2-c), (1-2-d), (1-3-a), (1-3-b), (1-3-d), (1-3-e), (1-3-g), (1-4-a), (1-4-b), (1-5-a) and (1-5-b). More preferred examples include compounds (1-3-a), (1-3-b) and (1-5-a).

Moreover, in compounds (1-4-a), (1-4-b), (1-5-a) and (1-5-b), also in a case where $Y^1$ is halogen, and at least one of $P^9$, one or two of $P^{11}$ and $P^{14}$ is acryloyloxy, and at least one thereof is methacryloyloxy, improvement of solubility in the liquid crystal composition due to reduction of symmetry of the molecule is expected, and such a case is preferred.

2. Synthesis Method

A method for synthesizing compound (1) will be described. Compound (1) can be prepared by suitably combining methods in synthetic organic chemistry. A method to for introducing an objective terminal group, ring and bonding group into a starting material is described in books such as Houben-Wyle, Methoden der Organische Chemie (Georg-Thieme Verlag, Stuttgart), Organic Syntheses (John Wily& Sons, Inc.), Organic Reactions (John Wily & Sons Inc.), Comprehensive Organic Synthesis (Pergamon Press) and New Experimental Chemistry Course (Shin Jikken Kagaku Koza in Japanese) (Maruzen Co., Ltd.).

2-1. Formation of Bonding Group Z

An example of a method for forming bonding groups $Z^1$ to $Z^3$ in compound (1) is as described in the scheme below. In the scheme, $MSG^1$ (or $MSG^2$) is a monovalent organic group having at least one ring. Monovalent organic groups represented by a plurality of $MSG^1$ (or $MSG^2$) may be identical or different. Compounds (1A) to (1I) correspond to compound (1). In formation of ester, a method for preparing a compound having —COO— is shown. A compound having —OCO— can also be prepared by the synthesis method. Any other asymmetrical bonding group can also be prepared in a similar manner.

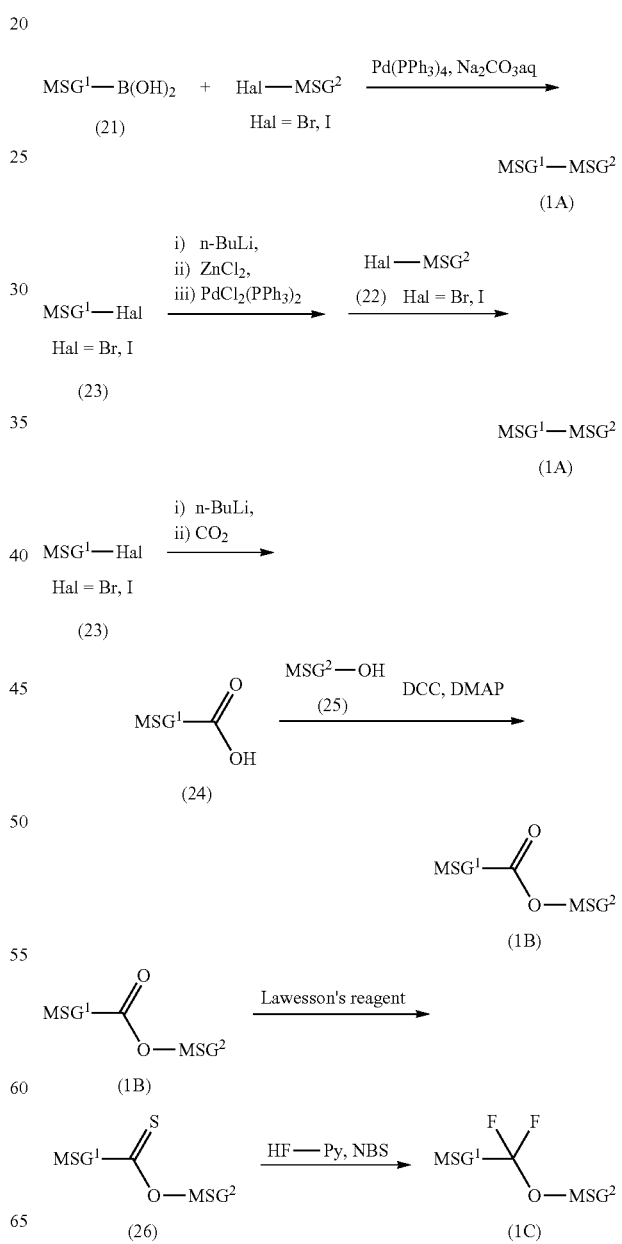

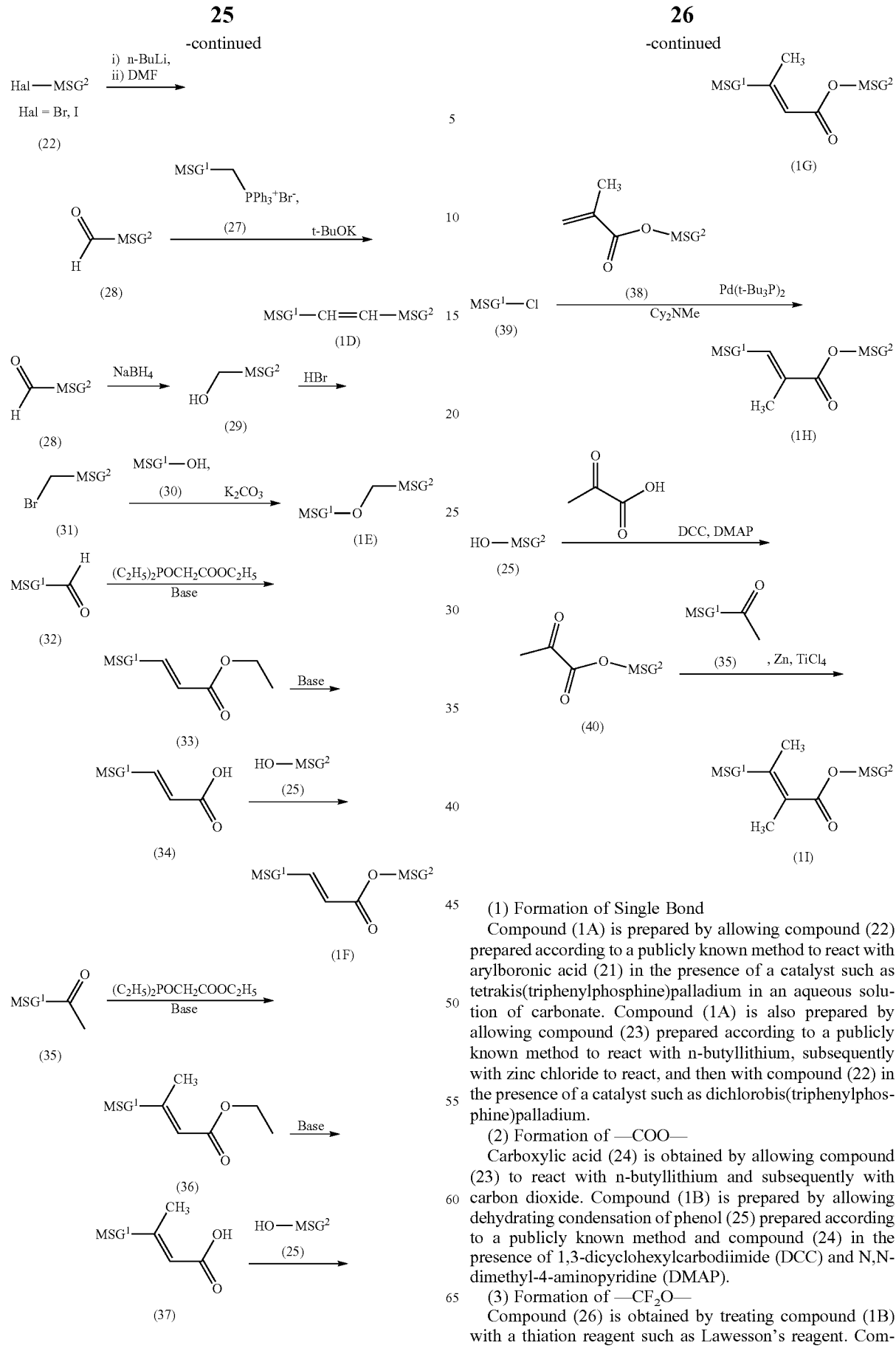

(1) Formation of Single Bond

Compound (1A) is prepared by allowing compound (22) prepared according to a publicly known method to react with arylboronic acid (21) in the presence of a catalyst such as tetrakis(triphenylphosphine)palladium in an aqueous solution of carbonate. Compound (1A) is also prepared by allowing compound (23) prepared according to a publicly known method to react with n-butyllithium, subsequently with zinc chloride to react, and then with compound (22) in the presence of a catalyst such as dichlorobis(triphenylphosphine)palladium.

(2) Formation of —COO—

Carboxylic acid (24) is obtained by allowing compound (23) to react with n-butyllithium and subsequently with carbon dioxide. Compound (1B) is prepared by allowing dehydrating condensation of phenol (25) prepared according to a publicly known method and compound (24) in the presence of 1,3-dicyclohexylcarbodiimide (DCC) and N,N-dimethyl-4-aminopyridine (DMAP).

(3) Formation of —CF$_2$O—

Compound (26) is obtained by treating compound (1B) with a thiation reagent such as Lawesson's reagent. Compound (1C) is prepared by fluorinating compound (26) with a hydrogen fluoride-pyridine complex and N-bromosuccinimide (NBS). Refer to M. Kuroboshi et al., Chem. Lett., 1992, and 827. Compound (1C) is also prepared by fluorinating compound (26) with (diethylamino)sulfur trifluoride (DAST). Refer to W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH=CH—

Aldehyde (28) is obtained by treating compound (22) with n-butyllithium, and subsequently allowing the resulting material to react with formamide such as N,N-dimethylformamide (DMF). Compound (1D) is prepared by allowing phosphorus ylide produced by treating phosphonium salt (27) prepared according to a known method with a base such as potassium tert-butoxide to react with aldehyde (28). A cis isomer may be generated depending on reaction conditions, and the cis isomer is isomerized into a trans isomer according to a known method, when necessary.

(5) Formation of —CH$_2$O—

Compound (29) is obtained by reducing compound (28) with a reducing agent such as sodium borohydride. Compound (31) is obtained by halogenating the obtained compound with hydrobromic acid or the like. Compound (1E) is prepared by allowing compound (31) to react with compound (30) in the presence of potassium carbonate or the like.

(6) Formation of —CH=CH—COO—

Phosphorus ylide is prepared by allowing a base such as sodium hydride to act on ethyl diethylphosphono acetate, and ester (33) is obtained by allowing the phosphorus ylide to react with aldehyde (32). Carboxylic acid (34) is obtained by hydrolyzing ester (33) in the presence of a base such as sodium hydroxide. Compound (1F) is prepared by allowing dehydrating condensation between the compound and compound (25).

(7) Formation of —C(CH$_3$)=CH—COO—

Phosphorus ylide is prepared by allowing a base such as sodium hydride to react with ethyl diethylphosphono acetate, and ester (36) is obtained by allowing the phosphorus ylide to react with methyl ketone (35). Next, carboxylic acid (37) is obtained by hydrolyzing ester (36) in the presence of a base such as sodium hydroxide, and then compound (1G) is prepared by dehydrating condensation with compound (25).

(8) Formation of —CH=C(CH$_3$)—COO—

Compound (1H) is prepared by allowing compound (38) prepared according to a known method to react with compound (39) prepared according to a known method, in the presence of a base such as N,N-dicyclohexylmethylamine (Cy$_2$NMe) and a catalyst such as bis(tri-tert-butylphosphine) palladium.

(9) Formation of —C(CH$_3$)=C(CH$_3$)—COO—

Compound (40) is obtained by dehydrating condensation between compound (25) and pyruvic acid. Compound (1I) is prepared by allowing compound (40) to react with compound (35) in the presence of zinc and titanium tetrachloride.

2-2. Formation of Linking Group S

In a compound in which the polymerizable group is —OCO-(M$^1$)C=CH (M$^2$), a method for forming linking group S will be described in sections (1) to (5). A compound in which a polymerizable group is vinyloxy (P-2) subjected to replacement or allyloxy (P-3) subjected to replacement will be described in section (6).

(1) Single Bond

An example of a method for forming compound (1) in which linking group S is a single bond is as described in the scheme below. In the scheme, MSG$^1$ is a monovalent organic group having at least one ring. Compounds (1J) to (1M) correspond to compound (1).

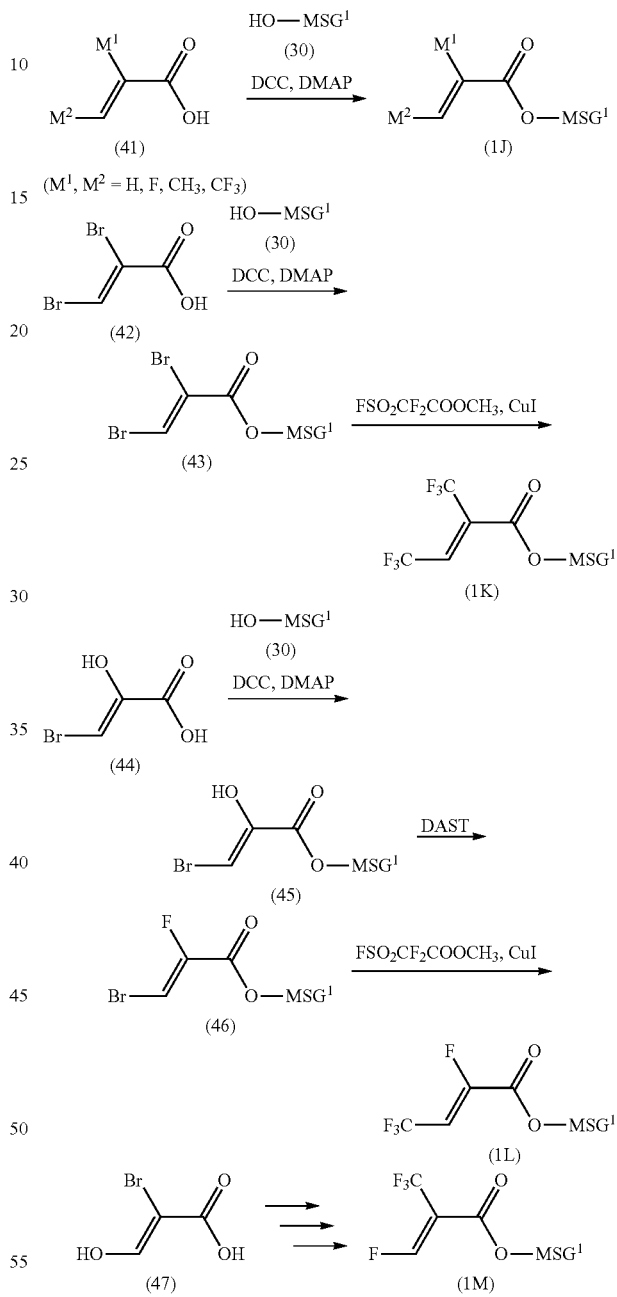

In the case where neither M$^1$ nor M$^2$ is —CF$_3$, in the case where M$^1$ is fluorine and M$^2$ is not —CF$_3$, or in the case where M$^1$ is —CF$_3$ and M$^2$ is not fluorine, carboxylic acid (41) shown in the above scheme is commercially available. Compound (1J) is prepared by allowing dehydrating condensation between carboxylic acid (41) and compound (30) in the presence of DDC and DMAP.

In the case where both M$^1$ and M$^2$ are —CF$_3$, compound (43) is obtained by allowing dehydrating condensation between carboxylic acid (42) and compound (30) in the presence of DCC and DMAP. Compound (1K) is prepared by allowing compound (43) to react with 2,2-difluoro-2-(fluorosulfonyl)methyl acetate in the presence of a copper iodide catalyst.

In the case where $M^1$ is fluorine and $M^2$ is —$CF_3$, compound (45) is obtained by allowing dehydrating condensation between carboxylic acid (44) and compound (30) in the presence of DCC and DMAP. Compound (46) is obtained by fluorinating compound (45) with a fluorinating agent such as DST. Compound (1L) is prepared by allowing compound (46) to react with 2,2-difluoro-2-(fluorosulfonyl)methyl acetate in the presence of a copper iodide catalyst.

In the case where $M^1$ is —$CF_3$ and $M^2$ is fluorine, compound (1M) is prepared by using carboxylic acid (47) as a starting material and according to the method described above.

An example of a method forming a linking group (S is not a single bond) in compound (1) is described in the scheme below. In the scheme, $MSG^1$ is a monovalent organic group having at least one ring. Compounds (1N) to (1Q) correspond to compound (1).

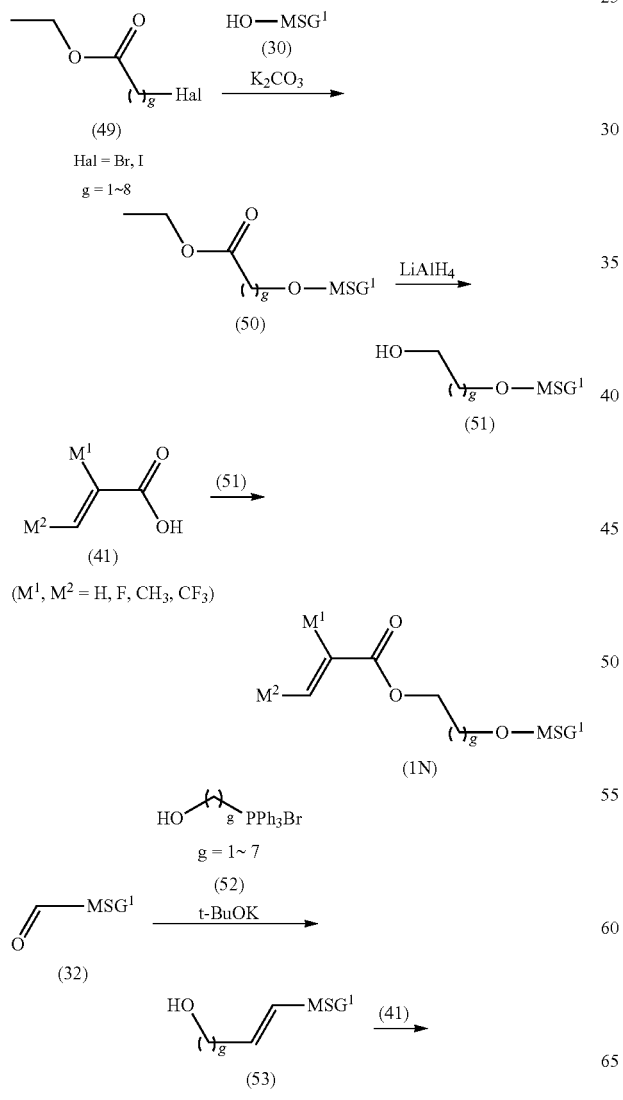

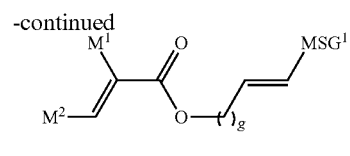

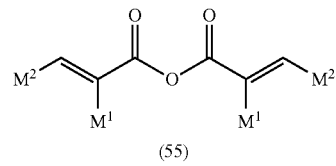

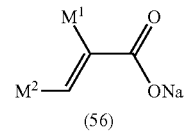

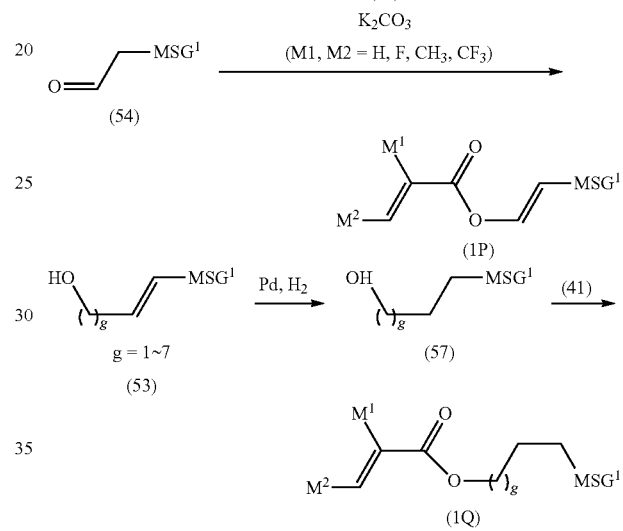

(2) Formation of —$(CH_2)_g$—O—

Compound (50) is obtained by allowing compound (49) prepared according to a publicly known method to react with compound (30) in the presence of potassium carbonate or the like. Compound (51) is obtained by reducing compound (50) with a reducing agent such as lithium aluminum hydride. Compound (1N) is obtained by dehydrating condensation between compound (51) and carboxylic acid (41).

(3) Formation of —$(CH_2)_g$—CH=CH—

Compound (53) is obtained by allowing phosphorus ylide generated by treating phosphonium salt (52) prepared according to a publicly known method with a base such as potassium tert-butoxide to react with aldehyde (32). Compound (10) is obtained by dehydrating condensation between compound (53) and carboxylic acid (41).

(4) Formation of —CH=CH—

Compound (1P) is obtained by allowing aldehyde (54) prepared according to a publicly known method to react with acid anhydride (55) and sodium carboxylate (56) in the presence of potassium carbonate or the like.

(5) Formation of —$(CH_2)_g$—$CH_2CH_2$—

Alcohol (57) is prepared by hydrogenating compound (53) in the presence of a catalyst such as palladium on carbon. Compound (1Q) is obtained by allowing dehydrating condensation between the alcohol and carboxylic acid (41).

(6) Group (P-2) and Group (P-3)

In a compound in which a polymerizable group is vinyloxy (P-2) subjected to replacement, a single bond is formed as described below. A compound having vinyloxy subjected to replacement is obtained by allowing HO-MGS$^1$ (30) to react with vinyl bromide subjected to replacement in the presence of potassium carbonate. In a compound in which the polymerizable group is allyloxy (P-3) subjected to replacement, a single bond is formed according to Williamson synthesis. More specifically, a compound having allyloxy subjected to replacement is obtained by a reaction between sodium salt of HO-MGS$^1$ (30) and allyl bromide subjected to replacement.

3. Polymerizable Composition

A polymerizable composition contains at least one of compound (1) as a first component. A component of the composition may be only the first component. The composition may also contain a second component, a third component or the like. A kind of the second component or the like depends on a kind of an objective polymer or application. The polymerizable composition may further contain any other polymerizable compound different from compound (1) as the second component. Preferred examples of other polymerizable compounds include acrylate, methacrylate, a vinyl compound, a vinyloxy compound, propenyl ether, ethylene oxide (oxirane, oxetane) or vinyl ketone. Further preferred examples include a compound having at least one of acryloyloxy or a compound having at least one of methacryloyloxy. Still further preferred examples also include a compound having acryloyloxy and methacryloyloxy.

Additional examples of other polymerizable compounds include compounds (M-1) to (M-12). In compounds (M-1) to (M-12), $R^{25}$, $R^{26}$ and $R^{27}$ are independently hydrogen or methyl; u, x and y are independently 0 or 1; v and w are independently 1 to 10; and $L^{21}$, $L^{22}$, $L^{23}$, $L^{24}$, $L^{25}$ and $L^{26}$ are independently hydrogen or fluorine.

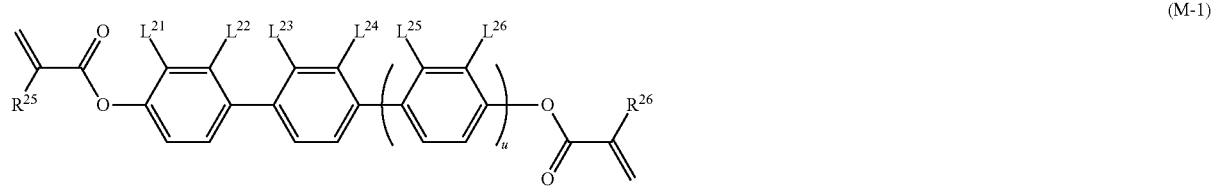

(M-1)

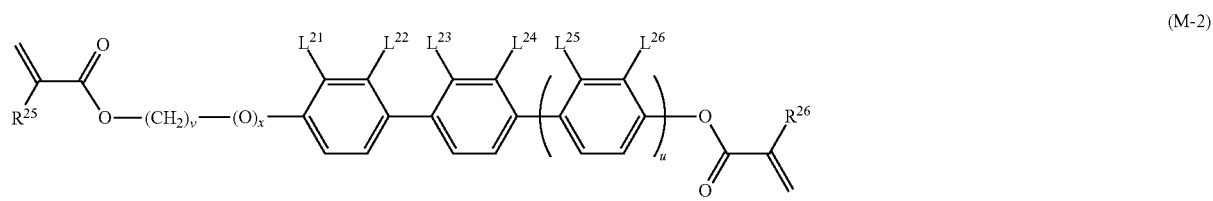

(M-2)

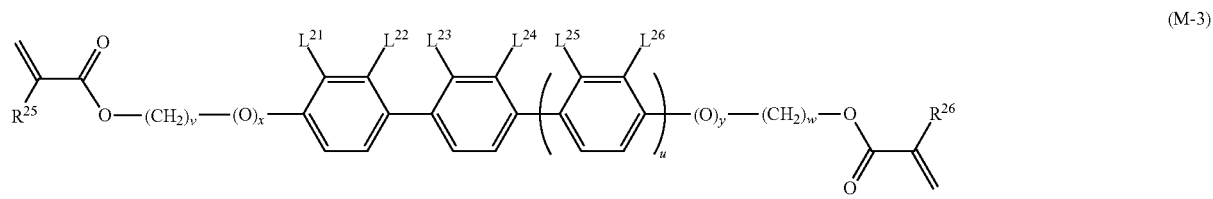

(M-3)

(M-4)                                            (M-5)

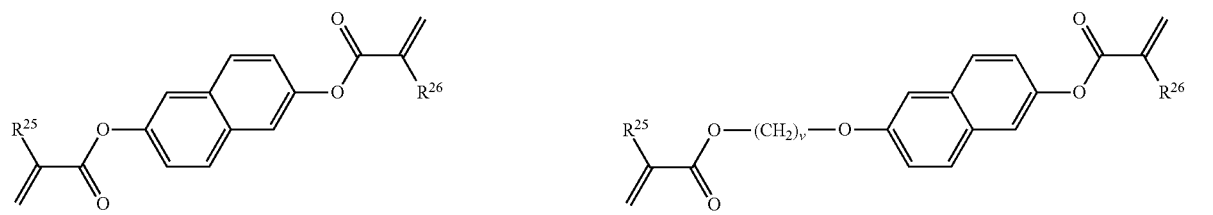

(M-6)

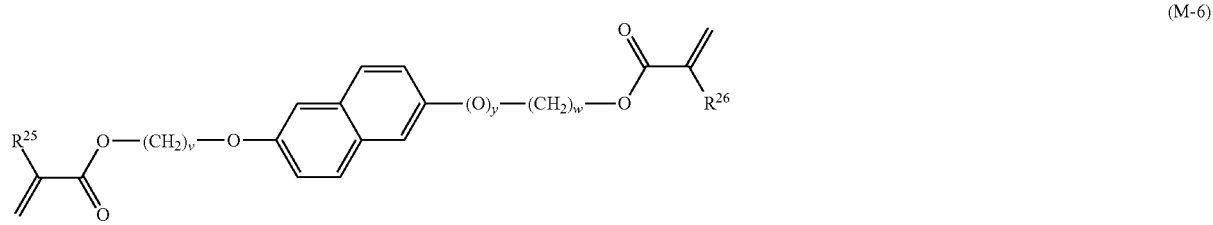

-continued

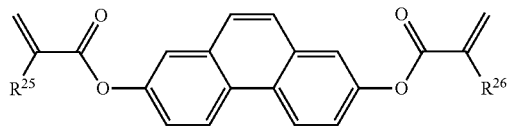
(M-7)

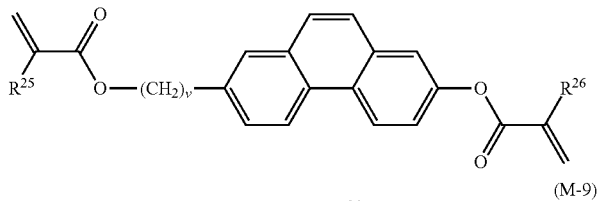
(M-8)

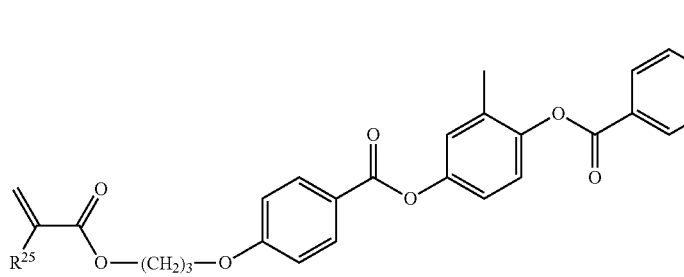
(M-9)

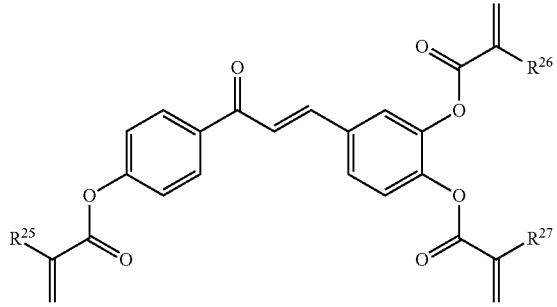
(M-10)

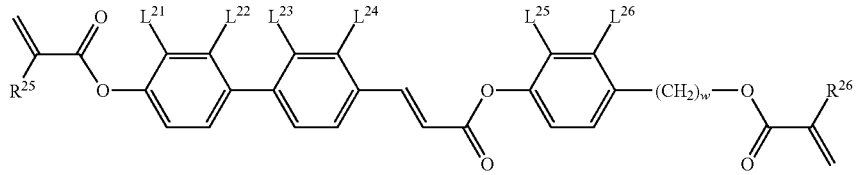
(M-11)

(M-12)

When the second component in the polymerizable composition is a polymerizable compound having the liquid crystal phase, the optically anisotropic body is formed by polymerizing the polymerizable compound while controlling alignment of liquid crystal molecules. The optically anisotropic body can be used for a phase difference film, a polarizing element, a circular polarizing element, an elliptic polarizing element, an antireflection film, a selective reflection film, a color compensation film, a viewing angle compensation film or the like. An additive such as the polymerization initiator may be added to the polymerizable composition for the purpose of adjusting physical properties of the optically anisotropic body.

The polymerizable composition may also contain the liquid crystal composition as the second component. In the case of aiming at a liquid crystal display device having the mode such as PS-TN, PS-IPS, PS-FFS, PSA-VA and PSA-OCB, the composition contains compound (1) as component A, and preferably further contains a compound selected from components B, C and D described below. Component B includes compounds (2) to (4). Component C includes compounds (5) to (7). Component D includes compound (8). When preparing such a composition, component B, C and D are preferably selected in consideration of magnitude of dielectric anisotropy or the like. The composition may contain any other liquid crystal compound different from components B, C and D. A composition in which the component is suitably selected has a high maximum temperature, a low minimum temperature, a small viscosity, a suitable optical anisotropy (namely, a large optical anisotropy or small optical anisotropy), a large dielectric anisotropy and a suitable elastic constant (namely, a large elastic constant or a small elastic constant).

The polymerizable composition is prepared by adding compound (1) to the liquid crystal composition. In such a composition, an amount of addition of compound (1), namely component A, is in the range of 0.05 wt % to 20 wt % based on the weight of the liquid crystal composition. A further preferred amount of addition is in the range of 0.1 wt % to 10 wt %. Most preferred amount of addition is in the range of 0.2 wt % to 1 wt %. At least one of other polymerizable compounds different from compound (1) may be further added thereto. In the above case, the amount of addition in a sum of compound (1) and any other polymerizable compound is preferably within the range described above. Physical properties of the polymer to be formed can be adjusted by suitably selecting any other polymerizable compound. Examples of other polymerizable compound include acrylate and methacrylate as previously described. The examples also include compounds (M-1) to (M-12).

Component B is a compound in which two terminal groups are alkyl or the like. Preferred examples of component B include compounds (2-1) to (2-11), compounds (3-1) to (3-19) and compounds (4-1) to (4-7). In the compound of component B, $R^{11}$ and $R^{12}$ are defined in a manner identical to the definitions of formulas (2) to (4) described in item 12.

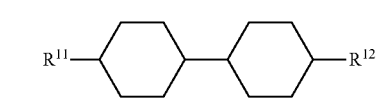

(2-1)

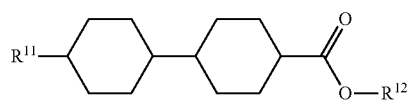

(2-2)

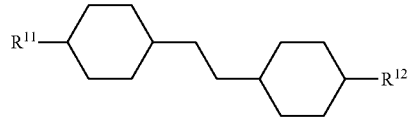

(2-3)

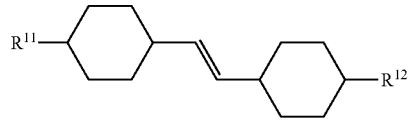

(2-4)

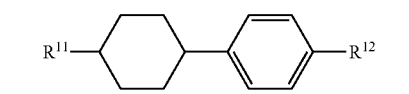

(2-5)

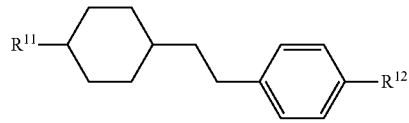

(2-6)

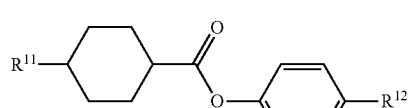

(2-7)

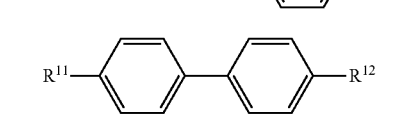

(2-8)

-continued

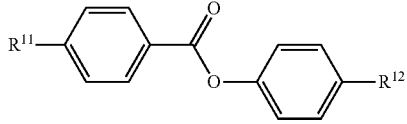

(2-9)

(2-10)

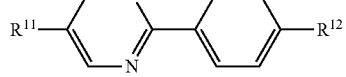

(2-11)

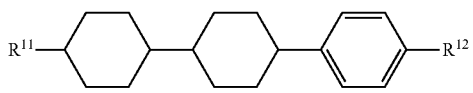

(3-1)

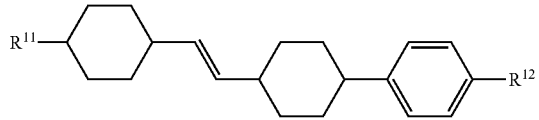

(3-2)

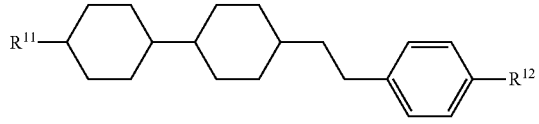

(3-3)

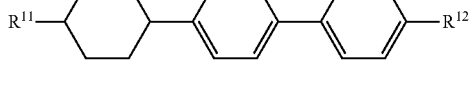

(3-4)

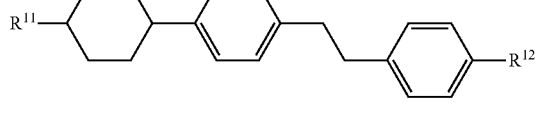

(3-5)

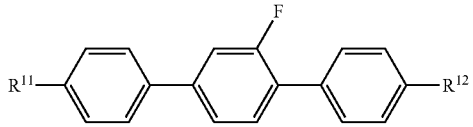

(3-6)

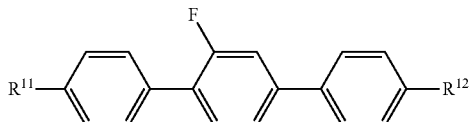

(3-7)

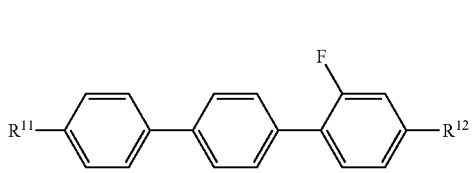

(3-8)

(3-9)

(3-10)

(3-11)
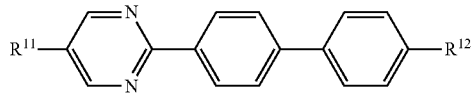

(3-12)
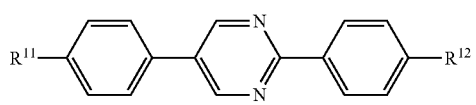

(3-13)
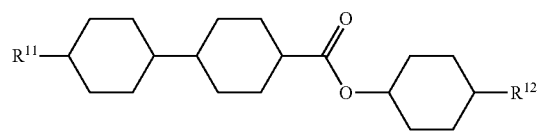

(3-14)
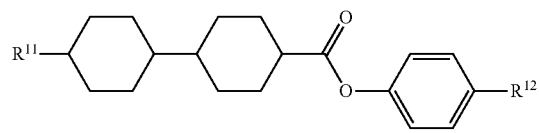

(3-15)
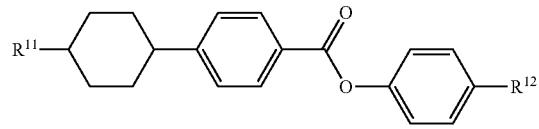

(3-16)
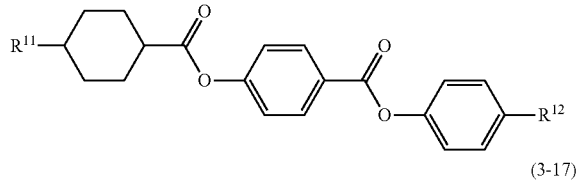

(3-17)
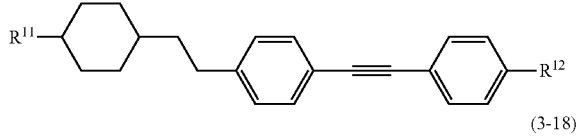

(3-18)
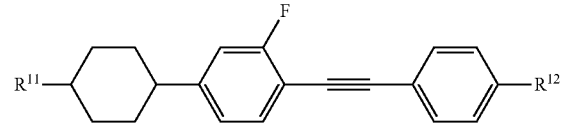

(3-19)
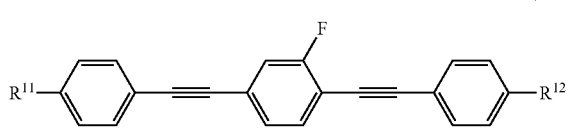

(4-1)
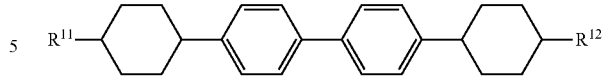

(4-2)
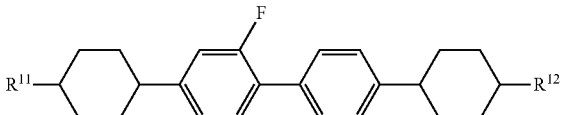

(4-3)
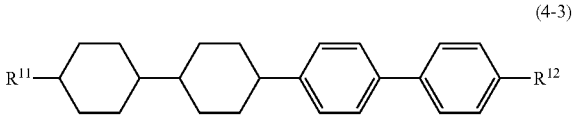

(4-4)
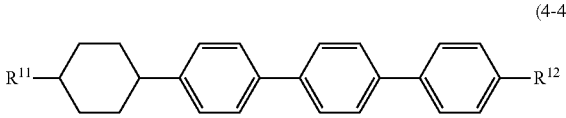

(4-5)
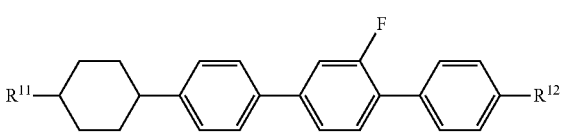

(4-6)
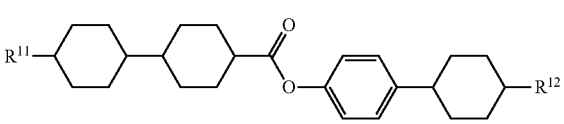

(4-7)
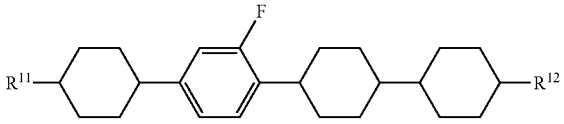

Component B has a small absolute value of dielectric anisotropy, and therefore is a compound close to neutrality. Compound (2) is effective mainly in adjusting the viscosity or the optical anisotropy. Compounds (3) and (4) are effective in extending the temperature range of the nematic phase by increasing the maximum temperature, or in adjusting the optical anisotropy.

If a content of component B is increased, the viscosity of the composition decreases, but the dielectric anisotropy thereof decreases. Thus, as long as a desired value of threshold voltage of the device is met, the content is preferably as large as possible. Accordingly, in the case where a composition for the mode such as PS-IPS and PSA-VA is prepared, the content of component B is preferably 30 wt % or more, and further preferably 40 wt % or more based on the weight of the liquid crystal composition.

Component C is a compound having a halogen-containing group or a fluorine-containing group at a right terminal. Preferred examples of component C include compounds (5-1) to (5-16), compounds (6-1) to (6-113) and compounds (7-1) to (7-57). In the compounds of component C, $R^{13}$ and $X^{11}$ are defined in a manner identical to the definitions of formulas (5) to (7) described in item 13.

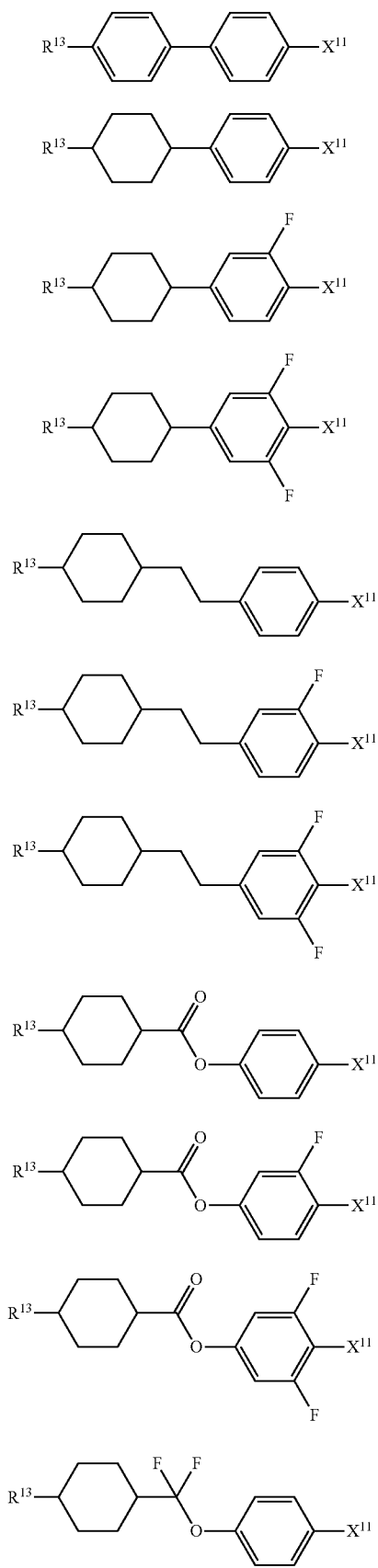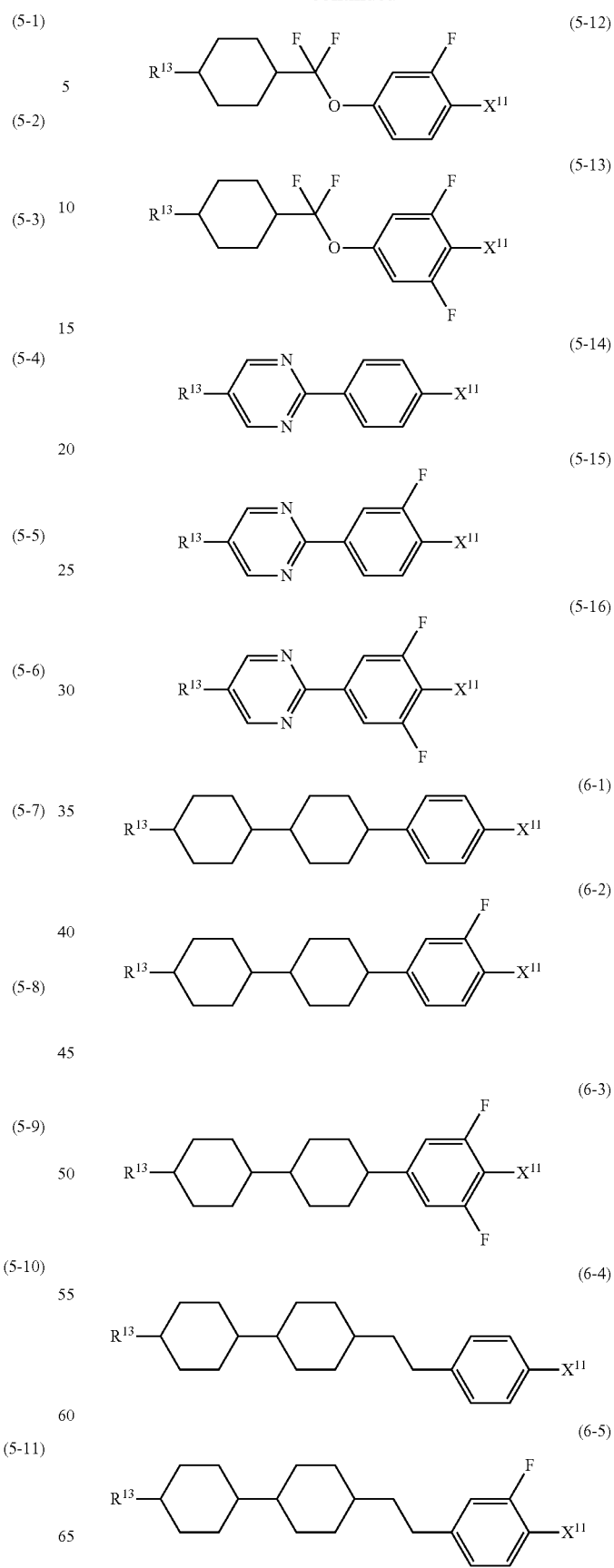

(6-6) 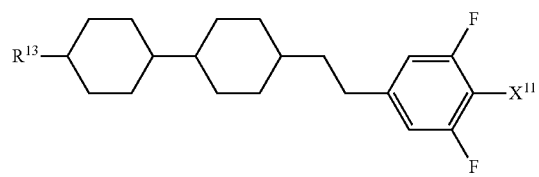
(6-7) 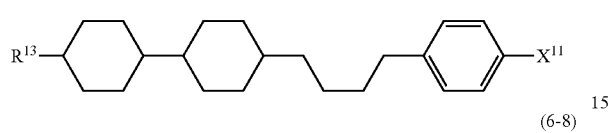
(6-8) 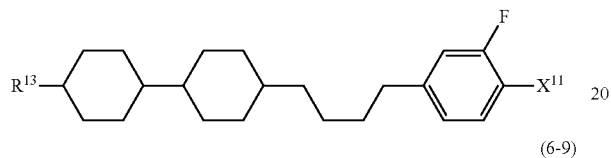
(6-9) 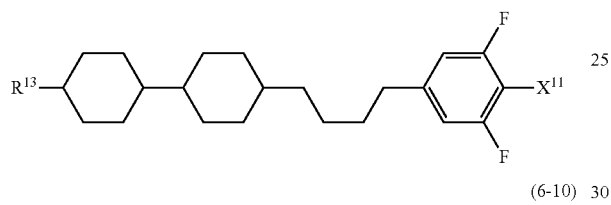
(6-10) 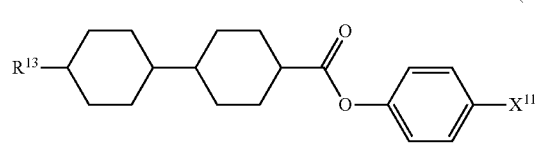
(6-11) 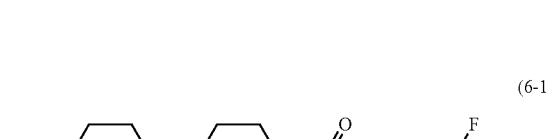
(6-12) 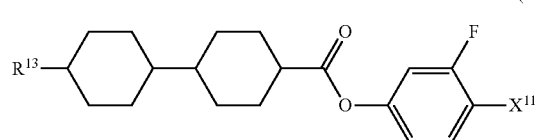
(6-13) 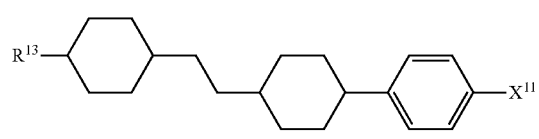
(6-14) 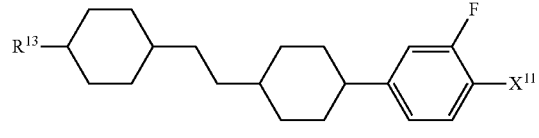
(6-15) 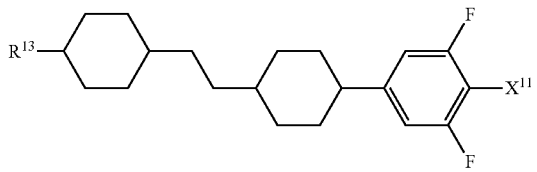
(6-16) 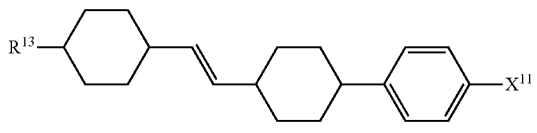
(6-17) 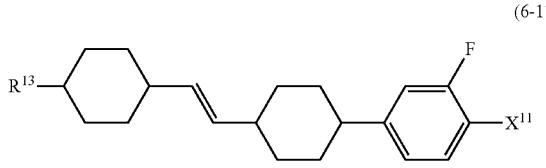
(6-18) 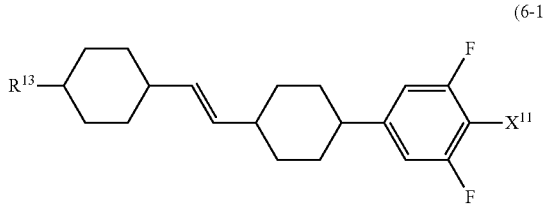
(6-19) 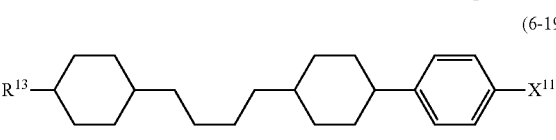
(6-20) 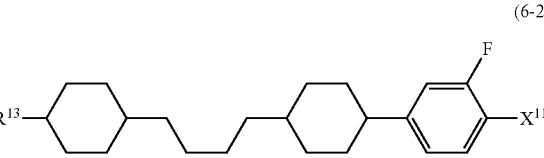
(6-21) 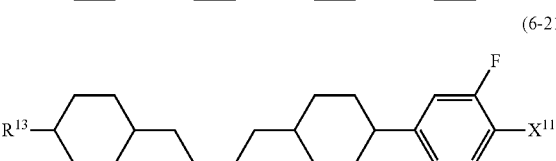
(6-22) 
(6-23) 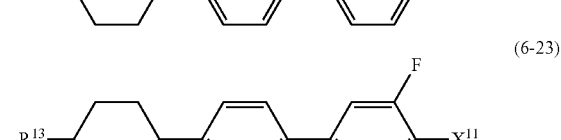
(6-24) 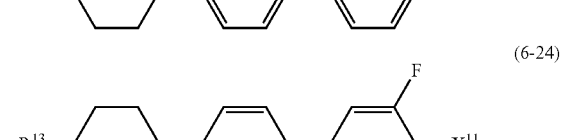

(6-25)
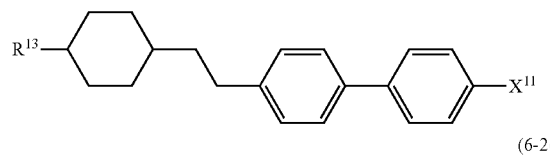
(6-26)
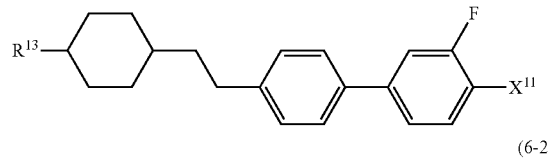
(6-27)
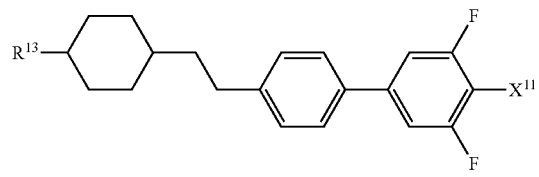
(6-28)
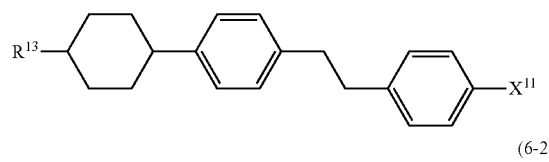
(6-29)
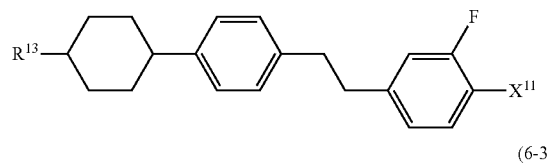
(6-30)
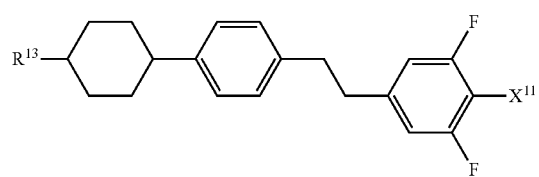
(6-31)
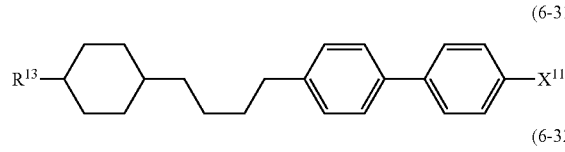
(6-32)
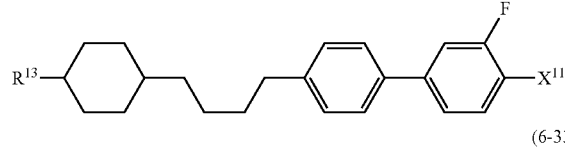
(6-33)
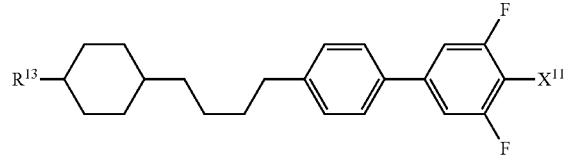
(6-34)
(6-35)
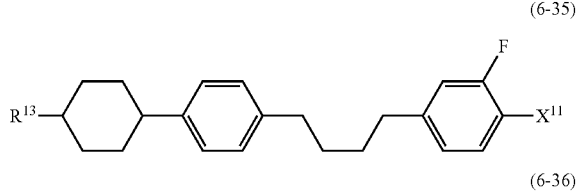
(6-36)
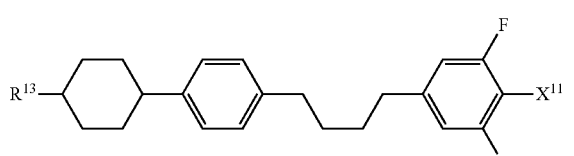
(6-37)
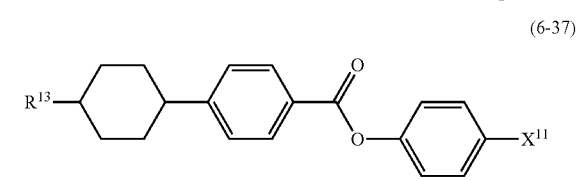
(6-38)
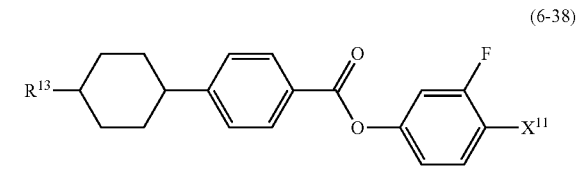
(6-39)
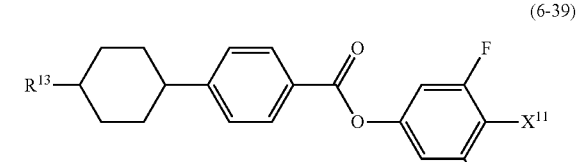
(6-40)
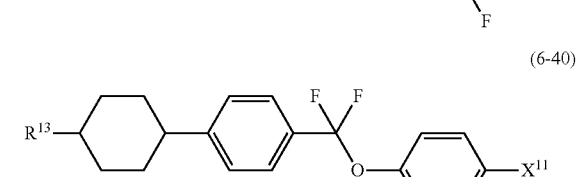
(6-41)
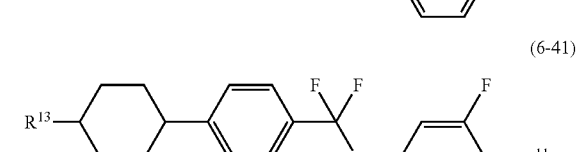
(6-42)
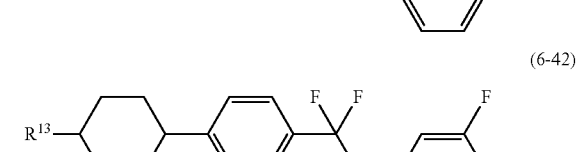
(6-43)

(6-44)
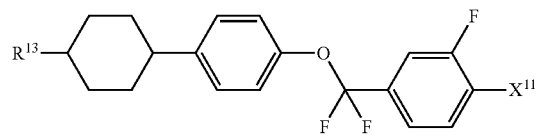
(6-45)
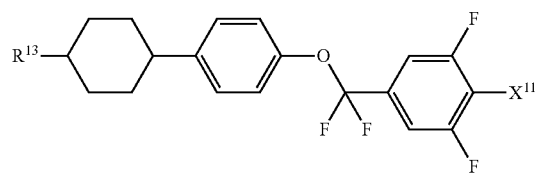
(6-46)
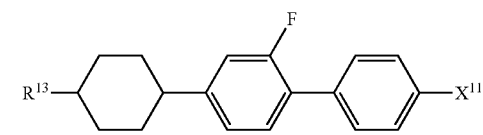
(6-47)
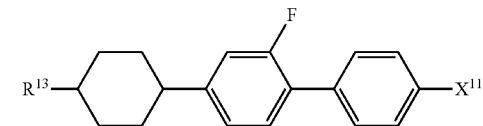
(6-48)
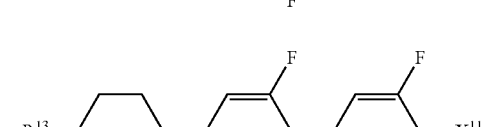
(6-49)
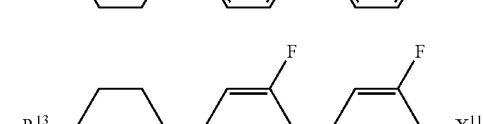
(6-50)
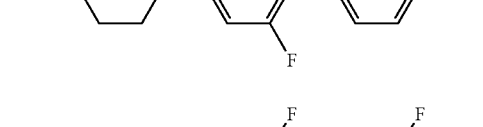
(6-51)
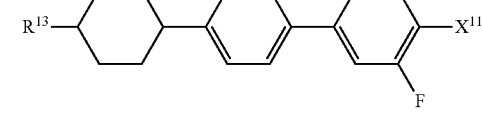
(6-52)
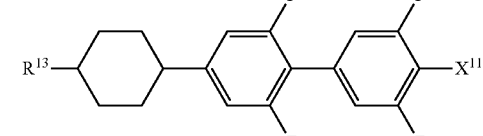
(6-53)
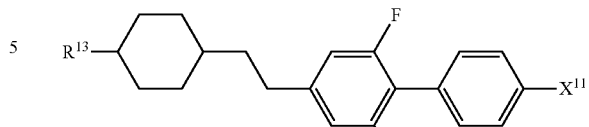
(6-54)
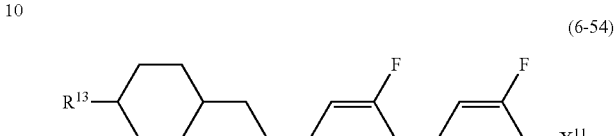
(6-55)
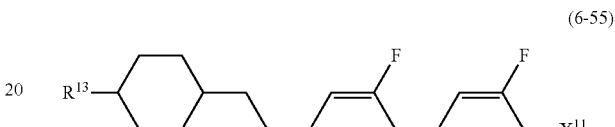
(6-56)
(6-57)
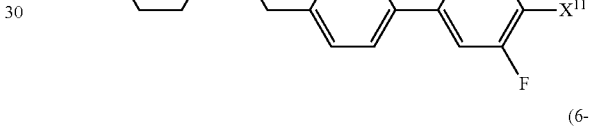
(6-58)
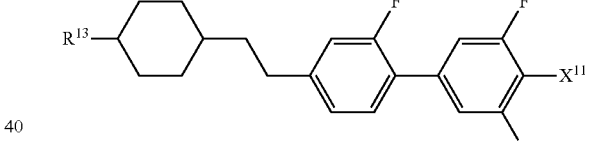
(6-59)
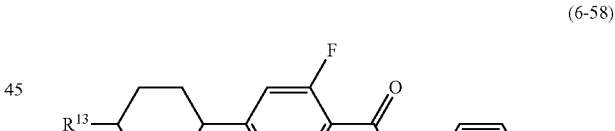
(6-60)
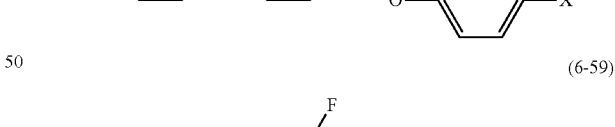

(6-61) 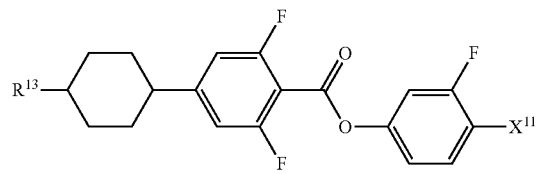
(6-62) 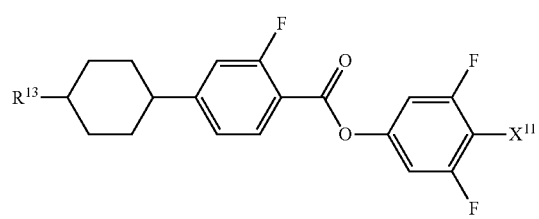
(6-63) 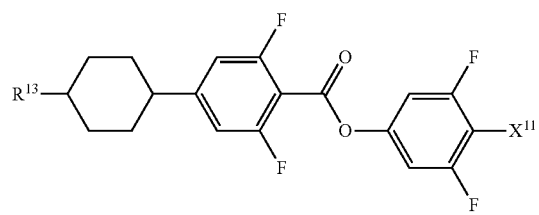
(6-64) 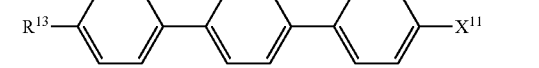
(6-65) 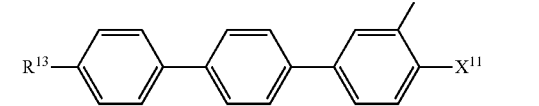
(6-66) 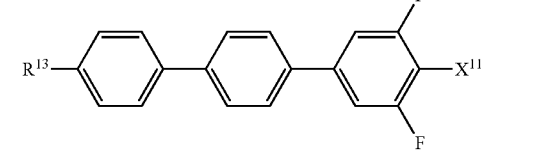
(6-67) 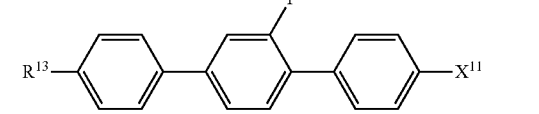
(6-68) 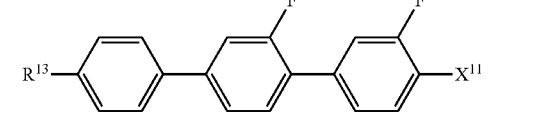
(6-69) 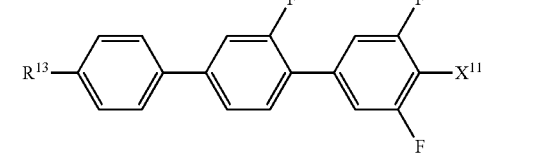
(6-70) 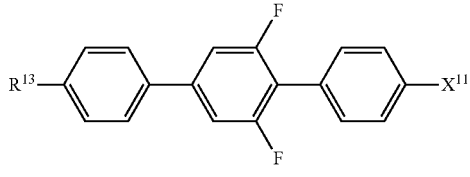
(6-71) 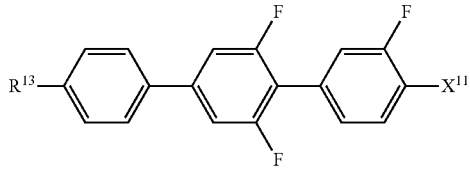
(6-72) 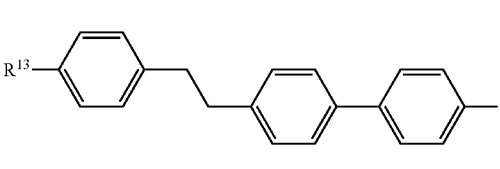
(6-73) 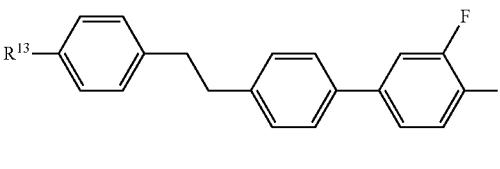
(6-74) 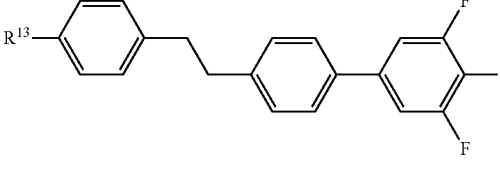
(6-75) 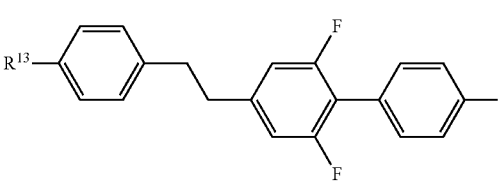
(6-76) 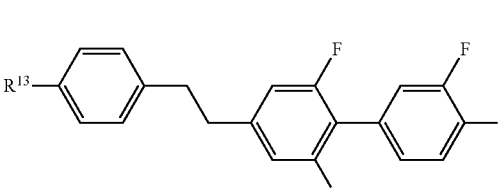
(6-77) 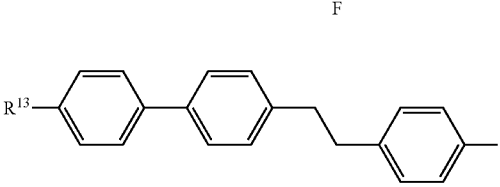
(6-78) 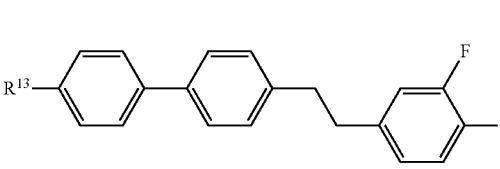

(6-79) 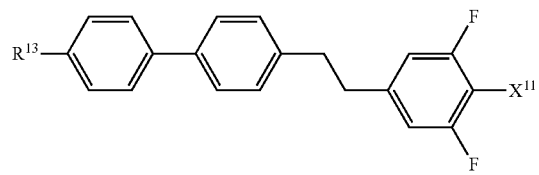
(6-80) 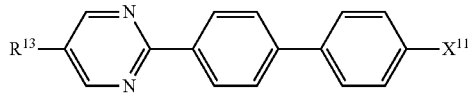
(6-81) 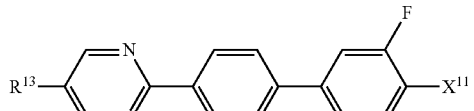
(6-82) 
(6-83) 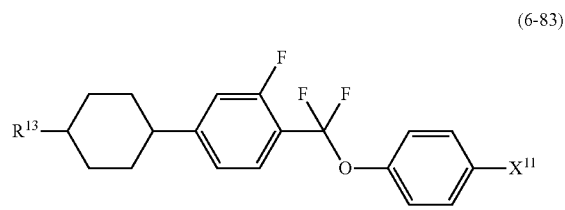
(6-84) 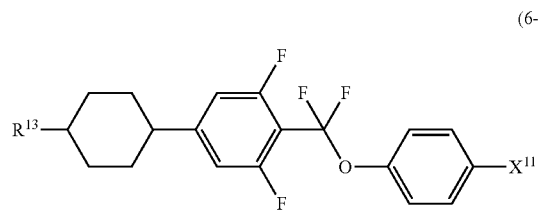
(6-85) 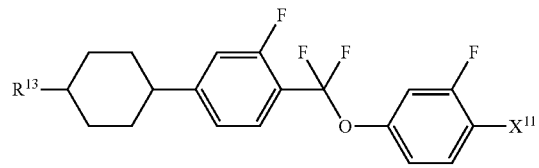
(6-86) 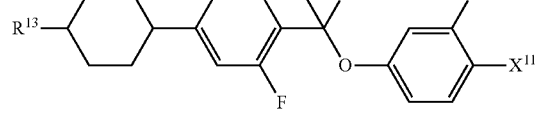
(6-87) 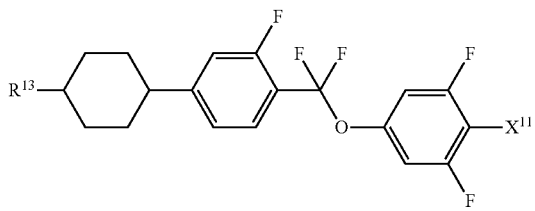
(6-88) 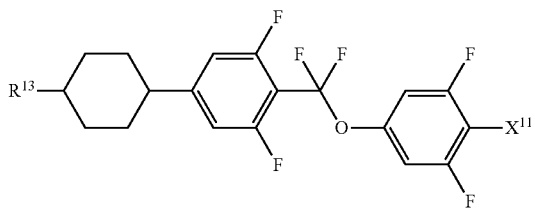
(6-89) 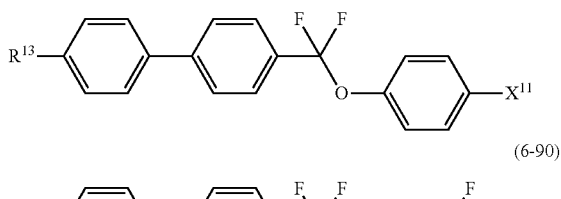
(6-90) 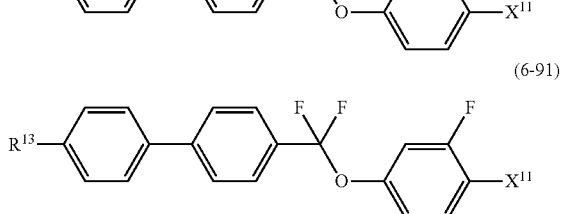
(6-91) 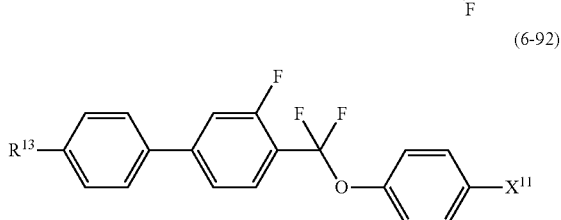
(6-92) 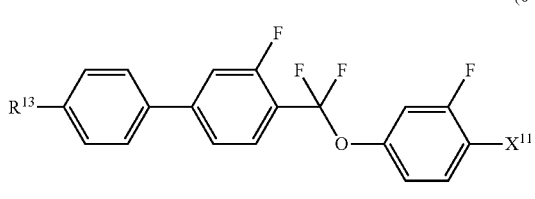
(6-93) 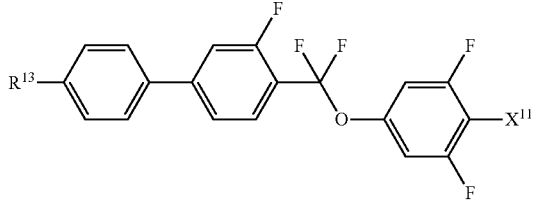
(6-94)

(6-95) 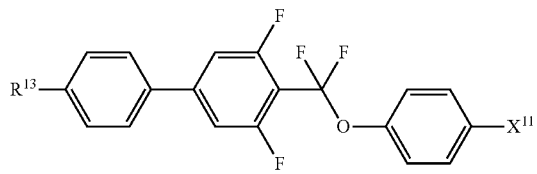
(6-96) 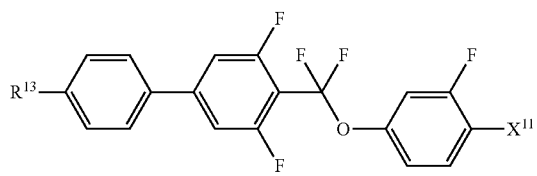
(6-97) 
(6-98) 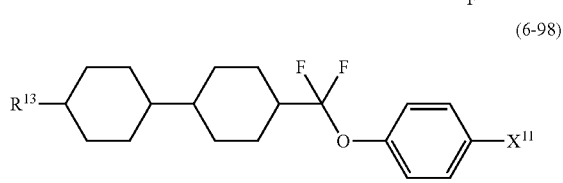
(6-99) 
(6-100) 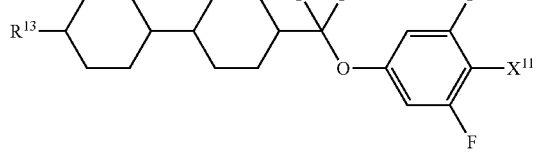
(6-101) 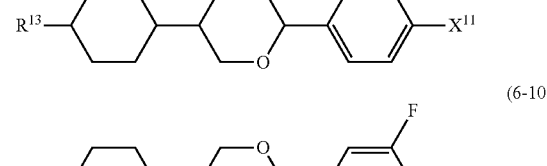
(6-102) 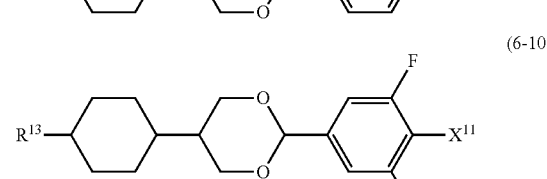
(6-103) 
(6-104) 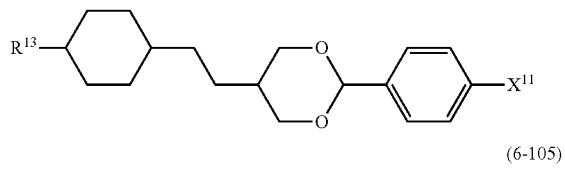
(6-105) 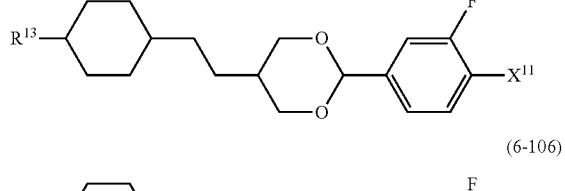
(6-106) 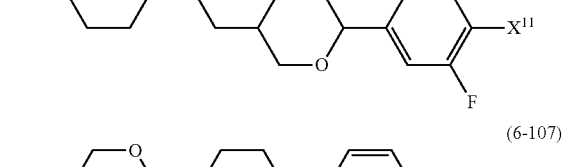
(6-107) 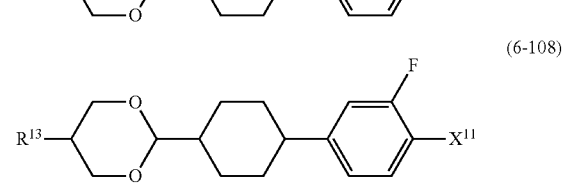
(6-108) 
(6-109) 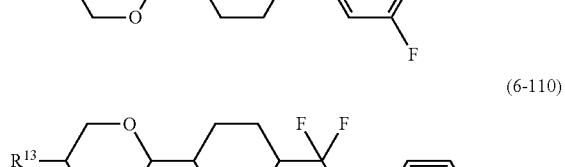
(6-110) 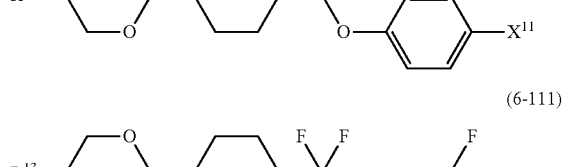
(6-111) 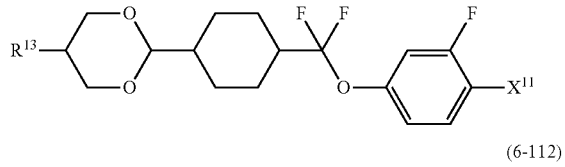
(6-112) 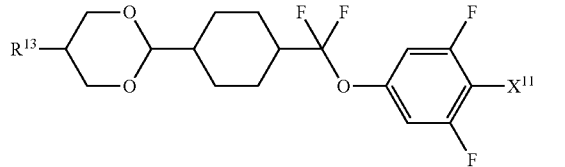

(6-113)
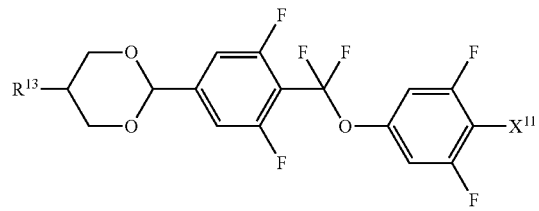
(7-1)
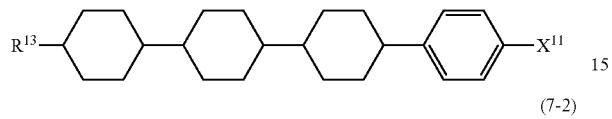
(7-2)
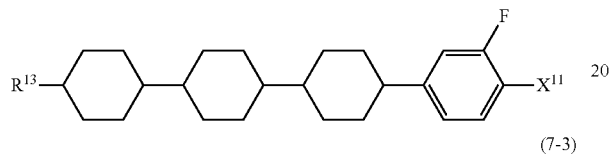
(7-3)
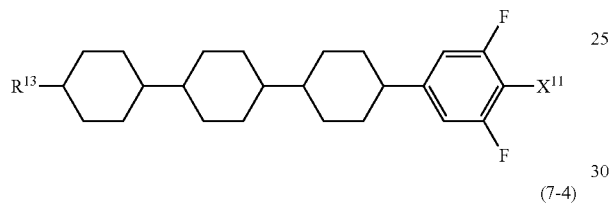
(7-4)
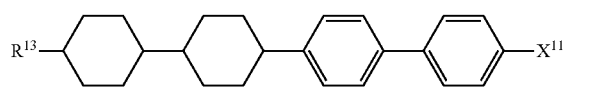
(7-5)
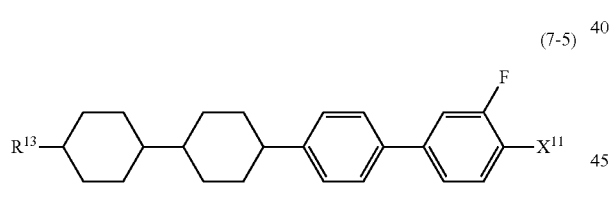
(7-6)
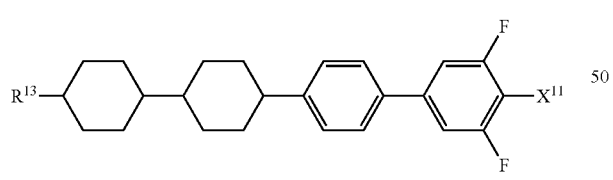
(7-7)
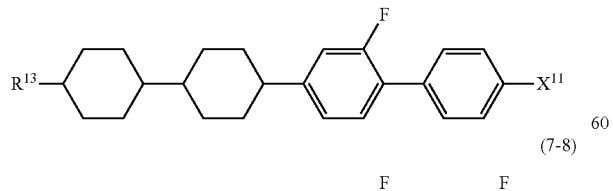
(7-8)
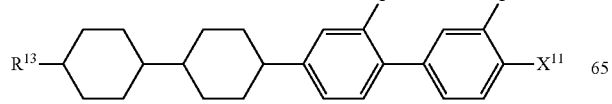
(7-9)
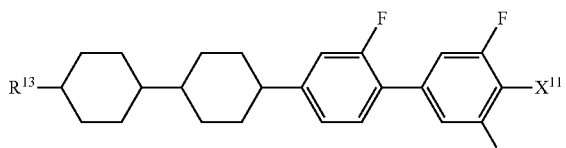
(7-10)
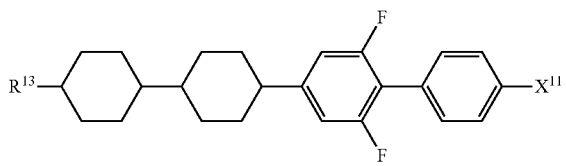
(7-11)
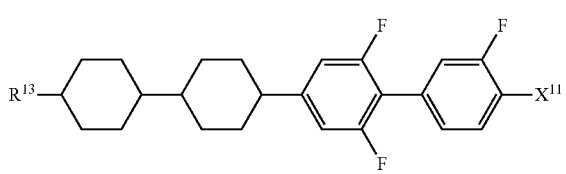
(7-12)
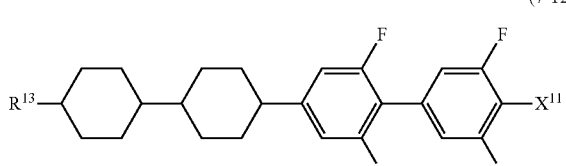
(7-13)
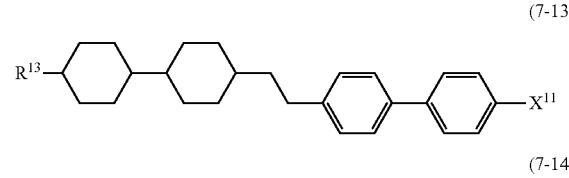
(7-14)
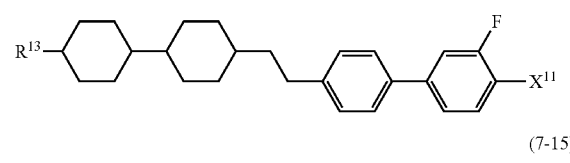
(7-15)
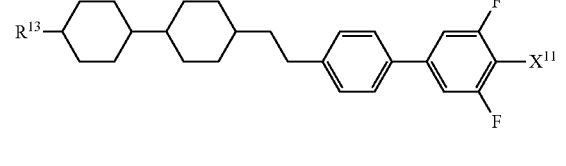
(7-16)
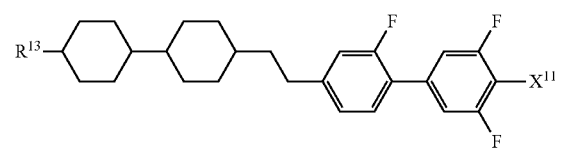
(7-17)
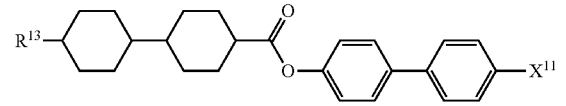

(7-18) 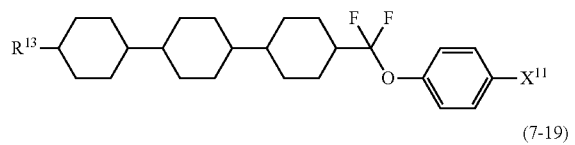
(7-19) 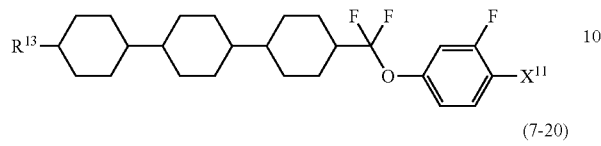
(7-20) 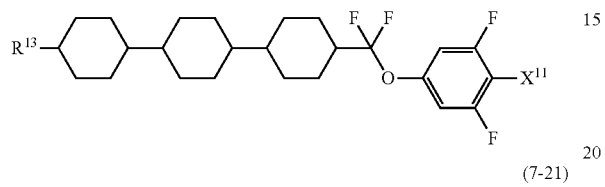
(7-21) 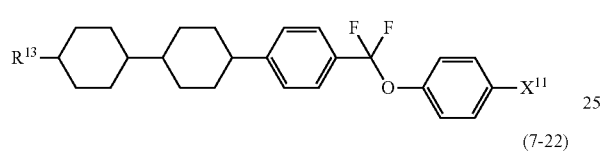
(7-22) 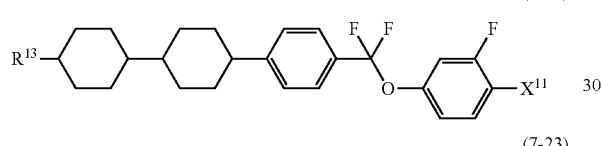
(7-23) 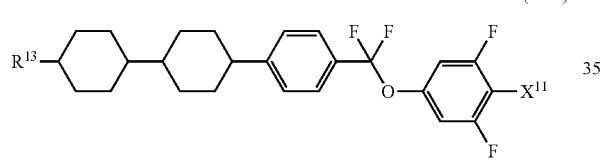
(7-24) 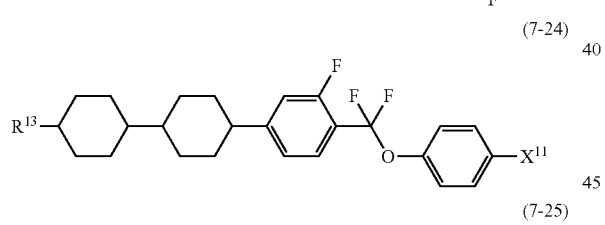
(7-25) 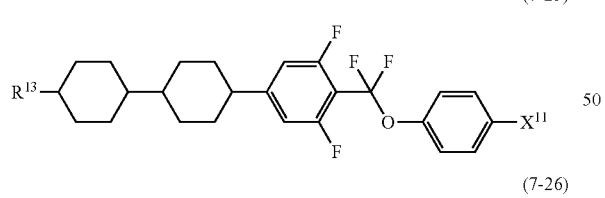
(7-26) 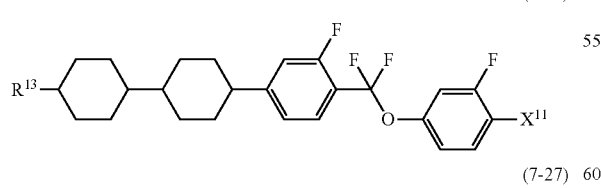
(7-27) 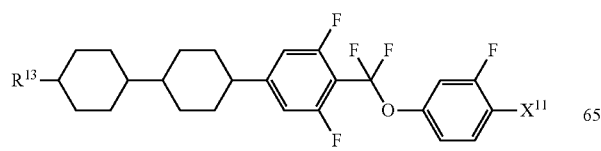
(7-28) 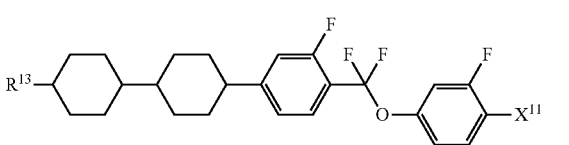
(7-29) 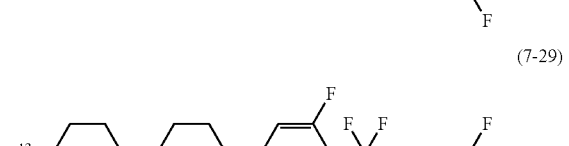
(7-30) 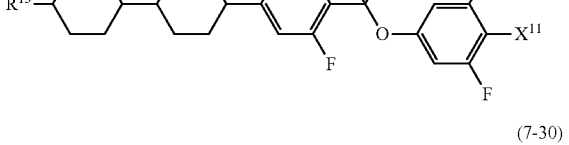
(7-31) 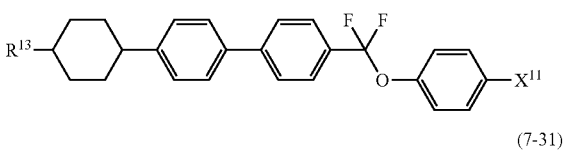
(7-32) 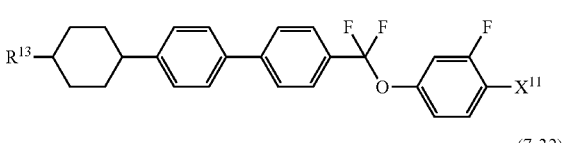
(7-33) 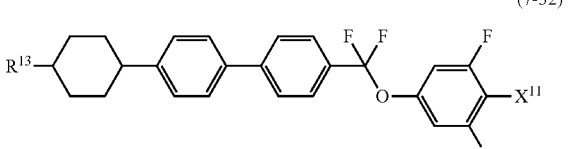
(7-34) 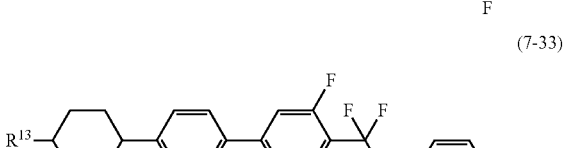
(7-35) 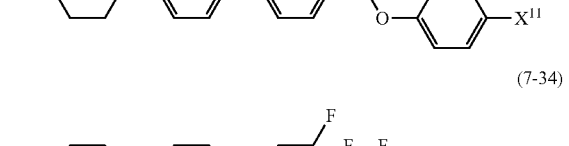
(7-36) 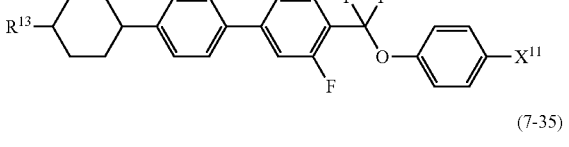
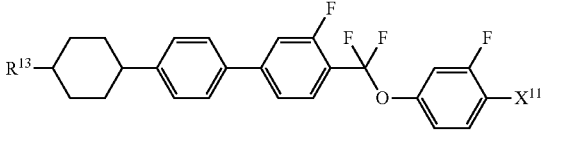
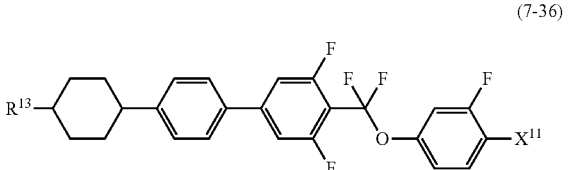

(7-37) 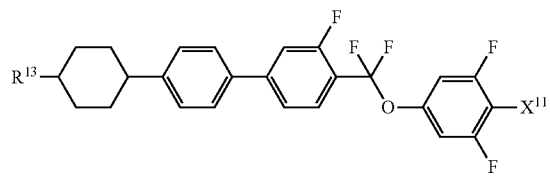
(7-38) 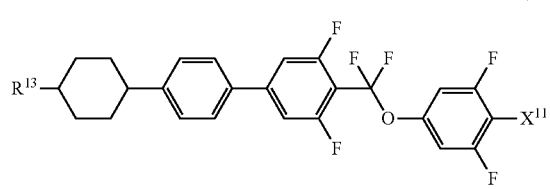
(7-39) 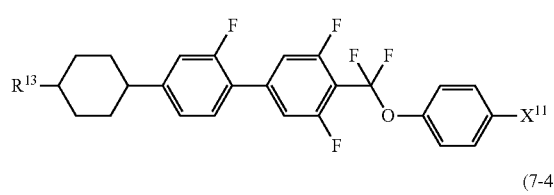
(7-40) 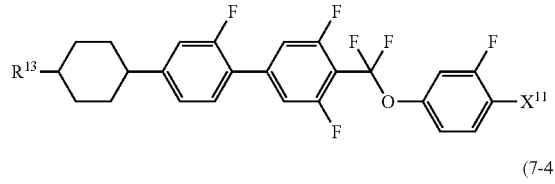
(7-41) 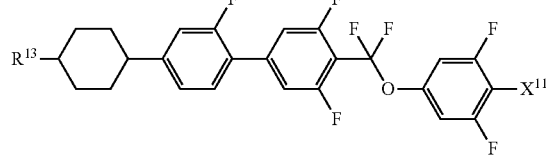
(7-42) 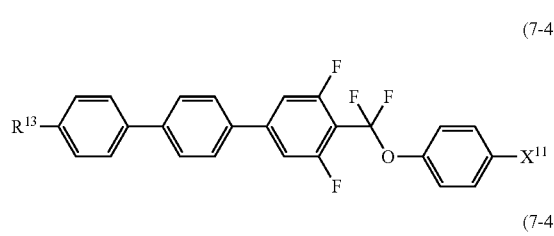
(7-43) 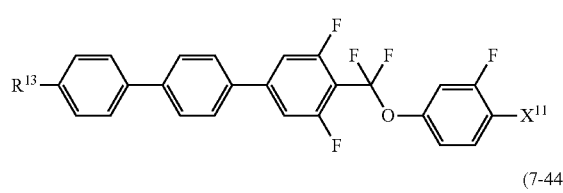
(7-44) 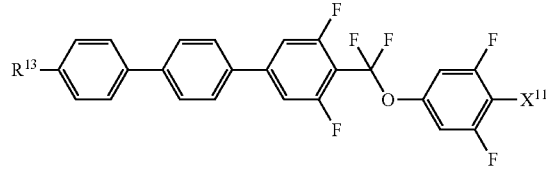
(7-45) 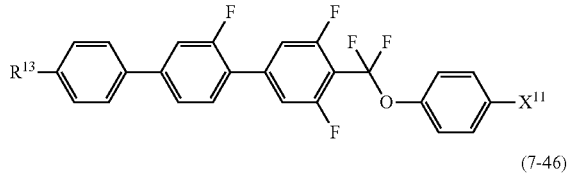
(7-46) 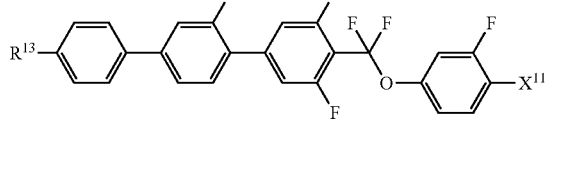
(7-47) 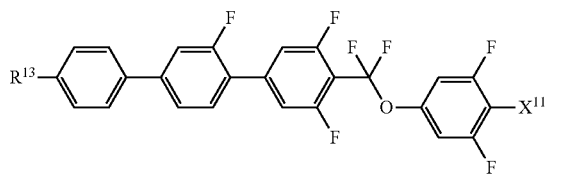
(7-48) 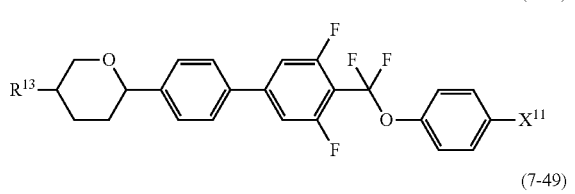
(7-49) 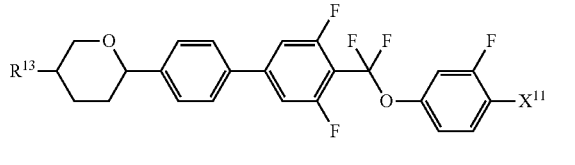
(7-50) 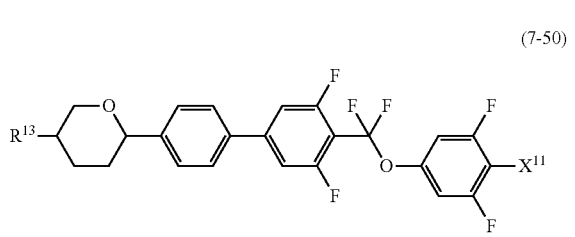
(7-51) 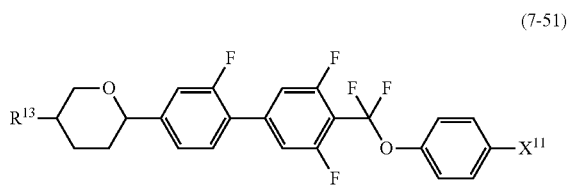
(7-52) 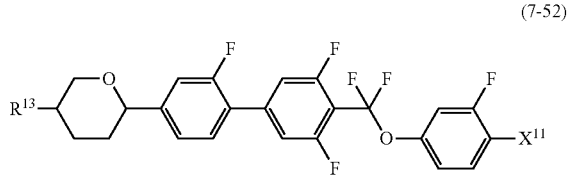

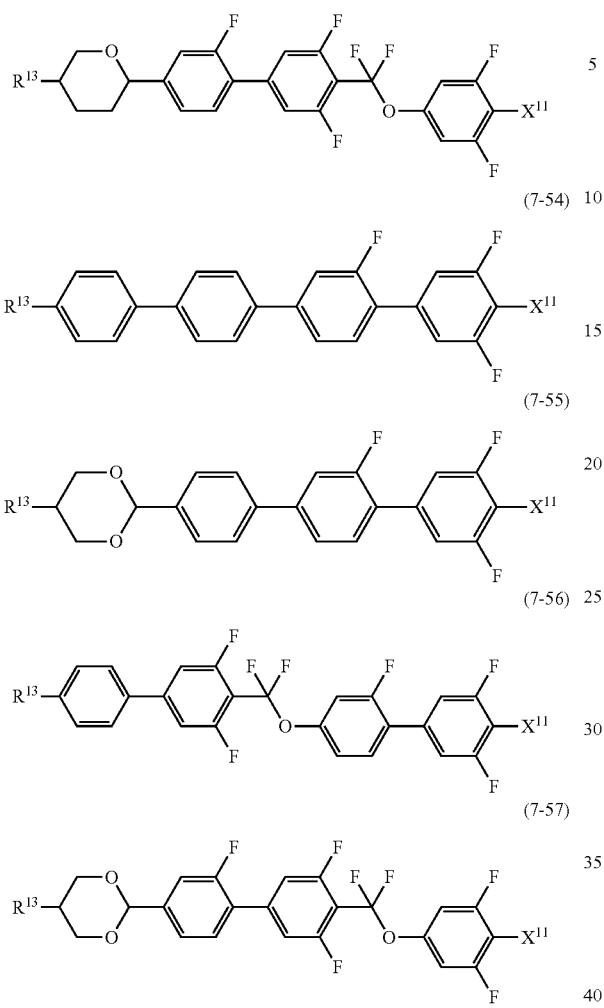

Component C has the positive dielectric anisotropy, and superb stability to heat, light and so forth, and therefore is used when a composition for the mode such as PS-IPS, PS-FFS and PSA-OCB is prepared. A content of component C is suitably in the range of 1 wt % to 99 wt %, preferably in the range of 10 wt % to 97 wt %, and further preferably in the range of 40 wt % to 95 wt %, based on the weight of the liquid crystal composition. When component C is added to a composition having the negative dielectric anisotropy, the content of component C is preferably 30 wt % or less based on the weight of the composition. When component C is added thereto, an elastic constant of the composition and a voltage-transmittance curve of the device can be adjusted.

Component D is compound (8) in which a right-terminal group is —C≡N or —C≡C—C≡N. Preferred examples of component D include compounds (8-1) to (8-64). In compound D, $R^{14}$ and $X^{12}$ are defined in a manner identical to the definitions of formula (8) described in item 14.

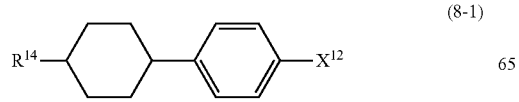

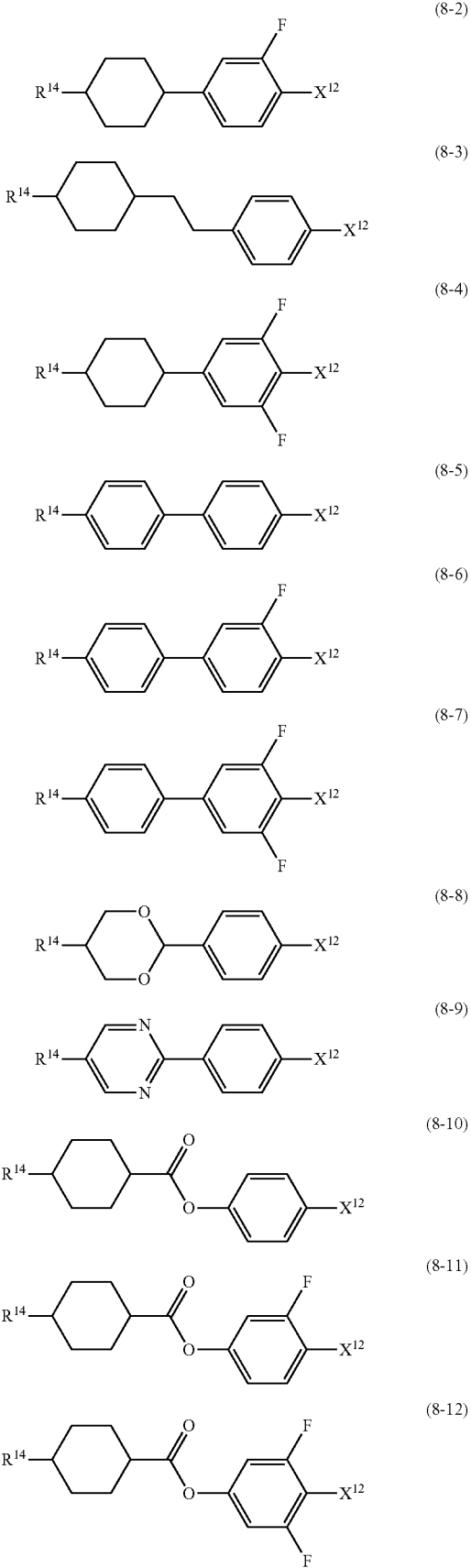

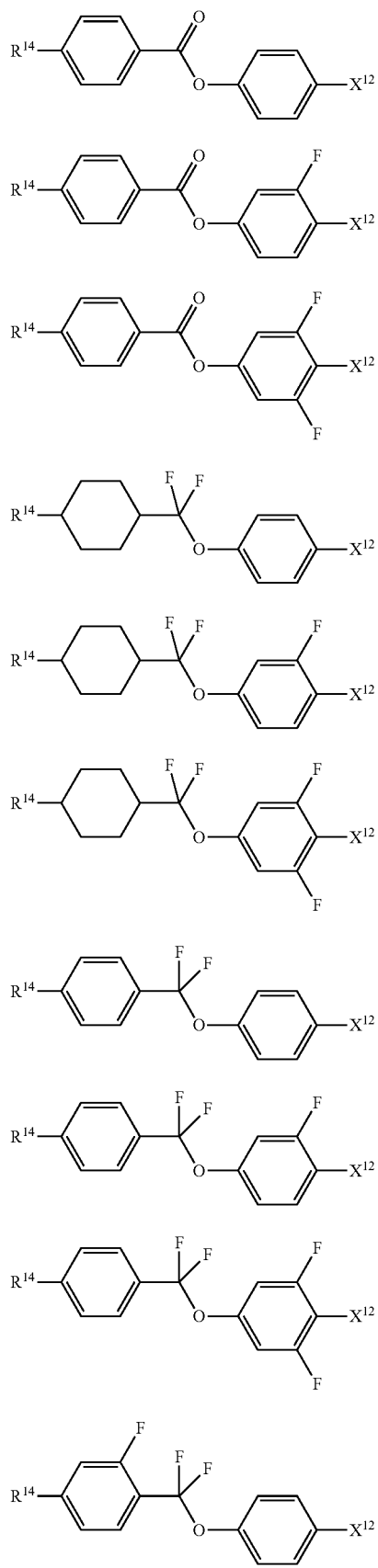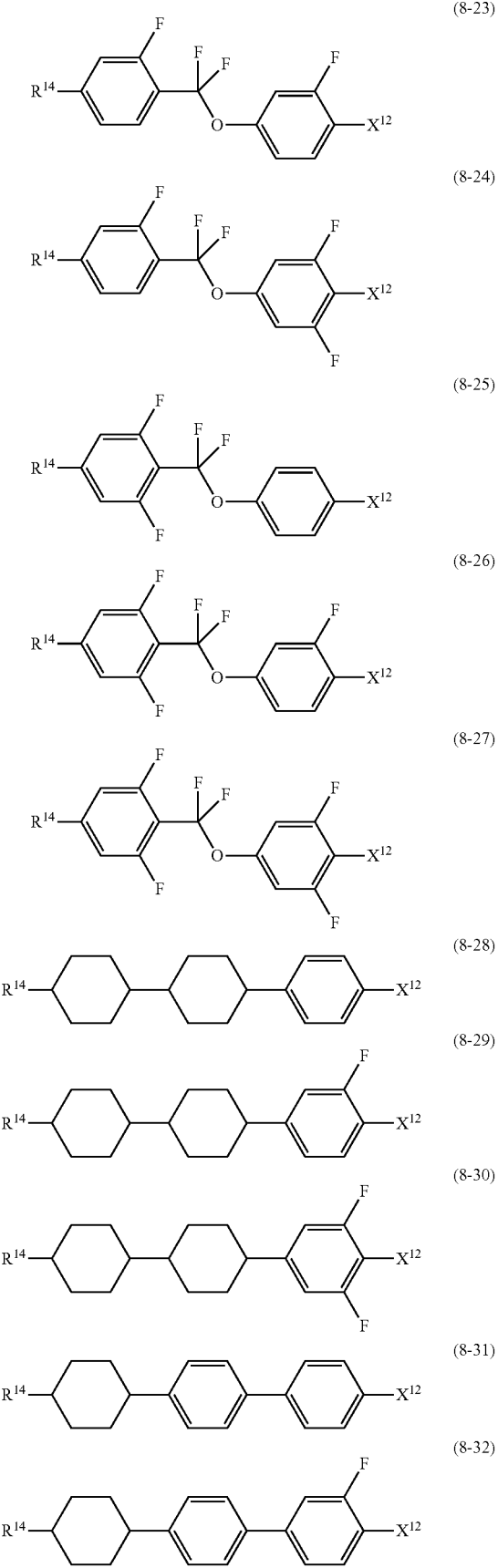

(8-33) 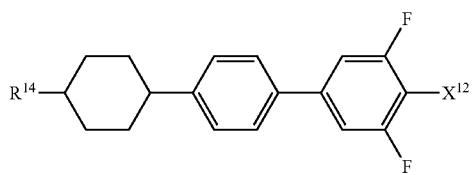
(8-34) 
(8-35) 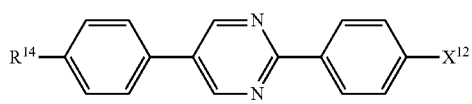
(8-36) 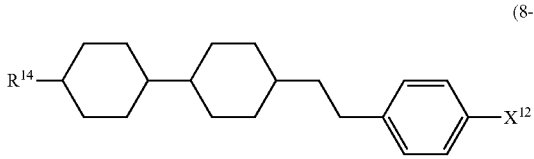
(8-37) 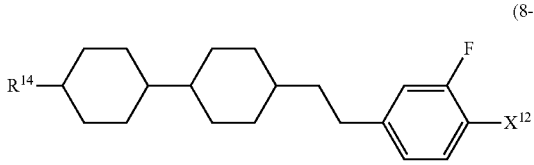
(8-38) 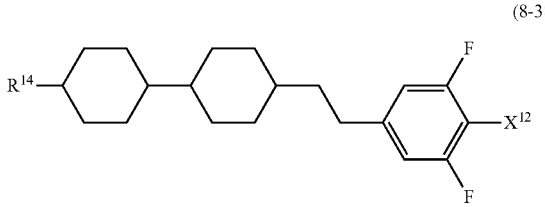
(8-39) 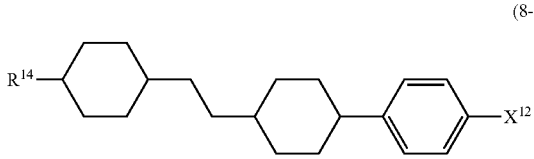
(8-40) 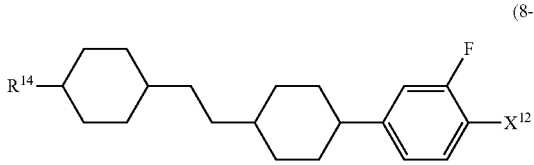
(8-41) 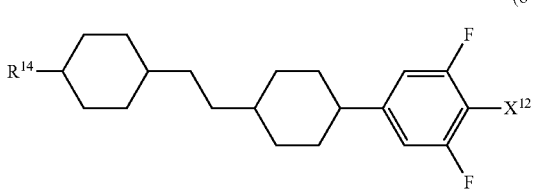
(8-42) 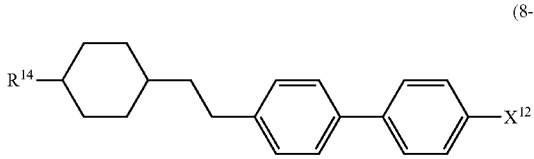
(8-43) 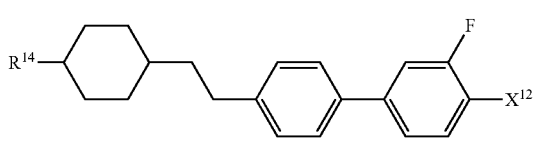
(8-44) 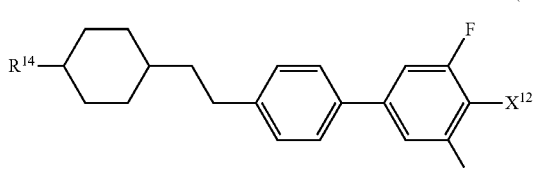
(8-45) 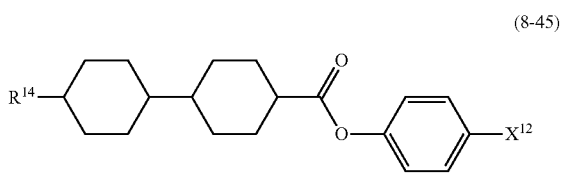
(8-46) 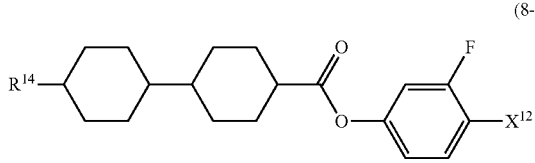
(8-47) 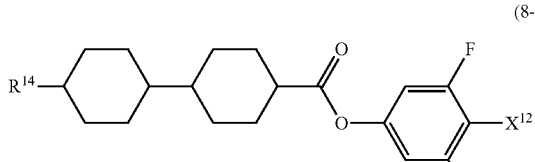
(8-48) 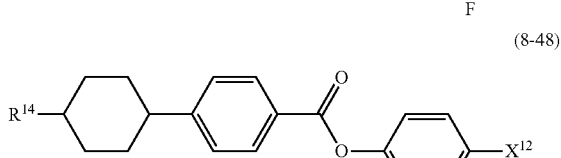
(8-49) 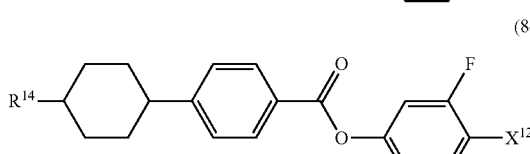
(8-50) 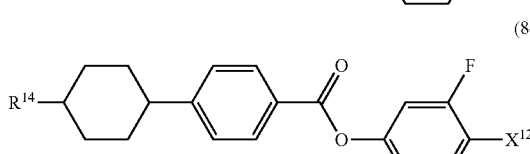
(8-51) 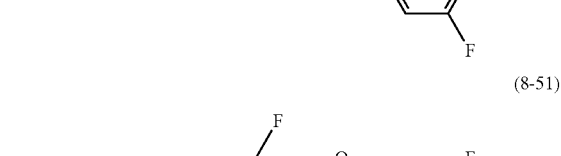

(8-52)
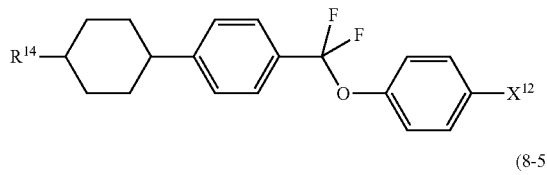

(8-53)
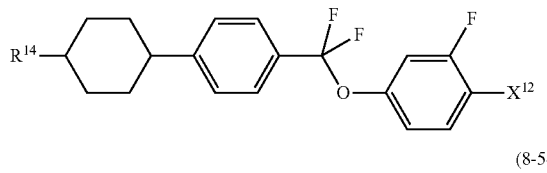

(8-54)
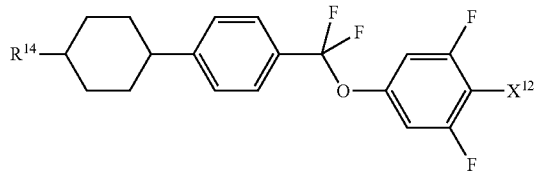

(8-55)
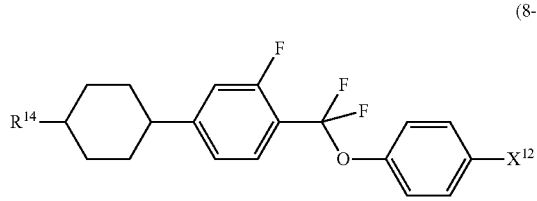

(8-56)
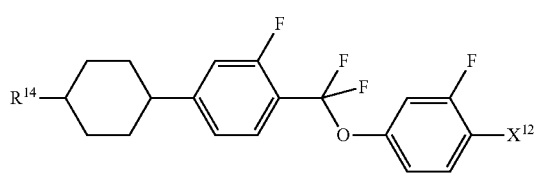

(8-57)
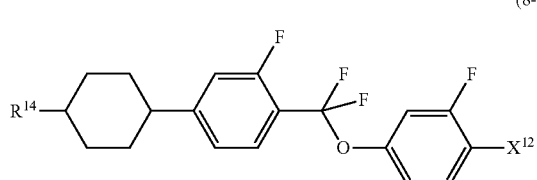

(8-58)
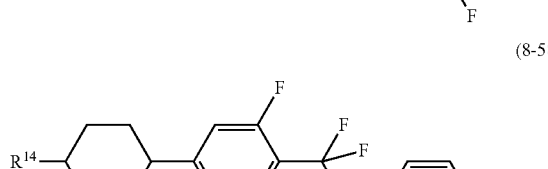

(8-59)
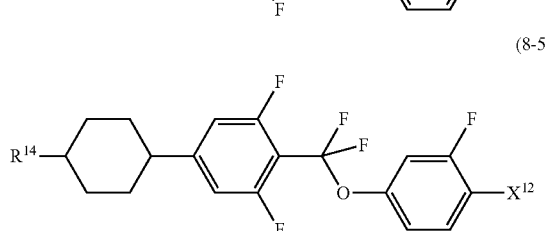

(8-60)
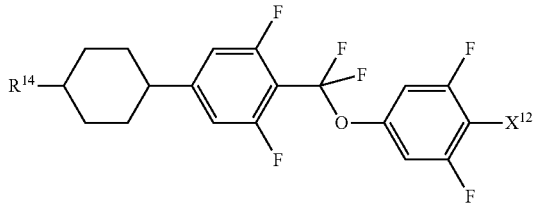

(8-61)

(8-62)
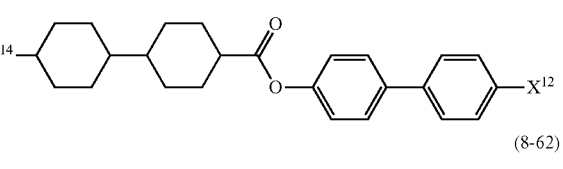

(8-63)
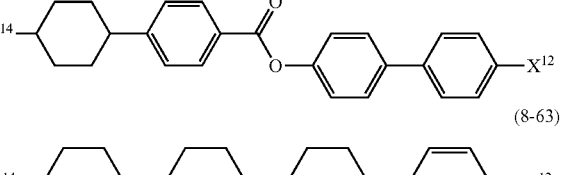

(8-64)
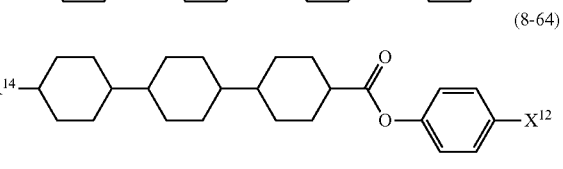

Component D has the positive dielectric anisotropy and a value thereof is large. Therefore, component D is mainly used when a composition for the mode such as the PS-TN mode is prepared. The dielectric anisotropy of the composition can be increased by adding component D. Component D is effective in extending the temperature range of the liquid crystal phase, adjusting the viscosity or adjusting the optical anisotropy. Component D is also useful in adjusting the voltage-transmittance curve of the device.

When a composition for the PS-TN mode or the like is prepared, a content of component D is suitably in the range of 1 wt % to 99 wt %, preferably in the range of 10 wt % to 97 wt %, and further preferably in the range of 40 wt % to 95 wt %, based on the weight of the liquid crystal composition. When component D is added to a composition having the negative dielectric anisotropy, the content of component D is preferably 30 wt % or less based on the weight of the composition. When component D is added thereto, the elastic constant of the composition and the voltage-transmittance curve of the device can be adjusted.

The polymerizable composition is prepared according to a method of dissolving required components at a temperature higher than room temperature, or the like. According to the application, an additive may be added to the composition. Examples of the additive includes an optically active compound, an antioxidant, a UV light absorber, a light stabilizer, a heat stabilizer, an antifoaming agent, a polymerization initiator and a polymerization inhibitor. Such additives are well known to those skilled in the art, and described in literature.

The optically active compound is effective in inducing a helical structure in the liquid crystal molecules to give a required twist angle, thereby being effective in preventing a reverse twist. A helical pitch can be adjusted by adding the optically active compound thereto. Two or more optically active compounds may be added for the purpose of adjusting temperature dependence of the helical pitch. Preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

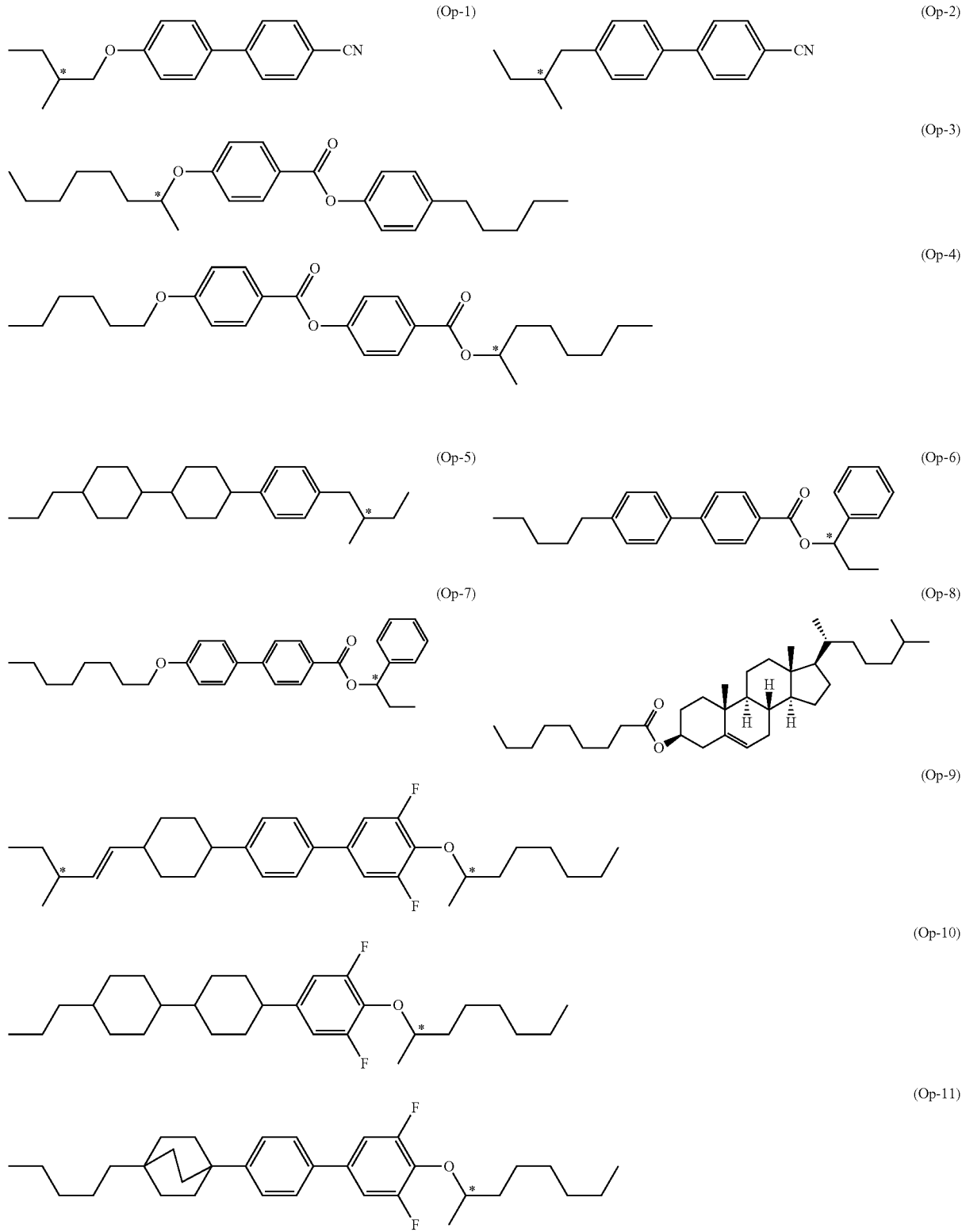

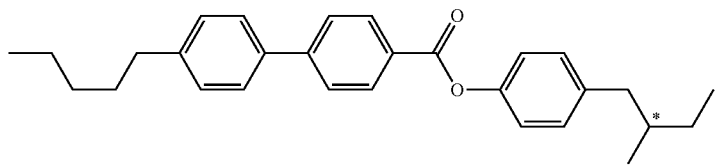
(Op-12)

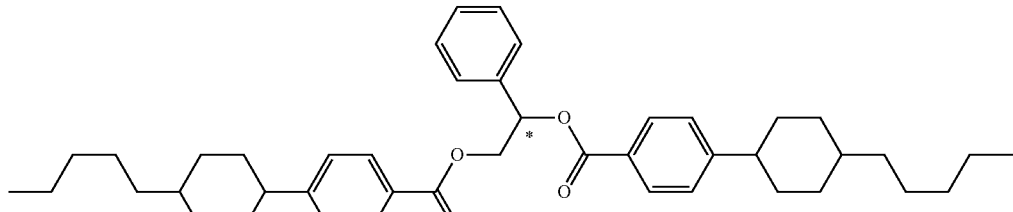
(Op-13)

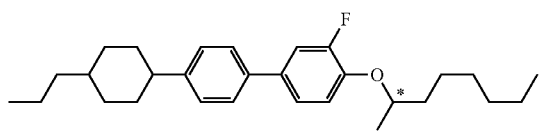
(Op-14)

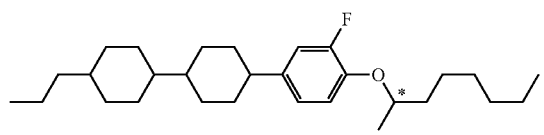
(Op-15)

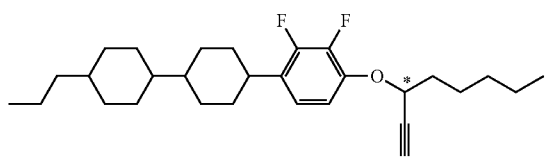
(Op-16)

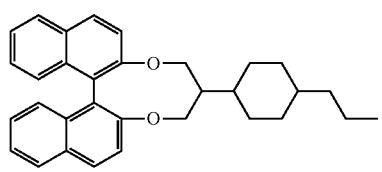
(Op-17)

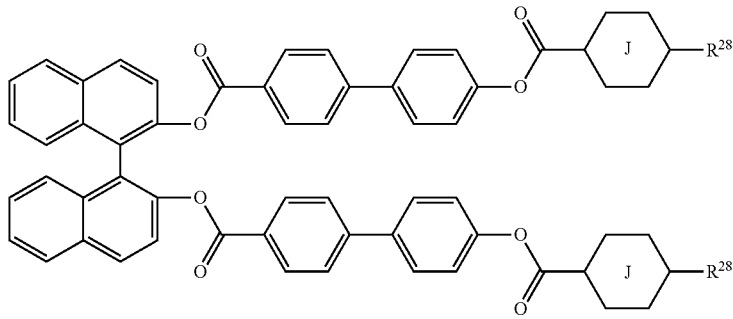
(Op-18)

The antioxidant is effective for maintaining the large voltage holding ratio. Preferred examples of the antioxidant include compounds (AO-1) and (AO-2) below, IRGANOX 415, IRGANOX 565, IRGANOX 1010, IRGANOX 1035, IRGANOX 3114 and IRGANOX 1098 (trade names: BASF SE). The UV light absorber is effective in preventing a decrease of the maximum temperature. Preferred examples of the UV light absorber include a benzophenone derivative, a benzoate derivative and a triazole derivative, and specific examples includes compounds (AO-3) and (AO-4) described below, TINUVIN 329, TINUVIN P, TINUVIN 326, TINUVIN 234, TINUVIN 213, TINUVIN 400, TINUVIN 328, TINUVIN 99-2 (trade names: BASF SE), and 1,4-diazabicyclo[2.2.2]octane (DABCO). The light stabilizer such as an amine having steric hindrance is preferred for maintaining the large voltage holding ratio. Preferred examples of the light stabilizers include compounds (AO-5) and (AO-6) described below, TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). The antifoaming agent is effective in preventing foam formation. Preferred examples of the antifoaming agent include dimethyl silicone oil and methylphenyl silicone oil.

(AO-1)

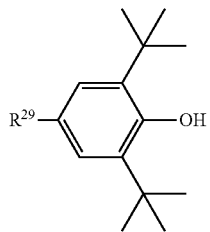

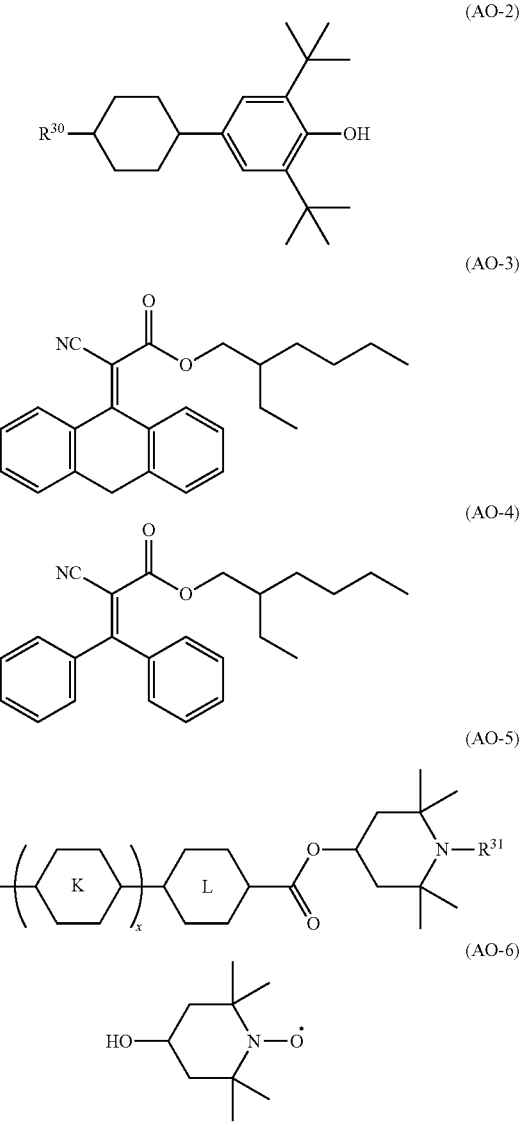

In compound (AO-1), $R^{29}$ is alkyl having 1 to 20 carbons, alkoxy having 1 to 20 carbons, —COOR$^{32}$ or —CH$_2$CH$_2$COOR$^{32}$, in which $R^{32}$ is alkyl having 1 to 20 carbons. In compounds (AO-2) and (AO-5), $R^{30}$ is alkyl having 1 to 20 carbons. In compound (AO-5), $R^{31}$ is hydrogen, methyl or O. (oxygen radical), and ring K and ring L are 1,4-cyclohexylene or 1,4-phenylene, and x is 0, 1 or 2.

4. Liquid Crystal Composite

Compound (1) has high polymerization reactivity, a high conversion ratio and a high solubility in a liquid crystal composition. A liquid crystal composite is formed by polymerizing a polymerizable composition containing compound (1) and the liquid crystal composition. Compound (1) forms a polymer in the liquid crystal composition by polymerization. The above polymer is effective in producing pretilt in liquid crystal molecules. Polymerization is preferably performed at temperature at which the polymerizable composition exhibits a liquid crystal phase. The polymerization progresses by heat, light or the like. A preferred reaction is photopolymerization. In order to prevent thermopolymerization from occurring simultaneously, the photopolymerization is preferably performed at 100° C. or lower, and may be performed in a state in which an electric field or a magnetic field is applied thereto.

The polymerization reactivity and the conversion ratio of compound (1) can be adjusted. Compound (1) is suitable for radical polymerization. An amount of remaining compound (1) can be decreased by optimizing a reaction temperature. Compound (1) can be quickly polymerized by adding the polymerization initiator. Specific examples of a photoradical polymerization initiator include TPO, 1173 and 4265 from Darocur series of Ciba Specialty Chemicals Inc. SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone/methyl p-dimethylaminobenzoate mixture and a benzophenone/methyltriethanolamine mixture.

The polymerization can be performed by adding the photoradical polymerization initiator to the polymerizable composition, and then irradiating the resulting mixture with UV light in a state in which the electric field is applied thereto. However, an unreacted polymerization initiator or a decomposition product of the polymerization initiator may possibly cause poor display such as image persistence in the device. The photopolymerization may be performed without adding the polymerization initiator in order to prevent such poor display. A preferred wavelength of light to be irradiated is in the range of 150 nanometers to 500 nanometers. A further preferred wavelength is in the range of 250 nanometers to 400 nanometers, and most preferred wavelength is in the range of 300 nanometers to 400 nanometers.

Upon storing the polymerizable compound, the polymerization inhibitor may be added thereto in order to prevent the polymerization. The polymerizable compound is ordinarily added to the composition without removing the polymerization inhibitor. Examples of the polymerization inhibitor include hydroquinone, a hydroquinone derivative such as methylhydroquinone, 4-tert-butylcatechol, 4-methoxyphenol and phenothiazine.

5. Liquid Crystal Display Device

An effect of a polymer in a liquid crystal display device is understood as described below. A polymerizable composition is a mixture of a liquid crystal compound, a polymerizable compound and so forth. Liquid crystal molecules are aligned in a direction of an electric field by applying the electric field to the composition. The polymerizable compounds are also aligned according to the above alignment. The polymerizable compound is polymerized by irradiating the composition with UV light while the alignment is maintained to form three-dimensional network structure. Even when the electric field is removed, the alignment of the polymers is maintained. The liquid crystal molecules are stabilized due to the effect of the polymers in a state in which the molecules are aligned in the direction of the electric field. Accordingly, a response time of the device is to be shortened.

The polymerization of the polymerizable composition is preferably performed within the display device. One example is as described below. A display device is arranged in which the device has two glass substrates provided with transparent electrodes and an alignment film. A polymerizable composition containing compound (1), a liquid crystal composition, an additive and so forth as a component is prepared. The composition is injected into the display device. While applying an electric field to the display device, compound (1) is polymerized by irradiating the device with UV light. A liquid crystal composite is formed by the polymerization. The liquid crystal display device having the liquid crystal composite can be easily produced by the above method. In the above method, rubbing treatment onto the alignment film may be omitted. In addition, a method may be adopted in which the liquid crystal molecules are stabilized in a state in which no electric field is applied.

When an amount of addition of the polymer is in the range of 0.1 wt % to 2 wt % based on the weight of the liquid crystal composition, a liquid crystal display device having the PSA mode is produced. The device having the PSA mode can be driven according to a driving mode such as active matrix (AM) and passive matrix (PM). Such devices can be applied to any of a reflective type, a transmissive type and a transflective type. A device having a polymer dispersed mode can also be produced by increasing the amount of addition of the polymer.

EXAMPLES

The invention will be described in more detail by way of Examples. The invention is not restricted by the Examples.

6. Example of Compound (1)

Compound (1) was prepared according to a procedure described in Example 1 or the like. A compound synthesized was identified by a method such as an NMR analysis. Physical properties of the compound were measured by methods described below.

NMR Analysis

As a measuring apparatus, DRX-500 (made by Bruker BioSpin Corporation) was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using $CFCl_3$ as an internal standard. In the explanation of nuclear magnetic resonance spectrum, s, d, t, q, quin, sex and m stand for a singlet, a doublet, a triplet, a quartet, a quintet, a sextet and a multiplet, respectively, and br means being broad.

HPLC Analysis

As a measuring apparatus, Prominence (LC-20 AD; SPD-20A) made by Shimadzu Corporation was used. As a column, YMC-Pack ODS-A (length: 150 mm, bore: 4.6 mm, particle diameter: 5 μm) made by YMC GmbH was used. As an eluate, acetonitrile and water were appropriately mixed and used. As a detector, a UV detector, an RI detector, a CORONA detector or the like was appropriately used. When the UV detector was used, a detection wavelength was adjusted to 254 nm. A sample was dissolved in acetonitrile and prepared to be a 0.1 weight % solution, and then 1 microliter of the solution was injected into a sample injector. As a recorder, C-R7 Aplus made by Shimadzu Corporation was used.

UV-Visible Spectrometry

As a measuring apparatus, PharmaSpec UV-1700 made by Shimadzu Corporation was used. A detection wavelength was adjusted in the range from 190 nm to 700 nm. A sample was dissolved in acetonitrile, and prepared to be a solution of 0.01 mmol per liter, and measurement was carried out by putting the solution in a quartz cell (optical path length 1 cm).

Sample for Measurement

Upon measuring phase structure and a transition temperature (clearing point, melting point, polymerization start temperature or the like), a liquid crystal compound itself was used as a sample. Upon measuring physical properties such as a maximum temperature of a nematic phase, viscosity, optical anisotropy and dielectric anisotropy, a mixture prepared by mixing the compound with a base liquid crystal was used as a sample.

Measuring Method

Physical properties were measured according to the methods described below. Most of the measuring methods are applied as described in the Standard of the Japan Electronics and Information Technology Industries Association (JEITA EIAJ ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a scanning calorimeter, Diamond DSC System, made by PerkinElmer, Inc., or a high-sensitivity differential scanning calorimeter, X-DSC7000, made by SII NanoTechnology Inc. was used. A sample was heated or cooled at a rate of 3° C. per minute, and a starting point of an endothermic peak or an exothermic peak associated with a phase change of the sample was calculated by extrapolation to determine the transition temperature. A melting point of a compound and a polymerization start temperature were also measured using the apparatus thereof. Temperature at which the compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to the liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point apparatus equipped with a polarizing microscope and was heated at a rate of 1° C. per minute. Temperature when part of the sample began to change from a nematic phase to an isotropic liquid was measured. A maximum temperature of the nematic phase may be occasionally abbreviated as "maximum temperature." When the sample was a mixture of a compound and the base liquid crystal, the maximum temperature was expressed in terms of symbol $T_{NI}$. When the sample was the mixture of the compound and component B, C, D or E, the maximum temperature was expressed in terms of symbol NI.

(4) Minimum Temperature of Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., Tc was expressed as $T_c \leq$ −20° C. A minimum temperature of the nematic phase may be occasionally abbreviated as "minimum temperature."

(5) Viscosity (Bulk Viscosity; $\eta$; 20° C. Measured at; mPa·s)

A cone-plate (E type) rotational viscometer made by Tokyo Keiki Inc. was used for measurement.

(6) Optical Anisotropy (Refractive Index Anisotropy; Measured at 25° C.; $\Delta n$)

Measurement was carried out by an Abbe refractometer having a polarizing plate mounted on an ocular, using light at a wavelength of 589 nanometers. A surface of a main prism was rubbed in one direction, and then a sample was added dropwise onto the main prism. The refractive index $n_{//}$ was measured when the direction of polarized light was parallel to the direction of rubbing. The refractive index $n_\perp$ was measured when the direction of polarized light was perpendicular to the direction of rubbing. A value of optical anisotropy was calculated from an equation: $\Delta n = n_{//} - n_\perp$.

(7) Specific Resistance ($\rho$; Measured at 25° C.; $\Omega$cm)

Into a vessel equipped with electrodes, 1.0 milliliter of sample was injected. A DC voltage (10 V) was applied to the vessel, and a DC current after 10 seconds was measured. A specific resistance was calculated from the following equation: (specific resistance)={(voltage)×(electric capacity of a vessel)}/{(direct current)×(dielectric constant of vacuum)}.

(8) Voltage Holding Ratio (VHR-1; Measured at 25° C.; %)

A TN device used for measurement had a polyimide alignment film and a distance (cell gap) between two glass substrates was 5 µm. A sample was put in the device, and then the device was sealed with a UV-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(9) Voltage Holding Ratio (VHR-2; Measured at 80° C.; %)

A voltage holding ratio was measured in procedures identical with the procedures described above except that the voltage holding ratio was measured at 80° C. in place of 25° C. The thus obtained results were expressed in terms of VHR-2.

Methods for measuring physical properties may be different between a sample having a positive dielectric anisotropy and a sample having a negative dielectric anisotropy. The measuring methods when the dielectric anisotropy is positive are described in sections (10) to (14).

(10) Viscosity (Rotational Viscosity; $\gamma 1$; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 µm. Voltage was applied stepwise to the device in the range of 16 V to 19.5 V at an increment of 0.5 V. After 0.2 second with no voltage application, voltage was applied repeatedly under conditions of only one rectangular wave (rectangular pulse; 0.2 second) and no application (2 seconds). A peak current and a peak time of a transient current generated by the applied voltage were measured. A value of rotational viscosity was obtained from the measured values according to calculating equation (8) on page 40 of the paper presented by M. Imai et al. A value of dielectric anisotropy required for the calculation was determined using the device by which the rotational viscosity was measured and by a method described below.

(11) Dielectric Anisotropy ($\Delta \varepsilon$; Measured at 25° C.)

A sample was put in a TN device in which a distance (cell gap) between two glass substrates was 9 µm and a twist angle was 80°. Sine waves (10 V, 1 kHz) were applied to the device, and after 2 sec, the dielectric constant $\varepsilon_{//}$ in the major axis direction of liquid crystal molecules was measured. Sine waves (0.5 V, 1 kHz) were applied to the device, and after 2 sec, the dielectric constant $\varepsilon_\perp$ in the minor axis direction of the liquid crystal molecules was measured. A value of dielectric anisotropy was calculated from an equation: $\Delta \varepsilon = \varepsilon_{//} - \varepsilon_\perp$.

(12) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 µm. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is expressed using a mean value of the thus determined $K_{11}$, $K_{22}$ and $K_{33}$.

(13) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/$\Delta n$ (µm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 90% transmittance.

(14) Response Time ($\tau$; Measured at 25° C.; ms)

An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 µm and a twist angle was 80°. Rectangular waves (60 Hz, 5 V, 0.5 seconds) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. Arise time (τr; millisecond) is a time taken to change 90% of transmissivity to 10%. A fall time (τf: millisecond) is a time taken to change 10% of transmissivity to 90%. Response time was expressed by a sum of the thus obtained rise time and fall time.

Example 1

Synthesis of Compound (1-3-12)

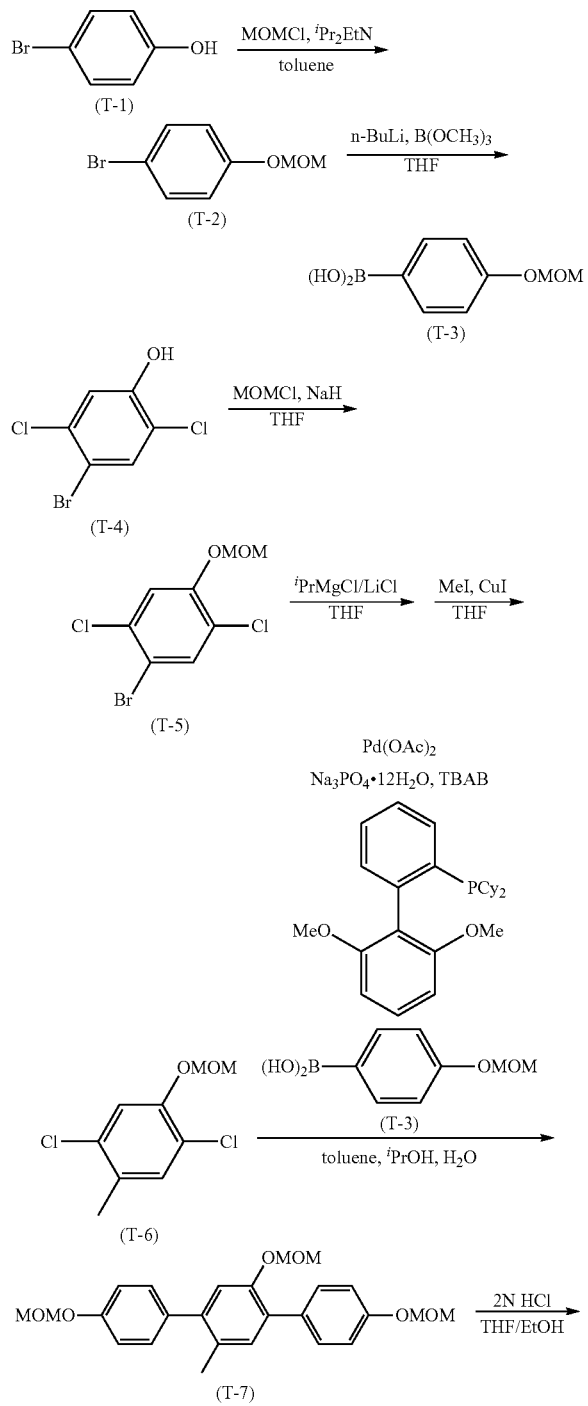

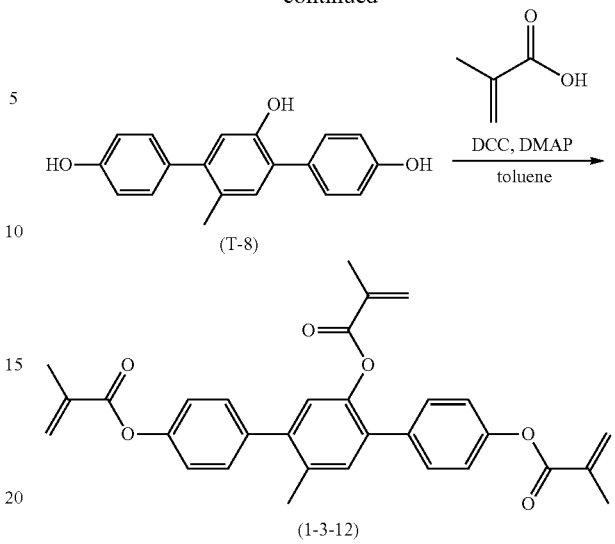

First Step:

A toluene (250 mL) solution of 4-bromophenol (T-1) (50.0 g, 289.01 mmol; Tokyo Chemical Industry Co., Ltd.) and diisopropyl ethylamine (56.03 g, 433.5 mmol) was ice-cooled, and chloromethyl methyl ether (34.9 g, 433.51 mmol) was added dropwise thereto. After the resulting mixture was stirred for 3 hours, the resulting reaction mixture was poured into a saturated aqueous solution of ammonium chloride (200 mL) and subjected to extraction with ethyl acetate. The resulting extracted solution was washed with water (300 mL) and saturated brine (200 mL), dried over anhydrous magnesium sulfate, and condensed under reduced pressure. The resulting residue was purified by column chromatography (eluent: toluene/heptane=2/1 (volume ratio)) to obtain compound (T-2) (57.6 g, 265.1 mol, 91.7%).

Second Step:

A THF (290 mL) solution of compound (T-2) (57.6 g, 265.1) obtained in the first step was cooled to −40° C., and n-BuLi (1.59 M, 200.3 mL, 318.4 mmol) was added dropwise thereto. After the resulting mixture was stirred at −40° C. for 2 hours, trimethoxy borate (35.85 g, 344.97 mmol) was added dropwise thereto. The resulting reaction mixture was stirred at room temperature for 8 hours, poured into a saturated aqueous solution of ammonium chloride (300 mL), and then subjected to extraction with ethyl acetate. The resulting extracted solution was washed with water (300 mL) and saturated brine (200 mL), dried over anhydrous magnesium sulfate, and condensed under reduced pressure to obtain compound (T-3) (32.7 g, 179.69 mol, 67.7%).

Third Step:

A THF (1,000 mL) solution of 4-bromo-2,5-dichlorophenol (T-4) (200.0 g, 826.80 mmol; Tokyo Chemical Industry Co., Ltd.) was ice-cooled, and 55% sodium hydride (43.3 g, 992.16 mmol) was added thereto by being divided into five, and the resulting mixture was stirred for 1 hour. Then, chloromethyl methyl ether (86.5 g, 1074.84 mmol) was added dropwise thereto. After the resulting mixture was stirred for 3 hours, the resulting reaction mixture was poured into a saturated aqueous solution of ammonium chloride (1,000 mL), and subjected to extraction with toluene. The resulting extracted solution was washed with water (200 mL) and saturated brine (200 mL), dried over anhydrous magnesium sulfate and condensed under reduced pressure.

The resulting residue was purified by column chromatography (eluent: toluene/heptane=2/1 (volume ratio)) to obtain compound (T-5) (235.8 g, 824.54 mol, 99.7%).

Fourth Step:

A tetrahydrofuran solution (1.3 M, 322.8 mL, 419.65 mmol, Aldrich) of isopropylmagnesium chloride-lithium chloride complex was cooled to 0° C., and a THF (500 mL) solution of compound (T-5) obtained in the third step (100.0 g, 349.71 mol) was added dropwise thereto. After the resulting mixture was stirred at 40° C. for 2 hours, copper iodide (3.3 g, 17.49 mmol) was added thereto, and then iodomethane (26.1 mL, 419.65 mmol) was added dropwise thereto. After the resulting mixture was stirred at room temperature for 8 hours, the resulting reaction mixture was poured into a saturated aqueous solution of ammonium chloride (300 mL) and subjected to extraction with ethyl acetate. The resulting extracted solution was washed with water (300 mL) and saturated brine (200 mL), dried over anhydrous magnesium sulfate and condensed under reduced pressure. The resulting residue was purified by column chromatography (eluent: toluene/heptane=2/1 (volume ratio)), and further recrystallized (methanol) to obtain compound (T-6) (64.7 g, 292.36 mol, 83.6%).

Fifth Step:

Compound (T-6) (30.0 g, 135.7 mmol) obtained in the fourth step, compound (T-3) (59.3 g, 325.67 mmol) obtained in the second step, palladium(II) acetate (0.152 g, 0.68 mmol), 2-dicyclohexylphosphino-2',6'-dimethoxybiphenyl (0.557 g, 1.36 mmol), sodium phosphate dodecahydrate (154.74 g, 407.09 mmol), tetrabutylammonium bromide (TBAB) (17.5 g, 54.28 mmol), toluene (200 mL), isopropanol (200 mL) and water (200 mL) were mixed, and the resulting mixture was refluxed under heating for 16 hours. After the resulting mixture was left to cool to room temperature, the resulting reaction mixture was subjected to filtration, and the resulting filtrate was washed with water (300 mL) and saturated brine (200 mL), dried over anhydrous magnesium sulfate and condensed under reduced pressure. The resulting residue was purified by column chromatography (eluent: toluene/ethyl acetate=9/1 (volume ratio)) to obtain compound (T-7) (57.0 g, 134.28 mmol, 98.9%).

Sixth Step:

To a THF:ethanol=1:1 mixed solution (300 mL) of compound (T-7) (57.0 g, 134.28 mmol) obtained in the fifth step, 2N hydrochloric acid (268.56 mL, 537.12 mmol) was added, and the resulting mixture was stirred at 70° C. for 3 hours. After the resulting mixture was cooled down to room temperature, the resulting reaction mixture was poured into water (500 mL) and subjected to extraction with ethyl acetate (500 mL). The resulting extracted solution was washed 5 times with water (100 mL), dried over anhydrous magnesium sulfate and condensed under reduced pressure to obtain compound (T-8) (31.8 g, 108.78 mmol, 81.0%).

Seventh Step:

Compound (T-8) (31.8 g, 108.78 mmol) obtained in the sixth step, methacrylic acid (32.8 g, 380.74 mmol) and N,N-dimethyl-4-aminopyridine (DMAP; 13.29 g, 108.78 mmol) were dissolved into toluene (500 mL), and ice-cooled. Dicyclohexylcarbodiimide (DCC; 78.55 g, 380.74 mmol) was added little by little while keeping solid, and then the resulting mixture was stirred at room temperature for 8 hours. The resulting reaction mixture was subjected to filtration through Celite, and the resulting filtrate was purified by column chromatography (eluent: toluene/ethyl acetate=19/1 (volume ratio)), and further recrystallized (heptane/ethyl acetate=1/1 (volume ratio)) to obtain compound (1-3-12) (28.2 g, 56.74 mmol, 52.2%).

Melting point: 120.7° C.

$^1$H-NMR (CDCl$_3$; δ ppm): 7.48 (d, 2H), 7.41 (d, 2H), 7.32 (s, 1H), 7.19 (d, 2H), 7.16 (d, 2H), 7.08 (s, 1H), 6.38 (s, 1H), 6.36 (s, 1H), 6.17 (s, 1H), 5.77 (s, 2H), 5.63 (s, 1H), 2.33 (s, 3H), 2.09 (s, 3H), 2.08 (s, 3H), 1.92 (s, 3H).

Example 2

Synthesis of Compound (1-3-1)

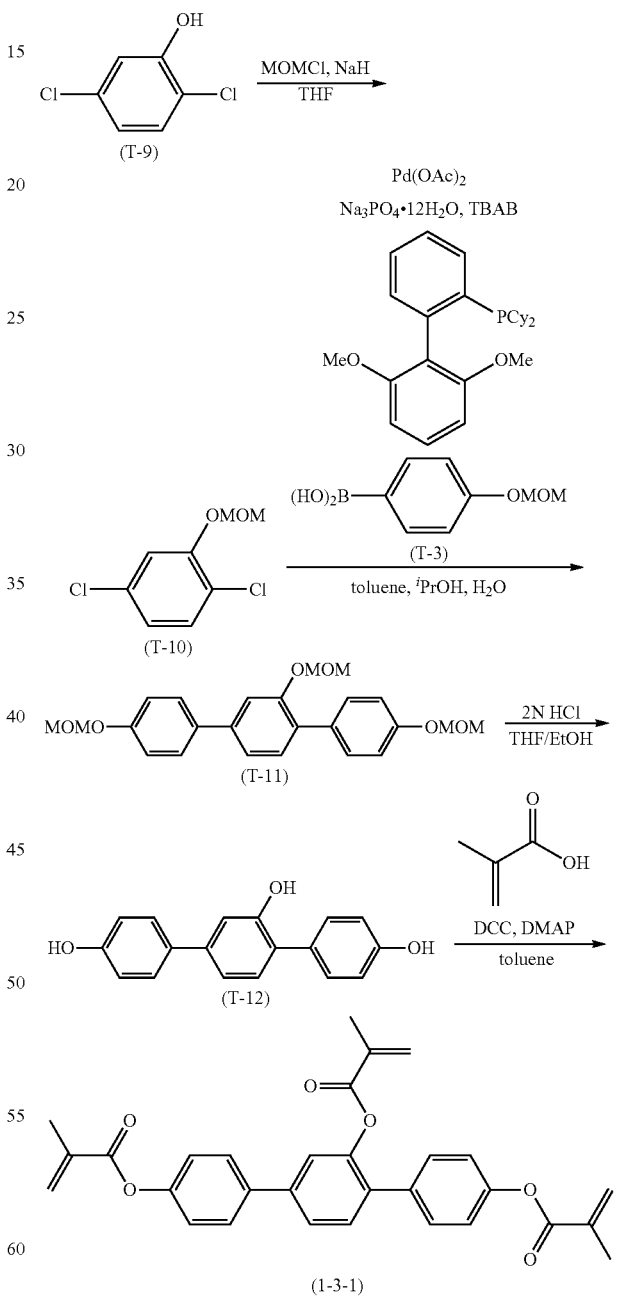

First Step:

A THF (500 mL) solution of 2,5-dichlorophenol (T-9) (50.0 g, 306.75 mmol; Tokyo Chemical Industry Co., Ltd.) was ice-cooled, and 55% sodium hydride (16.06 g, 368.10 mmol) was added thereto by being divided into three, and the resulting mixture was stirred for 1 hour. Then, chloromethyl methyl ether (29.6 g, 368.10 mmol) was added dropwise thereto. After the resulting mixture was stirred for 3 hours, the resulting reaction mixture was poured into a saturated aqueous solution of ammonium chloride (500 mL), and subjected to extraction with toluene. The resulting extracted solution was washed with water (200 mL) and saturated brine (200 mL), dried over anhydrous magnesium sulfate, and condensed under reduced pressure. The resulting residue was purified by column chromatography (eluent: toluene/heptane=2/1 (volume ratio)) to obtain compound (T-10) (63.0 g, 303.96 mol, 99.1%).

Second Step:

Compound (T-10) (23.0 g, 111.08 mmol) obtained in the first step, compound (T-3) (44.3 g, 233.27 mmol) obtained in the second step in Example 1, palladium(II) acetate (0.249 g, 1.11 mmol), 2-dicyclohexylphosphino-2',6'-dimethoxybiphenyl (0.912 g, 2.22 mmol), sodium phosphate dodecahydrate (126.68 g, 333.25 mmol), tetrabutylammonium bromide (TBAB) (17.9 g, 55.54 mmol), toluene (200 mL), isopropanol (200 mL) and water (200 mL) were mixed, and the resulting mixture was refluxed under heating for 16 hours. After the resulting mixture was cooled down to room temperature, the resulting reaction mixture was subjected to filtration, and the resulting filtrate was washed with water (300 mL) and saturated brine (200 mL), dried over anhydrous magnesium sulfate and condensed under reduced pressure. The resulting residue was purified by column chromatography (eluent: toluene/ethyl acetate=9/1 (volume ratio)) to obtain compound (T-11) (35.3 g, 85.83 mmol, 77.3%).

Third Step:

To a THF:ethanol=1:1 mixed solution (300 mL) of compound (T-11) (35.3 g, 134.28 mmol) obtained in the second step, 2N hydrochloric acid (268.56 mL, 537.12 mmol) was added, and the resulting mixture was stirred at 70° C. for 3 hours. After the resulting mixture was cooled down to room temperature, the resulting mixture was poured into water (500 mL) and subjected to extraction with ethyl acetate (500 mL). The resulting extracted solution was washed 5 times with water (100 mL), dried over anhydrous magnesium sulfate, and condensed under reduced pressure to obtain compound (T-12) (23.9 g, 85.88 mmol, 99.9%).

Fourth Step:

Compound (T-12) (23.9 g, 85.88 mmol) obtained in the third step, methacrylic acid (29.57 g, 343.51 mmol) and N,N-dimethyl-4-aminopyridine (DMAP; 10.49 g, 85.88 mmol) were dissolved into toluene (500 mL), and ice-cooled. After dicyclohexylcarbodiimide (DCC; 70.88 g, 343.51 mmol) was added little by little while keeping solid, the resulting mixture was stirred at room temperature for 8 hours. The resulting reaction mixture was subjected to filtration through Celite, and the resulting filtrate was purified by column chromatography (eluent: toluene/ethyl acetate=19/1 (volume ratio)), and further recrystallized (heptane/ethyl acetate=1/1 (volume ratio)) to obtain compound (1-3-1) (22.7 g, 47.00 mmol, 54.7%).

Melting point: 114.4° C.

$^{1}$H-NMR (CDCl$_{3}$; δ ppm): 7.65 (d, 2H), 7.60 to 7.45 (m, 4H), 7.40 (s, 1H), 7.21 (d, 2H), 7.16 (d, 2H), 6.38 (s, 1H), 6.37 (s, 1H), 6.20 (s, 1H), 5.78 (s, 2H), 5.66 (s, 1H), 2.08 (s, 6H), 1.94 (s, 3H).

Example 3

Synthesis of Compound (1-3-53)

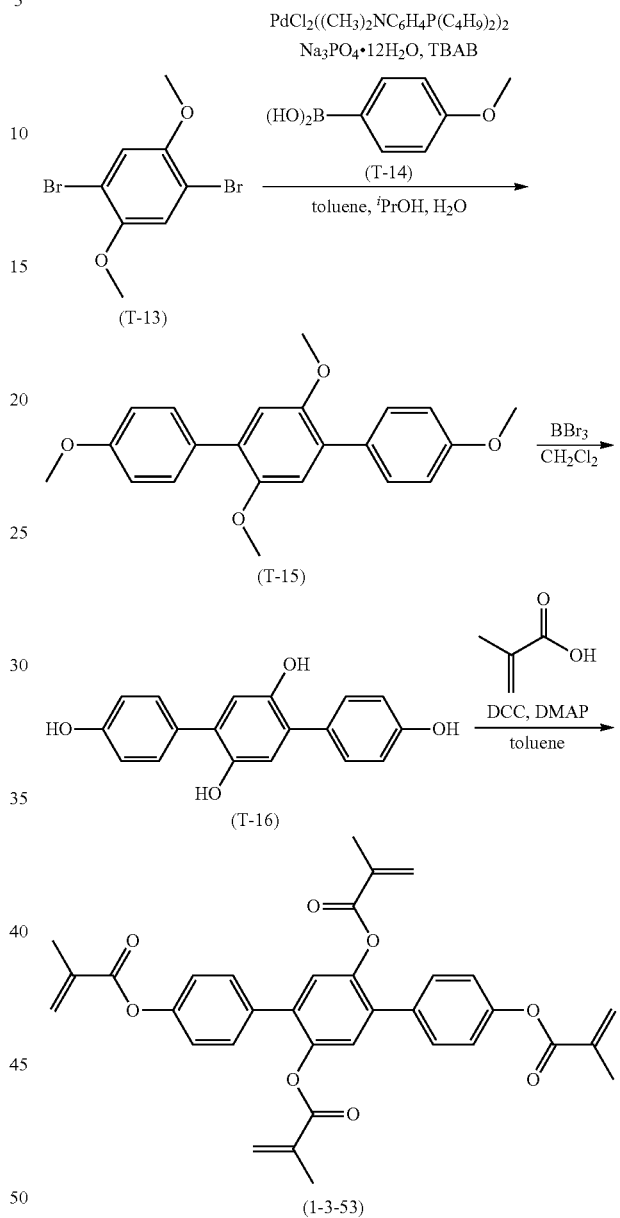

First Step:

Then, 1,4-dibromo-2,5-dimethoxybenzene (T-13) (25.0 g, 84.47 mmol, Tokyo Chemical Industry Co., Ltd.), 4-methoxyphenylboronic acid (T-14) (28.2 g, 185.84 mmol, Tokyo Chemical Industry Co., Ltd.), bis(di-tert-butyl-(4-dimethylaminophenyl)phosphine dichloropalladium(II) (0.30 g, 0.42 mmol), trisodium monophosphate dodecahydrate (96.33 g, 253.42 mmol), tetrabutylammonium bromide (TBAB) (5.45 g, 16.89 mmol), toluene (100 mL), isopropanol (100 mL) and water (100 mL) were mixed, and refluxed under heating for 5 hours. After the resulting mixture was cooled down to room temperature, the reaction mixture was subjected to filtration, and the resulting filtrate was washed with water (200 mL) and saturated brine (100 mL), dried over anhydrous magnesium sulfate and condensed under reduced pressure. The resulting residue was purified by column chromatography (eluent: toluene/ethyl acetate=9/1 (volume ratio)) to obtain compound (T-15) (27.9 g, 84.47 mmol, 94.3%).

Second Step:

Compound (T-15) (27.9 g, 5.80 mmol) obtained in the first step was dissolved into dichloromethane (200 mL) and cooled down to −60° C. After boron tribromide (99.7 g, 398.11 mmol) was added dropwise thereto, and the resulting mixture was stirred at −60° C. for 1 hour, and then heated to room temperature and further stirred for 8 hours. The resulting reaction mixture was poured into water (500 mL) and subjected to extraction with ethyl acetate (200 mL). The resulting extracted solution was washed with water (3 times with 100 mL) and saturated brine (100 mL), dried over anhydrous magnesium sulfate and condensed under reduced pressure to obtain compound (T-16) (23.0 g, 78.15 mmol, 98.1%).

Third Step:

Compound (T-16) (7.8 g, 26.50 mmol) obtained in the second step, methacrylic acid (9.13 g, 106.01 mmol) and N,N-dimethyl-4-aminopyridine (DMAP; 1.30 g, 10.60 mmol) were dissolved into toluene (100 mL) and ice-cooled. After dicyclohexylcarbodiimide (DCC; 24.06 g, 114.62 mmol) was added little by little while keeping solid, the resulting mixture was stirred at room temperature for 8 hours. The reaction mixture was subjected to filtration through Celite, and the resulting filtrate was purified by column chromatography (eluent: toluene/ethyl acetate=19/1 (volume ratio)) and further recrystallized (heptane/ethyl acetate=1/1 (volume ratio)) to obtain compound (1-3-53) (0.81 g, 1.42 mmol, 5.34%).

Melting point: 212.7° C.

$^{1}$H-NMR (CDCl$_3$; δ ppm): 7.49 (d, 4H), 7.26 (d, 4H), 7.16 (d, 2H), 6.36 (s, 2H), 6.19 (s, 2H), 5.77 (s, 2H), 5.66 (s, 2H), 2.07 (s, 6H), 1.93 (s, 6H).

Example 4

Synthesis of Compound (1-3-56)

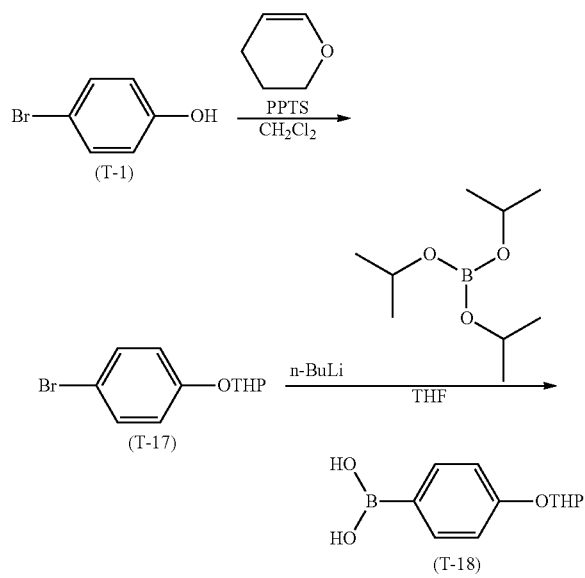

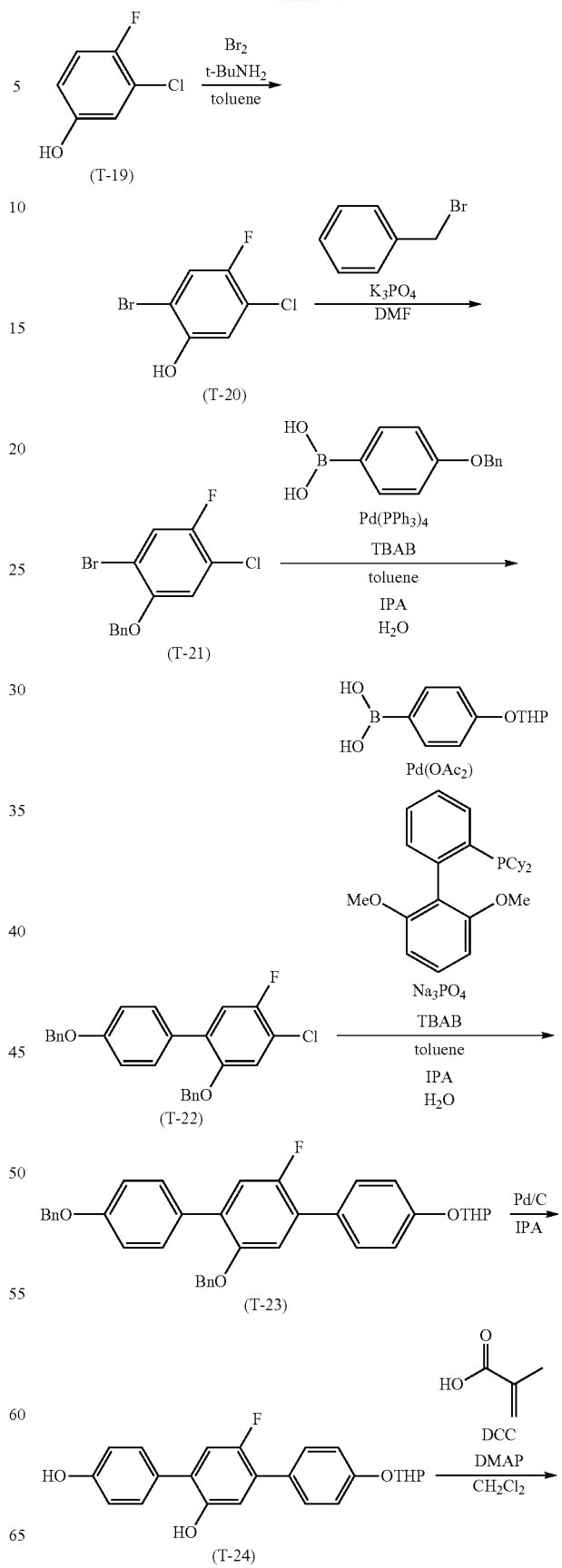

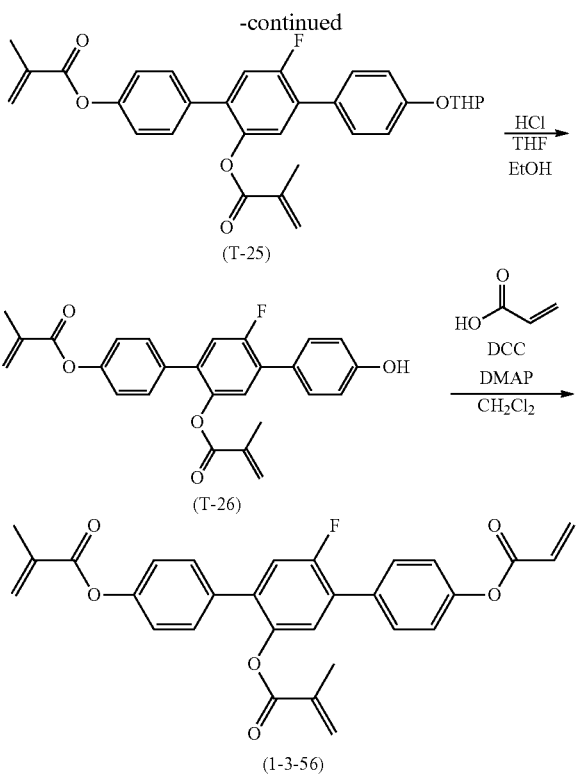

First Step:

To a dichloromethane (2,500 mL) solution of 4-bromophenol (T-1) (507.25 g, 2,932.0 mmol; Tokyo Chemical Industry Co., Ltd.) and pyridinium p-toluenesulfonate (50.72 g, 201.85 mmol), 3,4-dihydro-2H-pyran (69.71 g, 5864.0 mmol) was added dropwise. After the resulting mixture was stirred for 4 hours, the resulting reaction mixture was poured into a saturated aqueous solution of sodium hydrogencarbonate (2,000 mL) and subjected to extraction with ethyl acetate. The resulting extracted solution was washed with water (3,000 mL) and saturated brine (2,000 mL), dried over anhydrous magnesium sulfate and condensed under reduced pressure. The resulting residue was purified by column chromatography (eluent: toluene/heptane=2/1 (volume ratio)) to obtain compound (T-17) (723.7 g, 2,815.0 mmol, 96.1%).

Second Step:

A THF (3,600 mL) solution of compound (T-17) (723.7 g, 2,815.0 mmol) obtained in the first step was cooled to −40° C. and n-BuLi (1.59 M, 2,290 mL, 3,659.0 mmol) was added dropwise thereto. After the resulting mixture was stirred at −40° C. for 2 hours, triisopropoxy borane (688.16 g, 3,659.0 mmol) was added dropwise thereto. After the resulting mixture was stirred at room temperature for 8 hours, the resulting reaction mixture was poured into a saturated aqueous solution of ammonium chloride (4,000 mL) and subjected to extraction with ethyl acetate. The resulting extracted solution was washed with water (3,000 mL) and saturated brine (2,000 mL), dried over anhydrous magnesium sulfate and condensed under reduced pressure. The resulting residue was recrystallized (heptane) to obtain compound (T-18) (203.12 g, 914.77 mmol, 32.5%).

Third Step:

A toluene (360 mL) solution of t-butylamine (179.59 g, 2,455.4 mmol) was cooled to −30° C. and bromine (143.88 g, 900.31 mmol) was added dropwise thereto. After the resulting mixture was cooled to −70° C., 3-chloro-4-fluorophenol (T-19) (120 g, 818.83 mmol) was added dropwise thereto. After the resulting mixture was stirred at room temperature for 10 hours, the resulting reaction mixture was poured into 1 N hydrochloric acid (2,000 mL) and washed with water (2,000 mL). The resulting organic phase was dried over anhydrous magnesium sulfate and condensed under reduced pressure. The resulting residue was purified by column chromatography (eluent: heptane/ethyl acetate=5/1 (volume ratio)) to obtain compound (T-20) (105.17 g, 466.52 mmol, 57.0%).

Fourth Step:

Compound (T-20) (105.17 g, 466.52 mmol) obtained in the third step, potassium phosphate (159.59 g, 933.05 mmol) and N,N-dimethylformamide (1,000 mL) were mixed, benzyl bromide (108.92 g, 513.18 mmol) was added dropwise thereto, and then the resulting mixture was stirred at 70° C. for 4 hours. The resulting reaction mixture was subjected to filtration through Celite, and the resulting filtrate was poured into water (1,000 mL), and subjected to extraction with ethyl acetate. The resulting extracted solution was washed 5 times with water (200 mL), dried over anhydrous magnesium sulfate, and condensed under reduced pressure. The resulting residue was purified by column chromatography (eluent: toluene/heptane=1/1 (volume ratio)), and further recrystallized (ethanol) to obtain compound (T-21) (138.09 g, 437.60 mmol, 93.8%).

Fifth Step:

Compound (T-21) (138.09 g, 437.60 mmol) obtained in the fourth step, benzyloxyphenylboronic acid (109.77 g, 481.36 mmol), tetrakis(triphenylphosphine)palladium(0) (1.01 g, 0.88 mmol), potassium carbonate (120.95 g, 875.20 mmol), tetrabutylammonium bromide (TBAB; 35.27 g, 109.40 mmol), toluene (700 mL), isopropanol (700 mL) and water (300 mL) were mixed, and the resulting mixture was refluxed under heating for 16 hours. After the resulting mixture was cooled down to room temperature, the resulting reaction mixture was subjected to filtration, and the resulting filtrate was washed with water (900 mL) and saturated brine (600 mL), dried over anhydrous magnesium sulfate and condensed under reduced pressure. The resulting residue was purified by column chromatography (eluent: toluene/ethyl acetate=9/1 (volume ratio)) to obtain compound (T-22) (168.09 g, 401.28 mmol, 91.7%).

Sixth Step:

Compound (T-22) (168.09 g, 401.28 mmol) obtained in the fifth step, compound (T-18) (98.01 g, 441.41 mmol) obtained in the second step, palladium(II) acetate (0.45 g, 2.01 mmol), 2-dicyclohexylphosphino-2',6'-dimethoxybiphenyl (1.65 g, 4.01 mmol), sodium phosphate dodecahydrate (228.8 g, 601.92 mmol), tetrabutylammonium bromide (TBAB; 32.34 g, 100.32 mmol), toluene (840 mL), isopropanol (840 mL) and water (840 mL) were mixed, and the resulting mixture was refluxed under heating for 16 hours. After the resulting mixture was cooled down to room temperature, the resulting reaction mixture was subjected to filtration, and the resulting filtrate was washed with water (900 mL) and saturated brine (600 mL), dried over anhydrous magnesium sulfate and condensed under reduced pressure. The resulting residue was purified by column chromatography (eluent: toluene) to obtain compound (T-23) (218.91 g, 390.44 mmol, 97.3%).

Seventh Step:

To an isopropanol (2,200 mL) solution of compound (T-23) (218.91 g, 390.44 mmol) obtained in the sixth step, palladium on carbon (10.95 g) was added, hydrogen was added thereto, and the resulting mixture was stirred at room temperature for 16 hours. The resulting reaction mixture was subjected to filtration, and the resulting filtrate was purified by column chromatography (eluent: toluene/ethyl acetate=2/1 (volume ratio)) to obtain compound (T-24) (77.53 g, 203.81 mmol, 52.2%).

Eighth Step:

Compound (T-24) (77.53 g, 203.81 mmol) obtained in the seventh step, methacrylic acid (26.32 g, 305.72 mmol) and N,N-dimethyl-4-aminopyridine (DMAP; 6.22 g, 50.95 mmol) were dissolved into dichloromethane (780 mL), and ice-cooled. After dicyclohexylcarbodiimide (DCC; 63.08 g, 305.72 mmol) was added little by little thereto while keeping solid, the resulting mixture was stirred at room temperature for 8 hours. The resulting reaction mixture was subjected to filtration through Celite, and the resulting filtrate was purified by column chromatography (eluent: toluene/ethyl acetate=19/1 (volume ratio)), and further recrystallized (heptane/ethyl acetate=1/1 (volume ratio)) to obtain compound (T-25) (32.32 g, 62.57 mmol, 30.7%).

Ninth Step:

To a THF:ethanol=1:1 mixed solution (300 mL) of compound (T-25) (32.32 g, 62.57 mmol) obtained in the eighth step, 2 N hydrochloric acid (62.57 mL, 125.14 mmol) was added, and the resulting mixture was stirred at 70° C. for 3 hours. After the resulting mixture was cooled down to room temperature, the resulting reaction mixture was poured into water (500 mL) and subjected to extraction with ethyl acetate (500 mL). The resulting extracted solution was washed 5 times with water (100 mL), dried over anhydrous magnesium sulfate and condensed under reduced pressure to obtain compound (T-26) (26.95 g, 62.32 mmol, 99.6%).

Tenth Step:

Compound (T-26) (26.95 g, 62.32 mmol) obtained in the ninth step, acrylic acid (6.74 g, 93.48 mmol) and N,N-dimethyl-4-aminopyridine (DMAP; 1.90 g, 15.58 mmol) were dissolved into dichloromethane (300 mL), and ice-cooled. After dicyclohexylcarbodiimide (DCC; 19.29 g, 93.48 mmol) was added little by little thereto while keeping solid, the resulting mixture was stirred at room temperature for 8 hours. The resulting reaction mixture was subjected to filtration through Celite, and the resulting filtrate was purified by column chromatography (eluent: toluene/ethyl acetate=19/1 (volume ratio)), and further recrystallized (heptane/ethyl acetate=1/1 (volume ratio)) to obtain compound (1-3-56) (29.5 g, 60.64 mmol, 97.3%).

Melting point: 150.6° C.

$^1$H-NMR (CDCl$_3$; δ ppm): 7.63 (dd, 2H), 7.48 (m, 2H), 7.27 (m, 2H), 7.24 (m, 2H), 7.18 (m, 2H), 6.63 (dd, 1H), 6.38 (s, 1H), 6.20 (s, 1H), 6.05 (dd, 1H), 5.78 (s, 2H), 5.67 (s, 1H), 2.08 (s, 3H), 1.93 (s, 3H).

Example 5

Various compounds were prepared using corresponding starting materials according to techniques described in Examples 1 to 4, and confirmed to be objective compounds.

Compound (1-3-21)

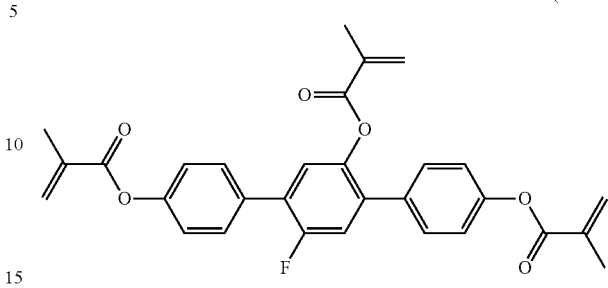

(1-3-21)

Melting point: 124.23° C.

$^1$H-NMR (CDCl$_3$; δ ppm): 7.63 (dd, 2H), 7.47 (d, 2H), 7.27 (d, 1H), 7.24 (d, 1H), 7.22 (d, 2H), 7.18 (d, 2H), 6.37 (s, 2H), 6.20 (s, 1H), 5.79 (dd, 2H), 5.67 (dd, 2H), 2.09 (s, 3H), 2.08 (s, 3H), 1.93 (s, 3H).

Compound (1-3-16)

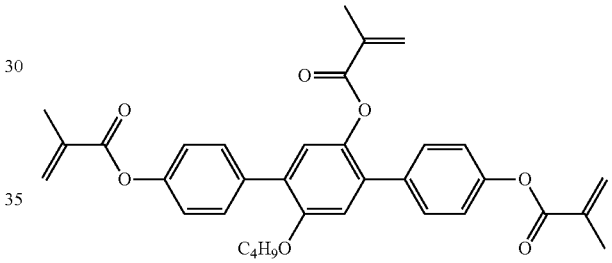

(1-3-16)

Melting point: 115.50° C.

$^1$H-NMR (CDCl$_3$; δ ppm): 7.48 (d, 2H), 7.41 (d, 2H), 7.32 (s, 1H), 7.19 (d, 2H), 7.16 (d, 2H), 7.08 (s, 1H), 6.38 (s, 1H), 6.36 (s, 1H), 6.17 (s, 1H), 5.77 (s, 2H), 5.63 (s, 1H), 4.06 (t, 3H), 2.09 (s, 3H), 2.08 (s, 3H), 1.92 (s, 3H), 1.76 (m, 2H), 1.45 (m, 2H), 0.90 (t, 3H).)

Compound (1-3-2)

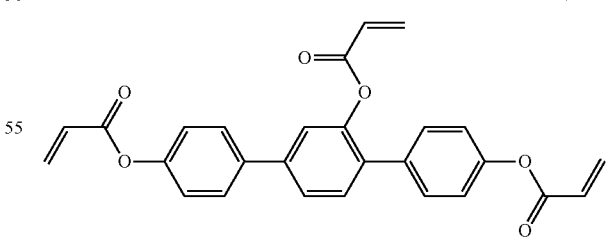

(1-3-2)

Melting point: 116.20° C.

$^1$H-NMR (CDCl$_3$; δ ppm): 7.65 (d, 2H), 7.60 (d, 1H), 7.47 (t, 2H), 7.24 (d, 2H), 7.22 (d, 2H), 6.71 (d, 1H), 6.68 (d, 1H), 6.56 (s, 1H), 6.52 (s, 1H), 6.40 (m, 2H), 6.28 (s, 1H), 6.23 (s, 1H), 6.11 (d, 1H), 6.09 (d, 1H), 6.00 (d, 1H).

Compound (1-3-23)

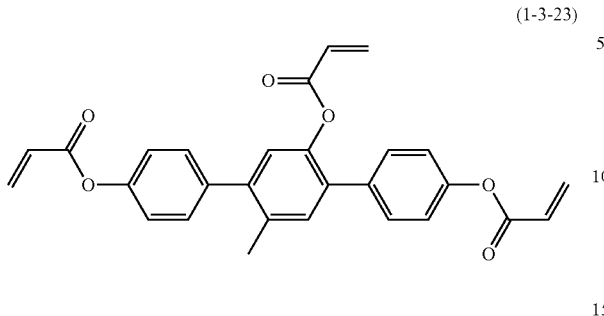

Melting point: 92.10° C.

¹H-NMR (CDCl₃; δ ppm): 7.49 (d, 2H), 7.41 (d, 2H), 7.33 (s, 1H), 7.21 (d, 2H), 7.19 (d, 2H), 7.08 (s, 1H), 6.68 (d, 1H), 6.56 (s, 1H), 6.52 (s, 1H), 6.40 (m, 2H), 6.28 (s, 1H), 6.23 (s, 1H), 6.11 (d, 1H), 6.09 (d, 1H), 6.00 (d, 1H), 2.46 (s, 3H).

Compound (1-3-40)

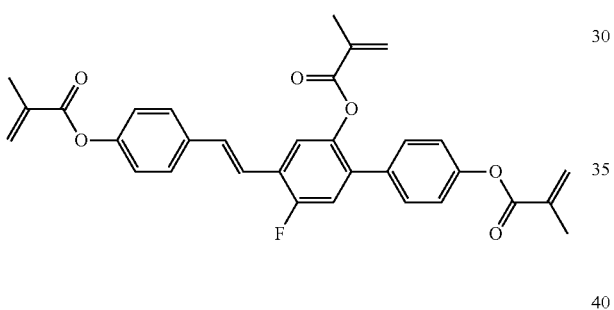

Melting point: 134.96° C.

¹H-NMR (CDCl₃; δ ppm): 7.51 (d, 2H), 7.45 (d, 2H), 7.42 (d, 1H), 7.21 to 7.13 (m, 8H), 6.37 (s, 2H), 6.21 (s, 1H), 5.77 (m, 2H), 5.68 (m, 1H), 2.08 (s, 6H), 1.94 (s, 3H).

Compound (1-2-1)

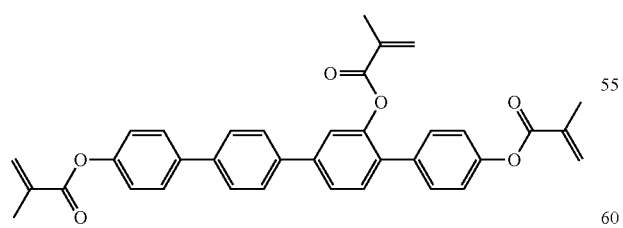

Melting point: 162.64° C.

¹H-NMR (CDCl₃; δ ppm): 7.71 (d, 2H), 7.66 (m, 4H), 7.60 (d, 1H), 7.51 (d, 2H), 7.48 (d, 2H), 7.22 (d, 2H), 7.17 (d, 2H), 6.38 (d, 2H), 6.22 (s, 1H), 5.78 (d, 2H), 5.67 (s, 1H), 2.09 (s, 3H), 2.08 (s, 3H), 1.95 (s, 3H).

Compound (1-3-13)

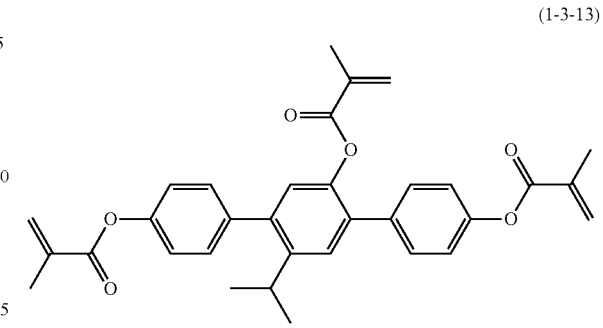

Melting point: 115.29° C.

¹H-NMR (CDCl₃; δ ppm): 7.49 (d, 2H), 7.40 (s, 1H), 7.37 (d, 2H), 7.18 (d, 2H), 7.17 (d, 2H), 7.02 (s, 1H), 6.38 (d, 2H), 6.16 (s, 1H), 5.78 (s, 2H), 5.62 (s, 1H), 3.11 (quin, 1H), 2.08 (d, 6H), 1.92 (s, 3H), 1.19 (d, 6H).

Compound (1-3-17)

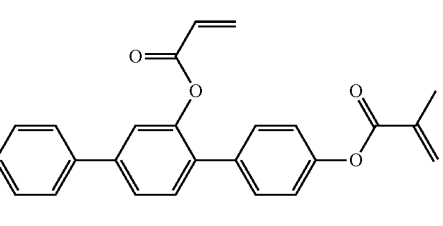

Melting point: 143.92° C.

¹H-NMR (CDCl₃; δ ppm): 7.64 (d, 2H), 7.55 (m, 1H), 7.48 (m, 3H), 7.40 (d, 1H), 7.22 (d, 2H), 7.17 (d, 2H), 6.49 (m, 1H), 6.37 (d, 2H), 6.20 (dd, 1H), 5.94 (dd, 1H), 5.78 (td, 2H), 2.09 (d, 6H).

Compound (1-3-28)

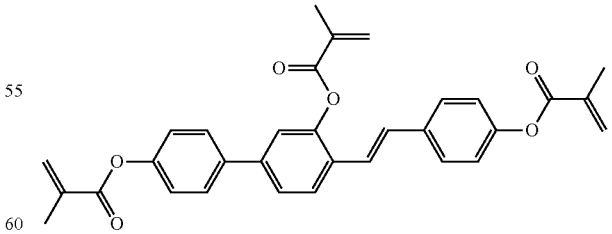

Melting point: 154.36° C.

¹H-NMR (CDCl₃; δ ppm): 7.52 (d, 2H), 7.53 (d, 1H), 7.44 (d, 2H), 7.40 (d, 2H), 7.23 to 7.11 (m, 7H), 6.37 (s, 2H), 6.21 (s, 1H), 5.77 (m, 2H), 5.68 (m, 1H), 2.08 (s, 6H), 1.94 (s, 3H).

Compound (1-3-34)

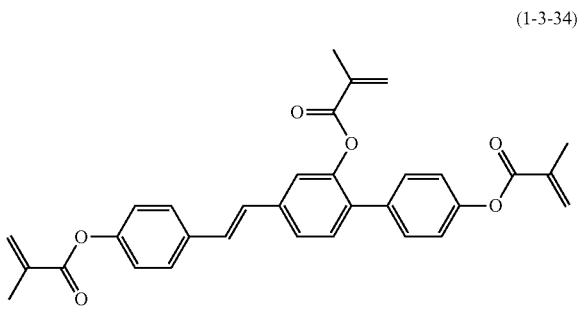 [SMILES: C=C(C)C(=O)Oc1ccc(/C=C/c2ccc(-c3ccc(OC(=O)C(=C)C)cc3)c(OC(=O)C(=C)C)c2)cc1]

Melting point: 153.47° C.

¹H-NMR (CDCl₃; δ ppm): 7.51 (d, 2H), 7.45 (d, 2H), 7.42 (d, 2H), 7.21 to 7.13 (m, 8H), 6.37 (s, 2H), 6.21 (s, 1H), 5.77 (m, 2H), 5.68 (m, 1H), 2.08 (s, 6H), 1.94 (s, 3H).

Compound (1-3-50)

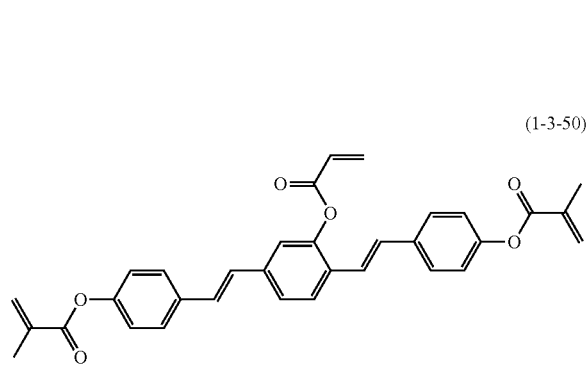 [SMILES: C=CC(=O)Oc1cc(/C=C/c2ccc(OC(=O)C(=C)C)cc2)ccc1/C=C/c1ccc(OC(=O)C(=C)C)cc1]

Melting point: 185.86° C.

¹H-NMR (CDCl₃; δ ppm): 7.68 (d, 2H), 7.52 (d, 2H), 7.48 (d, 2H), 7.39 (dd, 1H), 7.28 (d, 1H), 7.16 to 7.01 (m, 7H), 6.71 (m, 1H), 6.43 (m, 1H), 6.36 (s, 2H), 6.11 (m, 1H), 5.77 (t, 2H), 2.07 (m, 6H).

Compound (1-3-51)

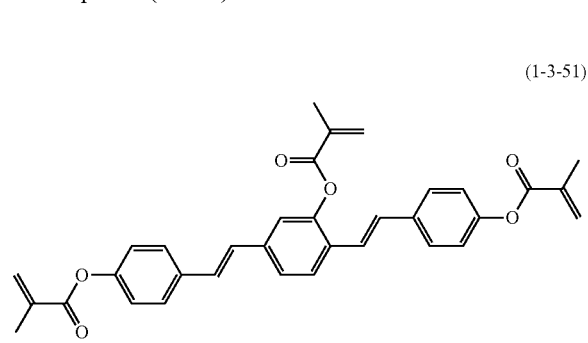

Melting point: 179.69° C.

¹H-NMR (CDCl₃; δ ppm): 7.68 (d, 2H), 7.52 (d, 2H), 7.48 (d, 2H), 7.39 (dd, 1H), 7.28 (d, 1H), 7.16 to 7.01 (m, 7H), 6.47 (s, 1H), 6.36 (s, 1H), 5.85 (t, 1H), 5.77 (t, 2H), 2.13 (m, 3H), 2.07 (m, 6H).

Compound (1-3-52)

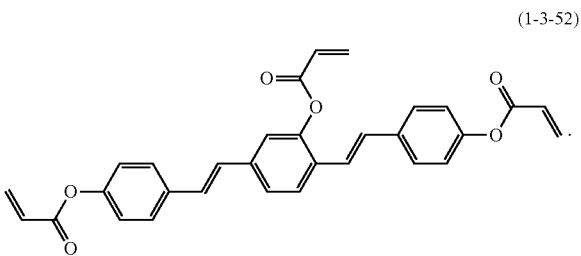 [SMILES: C=CC(=O)Oc1ccc(/C=C/c2ccc(/C=C/c3ccc(OC(=O)C=C)cc3)c(OC(=O)C=C)c2)cc1]

Melting point: 171.97° C.

¹H-NMR (CDCl₃; δ ppm): 7.69 (d, 1H), 7.52 (d, 2H), 7.49 (d, 2H), 7.40 (dd, 1H), 7.28 (d, 1H), 7.16 to 7.01 (m, 7H), 6.71 (dd, 1H), 6.62 (td, 1H), 6.43 (dd, 1H), 6.35 (dd, 1H), 6.31 (dd, 1H), 6.11 (dd, 1H), 6.02 (dd, 2H).

Compound (1-3-58)

Melting point: 114.44° C.

¹H-NMR (CDCl₃; δ ppm): 7.63 (dd, 2H), 7.47 (d, 1H), 7.27 (d, 1H), 7.22 (d, 2H), 7.18 (d, 2H), 6.37 (s, 2H), 6.20 (s, 1H), 5.79 (dd, 2H), 5.67 (dd, 2H), 2.09 (s, 3H), 2.08 (s, 3H), 1.93 (s, 3H).

Compound (1-3-64)

Melting point: 120.96° C.

¹H-NMR (CDCl₃; δ ppm): 7.63 (dd, 2H), 7.47 (d, 2H), 7.25 (m, 4H), 7.19 (d, 2H), 6.66 (dd, 1H), 6.62 (dd, 1H), 6.35 (m, 2H), 6.19 (s, 1H), 6.04 (m, 2H), 5.66 (t, 1H), 1.92 (s, 3H).

Compound (1-3-65)

Compound (1-3-154)

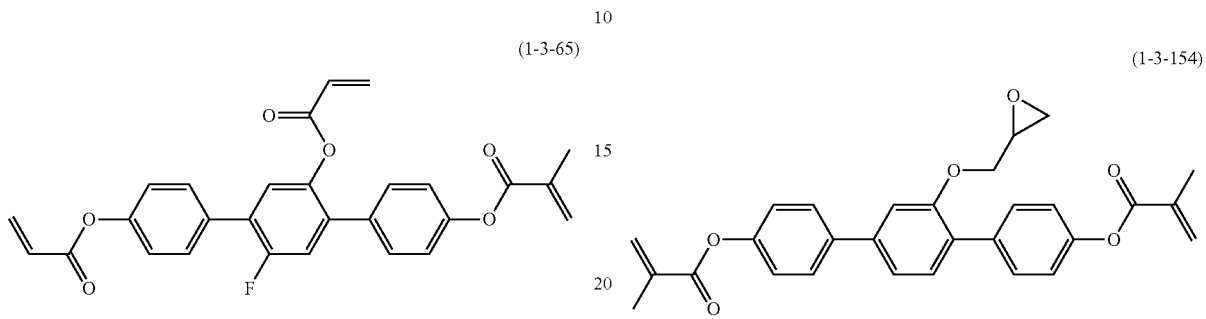

Melting point: 162.97° C.

$^1$H-NMR (CDCl$_3$; δ ppm): 7.62 (d, 2H), 7.47 (d, 2H), 7.25 (m, 4H), 7.18 (d, 2H), 6.64 (dd, 1H), 6.48 (dd, 1H), 6.39 to 6.32 (m, 2H), 6.18 (dd, 1H), 6.04 (dd, 1H), 5.94 (dd, 1H), 5.78 (t, 1H), 2.08 (s, 3H).

Compound (1-3-66)

Melting point: 130.13° C.

$^1$H-NMR (CDCl$_3$; δ ppm): 7.63 (t, 4H), 7.41 (d, 1H), 7.30 to 7.17 (m, 7H), 6.38 (s, 2H), 5.78 (d, 2H), 4.30 (dd, 1H), 4.05 (dd, 1H), 3.30 (s, 1H), 2.84 (t, 1H), 2.71 (dd, 1H), 2.09 (s, 6H).

Compound (1-3-155)

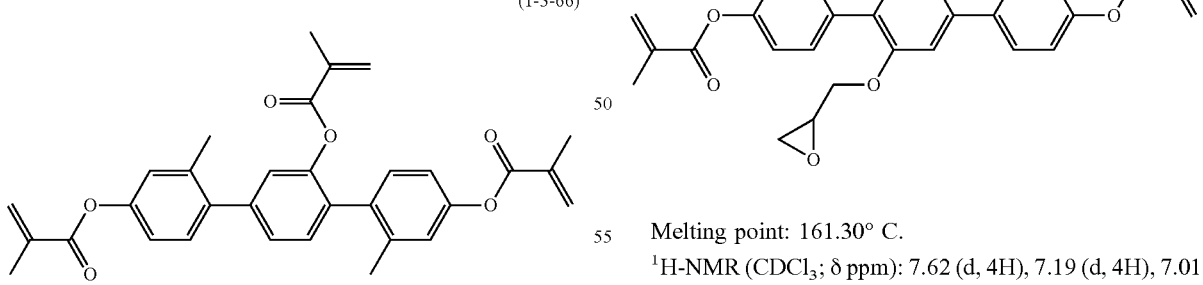

Melting point: 161.30° C.

$^1$H-NMR (CDCl$_3$; δ ppm): 7.62 (d, 4H), 7.19 (d, 4H), 7.01 (s, 2H), 6.38 (s, 2H), 5.78 (s, 2H), 4.30 (dd, 2H), 4.05 (dd, 2H), 3.30 (s, 2H), 2.84 (t, 2H), 2.71 (dd, 2H), 2.09 (s, 6H).

Example 6

Compounds (1-2-1) to (1-2-20) and compounds (1-3-1) to (1-3-182) shown below can be synthesized with referring to experimental operations described in Examples 1 to 5 and "2. Synthesis method."

Melting point: 93.43° C.

$^1$H-NMR (CDCl$_3$; δ ppm): 7.32 (t, 2H), 7.23 (t, 2H), 7.06 (s, 1H), 7.02 (m, 2H), 6.97 (d, 1H), 6.37 (d, 2H), 5.99 (s, 1H), 5.61 (d, 2H), 5.53 (s, 1H), 2.49 (s, 3H), 2.36 (s, 3H), 2.08 (d, 6H), 1.82 (s, 3H).

(1-2-1)
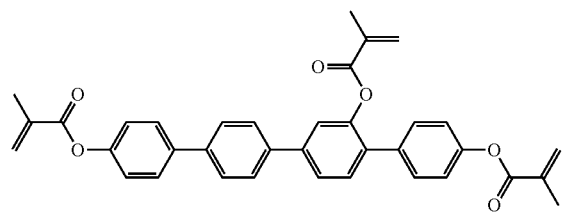
(1-2-2)
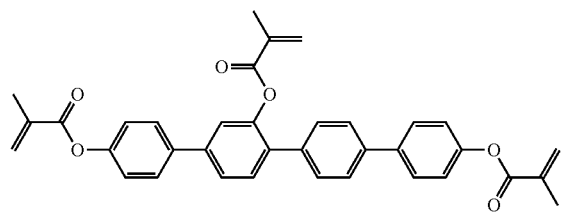
(1-2-3)
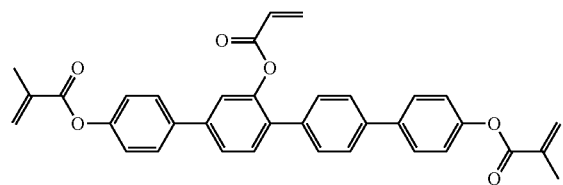
(1-2-4)
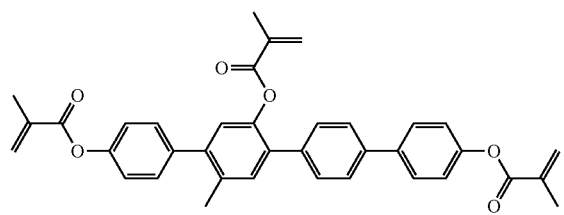
(1-2-5)
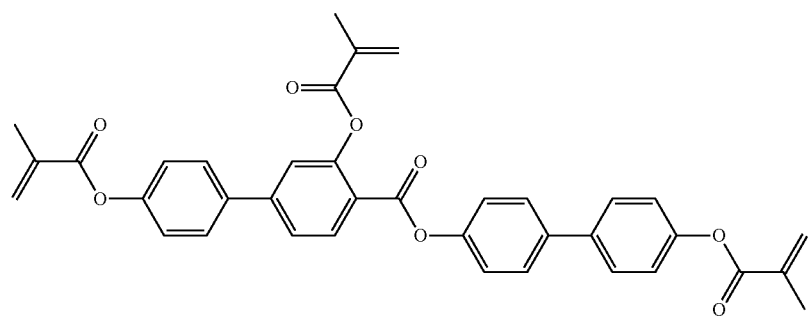
(1-2-6)
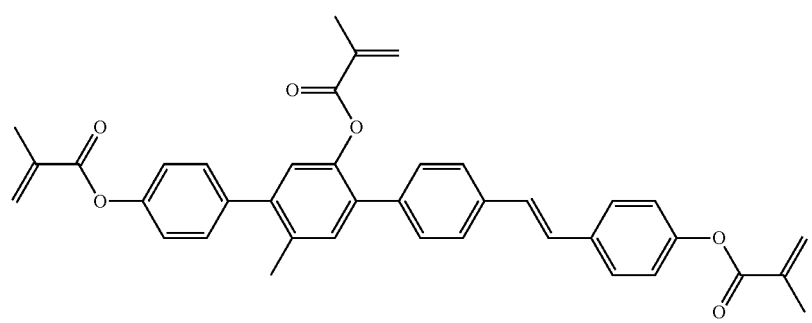
(1-2-7)
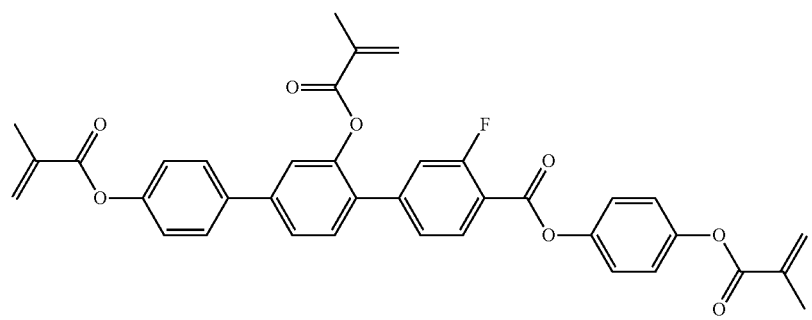

-continued
(1-2-8)
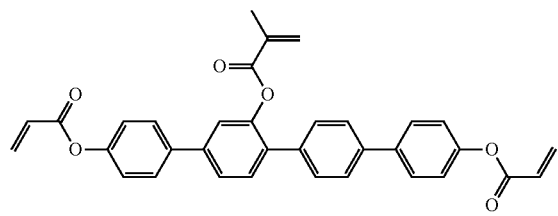
(1-2-9)
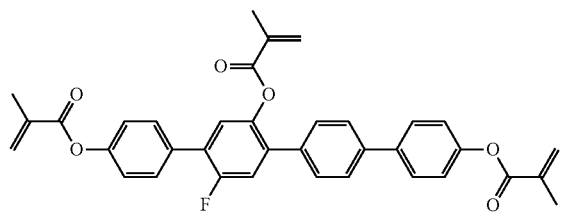
(1-2-10)
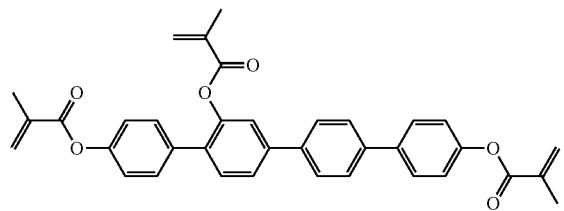
(1-2-11)
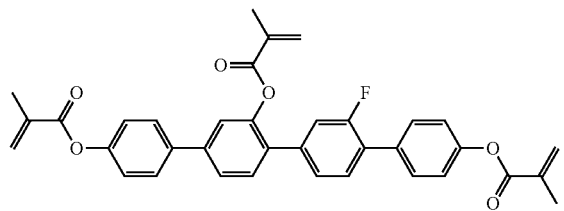
(1-2-12)
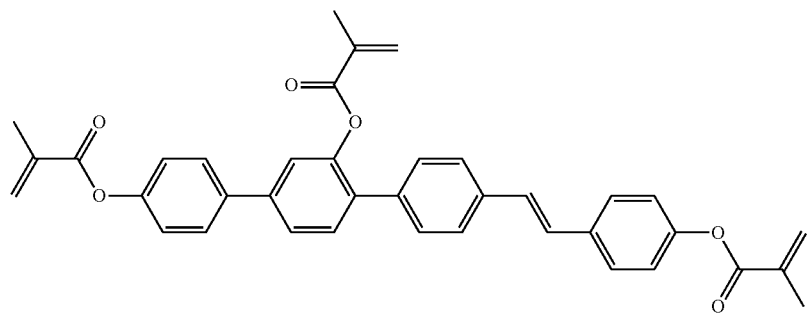
(1-2-13)
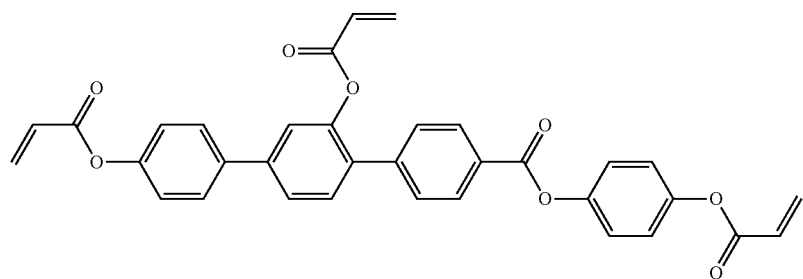
(1-2-14)
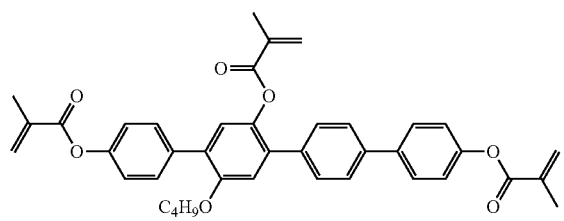
(1-2-15)
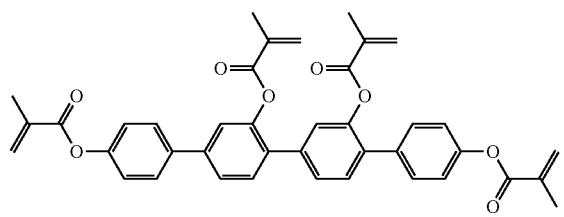

-continued
(1-2-16)
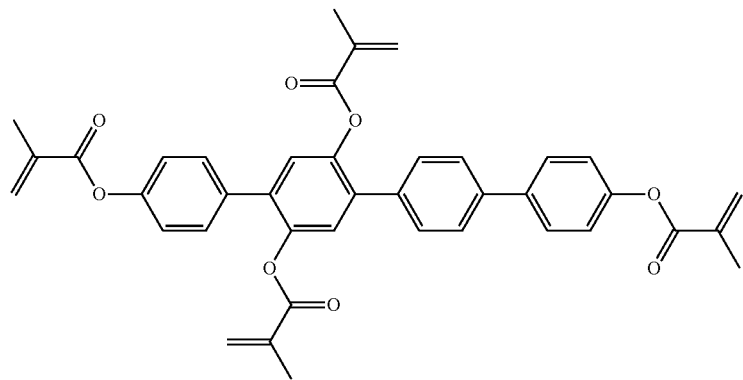
(1-2-17)
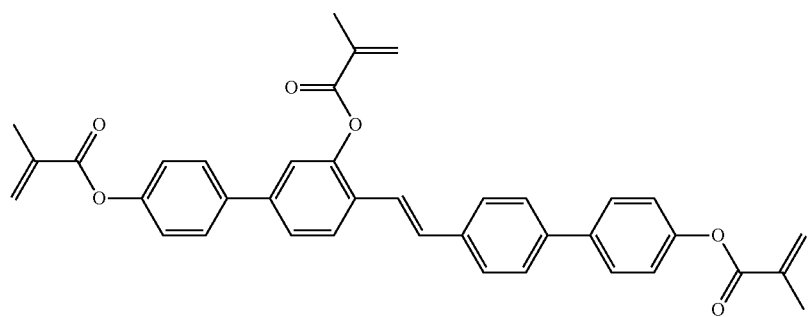
(1-2-18)
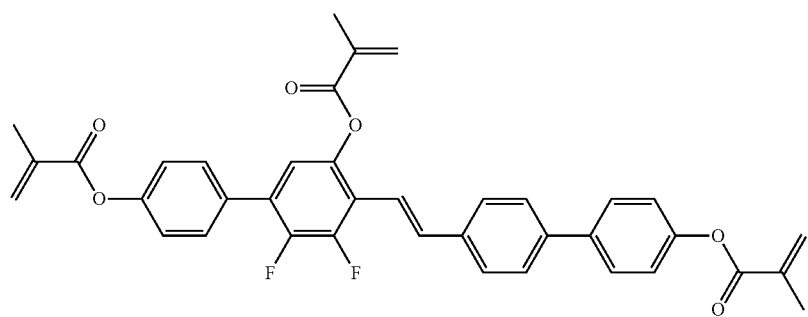
(1-2-19)
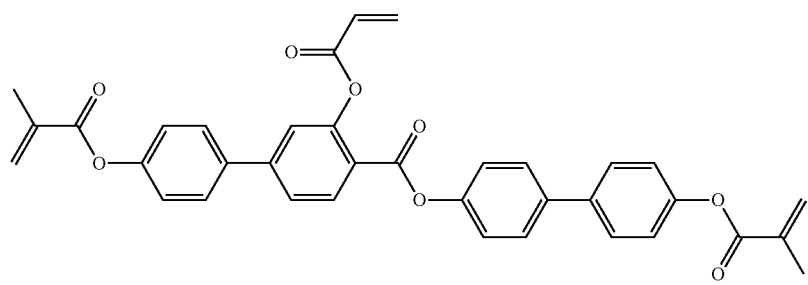
(1-2-20)
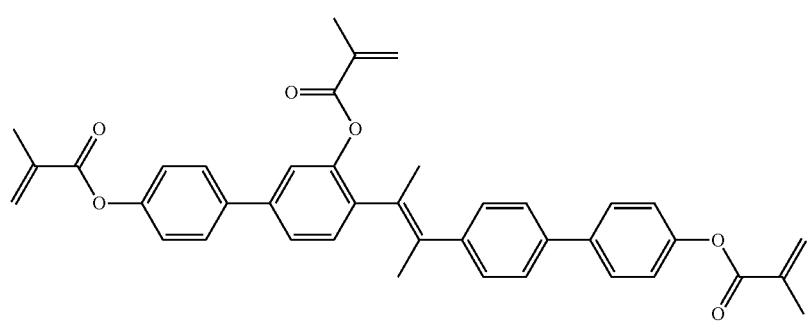

-continued
(1-3-1)
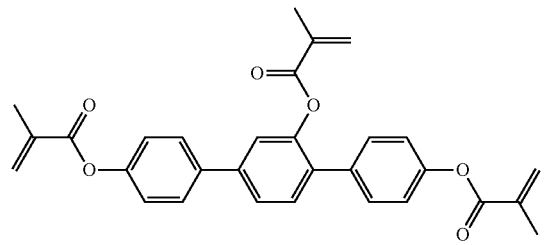
(1-3-2)
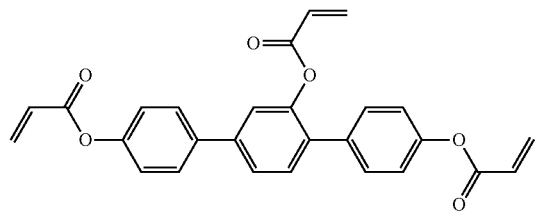
(1-3-3)
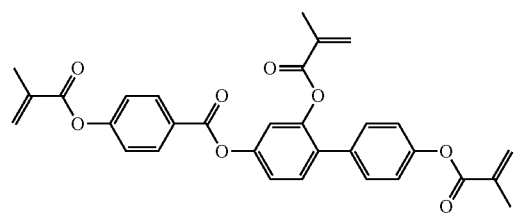
(1-3-4)
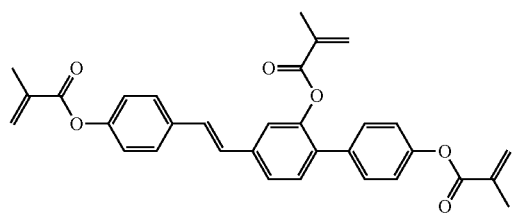
(1-3-5)
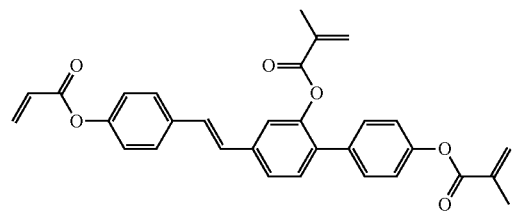
(1-3-6)
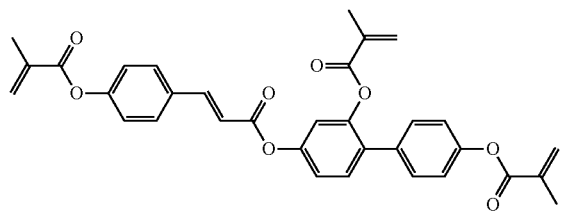
(1-3-7)
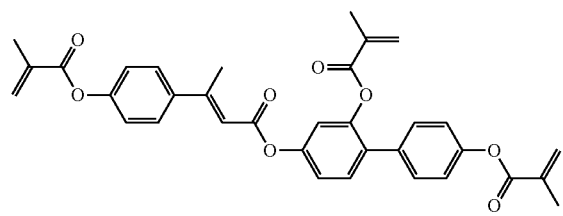
(1-3-8)
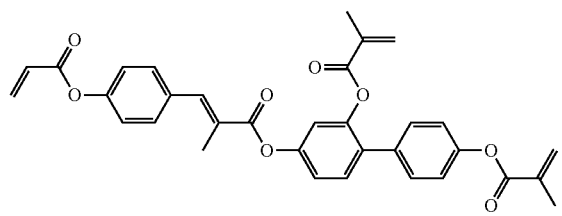
(1-3-9)
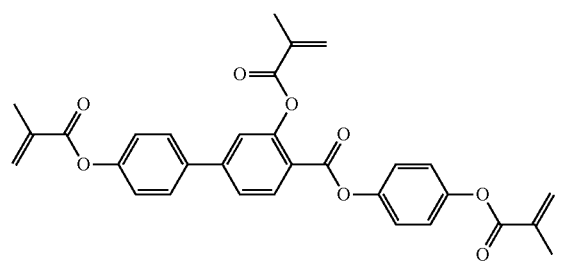
(1-3-10)
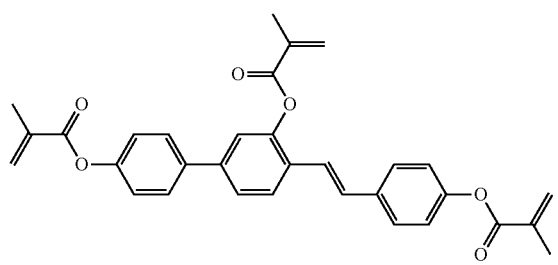
(1-3-11)
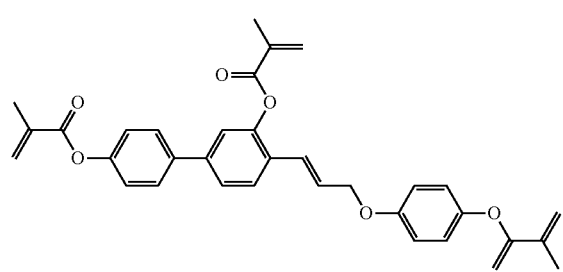
(1-3-12)
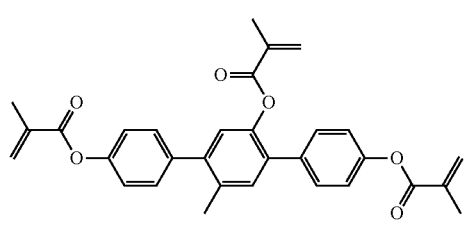 [SMILES: C=C(C)C(=C)Oc1cc(-c2ccc(OC(=O)C(=C)C)cc2)ccc1-c1ccc(OC(=O)C(=C)C)cc1]

(1-3-13)
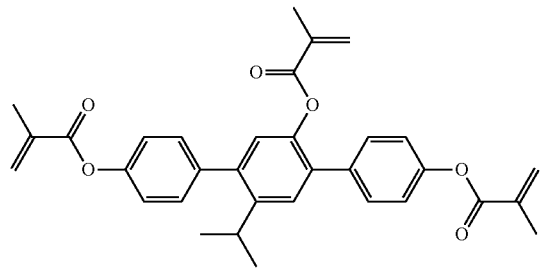
(1-3-14)
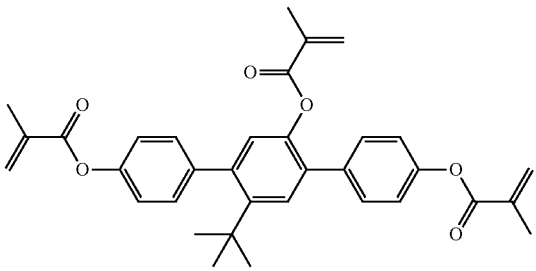
(1-3-15)
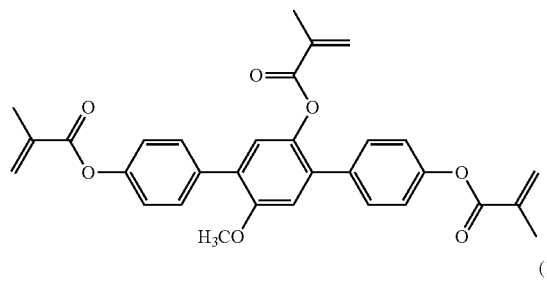
(1-3-16)
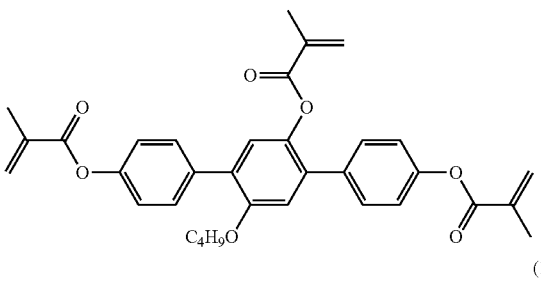
(1-3-17)
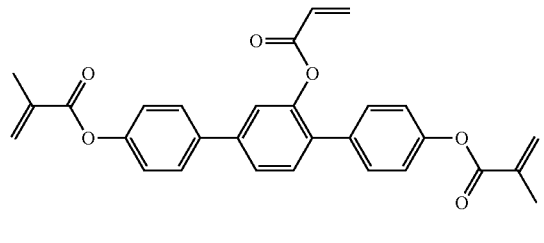
(1-3-18)
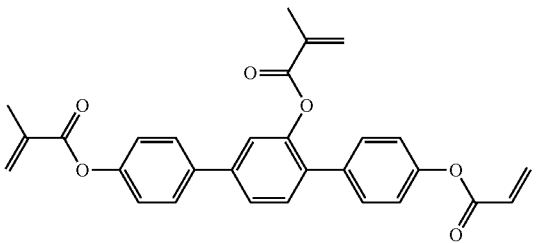
(1-3-19)
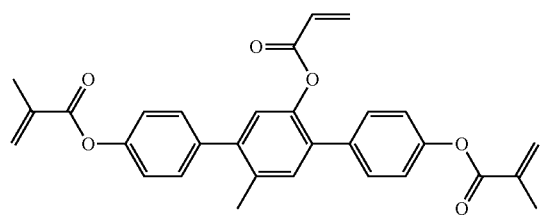
(1-3-20)
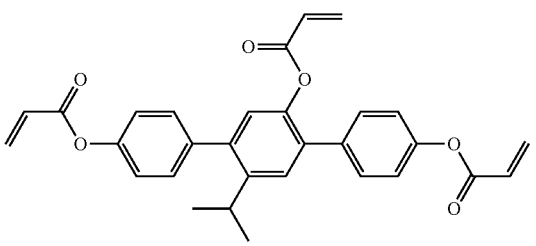
(1-3-21)
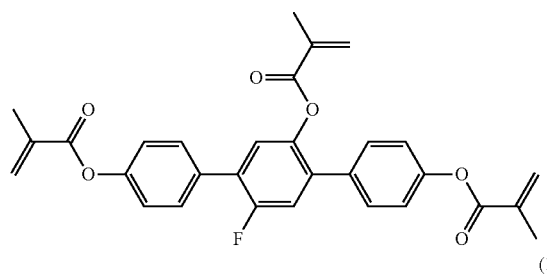
(1-3-22)
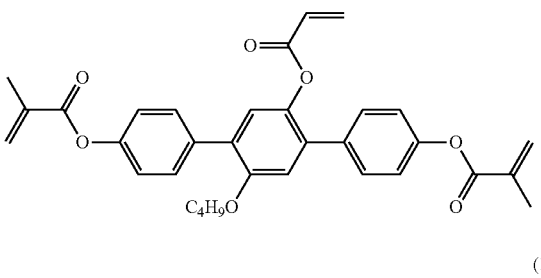
(1-3-23)
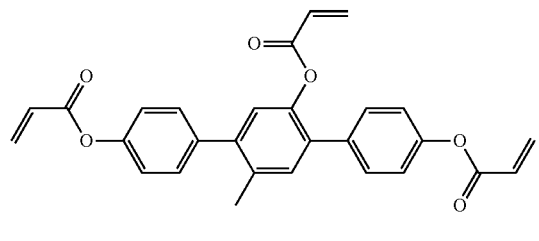
(1-3-24)
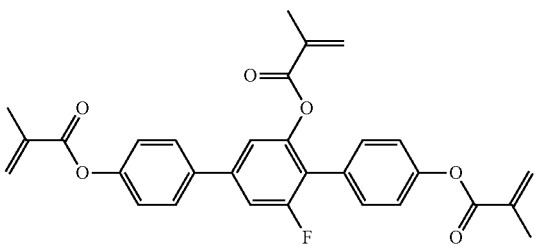

(1-3-25)
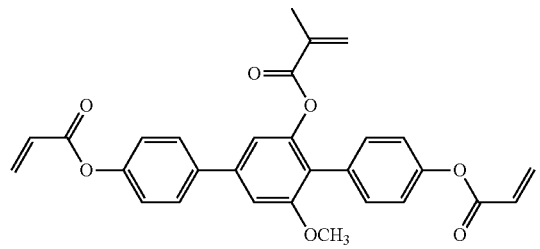
(1-3-26)
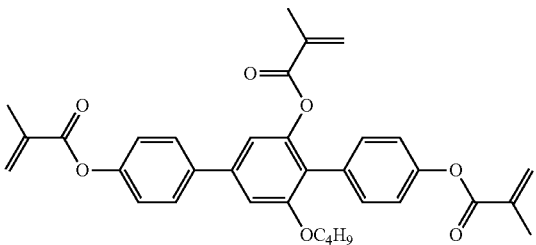
(1-3-27)
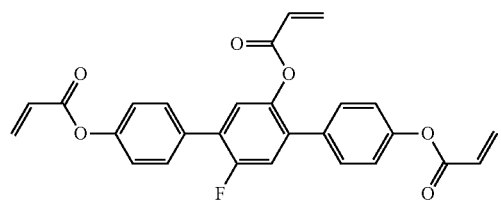
(1-3-28)
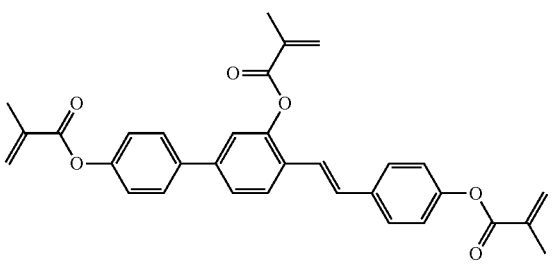
(1-3-29)
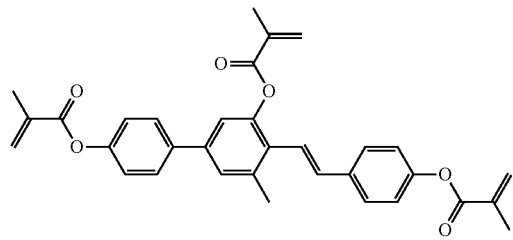
(1-3-30)
(no image)
(1-3-31)
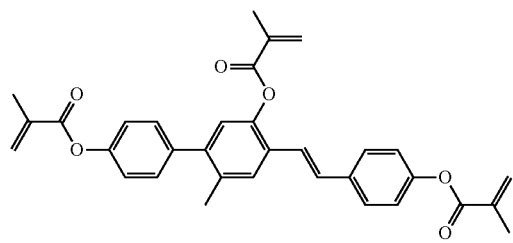
(1-3-32)
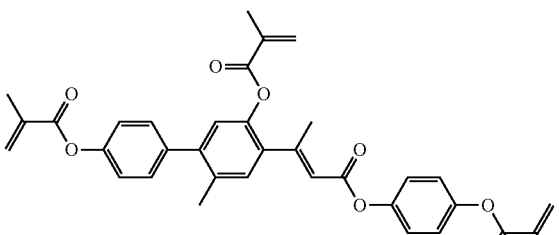
(1-3-33)
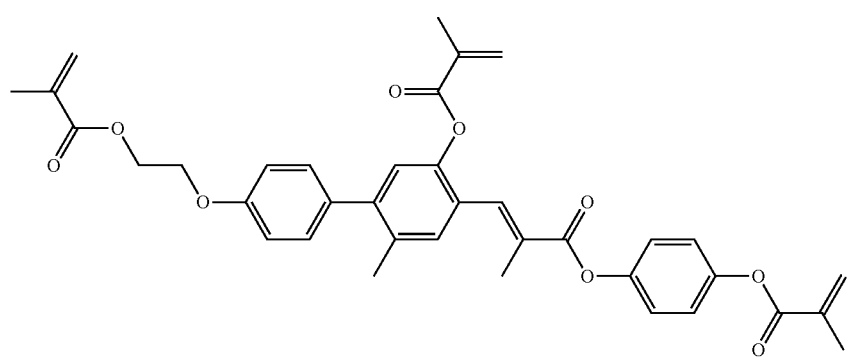

-continued
(1-3-34)
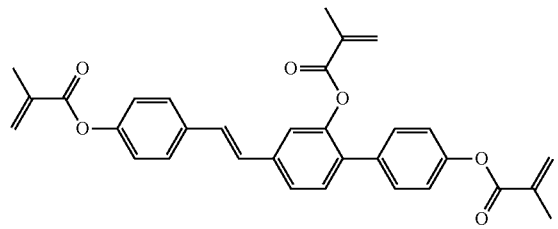
(1-3-35)
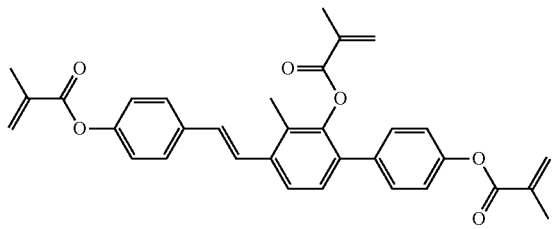
(1-3-36)
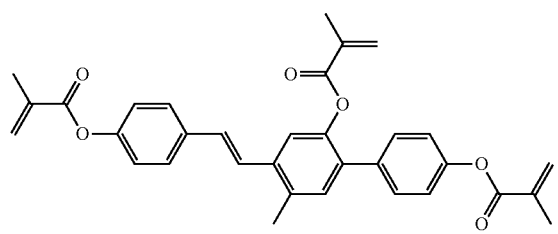
(1-3-37)
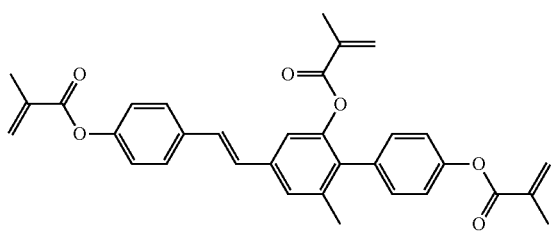
(1-3-38)
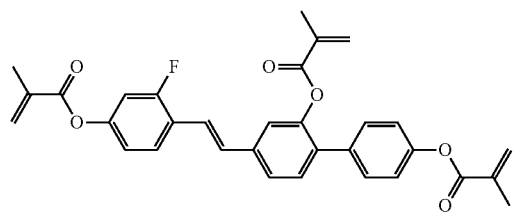
(1-3-39)
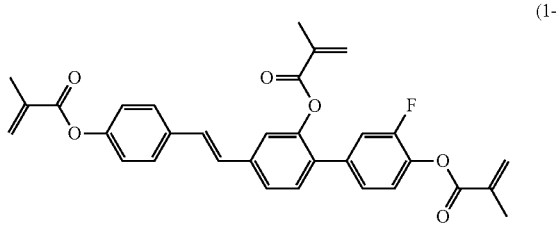
(1-3-40)
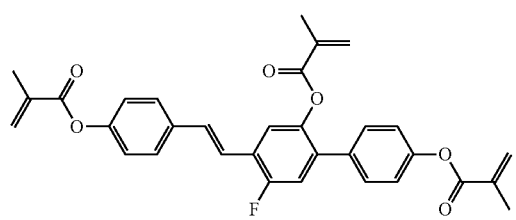
(1-3-41)
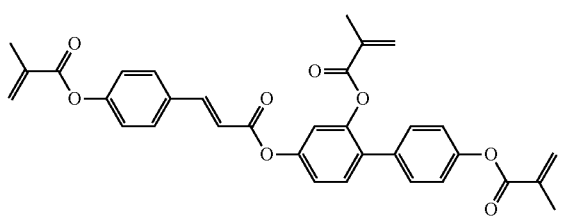
(1-3-42)
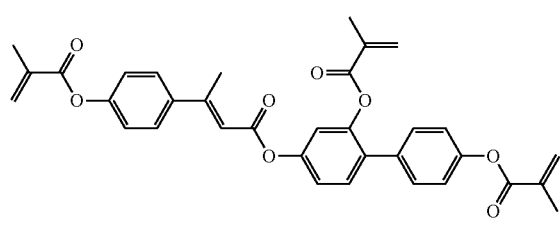
(1-3-43)
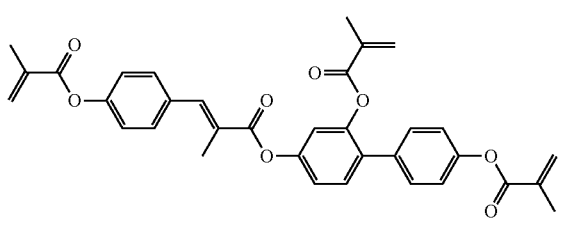
(1-3-44)
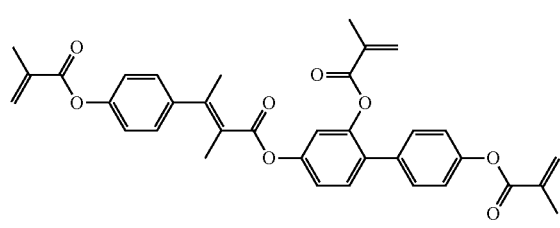
(1-3-45)
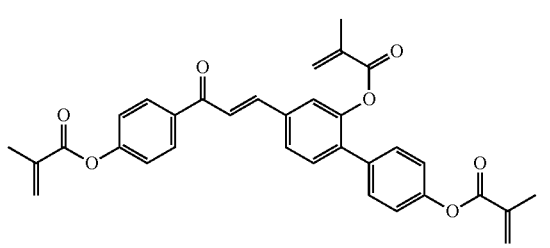

(1-3-46)
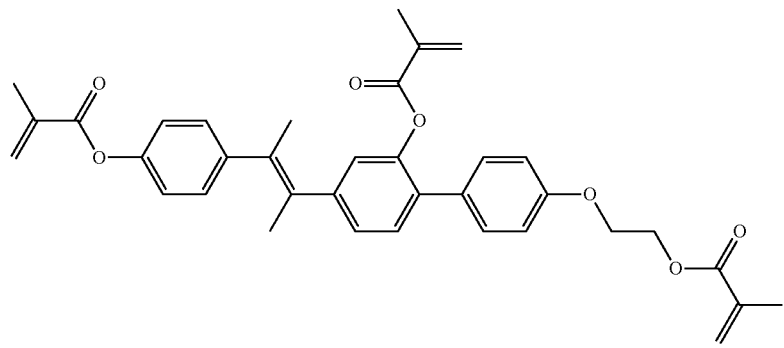
(1-3-47)
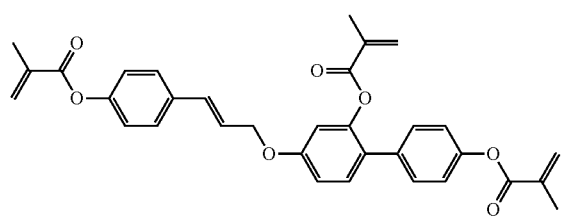
(1-3-48)
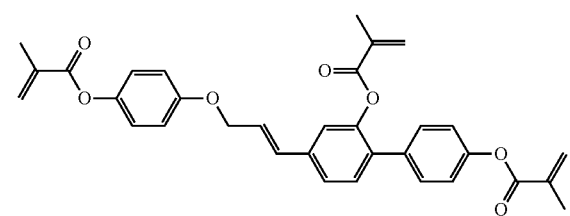
(1-3-49)
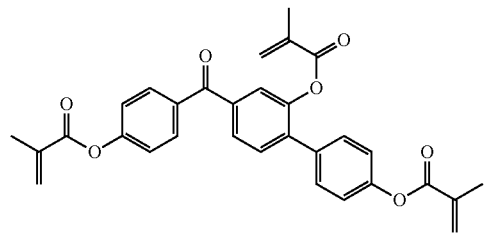
(1-3-50)
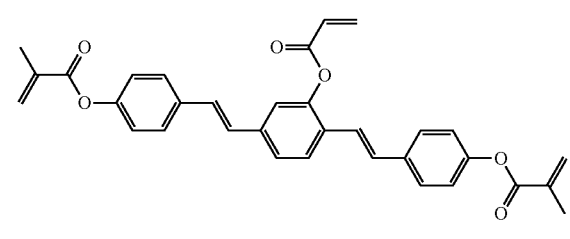
(1-3-51)
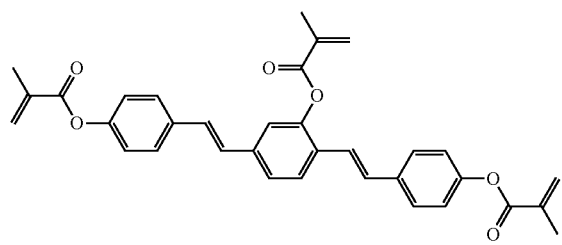
(1-3-52)
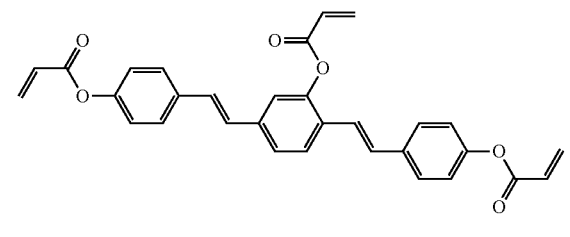
(1-3-53)
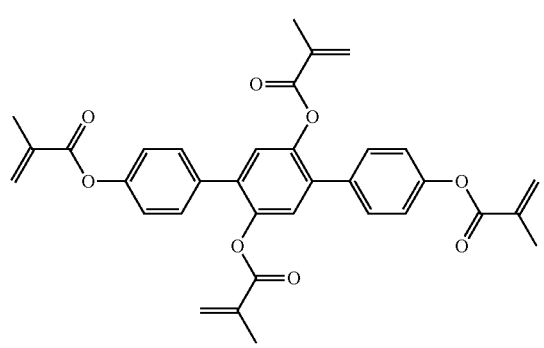
(1-3-54)
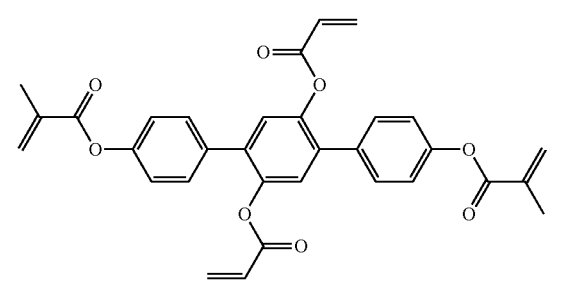

-continued
(1-3-55)
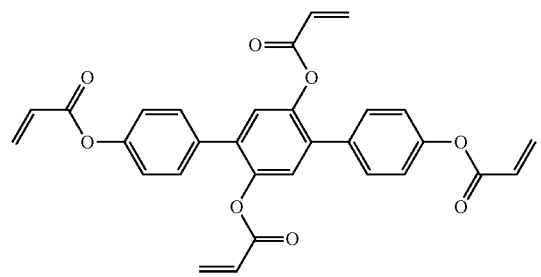
(1-3-56)
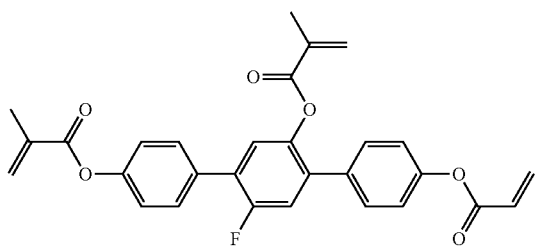
(1-3-57)
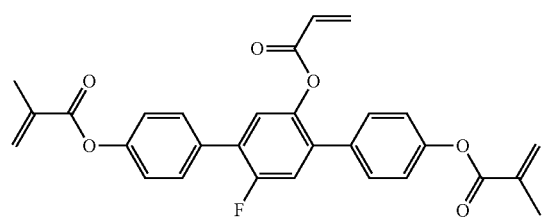
(1-3-58)
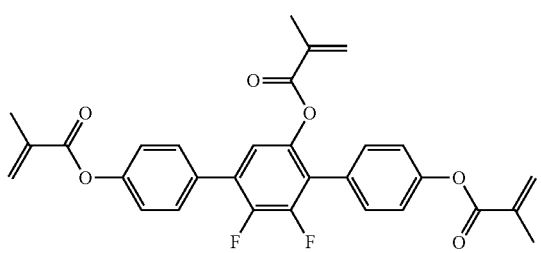
(1-3-59)
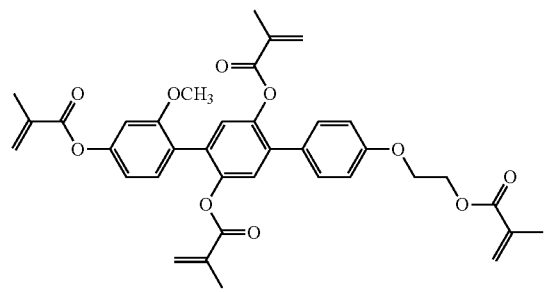
(1-3-60)
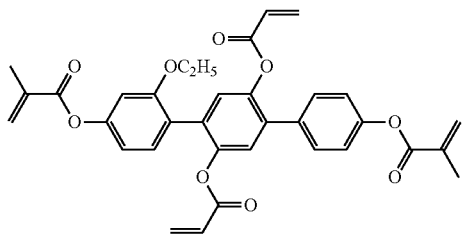
(1-3-61)
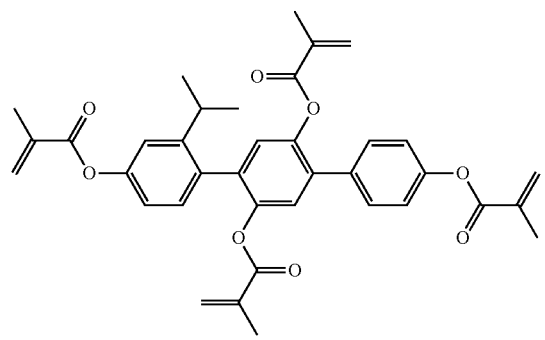
(1-3-62)
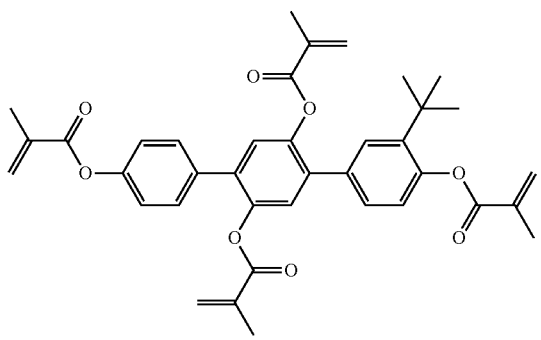
(1-3-63)
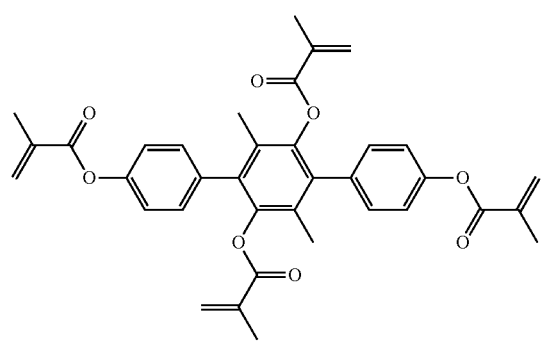
(1-3-64)
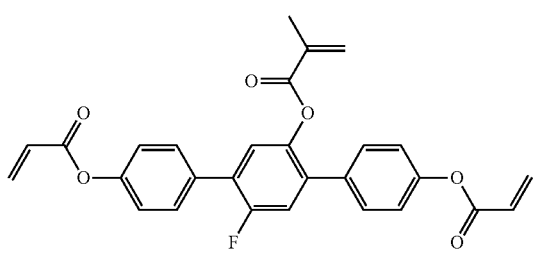

-continued
(1-3-65)
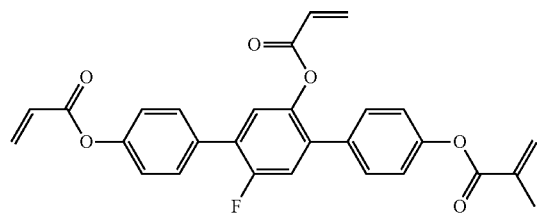
(1-3-66)
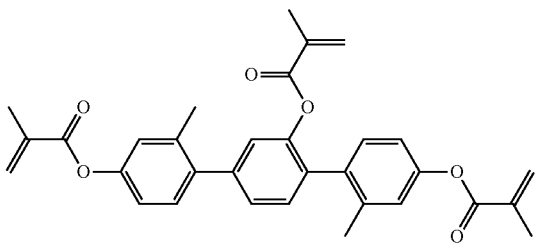
(1-3-67)
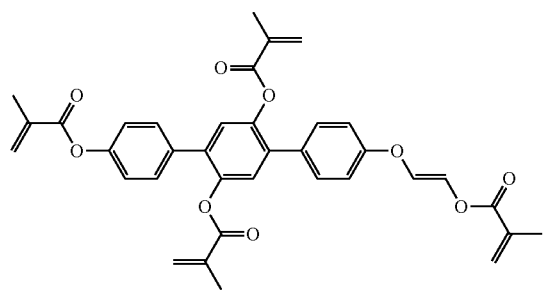
(1-3-68)
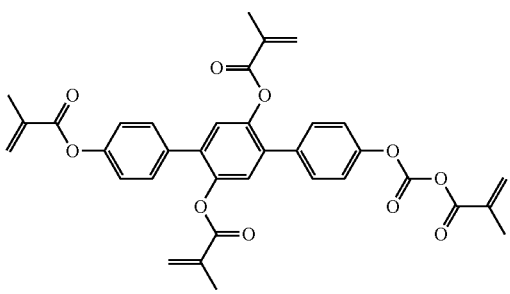
(1-3-69)
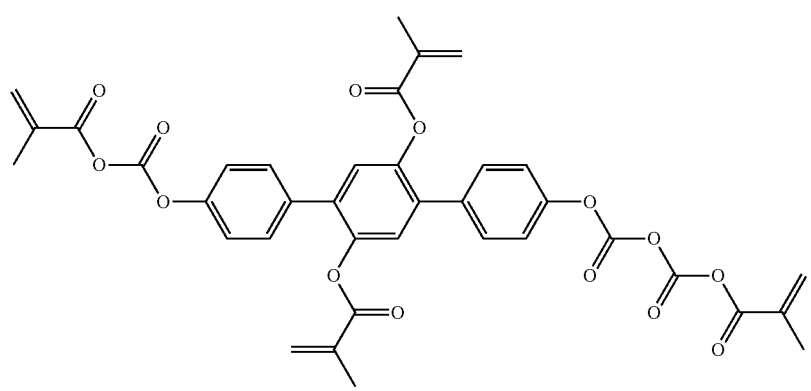
(1-3-70)
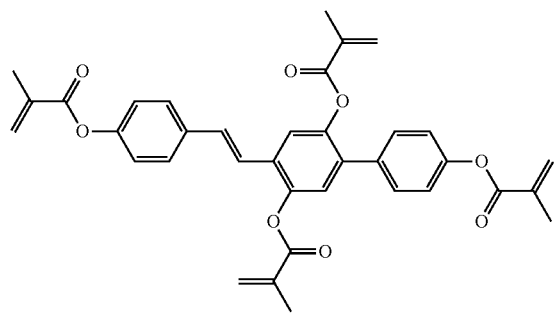
(1-3-71)
(1-3-72)
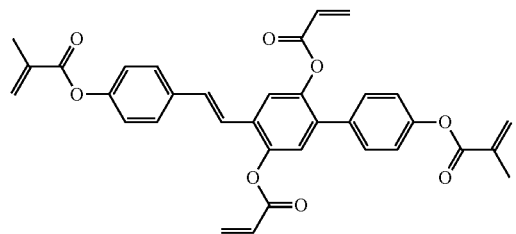
(1-3-73)
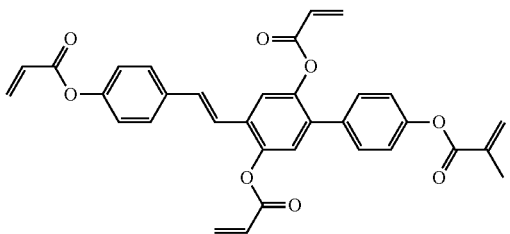

-continued
(1-3-74)
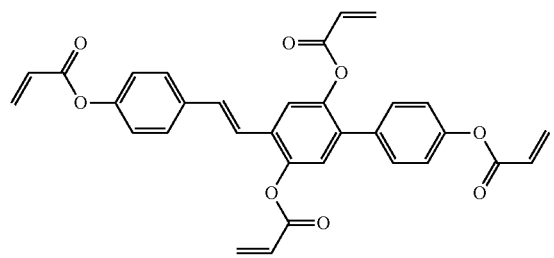
(1-3-75)
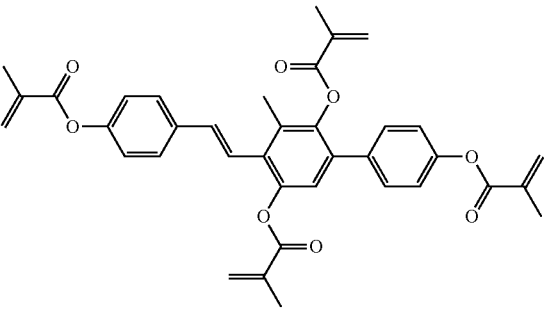
(1-3-76)
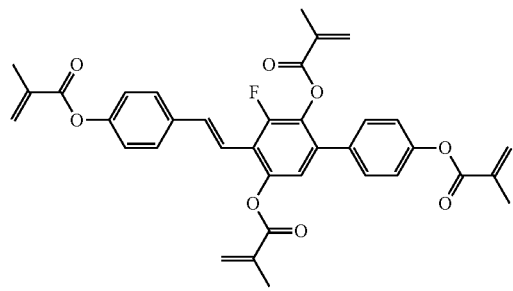
(1-3-77)
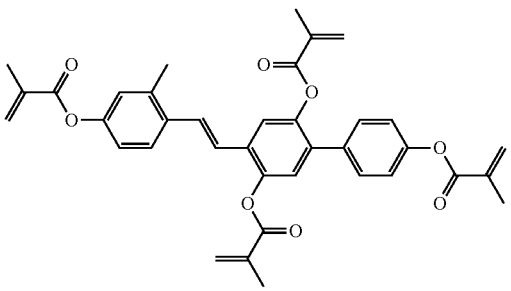
(1-3-78)
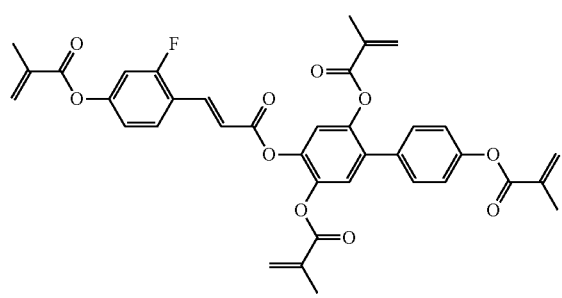
(1-3-79)
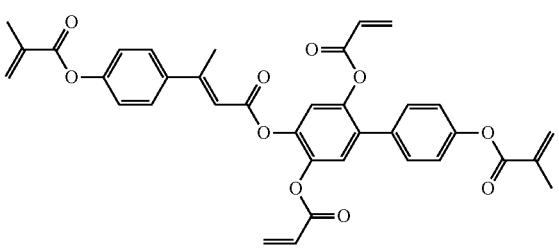
(1-3-80)
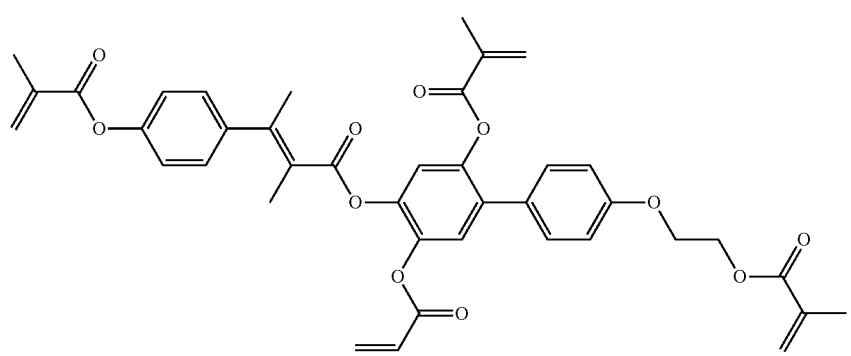
(1-3-81)
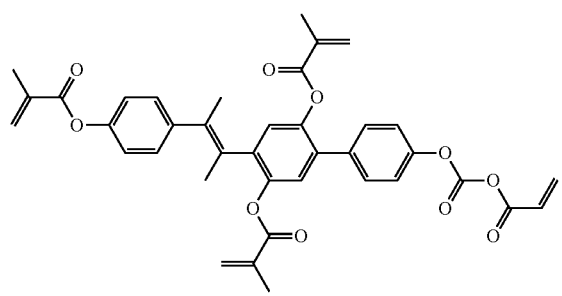
(1-3-82)
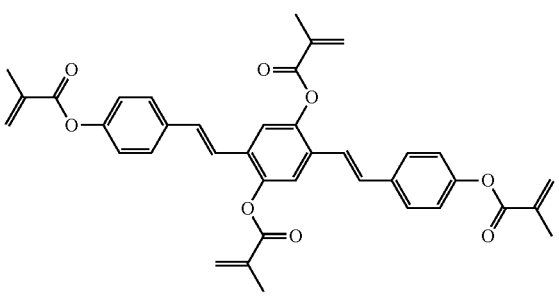

(1-3-83)
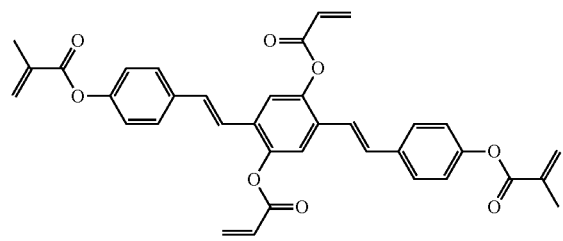
(1-3-84)
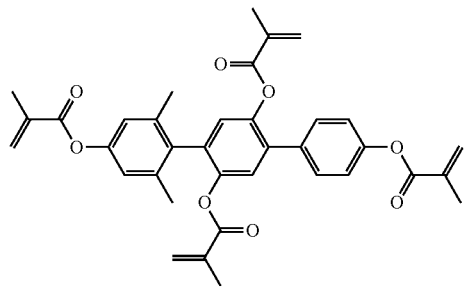
(1-3-85)
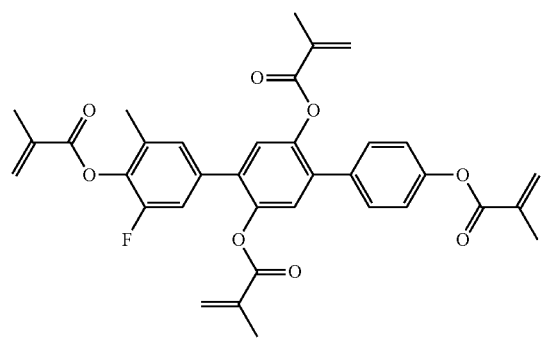
(1-3-86)
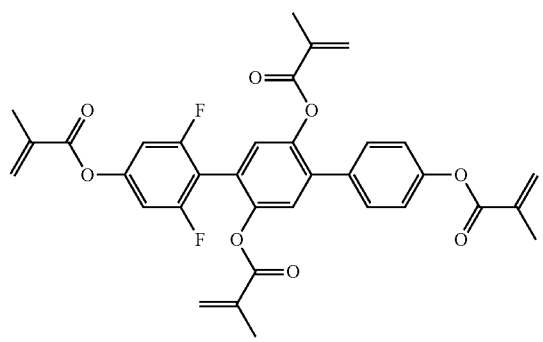
(1-3-87)
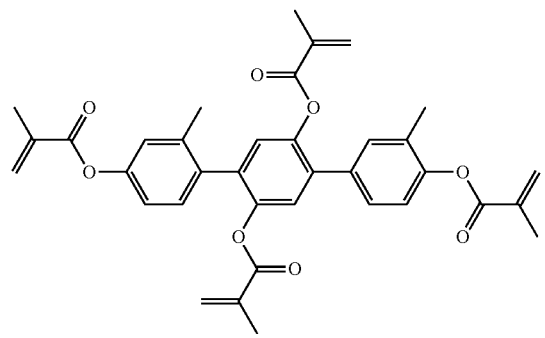
(1-3-88)
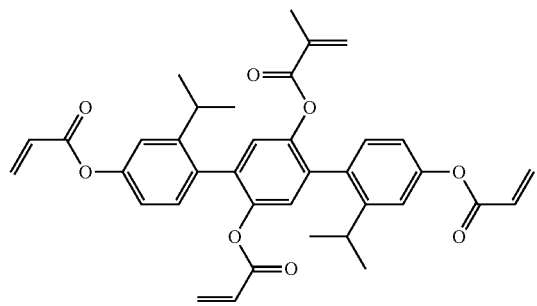
(1-3-89)
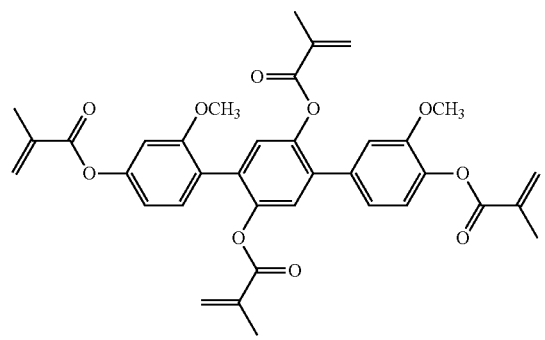
(1-3-90)
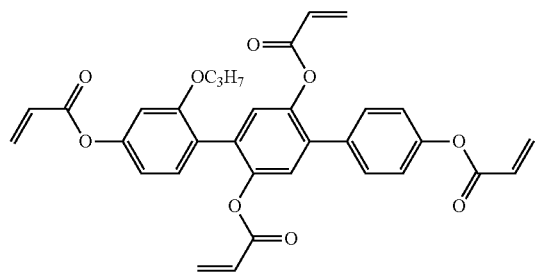

-continued
(1-3-91)
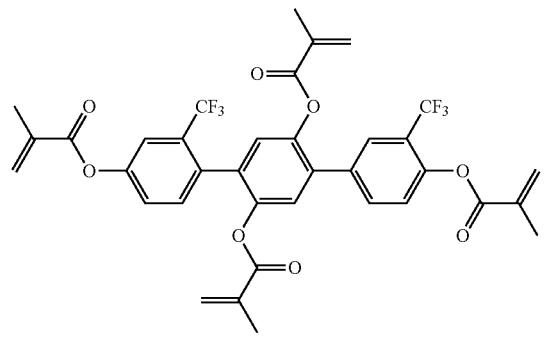
(1-3-92)
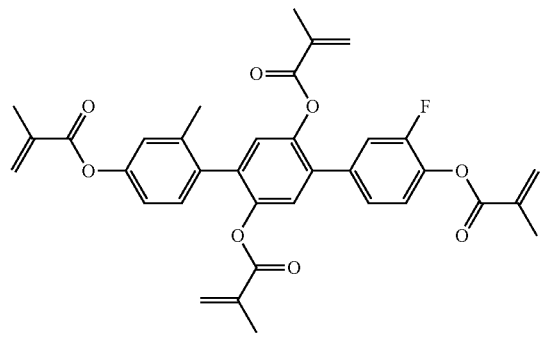
(1-3-93)
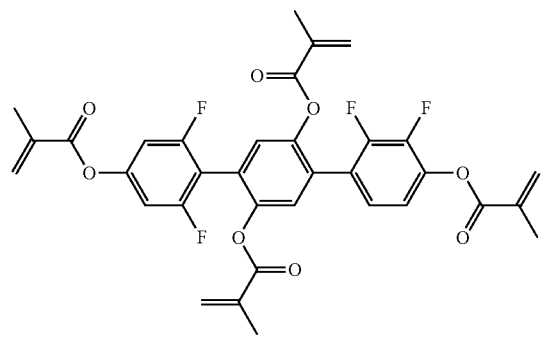
(1-3-94)
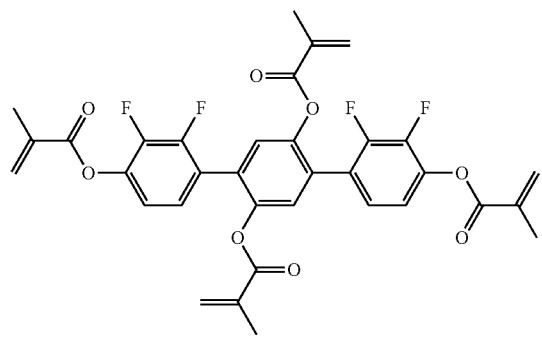
(1-3-96)
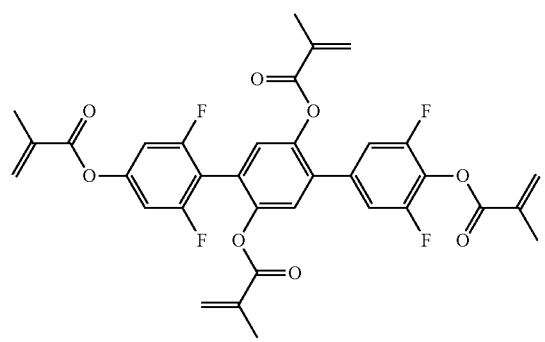
(1-3-97)
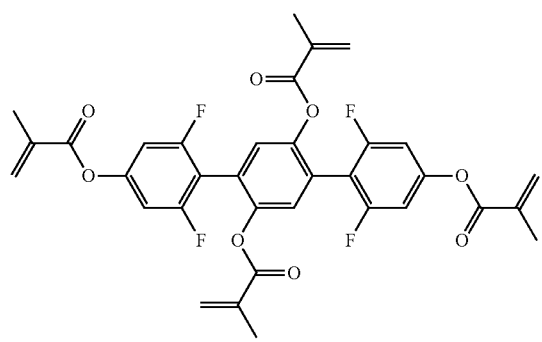
(1-3-98)
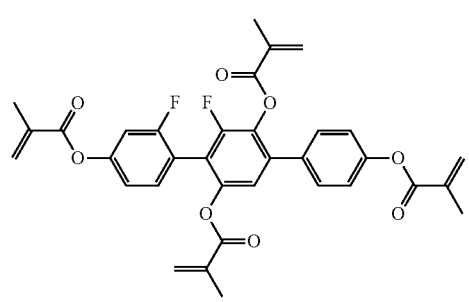
(1-3-99)
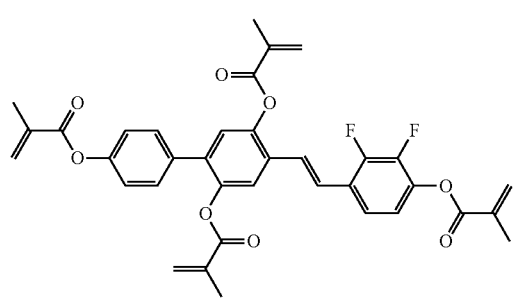

-continued
(1-3-100)
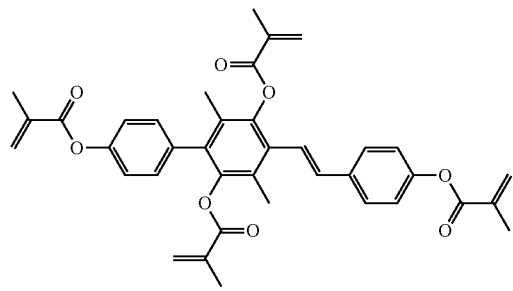
(1-3-101)
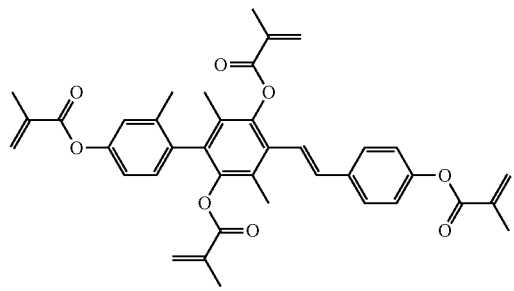
(1-3-102)
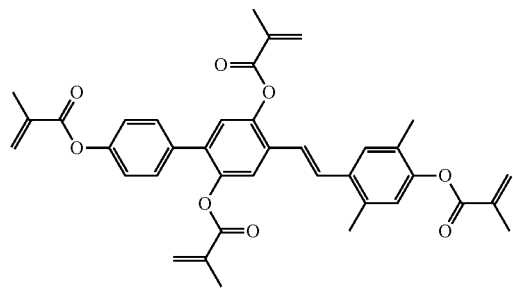
(1-3-103)
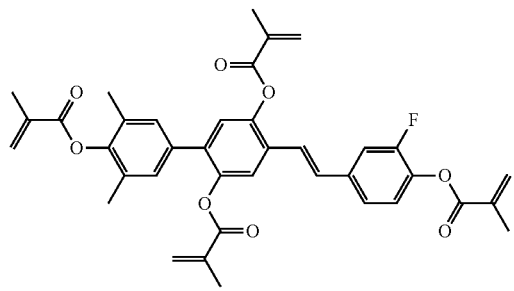
(1-3-104)
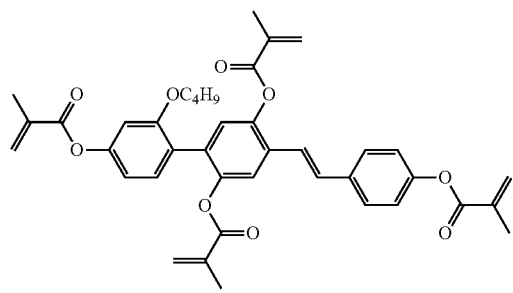
(1-3-105)
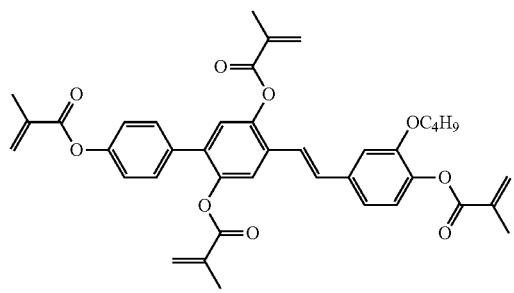
(1-3-106)
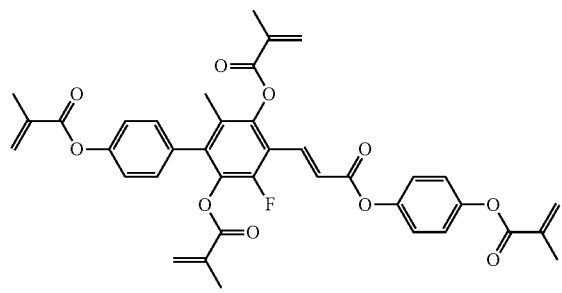
(1-3-107)
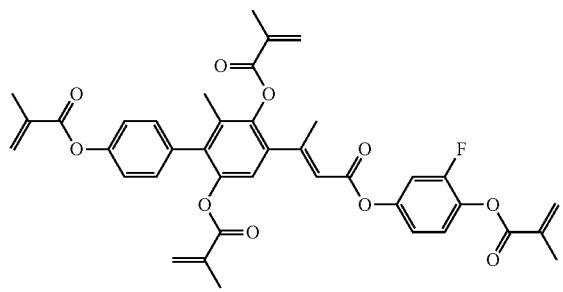
(1-3-108)
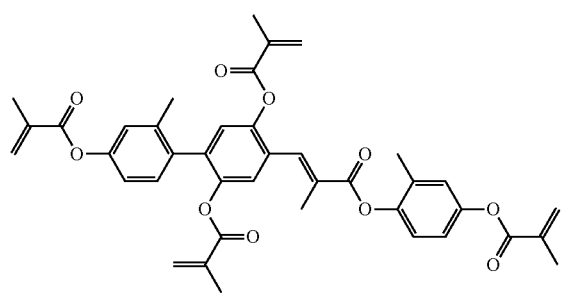
(1-3-109)
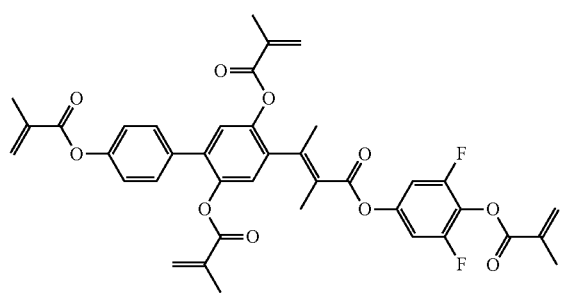

-continued
(1-3-110)
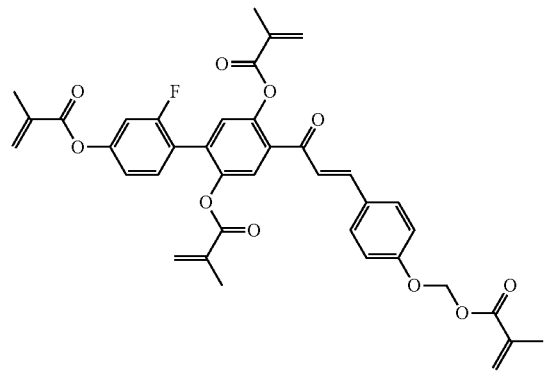
(1-3-111)
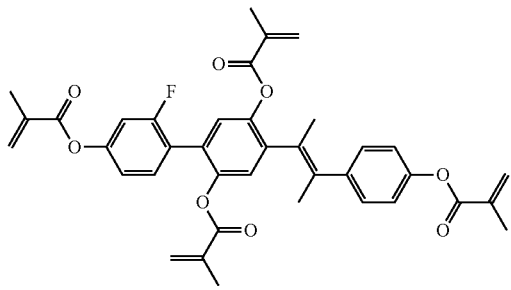
(1-3-112)
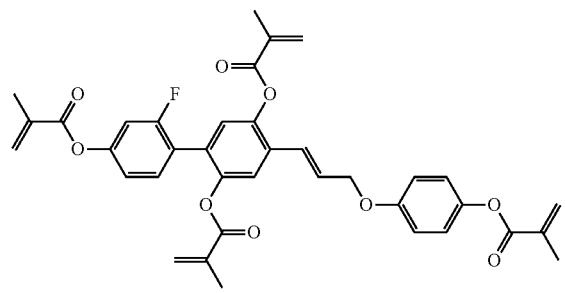
(1-3-113)
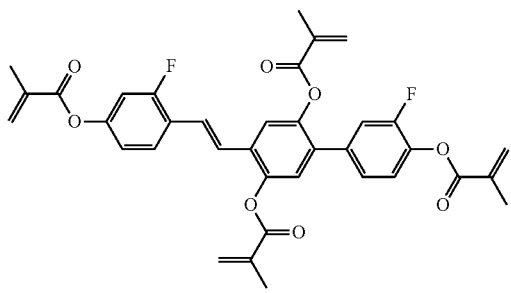
(1-3-114)
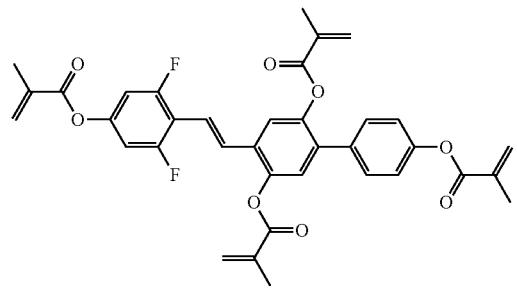
(1-3-115)
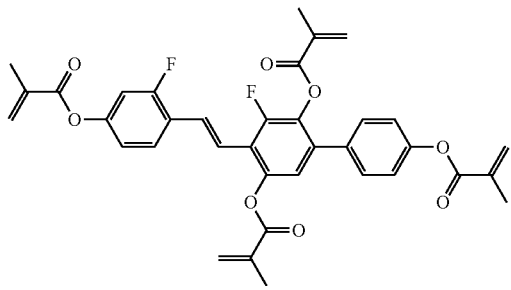
(1-3-116)
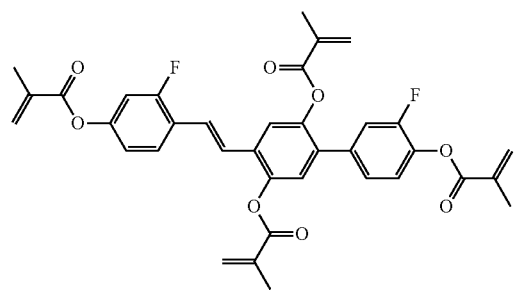
(1-3-117)
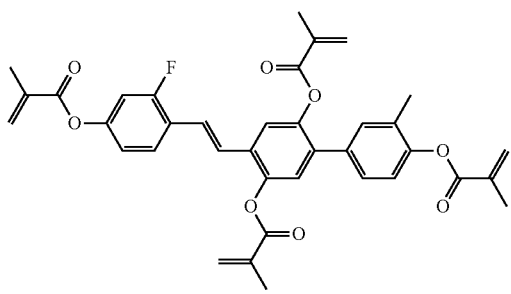
(1-3-118)
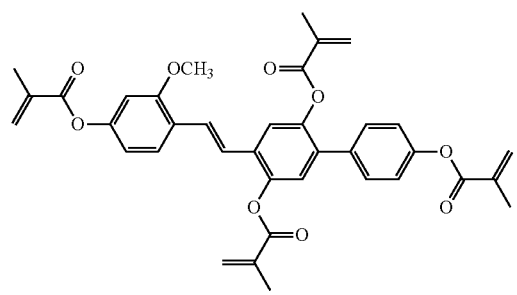
(1-3-119)
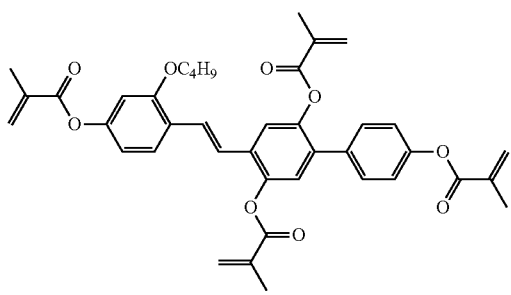

-continued
(1-3-120)
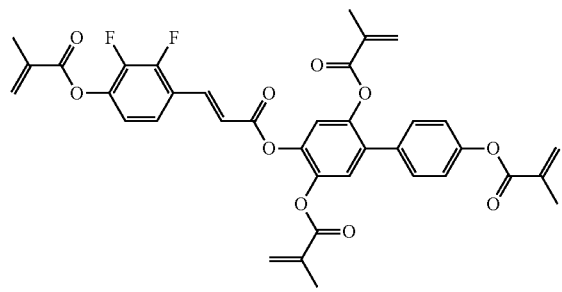
(1-3-121)
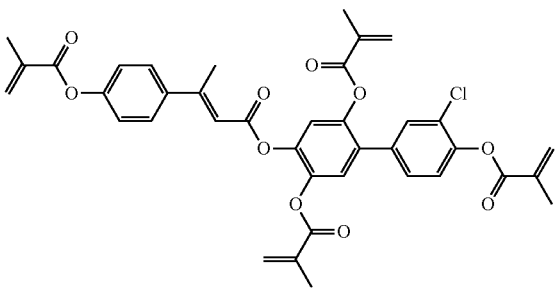
(1-3-122)
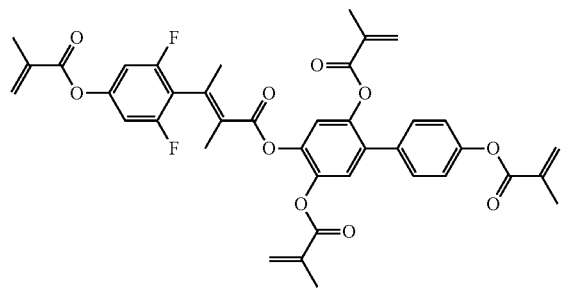
(1-3-123)
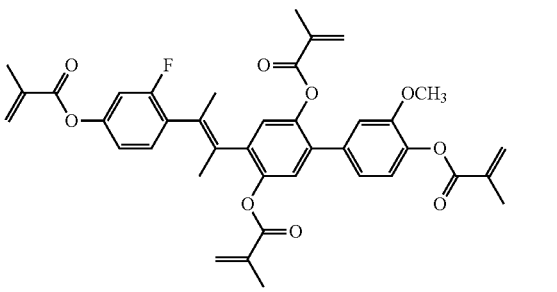
(1-3-124)
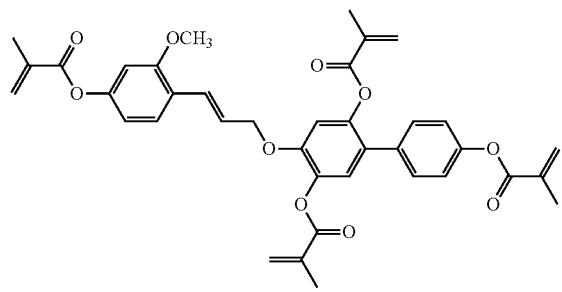
(1-3-125)
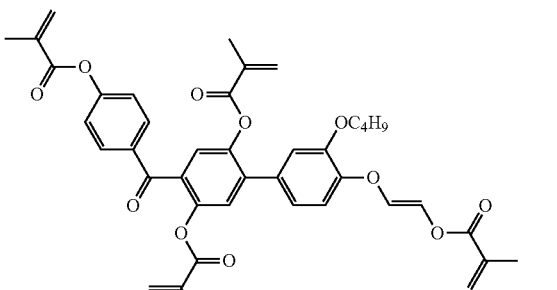
(1-3-126)
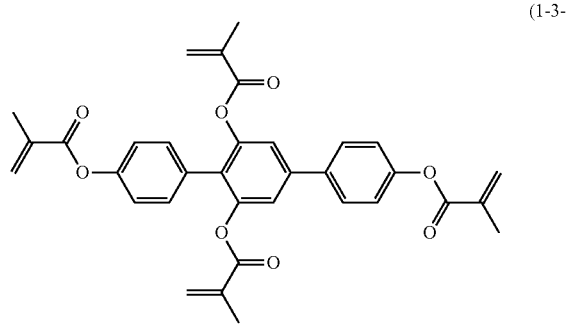
(1-3-127)
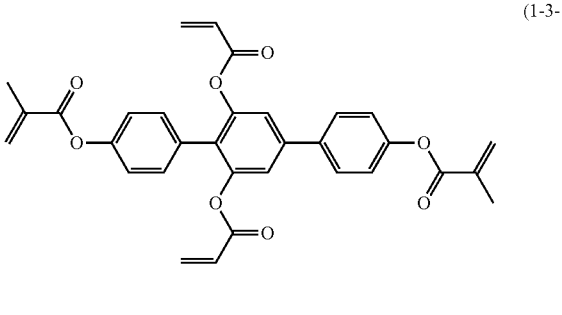
(1-3-128)
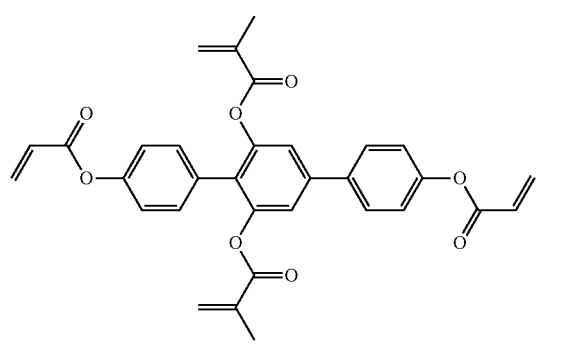
(1-3-129)
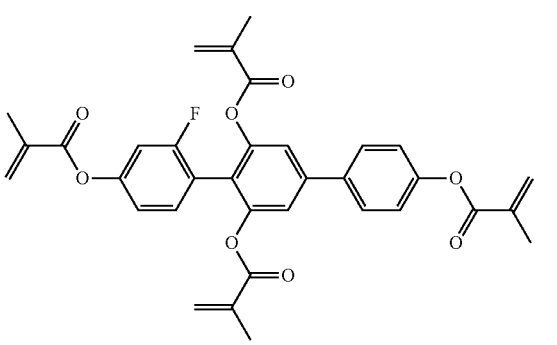

-continued
(1-3-130)
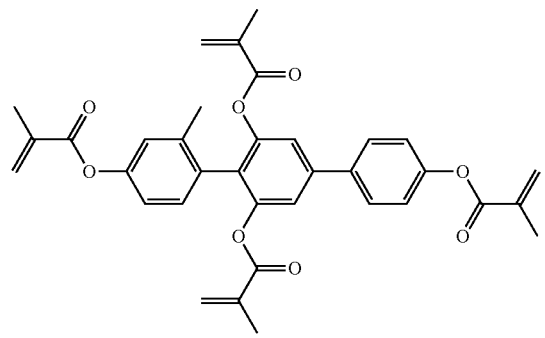
(1-3-131)
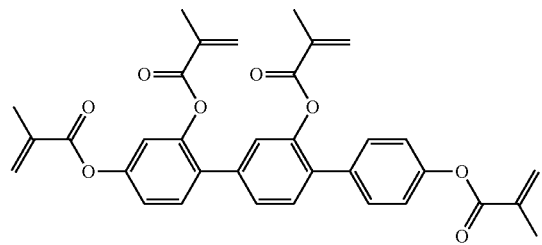
(1-3-132)
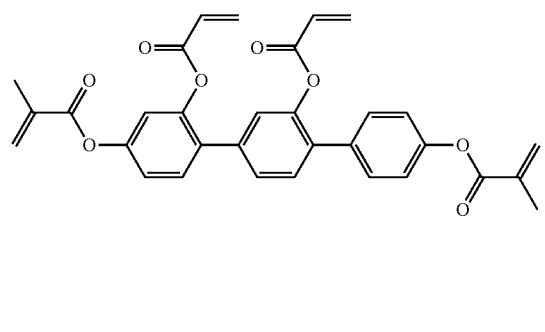
(1-3-133)
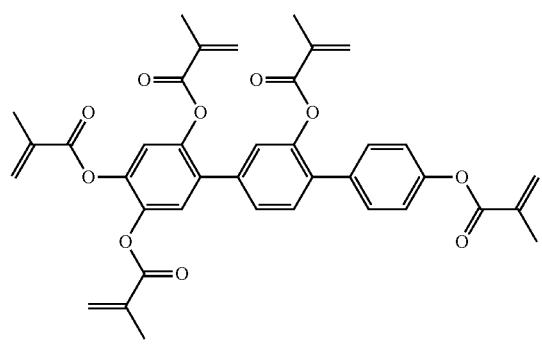
(1-3-134)
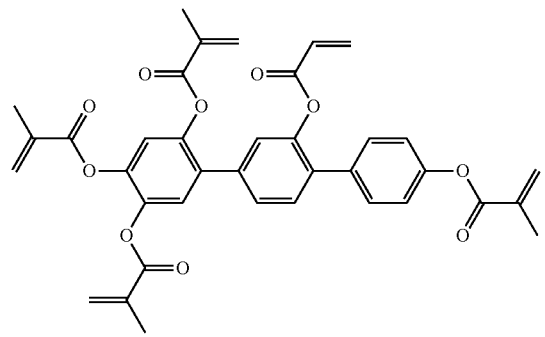
(1-3-135)
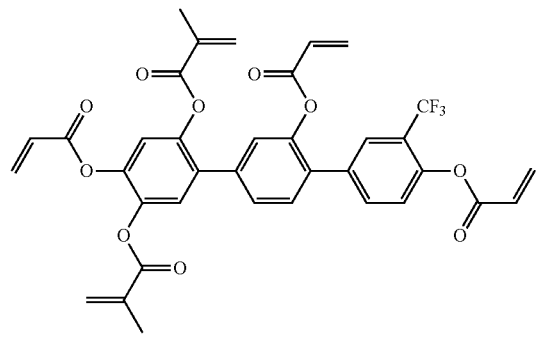
(1-3-136)
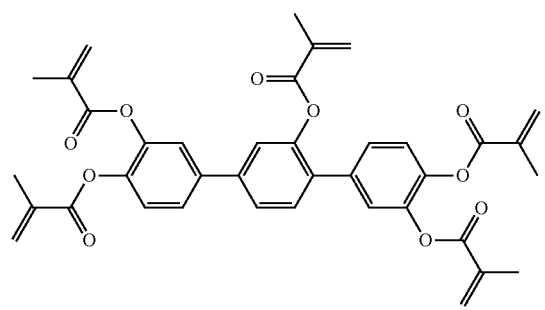
(1-3-137)
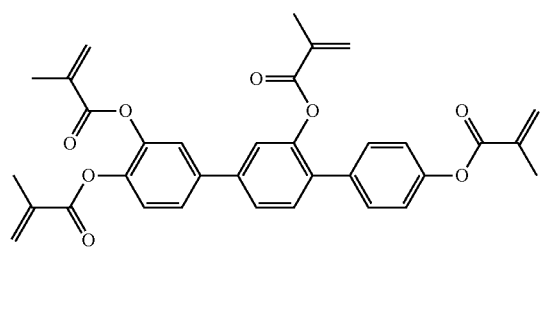

-continued
(1-3-138)
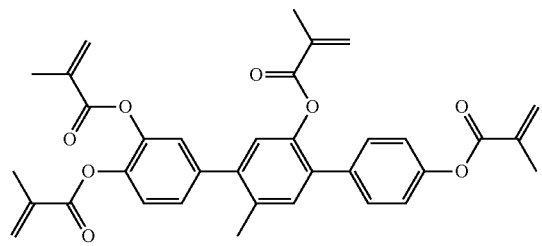
(1-3-139)
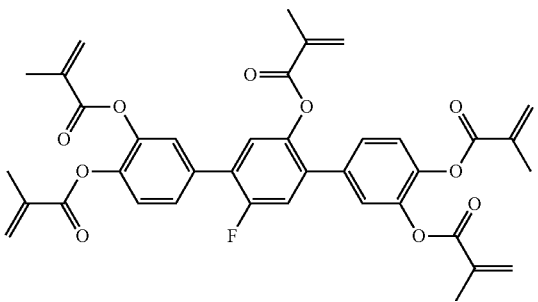
(1-3-140)
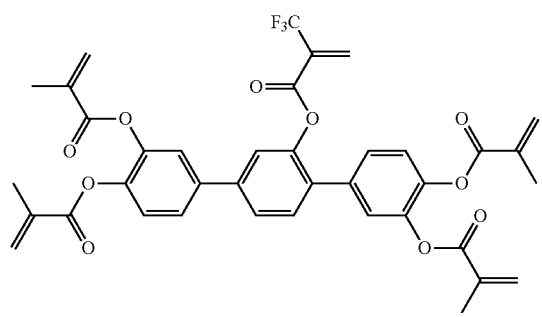
(1-3-141)
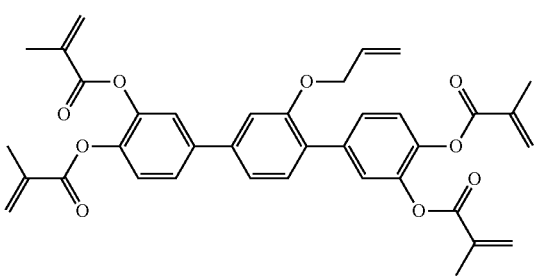
(1-3-142)
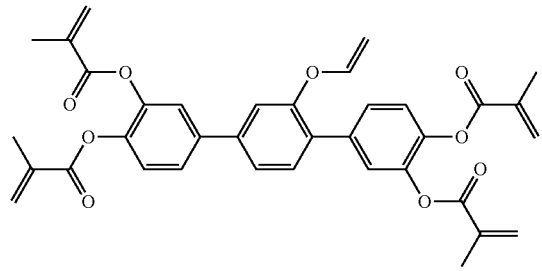
(1-3-143)
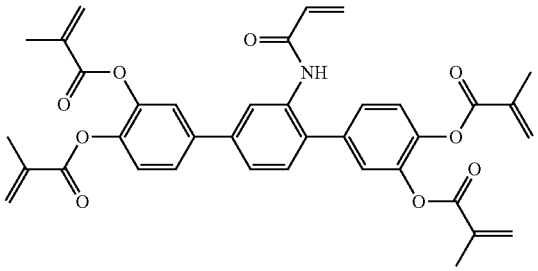
(1-3-144)
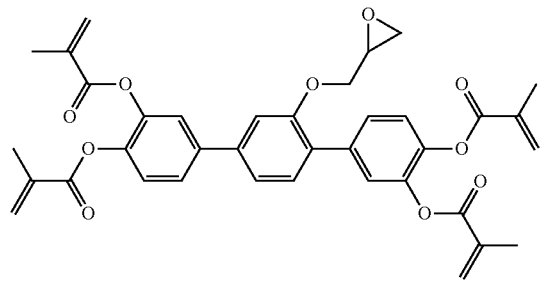
(1-3-145)
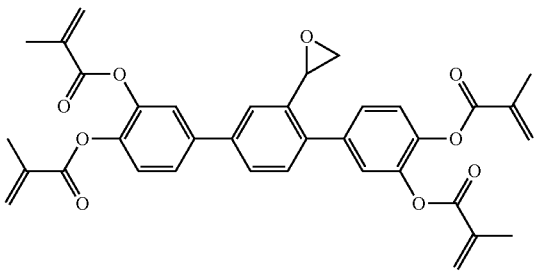
(1-3-146)
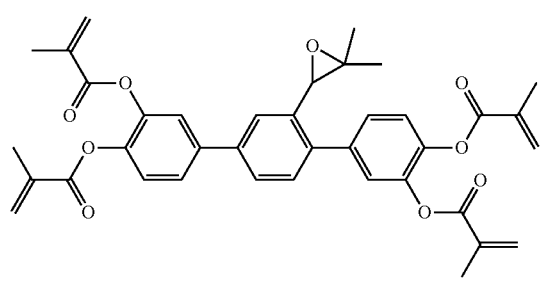
(1-3-147)
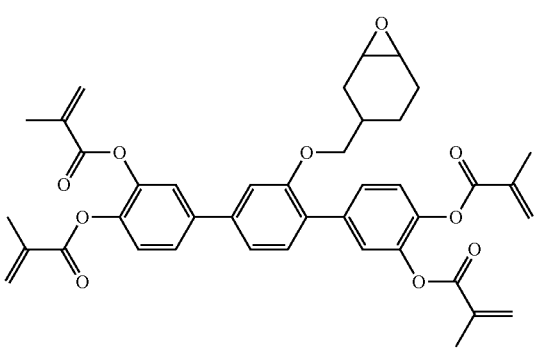

-continued
(1-3-148)
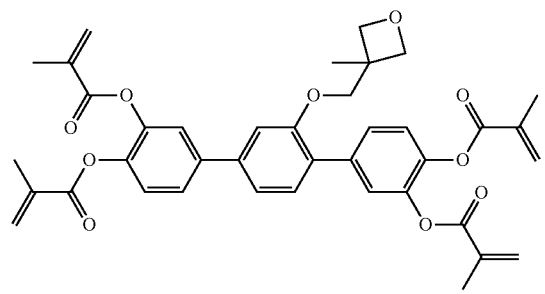
(1-3-149)
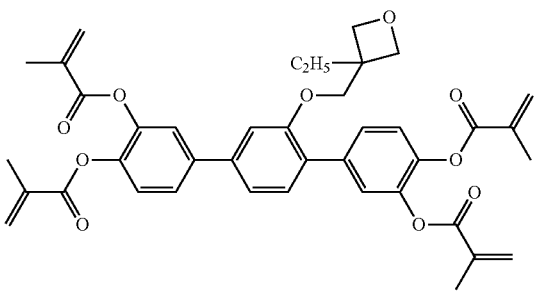
(1-3-150)
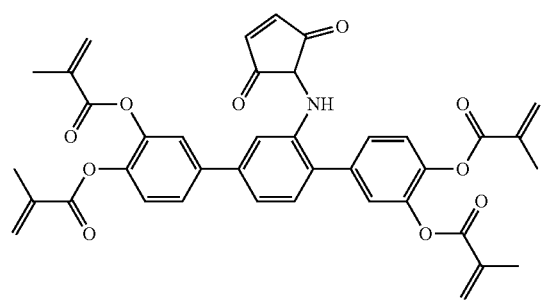
(1-3-151)
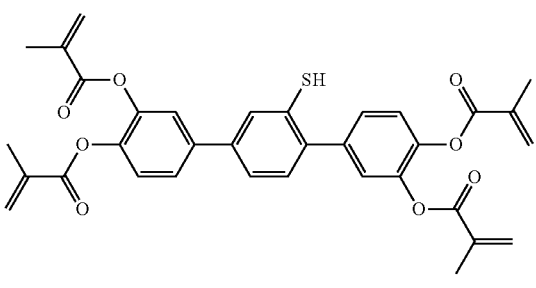
(1-3-152)
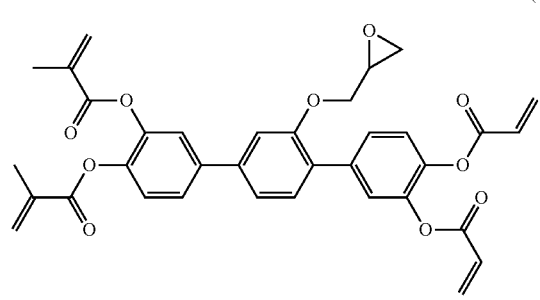
(1-3-153)
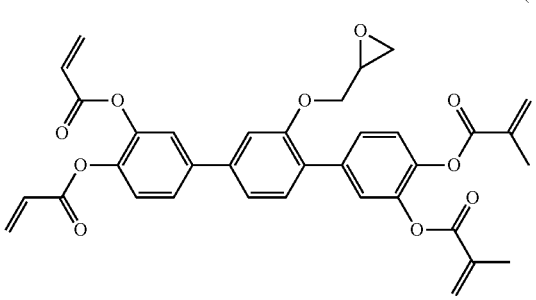
(1-3-154)
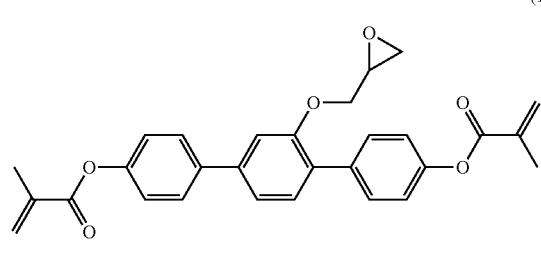
(1-3-155)
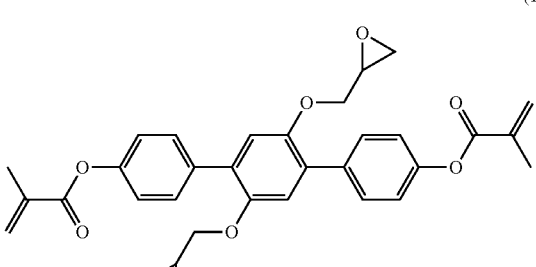
(1-3-156)
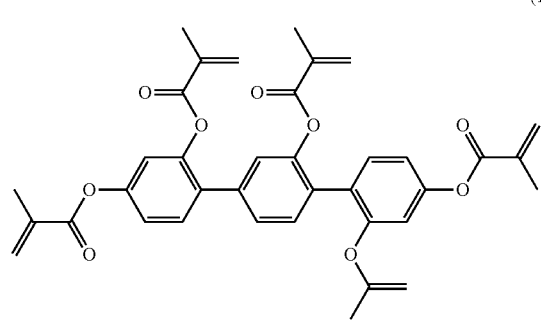
(1-3-157)
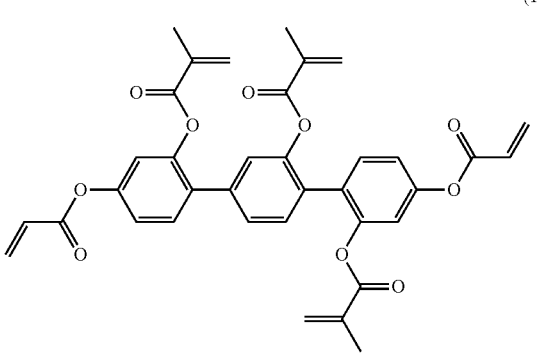

-continued
(1-3-158)
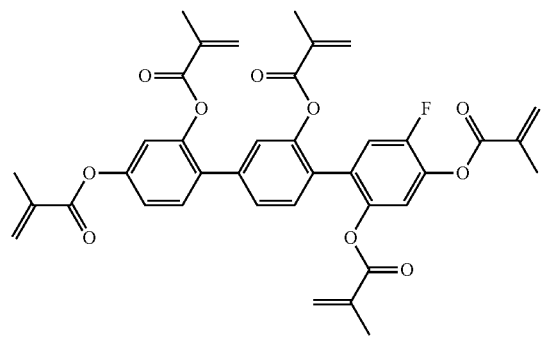
(1-3-159)
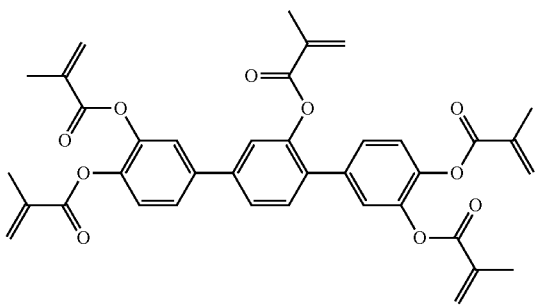
(1-3-160)
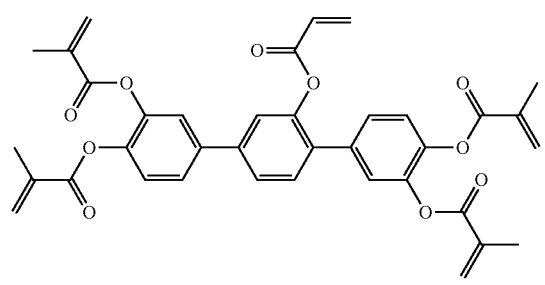
(1-3-161)
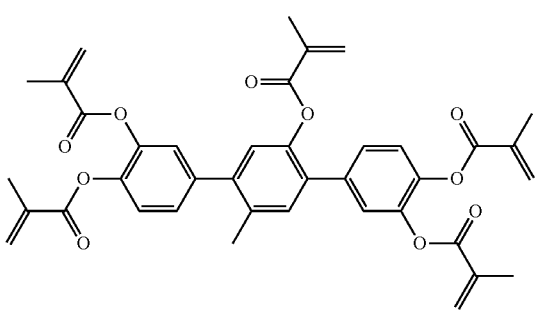
(1-3-162)
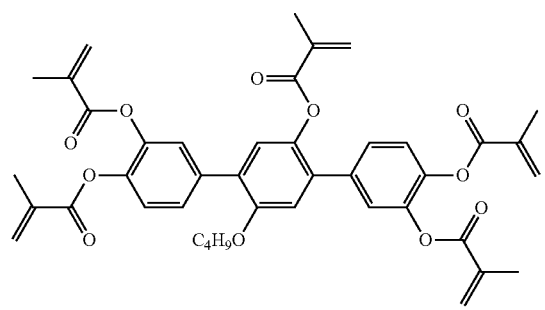
(1-3-163)
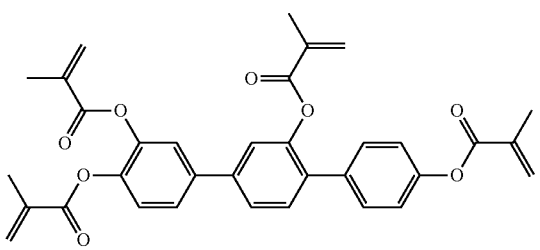
(1-3-164)
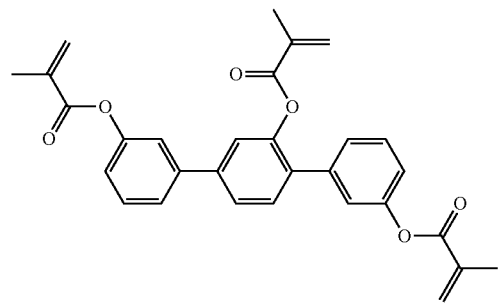
(1-3-165)
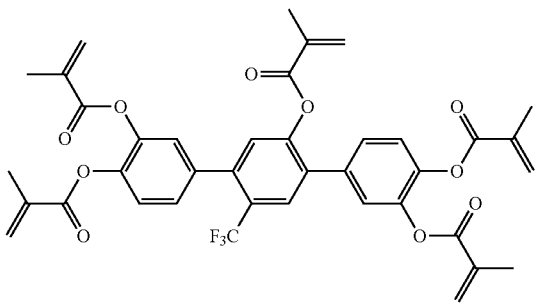

-continued
(1-3-166)
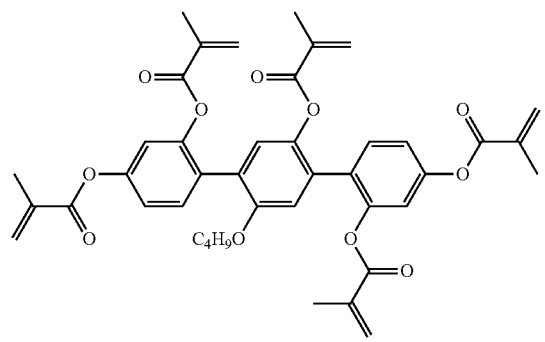
(1-3-167)
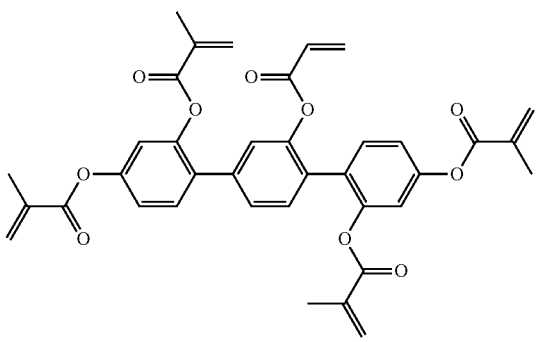
(1-3-168)
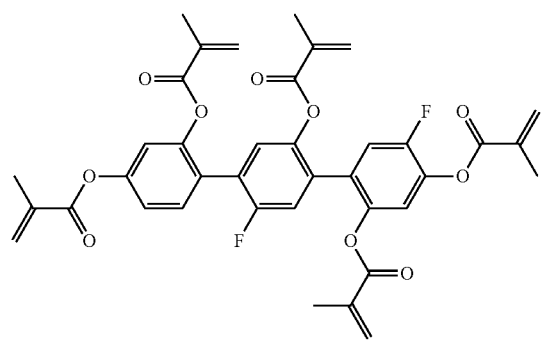
(1-3-169)
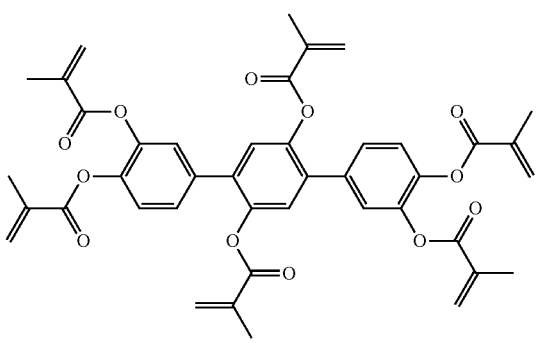
(1-3-170)
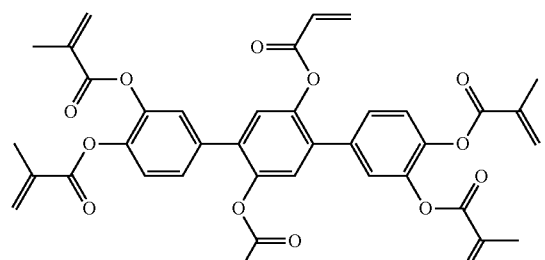
(1-3-171)
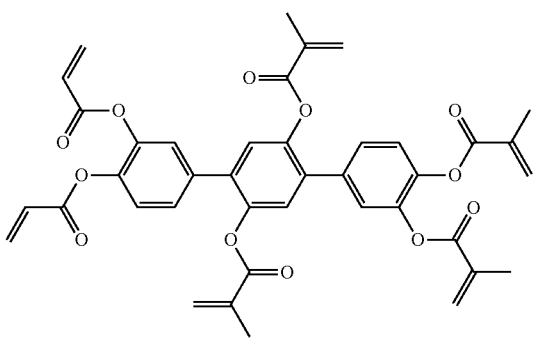
(1-3-172)
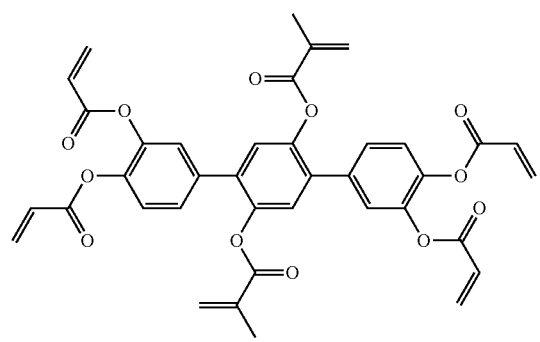
(1-3-173)
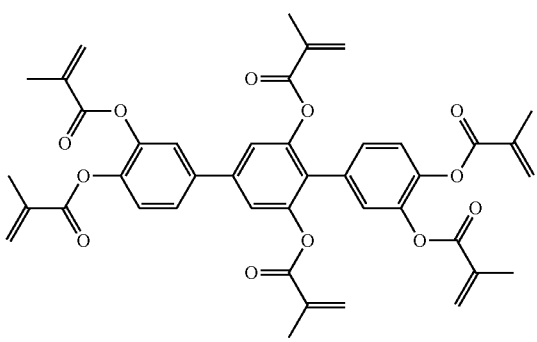

-continued
(1-3-174)
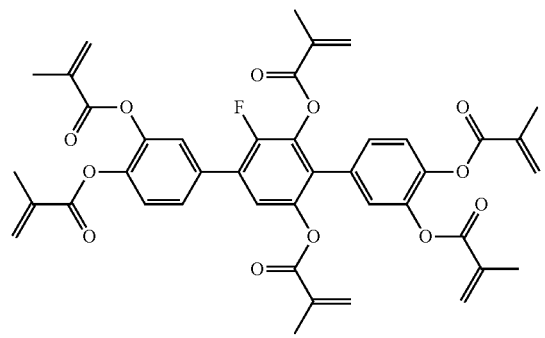
(1-3-175)
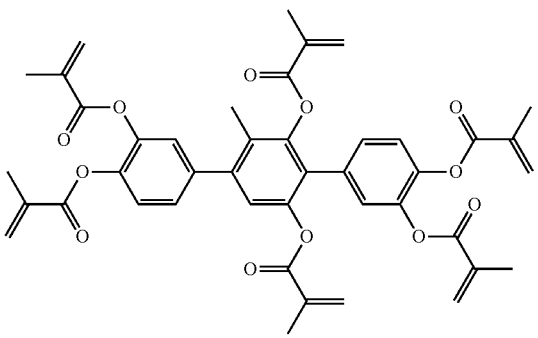
(1-3-176)
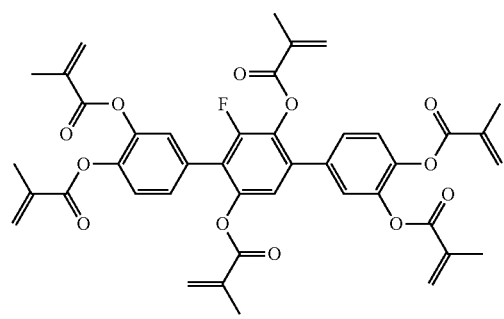
(1-3-177)
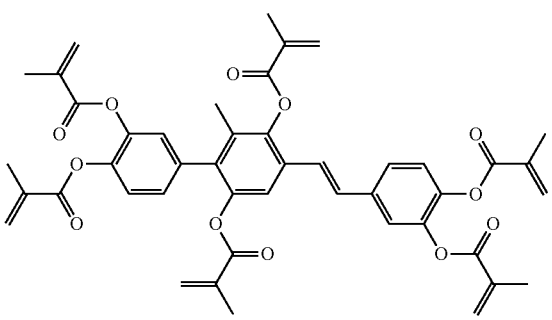
(1-3-178)
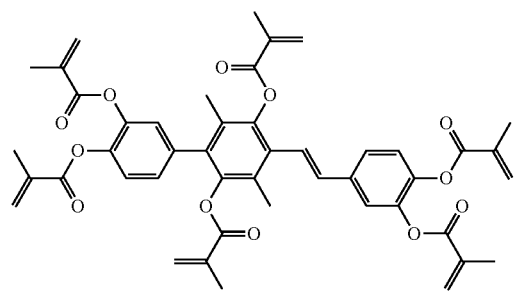
(1-3-179)
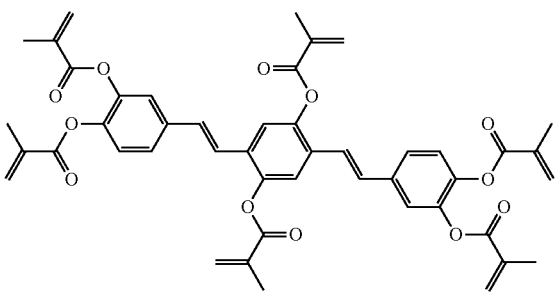
(1-3-180)
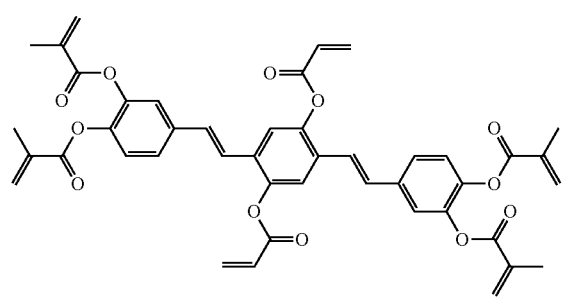
(1-3-181)
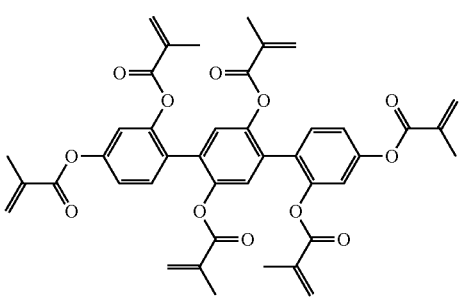

(1-3-182)

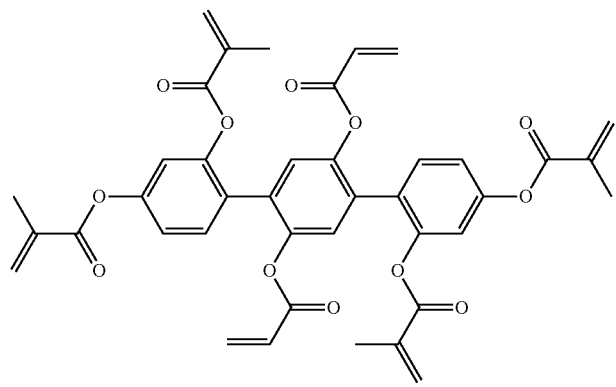

With regard to synthesis of Comparative Compound (R-1), [1,1'-biphenyl]-4,4'-diylbis(2-methacrylate), the synthesis was performed according to the reaction formula below to obtain a colorless crystal of Comparative Compound (R-1).

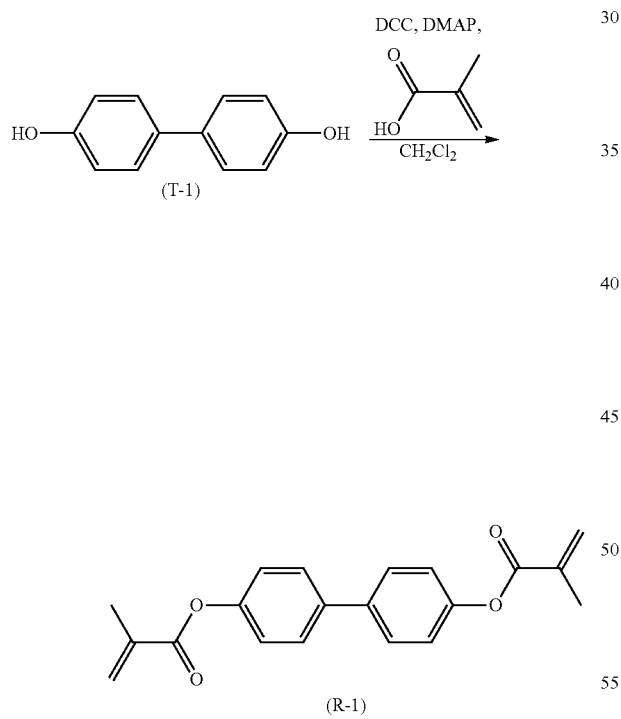

$^1$H-NMR (DMSO-d; δ ppm): 7.24 (d, 4H), 6.96 (d, 4H), 6.41 (d, 2H), 6.26 (d, 2H), 1.98 (s, 6H).

Physical properties of Comparative Compound (R-1) were as described below.

Melting point: 150.0° C.

Comparative Example 1

(Comparison of solubility in liquid crystal composition)

Compound (1-3-89) was added to liquid crystal composition A below at a proportion of 0.3 wt %, and the resulting mixture was heated at 50° C. for 30 minutes. The resulting solution was allowed to stand for two days at room temperature. Then, whether or not a crystal precipitated was visually observed. Meanwhile, Comparative Compound (R-1) was observed in a similar manner. The results are shown in Table 1. In symbols in Table 1, a symbol "O" represents no occurrence of crystal precipitation, and a symbol "x" represents occurrence of crystal precipitation. Table 1 shows that solubility of polymerizable compound of the invention in liquid crystal composition (A) is satisfactory. In addition, components and proportions thereof in liquid crystal composition (A) were as described below.

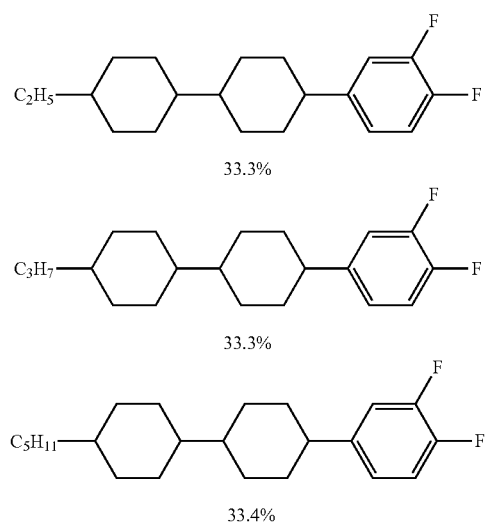

TABLE 1

Comparison of solubility in liquid crystal composition

| Compound | Structural formula | Solubility (for 2 days at room temperature) |
|---|---|---|
| Compound (1-3-1) | [structure: dimethacrylate terphenyl with methacryloyloxy substituent] | ○ |
| Comparative Compound (R-1) | [structure: biphenyl dimethacrylate] | X |

7. Example of Polymerizable Composition

The compounds in Examples were described using symbols according to the definitions in Table 2 below. In Table 2, a configuration of 1,4-cyclohexylene is trans. A parenthesized number next to a symbolized compound in Examples corresponds to the number of a compound. A symbol (-) means any other liquid crystal compound. A proportion (percentage) of a liquid crystal compound is expressed in terms of weight percent (wt %) based on the weight of the liquid crystal composition. Values of physical properties the polymerizable compositions were summarized in a last part. The physical properties were measured according to the methods described above, and measured values were directly described (without extrapolation).

TABLE 2

Method for Description of Compounds using Symbols
R-($A_1$)-$Z_1$-. . . -$Z_n$-($A_n$)-R'

| 1) Left-terminal Group R- | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$- | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |

| 2) Right-terminal Group -R' | Symbol |
|---|---|
| —$C_nH_{2n+1}$ | -n |
| —$OC_nH_{2n+1}$ | —On |
| —$COOCH_3$ | -EMe |
| —CH=$CH_2$ | —V |
| —CH=CH—$C_nH_{2n+1}$ | —Vn |
| —$C_nH_{2n}$—CH=$CH_2$ | -nV |
| —$C_mH_{2m}$—CH=CH—$C_nH_{2n+1}$ | -mVn |
| —CH=$CF_2$ | —VFF |
| —F | —F |
| —Cl | —CL |
| —$OCF_3$ | —OCF3 |

TABLE 2-continued

Method for Description of Compounds using Symbols
R-($A_1$)-$Z_1$-. . . -$Z_n$-($A_n$)-R'

| | |
|---|---|
| —$OCF_2H$ | —OCF2H |
| —$CF_3$ | —CF3 |
| —CF=CH—$CF_3$ | —FVCF3 |
| —C≡N | —C |

| 3) Bonding Group -$Z_n$- | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

| 4) Ring Structure -$A_n$- | Symbol |
|---|---|
| [cyclohexyl] | H |
| [phenyl] | B |
| [3-fluorophenyl] | B(F) |
| [2-fluorophenyl] | B(2F) |

TABLE 2-continued

Method for Description of Compounds using Symbols
R-(A$_1$)-Z$_1$-. . . -Z$_n$-(A$_n$)-R'

| | |
|---|---|
| 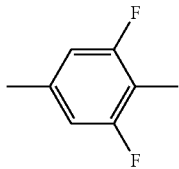 | B(F,F) |
| 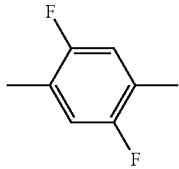 | B(2F,5F) |
| 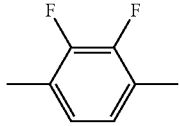 | B(2F,3F) |
| 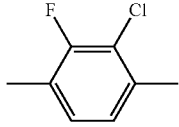 | B(2F,3CL) |
| 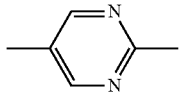 | Py |
| 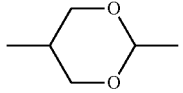 | G |
| 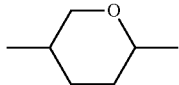 | dh |
| 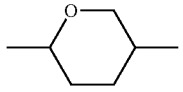 | Dh |
| 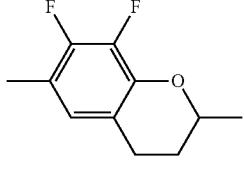 | Cro(7F,8F) |

TABLE 2-continued

Method for Description of Compounds using Symbols
R-(A$_1$)-Z$_1$-. . . -Z$_n$-(A$_n$)-R'

5) Examples of Description

Example 1 3-BB(F,F)XB(F,F)—F

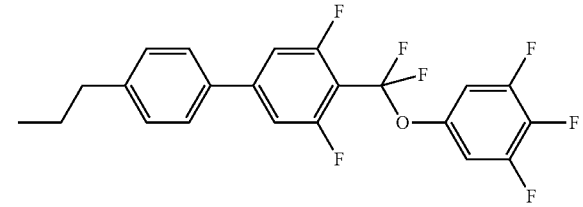 [SMILES: CCCc1ccc(-c2cc(F)c(C(F)(F)Oc3cc(F)c(F)c(F)c3)c(F)c2)cc1]

Example 2 3HBB(2F,3F)—O2

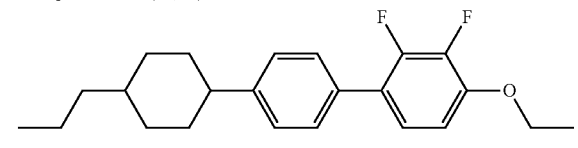

Example 3 3-HH-4

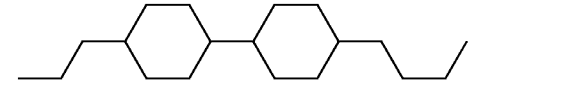 [SMILES: CCCCC1CCC(C2CCC(CCC)CC2)CC1]

Example 4 3HBB(F,F)—F

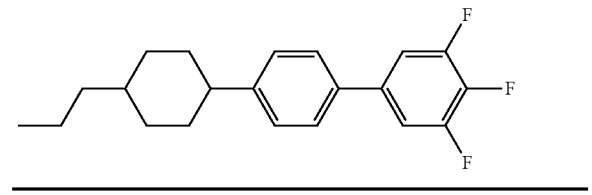

Example 7

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 8% |
| 5-PyBB-F | (6-80) | 10% |
| 5-HBB(F)B-2 | (4-5) | 10% |
| 5-HBB(F)B-3 | (4-5) | 12% |

Compound (1-3-1) below was added to the above composition at a proportion of 0.3 wt %.

(1-3-1)

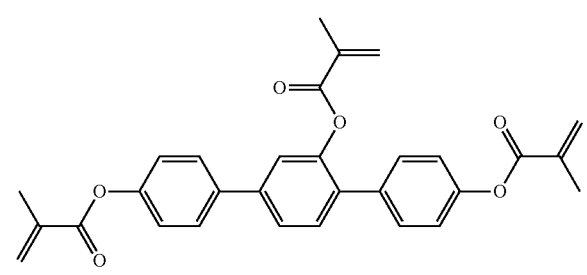

NI=101.2° C.; Δn=0.191; Δε=7.8; η=39.8 mPa·s.

Example 8

| | | |
|---|---|---|
| 2-HB-C | (8-1) | 5% |
| 3-HB-C | (8-1) | 12% |
| 3-HB-O2 | (2-5) | 13% |
| 2-BTB-1 | (2-10) | 3% |
| 3-HHB-F | (6-1) | 4% |
| 3-HHB-1 | (3-1) | 10% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

Compound (1-3-12) below was added to the above composition at a proportion of 0.25 wt %.

(1-3-12)

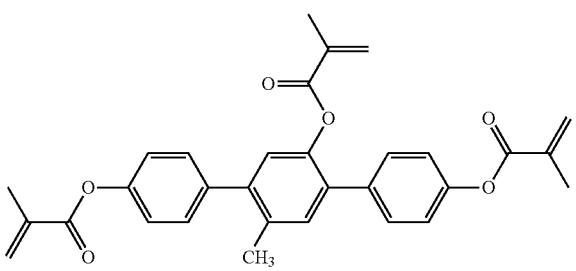

NI=103.3° C.; Δn=0.101; Δδ=4.6; η=18.5 mPa·s.

Example 9

| | | |
|---|---|---|
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 7% |
| 3-HBB(F)-F | (6-23) | 9% |
| 5-HBB(F)-F | (6-23) | 16% |
| 2-HBB-F | (6-22) | 4% |
| 3-HBB-F | (6-22) | 4% |
| 5-HBB-F | (6-22) | 5% |
| 3-HBB(F,F)-F | (6-24) | 5% |
| 5-HBB(F,F)-F | (6-24) | 10% |

Compound (1-3-54) below was added to the above composition at a proportion of 0.1 wt %.

(1-3-54)

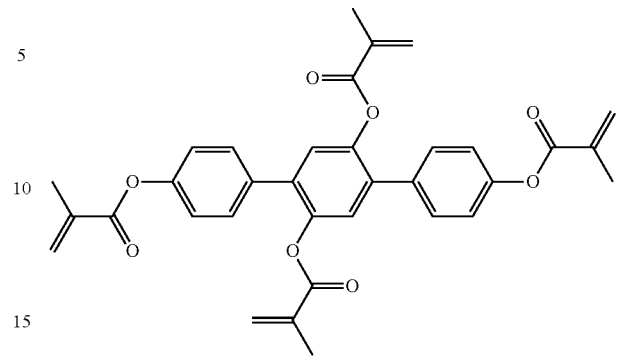

Example 10

| | | |
|---|---|---|
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 6% |
| 3-HBB(F,F)-F | (6-24) | 21% |
| 5-HBB(F,F)-F | (6-24) | 20% |
| 3-H2BB(F,F)-F | (6-27) | 10% |
| 5-HHBB(F,F)-F | (7-6) | 4% |
| 5-HHEBB-F | (7-17) | 2% |
| 3-HH2BB(F,F)-F | (7-15) | 4% |
| 1O1-HBBH-4 | (4-1) | 4% |
| 1O1-HBBH-5 | (4-1) | 4% |

Compound (1-8-16) below was added to the above composition at a proportion of 0.3 wt %.

(1-3-16)

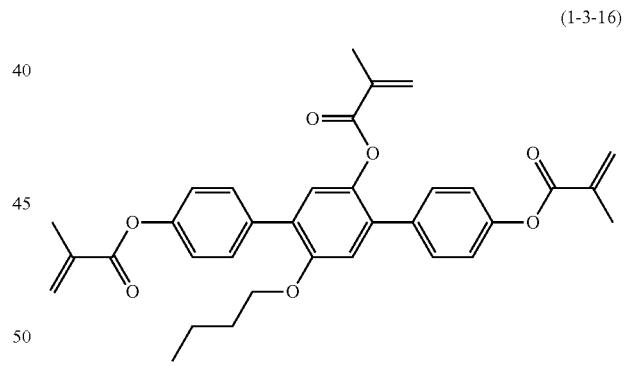

NI=99.6° C.; Δn=0.118; Δε=9.1; η=36.0 mPa·s.

Example 11

| | | |
|---|---|---|
| 5-HB-CL | (5-2) | 9% |
| 3-HH-4 | (2-1) | 8% |
| 3-HHB-1 | (3-1) | 7% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |

-continued

| | | |
|---|---|---|
| 3-HBEB(F,F)-F | (6-39) | 5% |
| 5-HBEB(F,F)-F | (6-39) | 3% |
| 3-HHBB(F,F)-F | (7-6) | 6% |

Compound (1-3-13) below was added to the above composition at a proportion of 0.2 wt %.

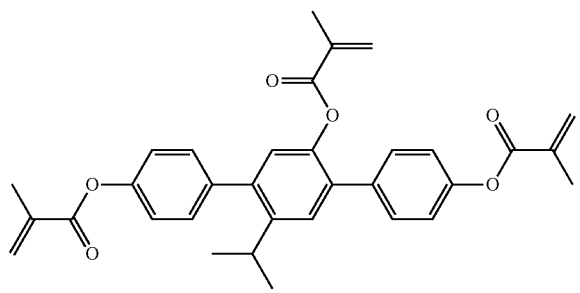

(1-3-13)

NI=83.4° C.; Δn=0.104; Δε=8.6; η=22.9 mPa·s.

Example 12

| | | |
|---|---|---|
| 5-HB-CL | (5-2) | 15% |
| 7-HB(F,F)-F | (5-4) | 3% |
| 3-HH-4 | (2-1) | 11% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 6% |
| 4-H2HB(F,F)-F | (6-15) | 5% |

Compound (1-3-17) below was added to the above composition at a proportion of 0.4 wt %.

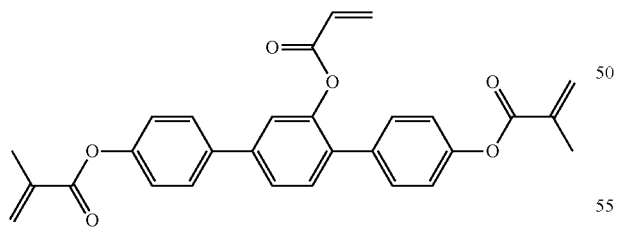

(1-3-17)

NI=72.3° C.; Δn=0.074; Δε=2.8; η=13.8 mPa·s.

Example 13

| | | |
|---|---|---|
| 5-HB-CL | (5-2) | 3% |
| 7-HB(F)-F | (5-3) | 7% |
| 3-HH-4 | (2-1) | 9% |
| 3-HH-EMe | (2-2) | 23% |

-continued

| | | |
|---|---|---|
| 3-HHEB-F | (6-10) | 10% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 5% |

Compound (1-3-2) below was added to the above composition at a proportion of 0.35 wt %.

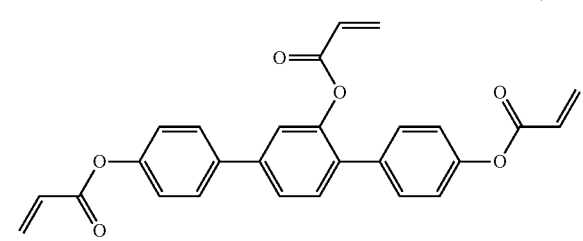

(1-3-2)

NI=81.7° C.; Δn=0.065; Δε=5.4; η=19.1 mPa·s.

Example 14

| | | |
|---|---|---|
| 1V2-BEB(F,F)-C | (8-15) | 6% |
| 3-HB-C | (8-1) | 16% |
| 2-BTB-1 | (2-10) | 10% |
| 5-HH-VFF | (2-1) | 30% |
| 3-HHB-1 | (3-1) | 4% |
| VFF-HHB-1 | (3-1) | 8% |
| VFF2-HHB-1 | (3-1) | 11% |
| 3-H2BTB-2 | (3-17) | 5% |
| 3-H2BTB-3 | (3-17) | 5% |
| 3-H2BTB-4 | (3-17) | 5% |

Compound (1-3-21) below was added to the above composition at a proportion of 0.15 wt %.

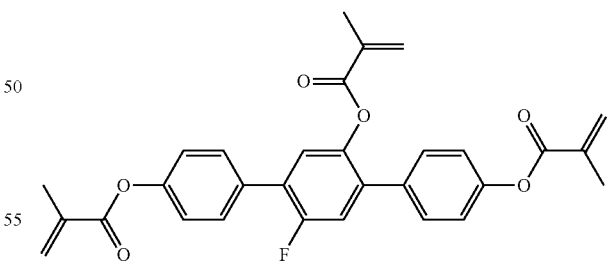

(1-3-21)

NI=83.9° C.; Δn=0.132; Δε=6.3; η=11.7 mPa·s.

Example 15

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 5% |

-continued

| | | |
|---|---|---|
| 5-BB(F)B(F,F)XB(F,F)-F | (7-47) | 4% |
| 3-HH-V | (2-1) | 41% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 11% |
| 3-HHBB(F,F)-F | (7-6) | 4% |

Compound (1-3-28) below was added to the above composition at a proportion of 0.25 wt %.

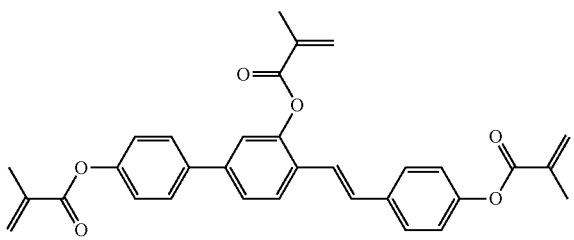

(1-3-28)

NI=83.0° C.; Δn=0.105; Δε=6.1; η=12.0 mPa·s.

Example 16

| | | |
|---|---|---|
| 3-GB(F)B(F,F)XB(F,F)-F | (7-57) | 5% |
| 3-BB(F)B(F,F)XB(F,F)-F | (7-47) | 1% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 5% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

Compound (1-3-34) below was added to the above composition at a proportion of 0.3 wt %.

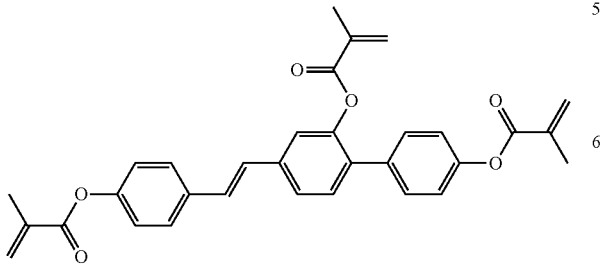

(1-3-34)

NI=82.5° C.; Δn=0.100; Δε=6.7; η=12.4 mPa·s.

Example 17

| | | |
|---|---|---|
| 3-HB-O2 | (2-5) | 10% |
| 5-HB-CL | (5-2) | 12% |
| 3-HBB(F,F)-F | (6-24) | 6% |
| 3-PyB(F)-F | (5-15) | 10% |
| 5-PyB(F)-F | (5-15) | 10% |
| 3-PyBB-F | (6-80) | 11% |
| 4-PyBB-F | (6-80) | 11% |
| 5-PyBB-F | (6-80) | 10% |
| 5-HBB(F)B-2 | (4-5) | 10% |
| 5-HBB(F)B-3 | (4-5) | 10% |

Compound (1-3-58) below was added to the above composition at a proportion of 0.3 wt %.

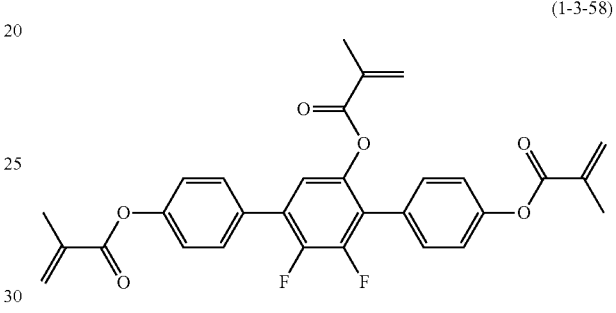

(1-3-58)

NI=101.7° C.; Δn=0.193; Δε=8.2; η=40.3 mPa·s.

Example 18

| | | |
|---|---|---|
| 5-HB-CL | (5-2) | 11% |
| 3-HH-4 | (2-1) | 8% |
| 3-HHB-1 | (3-1) | 5% |
| 3-HHB(F,F)-F | (6-3) | 8% |
| 3-HBB(F,F)-F | (6-24) | 18% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |
| 5-HB-O2 | (2-5) | 2% |

Compounds (1-3-1) and (1-3-12) below were added to the above composition at a proportion of 0.2 wt %, respectively.

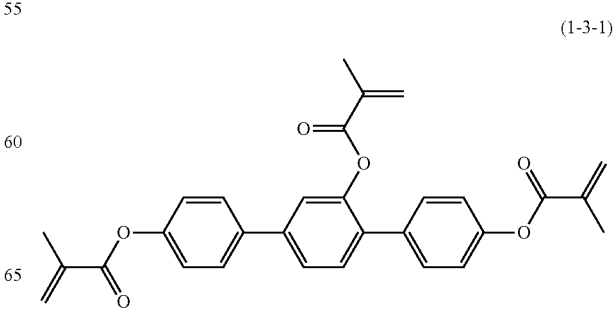

(1-3-1)

(1-3-12)

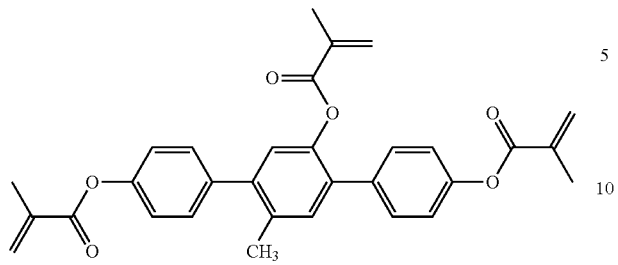

NI=79.9° C.; Δn=0.102; Δε=8.6; η=21.6 mPa·s.

Example 19

| | | |
|---|---|---|
| 3-HB-O2 | (2-5) | 10% |
| 5-HB-CL | (5-2) | 10% |
| 3-HBB(F,F)-F | (6-24) | 10% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 10% |
| 5-PyBB-F | (6-80) | 10% |
| 5-HBB(F)B-2 | (4-5) | 10% |
| 5-HBB(F)B-3 | (4-5) | 10% |

Compound (1-3-56) below was added to the above composition at a proportion of 0.3 wt %.

(1-3-56)

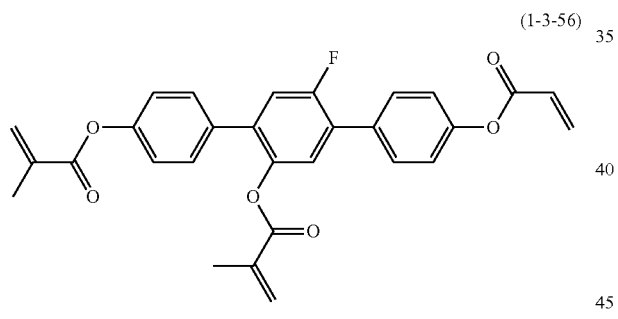

NI=100.8° C.; Δn=0.192; Δε=8.2; η=41.0 mPa·s.

Example 20

| | | |
|---|---|---|
| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

Compound (1-3-57) below was added to the above composition at a proportion of 0.25 wt %.

(1-3-57)

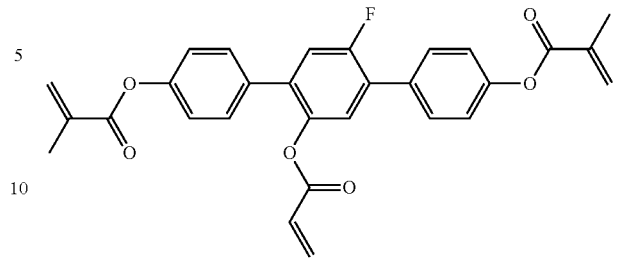

NI=100.5° C.; Δn=0.100; Δε=4.6; η=17.9 mPa·s.

Example 21

| | | |
|---|---|---|
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 21% |
| 5-HBB(F,F)-F | (6-24) | 20% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |

Compound (1-3-64) below was added to the above composition at a proportion of 0.1 wt %.

(1-3-64)

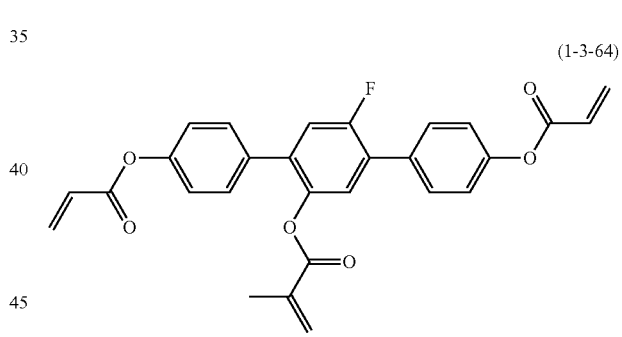

NI=97.8° C.; Δn=0.116; Δε=9.0; η=35.0 mPa·s.

Example 22

| | | |
|---|---|---|
| 5-HB-CL | (5-2) | 11% |
| 3-HH-4 | (2-1) | 8% |
| 3-HHB-1 | (3-1) | 5% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

Compound (1-3-65) below was added to the above composition at a proportion of 0.3 wt % respectively.

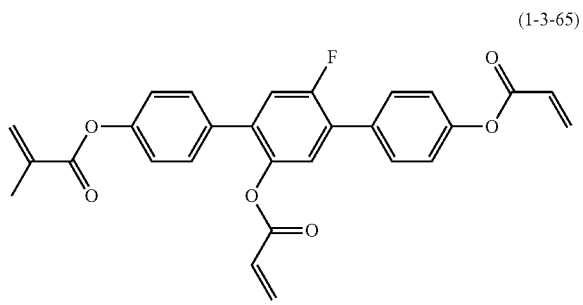
(1-3-65)

NI=80.2° C.; Δn=0.103; Δε=8.7; η=22.4 mPa·s.

Example 23

| 5-HB-CL       | (5-2)   | 3%  |
|---------------|---------|-----|
| 7-HB(F)-F     | (5-3)   | 7%  |
| 3-HH-4        | (2-1)   | 9%  |
| 3-HH-EMe      | (2-2)   | 23% |
| 3-HHEB-F      | (6-10)  | 8%  |
| 5-HHEB-F      | (6-10)  | 8%  |
| 3-HHEB(F,F)-F | (6-12)  | 10% |
| 4-HHEB(F,F)-F | (6-12)  | 5%  |
| 4-HGB(F,F)-F  | (6-103) | 5%  |
| 5-HGB(F,F)-F  | (6-103) | 6%  |
| 2-H2GB(F,F)-F | (6-106) | 4%  |
| 3-H2GB(F,F)-F | (6-106) | 5%  |
| 5-GHB(F,F)-F  | (6-109) | 7%  |

Compound (1-3-56) below was added to the above composition at a proportion of 0.2 wt %.

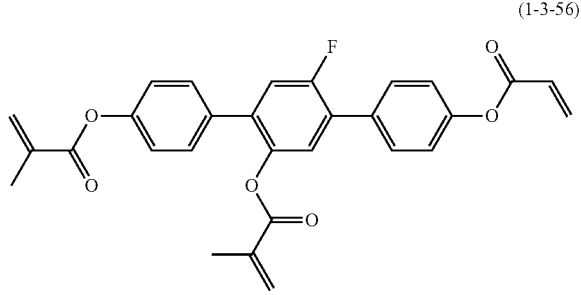 [SMILES: C=CC(=O)Oc1ccc(-c2cc(OC(=O)C(=C)C)c(-c3ccc(OC(=O)C(=C)C)cc3)cc2F)cc1]
(1-3-56)

NI=79.4° C.; Δn=0.064; Δε=5.7; η=19.9 mPa·s.

Example 24

| 1V2-BEB(F,F)-C | (8-15)  | 8%  |
|----------------|---------|-----|
| 3-HB-C         | (8-1)   | 16% |
| 2-BTB-1        | (2-10)  | 10% |
| 5-HH-VFF       | (2-1)   | 30% |
| 3-HHB-1        | (3-1)   | 4%  |
| VFF-HHB-1      | (3-1)   | 8%  |
| VFF2-HHB-1     | (3-1)   | 11% |
| 3-H2BTB-2      | (3-17)  | 5%  |
| 3-H2BTB-3      | (3-17)  | 4%  |
| 3-H2BTB-4      | (3-17)  | 4%  |

Compounds (1-3-56) and (1-3-65) below were added to the above composition at a proportion of 0.2 wt %, respectively.

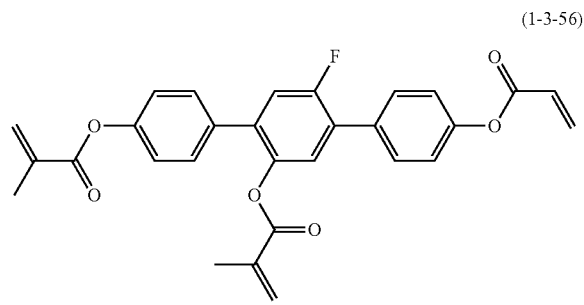 [SMILES: C=CC(=O)Oc1ccc(-c2cc(OC(=O)C(=C)C)c(-c3ccc(OC(=O)C(=C)C)cc3)cc2F)cc1]
(1-3-56)

(1-3-65)

NI=80.6° C.; Δn=0.131; Δε=7.7; η=12.4 mPa·s.

Example 25

| 5-HB(F)B(F,F)XB(F,F)-F | (7-41)  | 5%  |
|------------------------|---------|-----|
| 3-BB(F)B(F,F)XB(F,F)-F | (7-47)  | 3%  |
| 4-BB(F)B(F,F)XB(F,F)-F | (7-47)  | 7%  |
| 5-BB(F)B(F,F)XB(F,F)-F | (7-47)  | 3%  |
| 3-HH-V                 | (2-1)   | 41% |
| 3-HH-V1                | (2-1)   | 7%  |
| 3-HHEH-5               | (3-13)  | 3%  |
| 3-HHB-1                | (3-1)   | 4%  |
| V-HHB-1                | (3-1)   | 5%  |
| V2-BB(F)B-1            | (3-6)   | 5%  |
| 1V2-BB-F               | (5-1)   | 3%  |
| 3-BB(F,F)XB(F,F)-F     | (6-97)  | 11% |
| 3-HHBB(F,F)-F          | (7-6)   | 3%  |

Compound (1-3-57) below was added to the above composition at a proportion of 0.3 wt %.

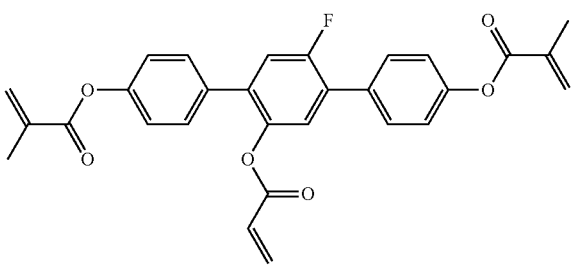
(1-3-57)

NI=81.9° C.; Δn=0.105; Δε=6.3; η=12.0 mPa·s.

Example 26

| 3-GB(F)B(F,F)XB(F,F)-F | (7-57) | 5% |
|------------------------|--------|-----|
| 3-BB(F)B(F,F)XB(F,F)-F | (7-47) | 3% |
| 4-BB(F)B(F,F)XB(F,F)-F | (7-47) | 7% |

| | | |
|---|---|---|
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

Compound (1-3-64) below was added to the above composition at a proportion of 0.3 wt %.

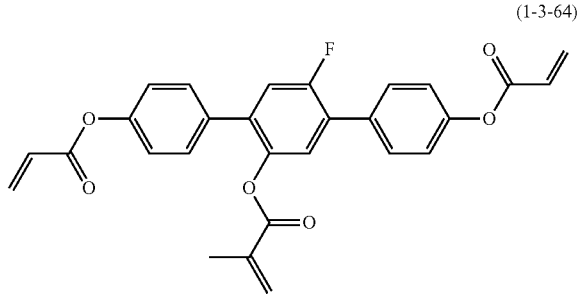 [SMILES: C=CC(=O)Oc1ccc(-c2cc(OC(=O)C(=C)C)c(-c3ccc(OC(=O)C=C)cc3)cc2F)cc1]

(1-3-64)

NI=81.3° C.; Δn=0.103; Δε=7.4; η=12.8 mPa·s.

Example 27

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 8% |
| 5-PyBB-F | (6-80) | 10% |
| 5-HBB(F)B-2 | (4-5) | 10% |
| 5-HBB(F)B-3 | (4-5) | 12% |

Compound (1-2-1) below was added to the above composition at a proportion of 0.3 wt %.

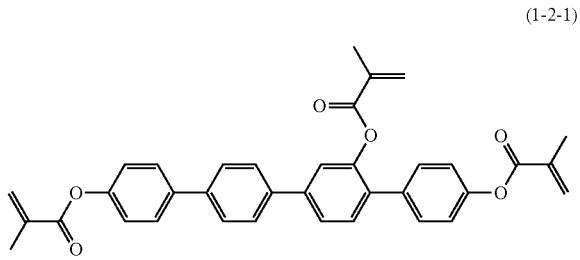 [SMILES: C=C(C)C(=O)Oc1ccc(-c2ccc(-c3ccc(-c4ccc(OC(=O)C(=C)C)cc4)c(OC(=O)C(=C)C)c3)cc2)cc1]

(1-2-1)

NI=101.2° C.; Δn=0.191; Δε=7.8; η=39.8 mPa·s.

Example 28

| | | |
|---|---|---|
| 2-HB-C | (8-1) | 5% |
| 3-HB-C | (8-1) | 12% |
| 3-HB-O2 | (2-5) | 13% |
| 2-BTB-1 | (2-10) | 3% |
| 3-HHB-F | (6-1) | 4% |
| 3-HHB-1 | (3-1) | 10% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

Compound (1-3-23) below was added to the above composition at a proportion of 0.25 wt % respectively.

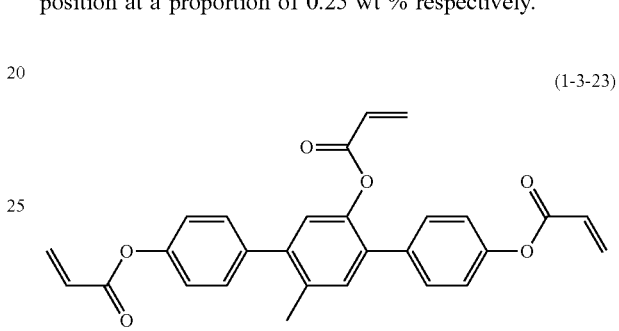

(1-3-23)

NI=103.3° C.; Δn=0.101; Δε=4.6; η=18.5 mPa·s.

Example 29

| | | |
|---|---|---|
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 7% |
| 3-HBB(F)-F | (6-23) | 9% |
| 5-HBB(F)-F | (6-23) | 16% |
| 2-HBB-F | (6-22) | 4% |
| 3-HBB-F | (6-22) | 4% |
| 5-HBB-F | (6-22) | 5% |
| 3-HBB(F,F)-F | (6-24) | 5% |
| 5-HBB(F,F)-F | (6-24) | 10% |

Compound (1-3-40) below was added to the above composition at a proportion of 0.1 wt %.

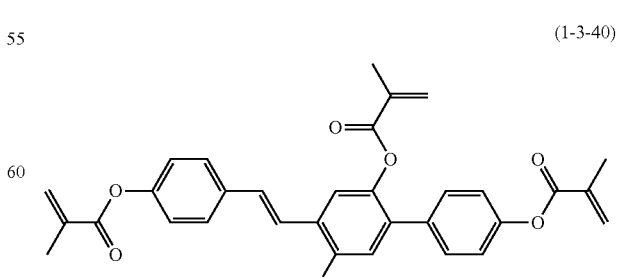

(1-3-40)

NI=86.7° C.; Δn=0.115; Δε=5.7; η=24.7 mPa·s.

Example 30

| | | |
|---|---|---|
| 3-HHB(F,F)-F | (6-3) | 9% |
| 3-H2HB(F,F)-F | (6-15) | 8% |
| 4-H2HB(F,F)-F | (6-15) | 8% |
| 5-H2HB(F,F)-F | (6-15) | 6% |
| 3-HBB(F,F)-F | (6-24) | 21% |
| 5-HBB(F,F)-F | (6-24) | 20% |
| 3-H2BB(F,F)-F | (6-27) | 10% |
| 5-HHBB(F,F)-F | (7-6) | 4% |
| 5-HHEBB-F | (7-17) | 2% |
| 3-HH2BB(F,F)-F | (7-15) | 4% |
| 1O1-HBBH-4 | (4-1) | 4% |
| 1O1-HBBH-5 | (4-1) | 4% |

Compound (1-3-50) below was added to the above composition at a proportion of 0.3 wt % respectively.

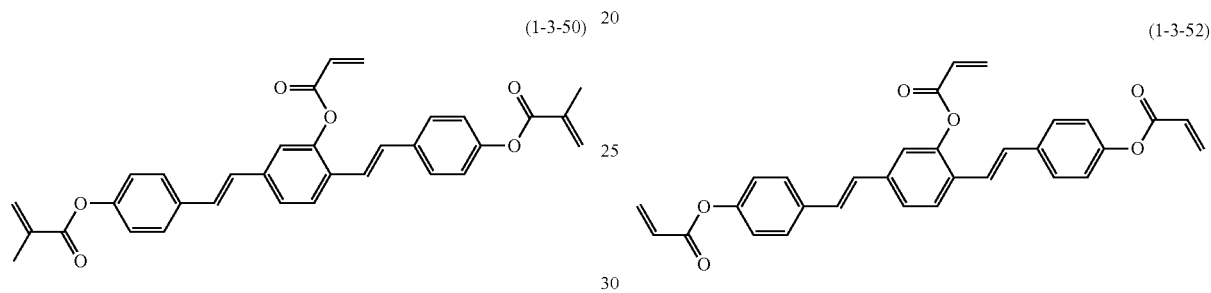

(1-3-50)

NI=99.6° C.; Δn=0.118; Δε=9.1; η=36.0 mPa·s.

Example 31

| | | |
|---|---|---|
| 5-HB-CL | (5-2) | 9% |
| 3-HH-4 | (2-1) | 8% |
| 3-HHB-1 | (3-1) | 7% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

Compound (1-3-51) below was added to the above composition at a proportion of 0.2 wt %.

(1-3-51)

NI=83.4° C.; Δn=0.104; Δε=8.6; η=22.9 mPa·s.

Example 32

| | | |
|---|---|---|
| 5-HB-CL | (5-2) | 15% |
| 7-HB(F,F)-F | (5-4) | 3% |
| 3-HH-4 | (2-1) | 11% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 6% |
| 4-H2HB(F,F)-F | (6-15) | 5% |

Compound (1-3-52) below was added to the above composition at a proportion of 0.4 wt %.

(1-3-52)

NI=72.3° C.; Δn=0.074; Δε=2.8; η=13.8 mPa·s.

Example 33

| | | |
|---|---|---|
| 5-HB-CL | (5-2) | 3% |
| 7-HB(F)-F | (5-3) | 7% |
| 3-HH-4 | (2-1) | 9% |
| 3-HH-EMe | (2-2) | 23% |
| 3-HHEB-F | (6-10) | 10% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 5% |

Compound (1-3-66) below was added to the above composition at a proportion of 0.35 wt %.

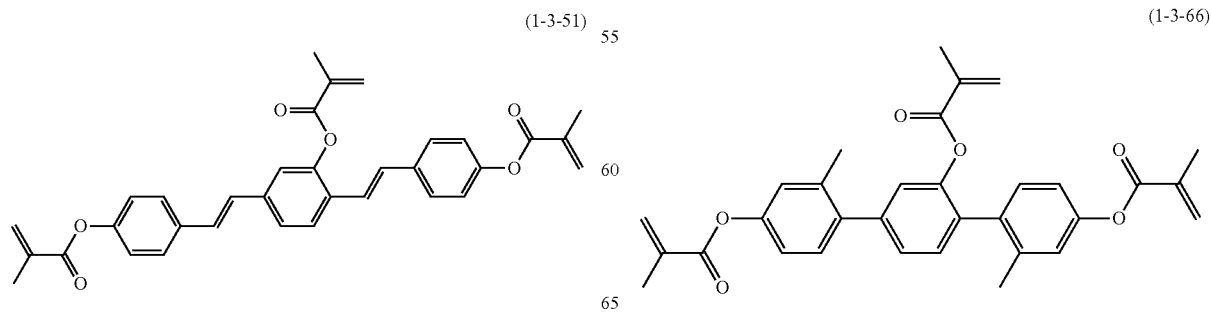

(1-3-66)

NI=81.7° C.; Δn=0.065; Δε=5.4; η=19.1 mPa·s.

Example 34

| | | |
|---|---|---|
| 1V2-BEB(F,F)-C | (8-15) | 6% |
| 3-HB-C | (8-1) | 16% |
| 2-BTB-1 | (2-10) | 10% |
| 5-HH-VFF | (2-1) | 30% |
| 3-HHB-1 | (3-1) | 4% |
| VFF-HHB-1 | (3-1) | 8% |
| VFF2-HHB-1 | (3-1) | 11% |
| 3-H2BTB-2 | (3-17) | 5% |
| 3-H2BTB-3 | (3-17) | 5% |
| 3-H2BTB-4 | (3-17) | 5% |

Compound (1-3-154) below was added to the above composition at a proportion of 0.15 wt %.

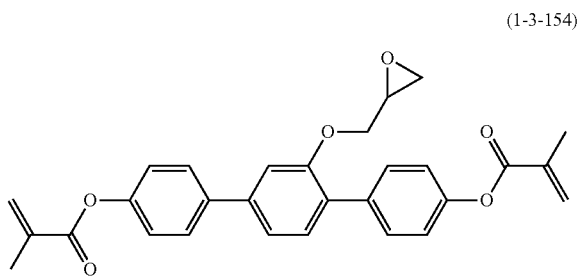 [SMILES: C=C(C)C(=O)Oc1ccc(-c2ccc(-c3ccc(OC(=O)C(=C)C)cc3)c(OCC3CO3)c2)cc1]

(1-3-154)

NI=83.9° C.; Δn=0.132; Δε=6.3; η=11.7 mPa·s.

Example 35

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 4% |
| 3-HH-V | (2-1) | 41% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 11% |
| 3-HHBB(F,F)-F | (7-6) | 4% |

Compounds (1-2-1) and (1-3-155) were added to the above composition at a proportion of 0.2 wt %, respectively.

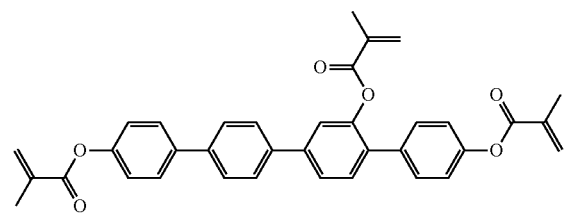

(1-2-1)

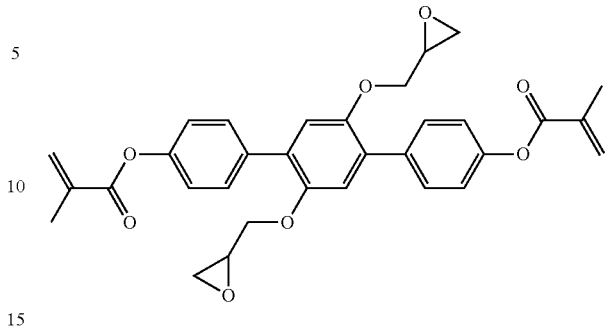

(1-3-155)

NI=83.0° C.; Δn=0.105; Δε=6.1; η=12.0 mPa·s.

INDUSTRIAL APPLICABILITY

A liquid crystal display device having a mode such as a PSA mode can be produced by polymerizing a polymerizable composition containing compound (1) and a liquid crystal composition. The polymerizable compound can also be used as a raw material of an optical anisotropic body.

The invention claimed is:

1. A polymerizable compound, represented by formula (1):

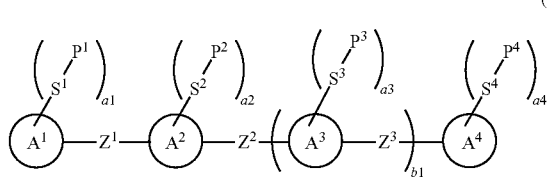

(1)

wherein in formula (1), $P^1$, $P^2$, $P^3$ and $P^4$ are a polymerizable group;

$S^1$, $S^2$, $S^3$ and $S^4$ are independently a single bond or alkylene having 1 to 10 carbons, and in the alkylene, at least one —$CH_2$— may be replaced by —O—, —COO—, —OCO— or —OCOO—, at least one —$CH_2$—$CH_2$— may be replaced by —CH=CH— or —C≡C—, and at least one hydrogen may be replaced by fluorine or chlorine;

a1, a3, and a4 are independently 0, 1, 2, 3 or 4, a2 is 1, 2, 3 or 4, and a sum of a1, a2, a3 and a4 is 3 to 10;

ring $A^1$ and ring $A^4$ are independently phenyl, pyrimidyl, pyridyl, naphthyl, cyclohexyl, cyclohexenyl, tetrahydropyranyl or 1,3-dioxanyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

ring $A^2$ and ring $A^3$ are independently 1,4-phenylene, pyrimidine-2,5-diyl, pyridine-2,5-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, 1,4-cyclohexylene, 1,4-cyclohexenylene, tetrahydropyran-2,5-diyl or 1,3-dioxane-2,5-diyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

$Z^1$, $Z^2$ and $Z^3$ are independently a single bond or alkylene having 1 to 10 carbons, and in the alkylene, at least one —$CH_2$— may be replaced by —O—, —CO—, —COO— or —OCO—, with a proviso that a total number of —COO— and —OCO— in $Z^1$, $Z^2$ and $Z^3$ is 0 or 1, at least one —$CH_2$—$CH_2$— may be replaced by —CH=CH—, —C($CH_3$)=CH—, —CH=C($CH_3$)— or —C($CH_3$)=C($CH_3$)—, and at least one hydrogen may be replaced by fluorine or chlorine; and b1 is 0 or 1.

2. The polymerizable compound of claim 1, wherein, in formula (1), $P^1$, $P^2$, $P^3$ and $P^4$ are acryloyloxy or methacryloyloxy;

$S^1$, $S^2$, $S^3$ and S4 are independently a single bond or alkylene having 1 to 10 carbons, and in the alkylene, one of —$CH_2$— may be replaced by —O—, —COO—, —OCO— or —OCOO—one of —$CH_2$—$CH_2$— may be replaced by —CH=CH— or —C≡C—, and at least one hydrogen may be replaced by fluorine or chlorine;

a1, a3 and a4 are independently 0, 1, 2, 3 or 4, a2 is 1, 2, 3 or 4, and a sum of a1, a2, a3 and a4 is 3 to 10;

ring $A^1$ and ring $A^4$ are independently phenyl, pyrimidyl, pyridyl or naphthyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

ring $A^2$ and ring $A^3$ are independently 1,4-phenylene, pyrimidine-2,5-diyl, pyridine-2,5-diyl, naphthalene-1,4-diyl, naphthalene-1,5-diyl, naphthalene-2,6-diyl, 1,4-cyclohexylene, tetrahydropyran-2,5-diyl or 1,3-dioxane-2,5-diyl, and in the rings, at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

$Z^1$, $Z^2$ and $Z^3$ are independently a single bond, alkylene having 1 to 5 carbons, —CO—, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—($CH_3$)C=CH—, —C($CH_3$)=C($CH_3$)—COO—, —OCO—C($CH_3$)=C($CH_3$)—, —CO—CH=CH—, —CH=CH—CO—, —C($CH_3$)=C($CH_3$)—, —CH=CH—$CH_2$O—, —$OCH_2$—CH=CH—, —CH=CH—$OCH_2$— or —$CH_2$O—CH=CH—, with a proviso that a total number of —COO— and —OCO— in $Z^1$, $Z^2$ and $Z^3$ is 0 or 1; and b1 is 0 or 1.

3. The polymerizable compound of claim 1, represented by formula (1-1):

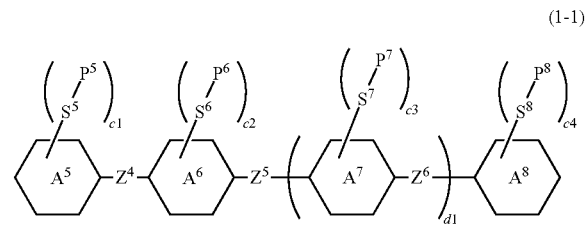

(1-1)

wherein, in formula (1-1), $P^5$, $P^6$, $P^7$ and $P^8$ are independently acryloyloxy or methacryloyloxy;

$S^5$, $S^6$, $S^7$ and $S^8$ are independently a single bond or alkylene having 1 to 5 carbons, and in the alkylene, one of —$CH_2$—may be replaced by —O—, —COO— or —OCO—, and one of —$CH_2$—$CH_2$—may be replaced by —CH=CH—;

c1, c3 and c4 are independently 0, 1 or 2, c2 is 1 or 2, and a sum of c1, c2, c3 and c4 is 3 to 6;

ring $A^5$ and ring $A^8$ are independently phenyl in which at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

ring $A^6$ and ring $A^7$ are independently 1,4-phenylene in which at least one hydrogen may be replaced by halogen, alkyl having 1 to 12 carbons, alkoxy having 1 to 12 carbons, alkyl having 1 to 12 carbons in which at least one hydrogen is replaced by halogen, or alkoxy having 1 to 12 carbons in which at least one hydrogen is replaced by halogen;

$Z^4$, $Z^5$ and $Z^6$ are independently a single bond, alkylene having 1 to 5 carbons, —CO—, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—($CH_3$)C=CH—, —C($CH_3$)=C($CH_3$)—COO—, —OCO—C($CH_3$)=C($CH_3$)—, —CO—CH=CH—, —CH=CH—CO—, —C($CH_3$)=C($CH_3$)—, —CH=CH—$CH_2$O—, —$OCH_2$—CH=CH—, —CH=CH—$OCH_2$— or —$CH_2$O—CH=CH—, with a proviso that a total number of —COO— and —OCO— in $Z^4$, $Z^5$ and $Z^6$ is 0 or 1; and d1 is 0 or 1.

4. The polymerizable compound of claim 1, represented by any one of formula (1-1-1) or (1-1-2):

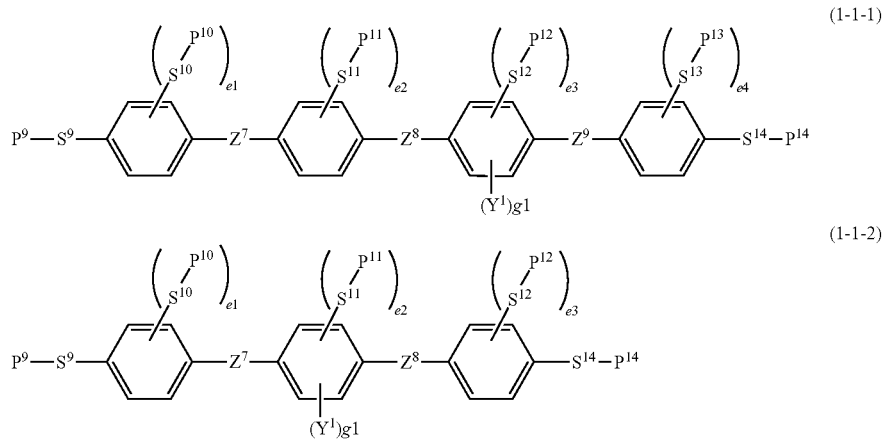

wherein, in formulas (1-1-1) and (1-1-2), $P^9$, $P^{10}$, $P^{11}$, $P^{12}$, $P^{13}$ and $P^{14}$ are independently acryloyloxy or methacryloyloxy;

$S^{11}$, $S^{12}$, $S^{13}$, $S^{14}$, $S^{15}$ and $S^{16}$ are independently a single bond or alkylene having 1 to 5 carbons, and in the alkylene, one of —$CH_2$— may be replaced by —O—, —COO— or —OCO—, and one of —$CH_2$—$CH_2$— may be replaced by —CH=CH—;

e1, e3 and e4 are independently 0, 1 or 2, e2 is 1 or 2, and a sum of e1, e2, e3 and e4 is 1 to 4;

$Z^7$, $Z^8$ and $Z^9$ are independently a single bond, alkylene having 1 to 5 carbons, —CO—, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—($CH_3$)C=CH—, —C($CH_3$)=C($CH_3$)—COO—, —OCO—C($CH_3$)=C($CH_3$)—, —CO—CH=CH—, —CH=CH—CO—, —C($CH_3$)=C($CH_3$)—, —CH=CH—$CH_2$O—, —O$CH_2$—CH=CH—, —CH=CH—O$CH_2$— or —$CH_2$O—CH=CH—, with a proviso that a total number of —COO— and —OCO— in $Z^7$, $Z^8$ and $Z^9$ in formula (1-1-1) or in $Z^7$ and $Z^8$ in formula (1-1-2) is 0 or 1;

g1 is 0, 1 or 2; and $Y^1$ is halogen, alkyl having 1 to 5 carbons, alkoxy having 1 to 5 carbons, alkyl having 1 to 5 carbons in which at least one hydrogen is replaced by halogen, or alkoxy having 1 to 5 carbons in which at least one hydrogen is replaced by halogen.

5. The polymerizable compound of claim 1, represented by formula (1-2) or (1-3):

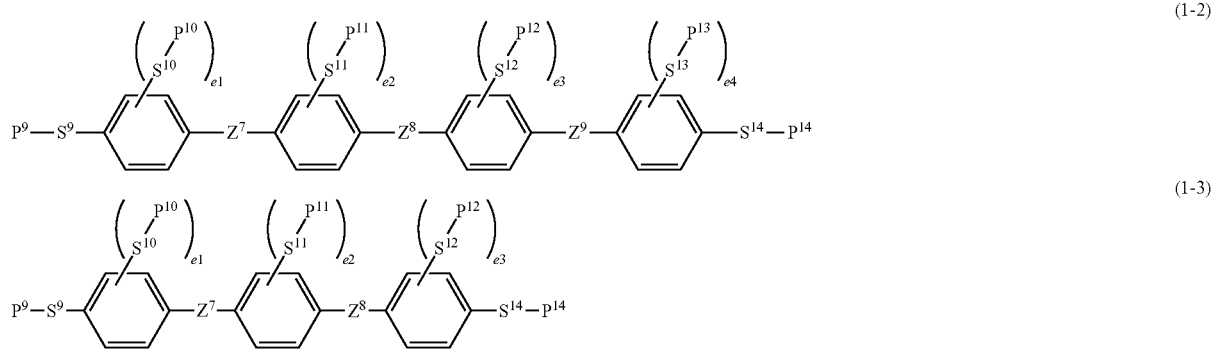

wherein, in formulas (1-2) and (1-3), $P^9$, $P^{10}$, $P^{11}$, $P^{12}$, $P^{13}$ and $P^{14}$ are independently acryloyloxy or methacryloyloxy;

$S^9$, $S^{10}$, $S^{11}$, $S^{12}$, $S^{13}$ and $S^{14}$ are independently a single bond or alkylene having 1 to 5 carbons, and in the alkylene, one of —$CH_2$— may be replaced by —O—, —COO— or —OCO—, and one of —$CH_2$—$CH_2$— may be replaced by —CH=CH—;

e1, e3 and e4 are independently 0, 1 or 2, e2 is 1 or 2, and a sum of e1, e2, e3 and e4 is 1 to 4;

$Z^7$, $Z^8$ and $Z^9$ are independently a single bond, alkylene having 1 to 5 carbons, —CO—, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—($CH_3$)C=CH—, —C($CH_3$)=C($CH_3$)—COO—, —OCO—C($CH_3$)=C($CH_3$)—, —CO—CH=CH—, —CH=CH—CO—, —C($CH_3$)=C($CH_3$)—, —CH=CH—$CH_2$O—, —O$CH_2$—CH=CH—, —CH=CH—O$CH_2$— or —$CH_2$—O—CH=CH—, with a proviso that a total number of —COO— and —OCO— in $Z^7$, $Z^8$ and $Z^9$ in formula (1-2) or in $Z^7$ and $Z^8$ in formula (1-3) is 0 or 1.

6. The polymerizable compound of claim 1, represented by formula (1-4) or (1-5):

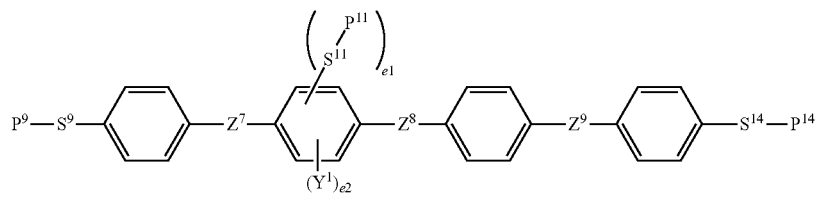
(1-4)

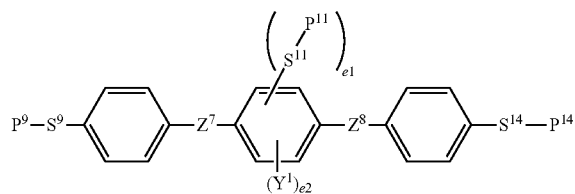
(1-5)

wherein, in formulas (1-4) and (1-5), $P^9$, $P^{11}$ and $P^{14}$ are independently acryloyloxy or methacryloyloxy;

$Y^1$ is halogen, alkyl having 1 to 5 carbons, alkoxy having 1 to 5 carbons, alkyl having 1 to 5 carbons in which at least one hydrogen is replaced by halogen, or alkoxy having 1 to 5 carbons in which at least one hydrogen is replaced by halogen;

$S^9$, $S^{11}$ and $S^{14}$ are independently a single bond, —CH$_2$—, —CH$_2$O—, —OCH$_2$—, —COO—, —OCO—, —CH=CH—, —CH=C—, —CH$_2$CH$_2$O—, —OCH$_2$CH$_2$—, —CH=CH—O— or —O—CH=CH—;

e1 is 1 or 2, and e2 is 0, 1 or 2; and $Z^7$, $Z^8$ and $Z^9$ are independently a single bond, —CO—, —COO—, —CH=CH—, —CH=CH—COO—, —C(CH$_3$)=CH—COO—, —CH=C(CH$_3$)—COO—, —C(CH$_3$)=C(CH$_3$)—COO—, —COCH=CH—, —C(CH$_3$)=C(CH$_3$)—, —CH=CH—CH$_2$O— or —CH=CH—OCH$_2$—, with a proviso that a total number of —COO— and —OCO— in $Z^7$, $Z^8$ and $Z^9$ in formula (1-4) or in $Z^7$ and $Z^8$ in formula (1-5) is 0 or 1.

7. The polymerizable compound of claim 6, wherein, in formula (1-4) or (1-5), at least one of $P^9$, e1 pieces of $P^{11}$, and $P^{14}$ is acryloyloxy, and at least one thereof is methacryloyloxy.

8. The polymerizable compound of claim 1, represented by formula (1-6) or (1-7):

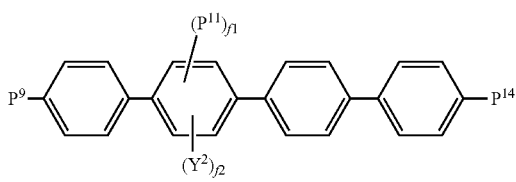
(1-6)

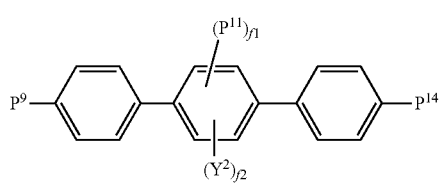
(1-7)

wherein, in formulas (1-6) and (1-7), $P^9$, $P^{11}$ and $P^{14}$ are independently acryloyloxy or methacryloyloxy;

$Y^2$ is halogen, alkyl having 1 to 5 carbons or alkoxy having 1 to 5 carbons; and f1 is 1 or 2, and f2 is 0, 1 or 2.

9. The polymerizable compound of claim 8, wherein, in formula (1-6) or (1-7), at least one of $P^9$, f1 pieces of $P^{11}$, and $P^{14}$ is acryloyloxy, and at least one thereof is methacryloyloxy.

10. The polymerizable compound of claim 1, represented by formula (1-8) or (1-9):

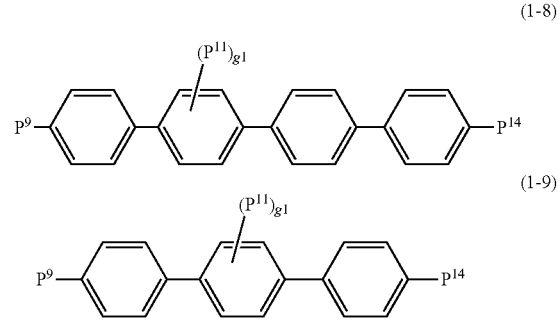
(1-8)

(1-9)

wherein, in formula (1-8) or (1-9), $P^9$, $P^{11}$ and $P^{14}$ are independently acryloyloxy or methacryloyloxy; and g1 is 1 or 2.

11. A polymerizable composition, containing at least one of the compounds of claim 1.

12. The polymerizable composition of claim 11, further containing at least one compound selected from the group of compounds represented by formulas (2) to (4):

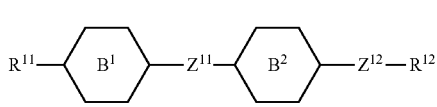
(2)

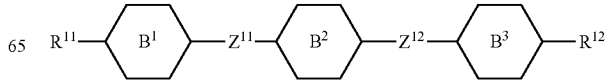
(3)

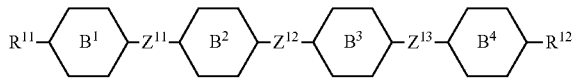
(4)

wherein, in formulas (2) to (4),
R$^{11}$ and R$^{12}$ are independently alkyl having 1 to 10 carbons or alkenyl having 2 to 12 carbons, and in the alkyl or the alkenyl, at least one —CH$_2$— may be replaced by —O— and at least one hydrogen may be replaced by fluorine;
ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and
Z$^{11}$, Z$^{12}$, and Z$^{13}$ are independently a single bond, —CH$_2$CH$_2$—, —CH=CH—, —C≡C— or —COO—.

13. The polymerizable composition of claim 11, further containing at least one compound selected from the group of compounds represented by formulas (5) to (7):

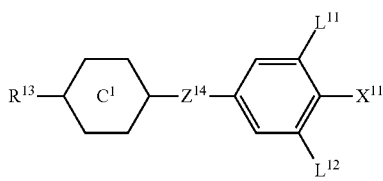
(5)

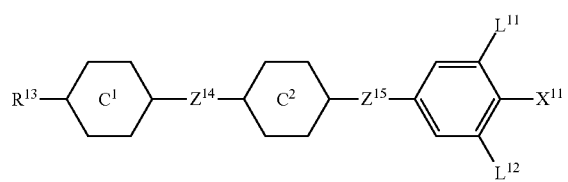
(6)

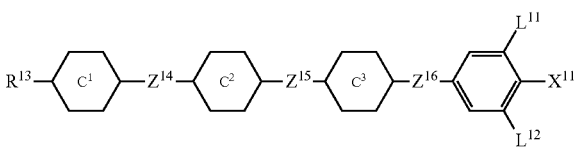
(7)

wherein, in formulas (5) to (7),
R$^{13}$ is alkyl having 1 to 10 carbons or alkenyl having 2 to 12 carbons, and in the alkyl or the alkenyl, at least one —CH$_2$— may be replaced by —O— and at least one hydrogen may be replaced by fluorine;
X$^{11}$ fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring C$^1$, ring C$^2$ and ring C$^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
Z$^{14}$, Z$^{15}$ and Z$^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and
L$^{11}$ and L$^{12}$ are independently hydrogen or fluorine.

14. The polymerizable composition of claim 11, further containing at least one compound selected from the group of compounds represented by formula (8):

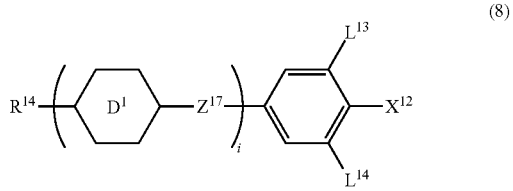
(8)

wherein, in formula (8),
R$^{14}$ is alkyl having 1 to 10 carbons or alkenyl having 2 to 12 carbons, and in the alkyl or the alkenyl, at least one —CH$_2$— may be replaced by —O— and at least one hydrogen may be replaced by fluorine;
X$^{12}$ is —C≡N or —C≡C—C≡N;
ring D$^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
Z$^{17}$ is a single bond, —CH$_2$CH$_2$—, —C≡C—, —COO—, —CF$_2$O—, —OCF$_2$— or —CH$_2$O—;
L$^{13}$ and L$^{14}$ are independently hydrogen or fluorine; and
i is 1, 2, 3 or 4.

15. A liquid crystal composite, formed by polymerization of the polymerizable composition of claim 11.

16. An optical anisotropic body, formed by polymerization of the polymerizable composition of claim 11.

17. A liquid crystal display device, including the polymerizable composition of claim 11.

18. A liquid crystal display device, including the liquid crystal composite of claim 15.

* * * * *